(12) United States Patent
Raymond et al.

(10) Patent No.: US 12,203,127 B2
(45) Date of Patent: Jan. 21, 2025

(54) METHODS FOR QUANTITATIVE GENETIC ANALYSIS OF CELL FREE DNA

(71) Applicant: Resolution Bioscience, Inc., Bellevue, WA (US)

(72) Inventors: Christopher K. Raymond, Seattle, WA (US); Lee P. Lim, Kirkland, WA (US); Christopher D. Armour, Kirkland, WA (US)

(*) Notice: Subject to any disclaimer, the term of this patent is extended or adjusted under 35 U.S.C. 154(b) by 181 days.

(21) Appl. No.: 15/727,887

(22) Filed: Oct. 9, 2017

(65) Prior Publication Data

US 2018/0179578 A1 Jun. 28, 2018

Related U.S. Application Data

(63) Continuation of application No. 14/466,741, filed on Aug. 22, 2014, now abandoned.

(51) Int. Cl.

| | | |
|---|---|---|
| *C12Q 1/6806* | (2018.01) | |
| *C12Q 1/6869* | (2018.01) | |
| *G16B 20/00* | (2019.01) | |
| *G16B 20/10* | (2019.01) | |
| *G16B 20/20* | (2019.01) | |
| *G16B 25/00* | (2019.01) | |
| *G16B 25/10* | (2019.01) | |
| *G16B 30/00* | (2019.01) | |
| *G16B 30/10* | (2019.01) | |

(52) U.S. Cl.
CPC ......... *C12Q 1/6806* (2013.01); *C12Q 1/6869* (2013.01); *G16B 20/00* (2019.02); *G16B 20/10* (2019.02); *G16B 20/20* (2019.02); *G16B 25/10* (2019.02); *G16B 30/00* (2019.02); *G16B 30/10* (2019.02); *G16B 25/00* (2019.02)

(58) Field of Classification Search
CPC .... C12Q 1/6806; C12Q 1/6869; G16B 25/00; G16B 30/00
See application file for complete search history.

(56) References Cited

U.S. PATENT DOCUMENTS

| | | |
|---|---|---|
| 5,185,243 A | 2/1993 | Ullman et al. |
| 5,512,445 A | 4/1996 | Yang et al. |
| 5,514,551 A | 5/1996 | Yang et al. |
| 5,591,582 A | 1/1997 | Bos et al. |
| 6,025,133 A | 2/2000 | Stull et al. |
| 6,025,139 A | 2/2000 | Yager et al. |
| 6,087,133 A | 7/2000 | Dattagupta et al. |
| 6,214,587 B1 | 4/2001 | Dattagupta et al. |
| 6,480,791 B1 | 11/2002 | Strathmann |
| 6,812,341 B1 | 11/2004 | Conrad |
| 7,081,527 B2 | 7/2006 | Cunningham et al. |
| 7,393,665 B2 | 7/2008 | Brenner |
| 7,537,897 B2 | 5/2009 | Brenner et al. |
| 7,585,631 B2 | 9/2009 | Cunningham et al. |
| 8,148,068 B2 | 4/2012 | Brenner |
| 8,168,385 B2 | 5/2012 | Brenner |
| 8,318,433 B2 | 11/2012 | Brenner |
| 8,370,079 B2 | 2/2013 | Sorenson et al. |
| 8,383,338 B2 | 2/2013 | Kitzman et al. |
| 8,470,996 B2 | 6/2013 | Brenner |
| 8,476,018 B2 | 7/2013 | Brenner |
| 8,481,292 B2 | 7/2013 | Casbon et al. |
| 8,722,368 B2 | 5/2014 | Casbon et al. |
| 8,741,811 B2 | 6/2014 | Lo et al. |
| 8,828,688 B2 | 9/2014 | Namsaraev |
| 8,835,358 B2 | 9/2014 | Fodor et al. |
| 8,865,410 B2 | 10/2014 | Shendure et al. |
| 8,999,642 B2 | 4/2015 | Sabot et al. |
| 9,018,365 B2 | 4/2015 | Brenner |
| 9,085,798 B2 | 7/2015 | Chee |
| 9,121,069 B2 | 9/2015 | Lo et al. |
| 9,216,172 B2 | 12/2015 | Kohno et al. |
| 9,290,808 B2 | 3/2016 | Fodor et al. |
| 9,290,809 B2 | 3/2016 | Fodor et al. |
| 9,297,011 B2 | 3/2016 | Downing et al. |
| 9,315,857 B2 | 4/2016 | Fu et al. |
| 9,340,830 B2 | 5/2016 | Lipson et al. |
| 9,410,954 B2 | 8/2016 | Boshoff et al. |
| 9,522,125 B1 | 12/2016 | Yao et al. |
| 9,546,399 B2 | 1/2017 | Amorese et al. |
| 9,598,731 B2 | 3/2017 | Talasaz |
| 9,624,489 B2 | 4/2017 | Sabot et al. |
| 9,702,002 B2 | 7/2017 | Boutell |
| 9,708,659 B2 | 7/2017 | Fodor et al. |
| 9,783,847 B2 | 10/2017 | Chee |
| 9,783,853 B2 | 10/2017 | Chinnaiyan et al. |
| 9,792,403 B2 | 10/2017 | Sun et al. |
| 9,816,137 B2 | 11/2017 | Fodor et al. |
| 9,834,822 B2 | 12/2017 | Talasaz |
| 9,840,743 B2 | 12/2017 | Talasaz |
| 9,850,523 B1 | 12/2017 | Chudova et al. |
| 9,902,992 B2 | 2/2018 | Talasaz et al. |
| 9,907,798 B2 | 3/2018 | Boshoff et al. |
| 9,920,366 B2 | 3/2018 | Eltoukhy et al. |

(Continued)

FOREIGN PATENT DOCUMENTS

| | | |
|---|---|---|
| CN | 101932729 A | 12/2010 |
| CN | 102264914 A | 11/2011 |

(Continued)

OTHER PUBLICATIONS

Horn ("Target Enrichment via DNA Hybridization Capture" in Ancient DNA: Methods and Protocols, Methods in Molecular Biology, (2012) vol. 840, ch. 21, pp. 177-188).*

(Continued)

*Primary Examiner* — Kaijiang Zhang
(74) *Attorney, Agent, or Firm* — Casimir Jones, S.C.; Thomas A. Isenbarger

(57) ABSTRACT

The invention provides a method for genetic analysis in individuals that reveals both the genetic sequences and chromosomal copy number of targeted and specific genomic loci in a single assay. The present invention further provides methods for the sensitive and specific detection of target gene sequences and gene expression profiles.

18 Claims, 27 Drawing Sheets

Specification includes a Sequence Listing.

(56) References Cited

U.S. PATENT DOCUMENTS

| | | | |
|---|---|---|---|
| 9,932,576 B2 | 4/2018 | Raymond et al. |
| 9,965,585 B2 | 5/2018 | Lo et al. |
| 10,000,800 B2 | 6/2018 | Chee |
| 10,000,814 B2 | 6/2018 | Cronin et al. |
| 10,011,870 B2 | 7/2018 | Zimmerman et al. |
| 10,047,394 B2 | 8/2018 | Fodor et al. |
| 10,059,991 B2 | 8/2018 | Fodor et al. |
| 10,087,482 B2 | 10/2018 | Korfhage et al. |
| 10,095,831 B2 | 10/2018 | Duenwald et al. |
| 10,119,165 B2 | 11/2018 | Chee |
| 10,202,646 B2 | 2/2019 | Fodor et al. |
| 10,208,296 B2 | 2/2019 | Iavarone et al. |
| 10,208,354 B2 | 2/2019 | Fernandez-Cuesta |
| 10,227,587 B2 | 3/2019 | Zhang et al. |
| 10,240,209 B2 | 3/2019 | Lo et al. |
| 10,266,883 B2 | 4/2019 | Chee |
| 10,266,889 B2 | 4/2019 | Behlke et al. |
| 10,287,630 B2 | 5/2019 | Xie et al. |
| 10,297,342 B2 | 5/2019 | Lo et al. |
| 10,329,627 B1 | 6/2019 | Beeler et al. |
| 10,378,063 B2 | 8/2019 | Stransky et al. |
| 10,378,064 B1 | 8/2019 | Schutz et al. |
| 10,388,403 B2 | 8/2019 | Rava et al. |
| 10,392,661 B2 | 8/2019 | Fodor et al. |
| 10,407,509 B2 | 9/2019 | Stransky et al. |
| 10,453,556 B2 | 10/2019 | Lo et al. |
| 10,494,678 B2 | 12/2019 | Talasaz |
| 10,501,793 B2 | 12/2019 | Chee |
| 10,501,810 B2 | 12/2019 | Talasaz |
| 10,538,759 B2 | 1/2020 | Stuelpnagel et al. |
| 10,577,601 B2 | 3/2020 | Shendure et al. |
| 10,597,653 B2 | 3/2020 | Sabot et al. |
| 10,597,708 B2 | 3/2020 | Zimmermann et al. |
| 10,597,709 B2 | 3/2020 | Zimmermann et al. |
| 10,619,203 B2 | 4/2020 | Fodor et al. |
| 10,619,214 B2 | 4/2020 | Lo et al. |
| 10,689,699 B2 | 6/2020 | Salk et al. |
| 10,704,085 B2 | 7/2020 | Talasaz et al. |
| 10,704,086 B2 | 7/2020 | Talasaz et al. |
| 10,705,087 B2 | 7/2020 | Takeuchi et al. |
| 10,741,270 B2 | 8/2020 | Lo et al. |
| 10,752,951 B2 | 8/2020 | Salk et al. |
| 10,793,916 B2 | 10/2020 | Talasaz |
| 10,801,063 B2 | 10/2020 | Eltoukhy et al. |
| 10,813,936 B2 | 10/2020 | Arrigo et al. |
| 10,815,533 B2 | 10/2020 | Lee et al. |
| 10,847,249 B2 | 11/2020 | Sun et al. |
| 10,876,152 B2 | 12/2020 | Talasaz et al. |
| 10,883,139 B2 | 1/2021 | Eltoukhy et al. |
| 10,889,858 B2 | 1/2021 | Talasaz et al. |
| 10,894,974 B2 | 1/2021 | Talasaz et al. |
| 10,907,149 B2 | 2/2021 | Raymond et al. |
| 10,921,311 B2 | 2/2021 | Takeuchi et al. |
| 10,947,600 B2 | 3/2021 | Talasaz |
| 10,982,265 B2 | 4/2021 | Talasaz et al. |
| 10,995,376 B1 | 5/2021 | Talasaz |
| 11,091,796 B2 | 8/2021 | Talasaz et al. |
| 11,142,759 B2 | 10/2021 | Sabot et al. |
| 11,186,875 B2 | 11/2021 | Carpten et al. |
| 11,186,878 B2 | 11/2021 | Beeler et al. |
| 11,230,589 B2 | 1/2022 | Lipson et al. |
| 11,319,594 B2 | 5/2022 | Raymond et al. |
| 11,319,597 B2 | 5/2022 | Talasaz |
| 11,339,391 B2 | 5/2022 | Raymond et al. |
| 11,525,162 B2 | 12/2022 | Padden |
| 11,578,372 B2 | 2/2023 | Hawryluk et al. |
| 11,633,402 B2 | 4/2023 | Kodama et al. |
| 11,643,694 B2 | 5/2023 | Mortimer et al. |
| 11,926,668 B2 | 3/2024 | Rietschel et al. |
| 2003/0148310 A1 | 8/2003 | Sorge |
| 2004/0058328 A1 | 3/2004 | Chan et al. |
| 2005/0032057 A1 | 2/2005 | Shoemaker et al. |
| 2007/0037139 A1 | 2/2007 | Tomono et al. |
| 2007/0117089 A1 | 5/2007 | Croker et al. |
| 2007/0117224 A1 | 5/2007 | Croker et al. |
| 2007/0128624 A1 | 6/2007 | Gormley et al. |
| 2007/0172873 A1 | 7/2007 | Brenner et al. |
| 2008/0038782 A1 | 2/2008 | Borns |
| 2009/0117573 A1* | 5/2009 | Fu ................ C12Q 1/6844 435/6.14 |
| 2009/0143243 A1 | 6/2009 | Gunning et al. |
| 2009/0191563 A1 | 7/2009 | Steemers et al. |
| 2009/0264305 A1 | 10/2009 | Brandon et al. |
| 2010/0093550 A1 | 4/2010 | Stuelpnagel et al. |
| 2010/0273219 A1 | 10/2010 | May et al. |
| 2011/0014657 A1 | 1/2011 | Rigatti et al. |
| 2011/0160078 A1* | 6/2011 | Fodor ................ G16B 30/00 506/9 |
| 2011/0294689 A1 | 12/2011 | Namsaraev |
| 2011/0313145 A1 | 12/2011 | Sharon et al. |
| 2012/0157322 A1* | 6/2012 | Myllykangas ....... C12Q 1/6806 506/2 |
| 2013/0288915 A1 | 10/2013 | Seligmann et al. |
| 2014/0100792 A1 | 4/2014 | Deciu et al. |
| 2014/0242581 A1 | 8/2014 | Johnson |
| 2014/0274731 A1 | 9/2014 | Raymond et al. |
| 2014/0274740 A1 | 9/2014 | Srinivasan et al. |
| 2015/0046180 A1 | 2/2015 | Futscher De Deus et al. |
| 2015/0072344 A1 | 3/2015 | Wiley |
| 2015/0111757 A1 | 4/2015 | Boyden et al. |
| 2015/0159222 A1 | 6/2015 | Gaulis et al. |
| 2015/0275289 A1 | 10/2015 | Otwinowski et al. |
| 2015/0376700 A1* | 12/2015 | Schnall-Levin ..... C12Q 1/6827 506/4 |
| 2016/0053253 A1 | 2/2016 | Salathia et al. |
| 2016/0053301 A1 | 2/2016 | Raymond et al. |
| 2017/0088887 A1 | 3/2017 | Makarov et al. |
| 2017/0096706 A1 | 4/2017 | Behlke et al. |
| 2017/0242960 A1* | 8/2017 | Rabinowitz .......... C12Q 1/6883 |
| 2017/0283869 A1 | 10/2017 | Fang et al. |
| 2017/0355984 A1 | 12/2017 | Evans et al. |
| 2017/0356053 A1 | 12/2017 | Otto et al. |
| 2018/0142234 A1 | 5/2018 | Raymond et al. |
| 2018/0163272 A1 | 6/2018 | Raymond et al. |
| 2018/0245072 A1 | 8/2018 | Raymond et al. |
| 2018/0300449 A1 | 10/2018 | Kermani et al. |
| 2018/0300456 A1 | 10/2018 | Eltoukhy et al. |
| 2018/0363066 A1 | 12/2018 | Chalmers et al. |
| 2019/0032118 A1 | 1/2019 | Lipson et al. |
| 2019/0136301 A1 | 5/2019 | Lipson et al. |
| 2019/0233897 A1 | 8/2019 | Cronin et al. |
| 2020/0048703 A1 | 2/2020 | Chee |
| 2020/0299775 A1 | 9/2020 | Hawryluk et al. |
| 2021/0198658 A1 | 7/2021 | Raymond et al. |
| 2022/0073906 A1 | 3/2022 | Guo et al. |
| 2022/0267763 A1 | 8/2022 | Raymond et al. |
| 2022/0325353 A1 | 10/2022 | Raymond et al. |

FOREIGN PATENT DOCUMENTS

| | | |
|---|---|---|
| CN | 102439177 A | 5/2012 |
| CN | 103103624 A | 5/2013 |
| CN | 103668471 A | 3/2014 |
| EP | 0709467 A2 | 5/1996 |
| EP | 0851033 A1 | 7/1998 |
| EP | 2940136 A1 | 11/2015 |
| EP | 3192869 A1 | 7/2017 |
| EP | 3202915 A1 | 8/2017 |
| EP | 3329039 A1 | 6/2018 |
| EP | 3363904 A2 | 8/2018 |
| EP | 3421613 A1 | 1/2019 |
| EP | 3470533 A1 | 4/2019 |
| EP | 3502273 A1 | 6/2019 |
| EP | 3551769 A2 | 10/2019 |
| EP | 3567120 A1 | 11/2019 |
| EP | 3374525 B1 | 1/2021 |
| JP | 2013-536679 A | 9/2013 |
| JP | 2014-512817 | 5/2014 |
| JP | 2017525371 A | 9/2017 |
| JP | 2019504618 A | 2/2019 |
| JP | 2019526257 A | 9/2019 |
| JP | 2020-516281 A | 6/2020 |
| WO | WO 1999/011819 A1 | 3/1999 |

(56) References Cited

FOREIGN PATENT DOCUMENTS

| WO | WO-9923258 A1 | 5/1999 | |
|---|---|---|---|
| WO | WO-0222890 A2 | 3/2002 | |
| WO | WO-200222890 A2 | 3/2002 | |
| WO | WO 2004/053127 A1 | 6/2004 | |
| WO | WO-2008070375 A2 | 6/2008 | |
| WO | WO 2009/076238 A2 | 6/2009 | |
| WO | WO 2009/091798 A1 | 7/2009 | |
| WO | WO2009099602 * | 8/2009 | ............. C12Q 1/68 |
| WO | WO-2010048605 A1 | 4/2010 | |
| WO | WO 2010/129937 A2 | 11/2010 | |
| WO | WO 2011/156529 A2 | 12/2011 | |
| WO | WO 2012/028746 A1 | 3/2012 | |
| WO | WO 2012/040387 A1 | 3/2012 | |
| WO | WO 2012/129363 A2 | 9/2012 | |
| WO | WO 2012/142213 A2 | 10/2012 | |
| WO | WO 2012/142334 A1 | 10/2012 | |
| WO | WO-2012138365 A1 | 10/2012 | |
| WO | WO 2012/148477 A1 | 11/2012 | |
| WO | WO 2014/052487 A1 | 4/2014 | |
| WO | WO 2014/055790 A2 | 4/2014 | |
| WO | WO 2014/071295 A1 | 5/2014 | |
| WO | WO 2014/093330 A1 | 6/2014 | |
| WO | WO 2014/093825 A1 | 6/2014 | |
| WO | WO 2014/122288 A1 | 8/2014 | |
| WO | WO 2015/134552 A1 | 9/2014 | |
| WO | WO 2015/117040 A1 | 8/2015 | |
| WO | WO 2016/022833 A1 | 2/2016 | |
| WO | WO 2016/028316 A1 | 2/2016 | |
| WO | WO 2016/037389 A1 | 3/2016 | |
| WO | WO 2016/040901 A1 | 3/2016 | |
| WO | WO 2016/094853 A1 | 6/2016 | |
| WO | WO 2016/109452 A1 | 7/2016 | |
| WO | WO-2017019322 A1 | 2/2017 | |
| WO | WO 2017/083562 A1 | 5/2017 | |
| WO | WO 2018/039463 A1 | 3/2018 | |
| WO | WO 2018/064629 A1 | 4/2018 | |
| WO | WO 2018/094183 A1 | 5/2018 | |
| WO | WO 2018/104908 A2 | 6/2018 | |
| WO | WO 2020/106906 A1 | 5/2020 | |
| WO | WO 2021/163546 | 8/2021 | |
| WO | WO-2022212574 A1 | 10/2022 | |

OTHER PUBLICATIONS

Mamanova (Nature Methods, v. 7 No. 2, Feb. 2010, p. 111-118).*
Porreca et al. (Nature Meth. 4:931-936, 2007, 16 pages with supplemental information).*
Atamaniuk et al., "Cell-free plasma DNA: a marker for apoptosis during hemodialysis." Clinical Chemistry (2006); 52.3: 523-526.
Blake, R. D., and Delcourt, S.G. "Thermodynamic effects of formamide on DNA stability." Nucleic Acids Research (1996); 24.11: 2095-2103.
Chan et al. "Cancer genome scanning in plasma: detection of tumor-associated copy number aberrations, singlenucleotide variants, and tu moral heterogeneity by massively parallel sequencing." Clinical Chemistry (2013); 59(1): 211-224.
Extended European Search Report in Application No. EP 13862440. 8, dated Oct. 11, 2016, 19 pages.
Hoeijmakers et al., "Linear amplification for deep sequencing." Nature Protocols (2011); 6.7: 1026-1036.
KAPA Biosystems "KAPA Library Quantification Kits Technical Data Sheet" (2011); 6 pages, www.kapabiosystems.com.
Leary et al. "Detection of chromosomal alterations in the circulation of cancer patients with whole-genome sequencing." Science Translational Medicine (2012); 4(162):162ra154.
Lin et al., "Exon array profiling detects EML4-ALK fusion in breast, colorectal, and non-small cell lung cancers." Molecular Cancer Research (2009); 7.9: 1466-1476.
Mano, H., "Non-solid oncogenes in solid tumors: EML4-ALK fusion genes in lung cancer." Cancer Science (2008); 99.12: 2349-2355.
McKernan et al., "Sequence and structural variation in a human genome uncovered by short-read, massively parallel ligation sequencing using two-base encoding." Genome Research (2009); 19.9: 1527-1541.
Melchior, W.B. and Hippel, P.H. "Alteration of the relative stability of dA· dT and dG· dC base pairs in DNA." Proceedings of the National Academy of Sciences USA (1973); 70.2: 298-302.
Meyer et al., "Targeted high-throughput sequencing of tagged nucleic acid samples." Nucleic Acids Research (2007); 35.15: e97, 5 pages.
Meyer et al., "From micrograms to picograms: quantitative PCR reduces the material demands of high-throughput sequencing" Nucleic Acids Research (2008); 36(1 ):e5.
Partial Supplementary European Search Report in European Application No. 13862440.8 dated Jul. 4, 2016, 11 pages.
PCT/US2013/074102, International Preliminary Report on Patentability dated Jun. 16, 2015.
PCT/US2014/052317, International Preliminary Report on Patentability dated Feb. 28, 2017, 8 pages.
PCT/US2013/074102, International Search Report and Written Opinion mailed Feb. 28, 2014.
PCT/US2014/052317, International Search Report and Written Opinion mailed Jan. 13, 2015, 13 pages.
PCT/US2016/061395, International Search Report and Written Opinion mailed Feb. 7, 2017, 14 pages.
Samorodnitsky, et al., "Comparison of Custom Capture for Targeted Next-Generation DNA Sequencing." The Journal of Molecular Diagnostics (2015); 17(1): 64-75.
Shevelev and Hübscher, "The 3'5' exonucleases", Nat Rev Mol Cell Biol., 3(5): 364-376 (2002).
Shiroguchi, et al., "Digital RNA sequencing minimizes sequence-dependent bias and amplification noise with optimized single-molecule barcodes." PNAS (2012); 109(4): 1347-1352, Supporting Information, 14 pages.
Stellwagen, Earle, et al. "Monovalent cation size and DNA conformational stability." Biochemistry (2011); 50.15: 3084-3094.
Taton, T. Andrew, et al. "Scanometric DNA array detection with nanoparticle probes." Science (2000); 289.5485: 1757-1760.
Vogelstein et al., "Cancer genome landscapes." Science (2013); 339.6127: 1546-1558.
Yegnasubramanian et al., "Preparation of Fragment Libraries for Next-Generation Sequencing on the Applied Biosystems SOLiD Platform." Methods in Enzymology (2013); 529: 185-200.
[Author Unknown] "SureSelectXT Target Enrichment System for Illumina Paired-End Multiplexed Sequencing Library". Protocol, Version C3, Sep. 2019, Agilent Technologies, @ Agilent Technologies, Inc. 2010-2019, 100 pages.
Extended European Search Report in Application No. EP 19153893. 3, dated Sep. 17, 2019, 9 pages.
Wisegeek, "How many species of bacteria are there?" WiseGeek. com, accessed Jan. 21, 2014, 2 pages. (Year: 2014).
Wikipedia, "List of sequenced bacterial genomes" Wikipedia.com, accessed Jan. 24, 2014, 57 pages. (Year: 2014).
Begley, Sharon, "Psst, The Human Genome Was Never Completely Sequenced. Some Scientists Say It Should Be", STAT News, Jun. 20, 2017 (Year: 2017), downloaded Sep. 3, 2018 from https://www.statnews.com/2017 /06/20/human-genome-not-fully-sequenced/, 8 pages.
Beltran, et al., "Circulating tumor DNA profile recognizes transformation to castration-resistant neuroendocrine prostate cancer". J Clin Invest (Apr. 1, 2020); 130(4): 1653-1668.
Cheng, et al., "Memorial Sloan Kettering-Integrated Mutation Profiling of Actionable Cancer Targets (MSK-Impact): A Hybridization Capture-Based Next-Generation Sequencing Clinical Assay for Solid Tumor Molecular Oncology". J Mol Diagn. (May 2015); 17(3): 251-264. Epub Mar. 20, 2015.
Extended European Search Report in Application No. EP 16865029. 9, dated Apr. 29, 2019, 11 pages.
Extended European Search Report in Application No. EP 17844424. 6, dated Mar. 27, 2020, 8 pages.
Extended European Search Report in Application No. EP 21152311. 3, dated Sep. 7, 2021, 14 pages.

(56) References Cited

OTHER PUBLICATIONS

Fakruddin, et al., "Nucleic acid amplification: Alternative methods of polymerase chain reaction". Journal of Pharmacy and Bioallied Sciences (Oct.-Dec. 2013); 5(4): 245-252.
Forster, et al., "A human gut bacterial genome and culture collection for improved metagenomic analyses". Nat Biotechnol. (Feb. 2019); 37(2): 186-192. Epub Feb. 4, 2019.
Jacobs, et al., "The thermal stability of oligonucleotide duplexes is sequence independent in tetraalkylammonium salt solutions: application to identifying recombinant DNA clones". Nucleic Acids Res. (May 25, 1988); 16(10): 4637-4650.
Miura, et al., "Highly efficient single-stranded DNA ligation technique improves low-input whole-genome bisulfite sequencing by post-bisulfite adaptor tagging." Nucleic Acids Research (Sep. 5, 2019); 47(15): e85-e85, p. 1-10. Epub May 22, 2019.
PCT/US2016/061395, International Preliminary Report on Patentability dated May 15, 2018, 10 pages.
PCT/US2017/048434, International Search Report and Written Opinion mailed Dec. 26, 2017, 15 pages.
PCT/US2017/048434, International Preliminary Report on Patentability dated Feb. 26, 2019, 10 pages.
PCT/US2021/049448, International Search Report and Written Opinion mailed Dec. 28, 2021, 12 pages.
Piovesan, et al., "On the length, weight and GC content of the human genome". BMC Res Notes (Feb. 27, 2019); 12: 106, 7 pages.
Rittié and Perbal, "Enzymes used in molecular biology: a useful guide". J. Cell Commun. Signal. (Jun. 2008); 2 (1-2): 25-45. Epub Sep. 3, 2008.
Oxford Dictionary of Biochemistry and Molecular Biology, Definition of "base composition", general eds Attwood, et al. Revised Edition (2000), 3 pages.
Zhou, et al., "Systematic evaluation of library preparation methods and sequencing platforms for high-throughput whole genome bisulfite sequencing." Scientific Reports (2019); 9: 10383, 16 pages.
[Author Unknown] "TruSeq™ RNA and DNA Library Preparation Kits v2". Data Sheet: Illumina® Sequencing, @ 2011, 2014 Illumina, Inc., Pub. No. 770-2009-039 Current as of Nov. 17, 2014, 4 pages.
Hess, et al., "Library preparation for next generation sequencing: A review of automation strategies". Biotechnol Adv. (Jul.-Aug. 2020); 41: 107537, 14 pages. Epub Mar. 19, 2020.
Hong and Shin, "Bisulfite-Converted DNA Quantity Evaluation: A Multiplex Quantitative Real-Time PCR System for Evaluation of Bisulfite Conversion". Front Genet. (Feb. 25, 2021); 12: 618955. eCollection 2021.
Ma, et al., "Pan-cancer genome and transcriptome analyses of 1,699 paediatric leukaemias and solid tumours". Nature (2018); 55: 371-376. Epub Feb. 28, 2018.
Malone, et al., "Molecular profiling for precision cancer therapies". Genome Med. (Jan. 14, 2020); 12(1): 8, 19 pages.
Manier, et al., "Whole-exome sequencing of cell-free DNA and circulating tumor cells in multiple myeloma". Nat Commun. (Apr. 27, 2018); 9(1): 1691, 11 pages.
Wang, et al., "Enzymatic approaches for profiling cytosine methylation and hydroxymethylation". Mol Metab. (Mar. 2022); 57: 101314. Epub Aug. 8, 2021.
Wang, et al., "Low-pass genome sequencing versus chromosomal microarray analysis: implementation in prenatal diagnosis". Genet Med. (Mar. 2020); 22(3): 500-510. Epub Aug. 26, 2019.
[Author Unknown] "An introduction to Next-Generation Sequencing Technology". Brochure, @ 2017, Illumina, Inc., Pub. No. 770-2012-008-B, ["retrieved date unknown"], https://www.illumina.com/content/dam/illumina-marketing/documents/products/illumina_sequencing_introduction.pdf, 16 pages.
Biswas, et al., "Sample quality control in agilent NGS solutions", Agilent (2018), 1-14, URL: https://www.agilent.com/cs/library/applications/application-ngs-electrophoresis-samplequalitycontrol-tapestation-5994-0127en-agilent.pdf.
International Search Report and Written Opinion for International Application No. PCT/US2022/022640, mailed Jul. 25, 2022, 15 pages.

Jang, et al., "Quality control probes for spot-uniformity and quantitative analysis of oligonucleotide array", Journal of Microbiology and Biotechnology (2009); 19(7): 658-665.
[Author Unknown] "NGS Library Preparation for Whole Genome Bisulfite Sequencing (WGBS) on Illumina® Sequencing Platforms", QIAGEN, Cat # 180495 ["retrieved date unknown"] https://www.qiagen.com/US/resources/resourcedetail?id=20735cc3-6bec-4865-9d97-8cb574840500lang=en, Oct. 2016; pp. 1-10.
[Author Unknown] "QIAseq™ Methyl Library Handbook for DNA library construction for whole genome bisulfite sequencing on Illumina® sequencing platforms", QIAGEN, Cat # 180502 ["retrieved date unknown"] https://www.qiagen.com/us/products/discovery-and-translational-research/next-generation-sequencing/dna-methylation-analysis/qiaseq-methyl-library-kit/, Nov. 2017; pp. 1-40.
[Author Unknown] "QIAseq® Targeted Methyl Panel Handbook Targeted next-generation sequencing of methylated DNA", QIAGEN, Cat # 335501 ["retrieved date unknown"] https://www.qiagen.com/us/products/discovery-and-translational-research/next-generation-sequencing/dna-methylation-analysis/qiaseq-targeted-methyl-panels/, Oct. 2019; pp. 1-60.
Cheng Jie et al., "Construction of chlamys farreri Fosmid Library and analysis of Genomic Structure", Journal of Ocean University of China, Jan. 2008, vol. 38(01); 078-088 and English abstract, 11 pages.
Diaz Jr. and Bardelli, "Liquid biopsies: genotyping circulating tumor DNA". J Clin Oncol. Feb. 20, 2014; 32(6): 579-586. Epub Jan. 21, 2014.
European Patent Application No. 19153893.3: Agilent Resolution ctDx First Technical Information, submitted with Response to Summons to Attend Oral Proceedings as "Annex B", on Mar. 17, 2023; 50 pages.
European Patent Application No. 19153893.3: Auxiliary Request 1, submitted with Response to Summons to Attend Oral Proceedings, on Mar. 17, 2023; 2 pages.
European Patent Application No. 19153893.3: Auxiliary Request 10, submitted with Response to Summons to Attend Oral Proceedings, on Apr. 17, 2023; 2 pages.
European Patent Application No. 19153893.3: Auxiliary Request 2, submitted with Response to Summons to Attend Oral Proceedings, on Mar. 17, 2023; 2 pages.
European Patent Application No. 19153893.3: Auxiliary Request 3, submitted with Response to Summons to Attend Oral Proceedings, on Mar. 17, 2023; 2 pages.
European Patent Application No. 19153893.3: Auxiliary Request 4, submitted with Response to Summons to Attend Oral Proceedings, on Mar. 17, 2023; 2 pages.
European Patent Application No. 19153893.3: Auxiliary Request 5, submitted with Response to Summons to Attend Oral Proceedings, on Mar. 17, 2023; 2 pages.
European Patent Application No. 19153893.3: Auxiliary Request 6, submitted with Response to Summons to Attend Oral Proceedings, on Mar. 17, 2023; 2 pages.
European Patent Application No. 19153893.3: Auxiliary Request 7, submitted with Response to Summons to Attend Oral Proceedings, on Mar. 17, 2023; 2 pages.
European Patent Application No. 19153893.3: Auxiliary Request 8, submitted with Response to Summons to Attend Oral Proceedings, on Apr. 17, 2023; 2 pages.
European Patent Application No. 19153893.3: Auxiliary Request 9, submitted with Response to Summons to Attend Oral Proceedings, on Apr. 17, 2023; 2 pages.
European Patent Application No. 19153893.3: Companion Diagnostics, submitted with Response to Summons to Attend Oral Proceedings as "Annex C", on Mar. 17, 2023; 2 pages.
European Patent Application No. 19153893.3: Declaration of Paul Stull with Exhibit B, signed Mar. 16, 2023, submitted with Response to Summons to Attend Oral Proceedings on Mar. 17, 2023; 8 total pages.
European Patent Application No. 19153893.3: Letter from Donna Roscoe, Ph.D. of Center for Devices and Radiological Health to Chris Pretzinger of Resolution Bioscience, Inc., signed Mar. 16, 2023, submitted with Response to Summons to Attend Oral Proceedings as "Annex A", on Mar. 17, 2023; 6 total pages.

(56) References Cited

OTHER PUBLICATIONS

European Patent Application No. 19153893.3: Main Request, submitted with Response to Summons to Attend Oral Proceedings, on Mar. 17, 2023; 2 pages.

European Patent Application No. 19153893.3: Response to Summons to Attend Oral Proceedings, dated Mar. 17, 2023; 31 pages.

Hocking, et al., "Liquid biopsies for liquid tumors: emerging potential of circulating free nucleic acid evaluation for the management of hematologic malignancies". Cancer Biol Med. Jun. 2016; 13(2): 215-225.

Jung, et al., "Cell-free DNA in the blood as a solid tumor biomarker—A critical appraisal of the literature". Clin Chim Acta. Nov. 11, 2010; 411(21-22): 1611-1624. Epub Aug. 2, 2010.

Kivioja, T., et al., "Counting absolute Nos. of molecules using unique molecular identifiers", Nature Methods (Nov. 20, 2011); 9(1): 72-74.

PCT/US2021/049448, International Preliminary Report on Patentability dated Mar. 23, 2023, 7 pages.

Pollak, Julia, et al., "Analytical validation of the Agilent Resolution ctDx HRD plasma assay used to identify mCRPC patients with mutations, including homozygous deletions, in DNA repair genes as a companion diagnostic for niraparib". Poster Abstract# 52 RA# PR7000-3277, [publication date unknown], 1 page.

Sparks et al., Selective analysis of cell-free DNA in maternal blood for evaluation of fetal trisomy. Prenat Diagn. Jan. 2012;32(1):3-9.

Cunningham, et al., "Abstract 881. Rapid Detection of Mycoplasma pneumoniae from Clinical Specimens by Transcription-Mediated Amplification". ICAAC 40th Anniversary, Toronto, Sept. 17-20, 2000, 2 pages.

Stull and Blanchard, "Improvement in the Dispersion of Silica Nanoparticles". 241st ACS National Meeting, Mar. 28-31, 2011, Abstract, 1 page.

Stull and Blanchard, "Surface coatings on anisotropic nanoparticles". 246th ACS National Meeting, Sep. 11-12, 2013, Abstract, 1 page.

Parham et al., Specific magnetic bead based capture of genomic DNA from clinical samples: application to the detection of group B streptococci in vaginal/anal swabs. Clin Chem. Sep. 2007;53(9): 1570-6.

Spiro et al., A bead-based method for multiplexed identification and quantitation of DNA sequences using flow cytometry. Appl Environ Microbiol. Oct. 2000;66(10):4258-65.

\* cited by examiner

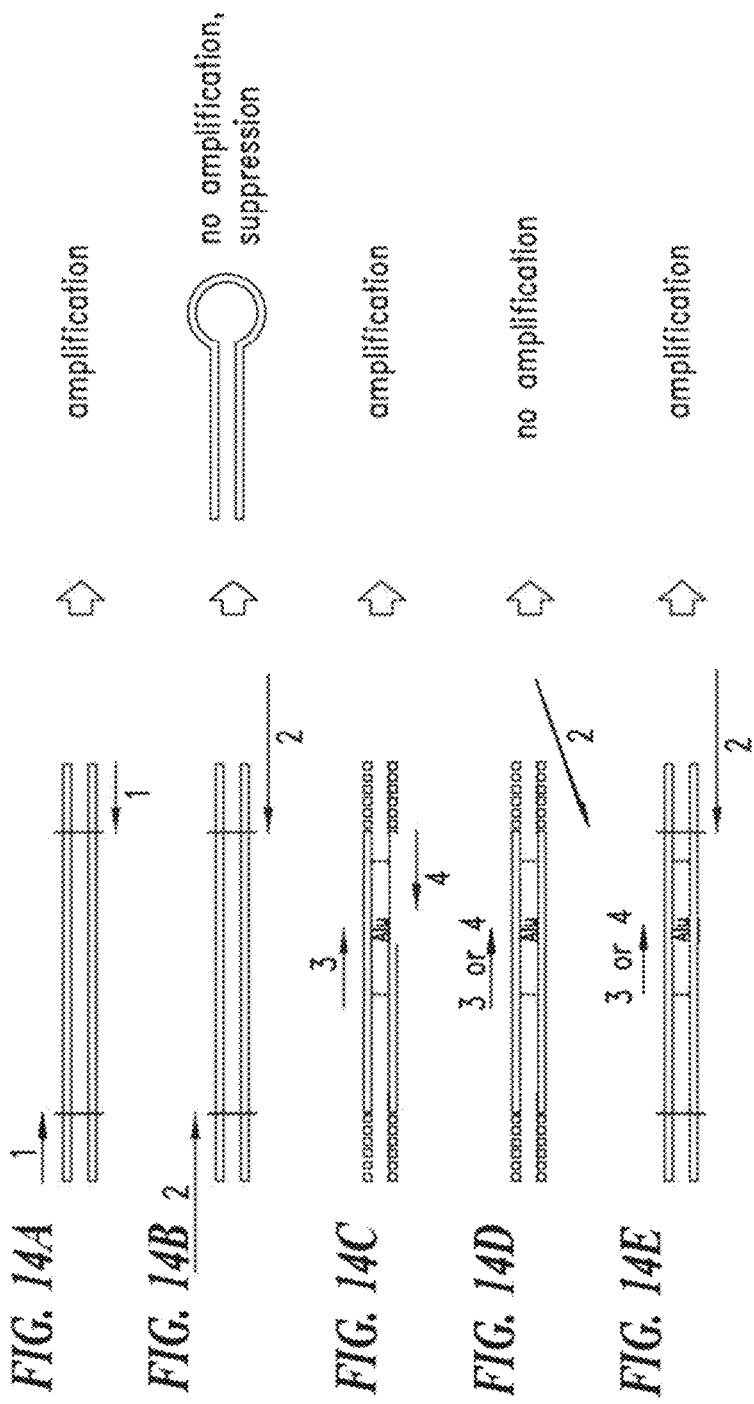

METHODS FOR QUANTITATIVE GENETIC ANALYSIS OF CELL FREE DNA

CROSS-REFERENCE TO RELATED APPLICATIONS

This application is a continuation of U.S. patent application Ser. No. 14/466,741, filed Aug. 22, 2014, which is incorporated herein by reference in its entirety.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is CLFK_002_01US_ST25.txt. The text file is 117 KB, was created on Oct. 6, 2017 and is being submitted electronically via EFS-Web.

BACKGROUND OF THE INVENTION

Technical Field

The invention relates generally to compositions and methods for the quantitative genetic analysis of cell free DNA (cfDNA). In particular, the present invention relates to improved targeted sequence capture compositions and methods for the genetic characterization and analysis of cfDNA.

Description of the Related Art

It is becoming increasing clear that most, if not all, of the most common human cancers are diseases of the human genome. The emerging picture is that somatic mutations accumulate during an individual's lifetime, some of which increase the probability that the cell in which they are harbored can develop into a tumor (Vogelstein et al., Science 339(6127): 1546-1558 (2013)). With just the wrong combination of accumulated mutational events, a precancerous growth loses constraints that keep uncontrolled proliferation in check and the resulting cell mass becomes a cancer. The constellations of mutations that are necessary and sufficient to cause cancer are often collectively referred to as "driver mutations." One of the themes that have emerged from recent and intensive molecular analysis is that cancer, once thought of as a single, tissue-specific disease, is in fact a group of related diseases, each with a unique molecular pathology. The human genome project laid the groundwork for genome-wide analysis of cancers.

For example, the introduction of next-generation sequencing technologies (2004-present) has accelerated the discovery pace of causal genomic factors that underlie the diagnosis of NSCLC, making it clear that NSCLC is really a family of related diseases, each of which may be responsive to a different targeted therapy.

The art lacks reliable and robust molecular analysis methods for the analysis of genetic diseases. Traditionally, molecular diagnostics have consisted of antibody-based tests (immunohistochemistry), in-situ hybridization with DNA probes (fluorescence in situ hybridization), and hybridization or PCR-based tests that query specific nucleotide sequences. Until recently, DNA sequencing as a molecular diagnostic tool has been generally limited to the coding exons of one or two genes. While DNA sequencing has been used in the diagnosis and treatment of solid cancers, one of the most significant drawbacks of these methods is that they require direct access to tumor tissues. Such material is often difficult to obtain from the initial biopsy used to diagnose the disease and virtually impossible to obtain in multiple repetitions over time. Similarly, biopsies are not possible in patients with inaccessible tumors and not practical in individuals suffering from metastatic disease.

Thus, the vast potential of molecular diagnostics for genetic diseases; fetal testing; paternity testing; predicting response to drug treatment; diagnosing or monitoring a medical condition; mendelian disorders; genetic mosaicism; pathogen screening; microbiome profiling; and organ transplant monitoring; has yet to be realized. To date, existing molecular diagnostics approaches lack efficient solutions to clone and amplify individual DNA molecules, as well as solutions to efficiently target sequencing to specific genomic loci, with sensitivity sufficient to discriminate true positive test results from false positive signals that arise during sample processing.

BRIEF SUMMARY OF THE INVENTION

The invention relates generally to compositions and methods for improved compositions and methods for the genetic analysis of cfDNA.

In various embodiments, a method for genetic analysis of cell-free DNA (cfDNA) is provided, comprising: treating cfDNA with one or more end-repair enzymes to generate end-repaired cfDNA; ligating one or more adaptors to each end of the end-repaired cfDNA to generate a cfDNA library; amplifying the cfDNA library to generate cfDNA library clones; determining the number of genome equivalents in the cfDNA clone library; and performing a quantitative genetic analysis of one or more target genetic loci in the cfDNA library clones.

In a particular embodiment, the method further comprises isolating cfDNA from a biological sample of a subject.

In an additional embodiment, the cfDNA is isolated from a biological sample selected from the group consisting of: amniotic fluid, blood, plasma, serum, semen, lymphatic fluid, cerebral spinal fluid, ocular fluid, urine, saliva, stool, mucous, and sweat.

In a certain embodiment, the one or more adaptors comprise a plurality of adaptor species.

In a particular embodiment, the one or more adaptors each comprise a primer binding site for amplification of the cfDNA library.

In a further embodiment, the one or more adaptors each comprise one or more unique read codes.

In an additional embodiment, the one or more adaptors each comprise one or more sample codes for sample multiplexing.

In another embodiment, the one or more adaptors each comprise one or more sequences for DNA sequencing.

In a particular embodiment, qPCR is performed on the cfDNA clone library and a qPCR measurement is compared to standards of known genome equivalents to determine the genome equivalents of the cfDNA clone library.

In another particular embodiment, qPCR is performed with a primer that binds to an Alu sequence and a primer that binds to a sequence in an adaptor.

In a certain embodiment, the quantitative genetic analysis is performed on a plurality of genetic loci in the cfDNA library clones.

In a further embodiment, the quantitative genetic analysis is performed on a plurality of genetic loci in a plurality of cfDNA clone libraries.

In an additional embodiment, the quantitative genetic analysis comprises hybridizing one or more capture probes to a target genetic locus to form capture probe-cfDNA clone complexes.

In a particular embodiment, the quantitative genetic analysis comprises isolating the capture probe-cfDNA clone complexes.

In a certain embodiment, the quantitative genetic analysis comprises amplification of the cfDNA clone sequence in the isolated hybridized capture probe-cfDNA clone complexes.

In a further embodiment, the quantitative genetic analysis comprises DNA sequencing to generate a plurality of sequencing reads.

In another embodiment, the quantitative genetic analysis comprises bioinformatic analysis of the plurality of sequencing reads.

In a particular embodiment, bioinformatics analysis is used: to quantify the number of genome equivalents analyzed in the cfDNA clone library; to detect genetic variants in a target genetic locus; to detect mutations within a target genetic locus; to detect genetic fusions within a target genetic locus; and to measure copy number fluctuations within a target genetic locus.

In an additional embodiment, the subject does not have a genetic disease.

In a certain embodiment, the subject has not been diagnosed with a genetic disease.

In another certain embodiment, the subject has been diagnosed with a genetic disease.

In another embodiment, the quantitative genetic analysis is used to identify or detect one or more genetic lesions that cause or associated with the genetic disease.

In a certain embodiment, the genetic lesion comprises a nucleotide transition or transversion, a nucleotide insertion or deletion, a genomic rearrangement, a change in copy number, or a gene fusion.

In a particular embodiment, the genetic lesion comprises a genomic rearrangement that fuses the 3' coding region of the ALK gene to another gene.

In a particular embodiment, the 3' coding region of the ALK gene is fused to the EML4 gene.

In another embodiment, the genetic disease is cancer.

In a further embodiment, the subject is pregnant.

In an additional embodiment, the quantitative genetic analysis is used to identify or detect one or more genetic variants or genetic lesions of one or more target genetic loci in fetal cfDNA.

In a particular embodiment, the subject is a transplant recipient.

In an additional embodiment, the quantitative genetic analysis is used to identify or detect donor cfDNA in the subject.

In various embodiments, a method of predicting, diagnosing, or monitoring a genetic disease in a subject is provided, comprising: isolating or obtaining cfDNA from a biological sample of a subject; treating the cfDNA with one or more end-repair enzymes to generate end-repaired cfDNA; ligating one or more adaptors to each end of the end-repaired cfDNA to generate a cfDNA library; amplifying the cfDNA library to generate a cfDNA clone library; determining the number of genome equivalents in the cfDNA clone library; and performing a quantitative genetic analysis of one or more target genetic loci associated with the genetic disease in the cfDNA clone library, wherein the identification or detection of one or more genetic lesions in the one or more target genetic loci is prognostic for, diagnostic of, or monitors the progression of the genetic disease.

In an additional embodiment, the cfDNA is isolated from a biological sample selected from the group consisting of: amniotic fluid, blood, plasma, serum, semen, lymphatic fluid, cerebral spinal fluid, ocular fluid, urine, saliva, stool, mucous, and sweat.

In a certain embodiment, the genetic lesion comprises a nucleotide transition or transversion, a nucleotide insertion or deletion, a genomic rearrangement, a change in copy number, or a gene fusion.

In a particular embodiment, the genetic lesion comprises a genomic rearrangement that fuses the 3' coding region of the ALK gene to another gene.

In a further embodiment, the 3' coding region of the ALK gene is fused to the EML4 gene.

In a particular embodiment, the genetic disease is cancer.

In various embodiments, a companion diagnostic for a genetic disease is provided comprising: isolating or obtaining cfDNA from a biological sample of a subject; treating the cfDNA with one or more end-repair enzymes to generate end-repaired cfDNA; ligating one or more adaptors to each end of the end-repaired cfDNA to generate a cfDNA library; amplifying the cfDNA library to generate a cfDNA clone library; determining the number of genome equivalents in the cfDNA clone library; and performing a quantitative genetic analysis of one or more biomarkers associated with the genetic disease in the cfDNA clone library, wherein detection of, or failure to detect, at least one of the one or more biomarkers indicates whether the subject should be treated for the genetic disease.

In a particular embodiment, the cfDNA is isolated from a biological sample selected from the group consisting of: amniotic fluid, blood, plasma, serum, semen, lymphatic fluid, cerebral spinal fluid, ocular fluid, urine, saliva, stool, mucous, and sweat.

In an additional embodiment, the biomarker is a genetic lesion.

In a particular embodiment, the genetic lesion comprises a nucleotide transition or transversion, a nucleotide insertion or deletion, a genomic rearrangement, a change in copy number, or a gene fusion.

In an additional embodiment, the genetic lesion comprises a genomic rearrangement that fuses the 3' coding region of the ALK gene to another gene.

In a further embodiment, the 3' coding region of the ALK gene is fused to the EML4 gene.

In a certain embodiment, the genetic disease is cancer.

BRIEF DESCRIPTION OF THE SEVERAL VIEWS OF THE DRAWINGS

FIG. 9A shows a representative example of the size distribution of cell-free DNA (cfDNA) libraries. The dominant band is consistent with a collection of 170±10 bp fragments ligated to 90 bp of adaptors. FIG. 9B shows a published gel image of cfDNA and a representative cfDNA library generated using the methods disclosed and/or contemplated herein. The qualitative "ladder" appearance is conserved in the library, but the library is shifted to higher mass by the addition of 90 bp of adaptor sequences. FIG. 9C shows a representative example of genomic, plasma-derived cfDNA libraries from Ovarian cancer patients (OvC) and "healthy donors" (HD).

FIG. 14A-FIG. 14E show a schematic of the core elements of a qPCR genome equivalent measurement assay that couples an genomic repeat specific primer (e.g., Alu) and a long adaptor-specific primer. FIG. 14A shows standard library amplification using a single, 25 nt primer named ACA2 (primer 1). FIG. 14B shows longer, 58 nt versions of the ACA2 primer (primer 2) do not amplify genomic libraries because of stem-loop suppression. FIG. 14C shows forward and reverse primers directed to a consensus human Alu repeat element (primers 3 and 4) recognize 1000's of loci and readily amplify genomic DNA. FIG. 14D shows a single Alu primer alone, either forward or reverse (primer 3 or primer 4), coupled with the long ACA2 primer (primer 2) do not amplify genomic DNA. FIG. 14E shows the same primer pair as in FIG. 14D readily amplifies genomic cfDNA library clones that contain Alu sequences.

FIG. 15A shows amplification of 10 pg of a standard genomic library with various PCR primers. The x-axis specifies PCR primers used for amplification and the Y-axis (log scale) indicates the PCR signal measured in units of fg/µL. The standard ACA2 primer produced a strong signal, as expected. The ACA2 long primer failed to produce signal owing to PCR suppression. The two Alu primer pairs both produced signal at 1% the amount of ACA2, suggesting that 1% of clones possess an amplifiable Alu sequence. The combination of any Alu primer with the long ACA2 primer also produced signal in ~1% of clones. FIG. 15B shows validation against 10 pg of genomic DNA (left four samples) or 10 pg of library DNA (right four clones). Alu primer pairs amplify comparable signal from genomic DNA or a genomic library. In contrast, primer pairs consisting of an Alu primer and a long ACA2 primer amplify genomic DNA poorly (L+A1F) or not at all (L+A1R). These same pairs exhibit amplification of library that slightly exceeds the signal from Alu primer pairs.

FIG. 17A shows fine structure of the adaptor ligation strand. Details relating to each numbered element are provided in Example 4. FIG. 17B shows the duplex formed between 45 nt ligation strands and 12 nt partner oligo strand creates a blunt-end ligation substrate compatible with end-repaired cfDNA fragments (solid bars). FIG. 17C shows, following ligation, the complement to the ligation strand is created by a DNA polymerase-mediated fill-in reaction.

DETAILED DESCRIPTION OF THE INVENTION

A. Overview

Figure 1:
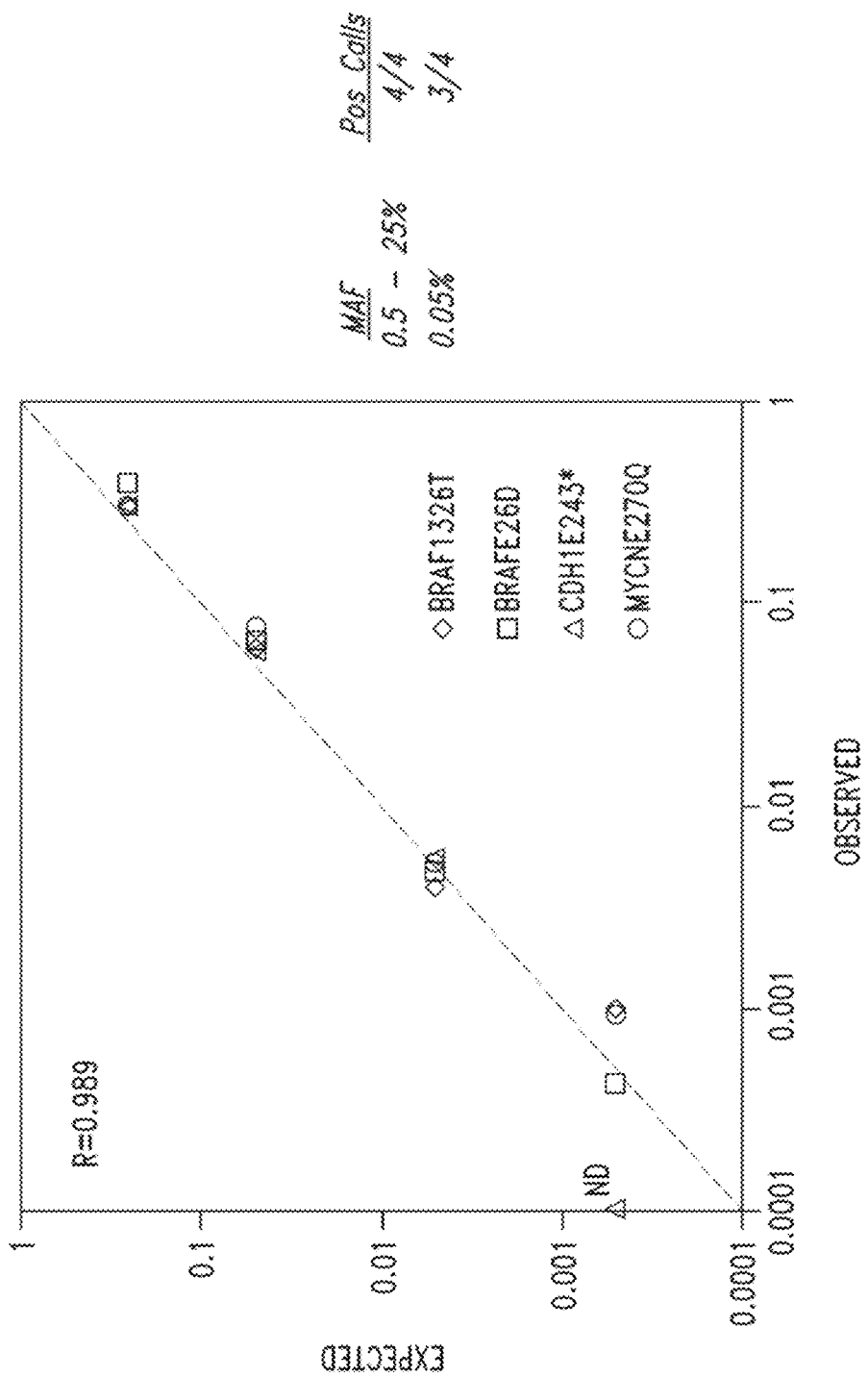
FIG. 1 shows the expected versus observed variant frequencies as a function of admix dilution in the absence of unique read filtering. In the absence of unique read filtering, random base changes at these four selected positions occurred with measurable, non-zero frequencies; thus, demonstrating a lack of sensitivity to detect the particular single nucleotide variants (SNV).

The present invention contemplates, in part, compositions and methods for the quantitative genetic analysis of the genetic state of an individual using cell-free DNA (cfDNA). As used herein, the term "genetic state" refers to the sequence of one or more target genome sequences in the genome in relation to a non-causal normal sequence or in relation to a sequence that is causal for a genetic condition or disease. In one embodiment, analyzing the genetic state refers to identifying, quantifying, or monitoring a genetic variant in a target genetic locus, wherein the variant varies with respect to a reference sequence (e.g., a normal or mutated sequence). The present inventors have provided solutions to the molecular diagnostic problems of genetic conditions or diseases associated with lack of sensitivity to discriminate true positives from false positives, inefficient cloning and amplification of individual DNA molecules, and inefficient targeted sequencing to specific genomic loci. The solutions contemplated herein comprise compositions and methods for reliable and robust quantitative genetic analysis with sensitivity sufficient to discriminate true positive test results from false positive signals that arise during sample processing.

Next-generation sequencing technology has afforded the opportunity to add broad genomic surveys to molecular diagnosis in a variety of scenarios including cancers, fetal diagnostics, paternity testing, pathogen screening and organ transplant monitoring. In the context of genetic diseases, next-generation sequencing information is being used in a clinical setting to identify mutations within genes that are likely to alter gene function, to identify the gain or loss of genetic material within cells, and to identify genomic rearrangements that are not found in normal, healthy cells. The results of these broad diagnostic surveys are often used to guide patient treatment.

However, the potential benefits of DNA sequencing in diagnosis and treatment of the genetic state of an individual or genetic conditions or diseases is outweighed by the need to directly access affected tissues to obtain samples. Such material is often difficult to obtain from the initial biopsy used to diagnose the disease and virtually impossible to obtain in multiple repetitions over time. Similarly, in cancer patients, biopsies are not possible in patients with inaccessible tumors and not practical in individuals suffering from metastatic disease. In contrast, the present inventors' approach derives from the fact that all tissues require access to the vasculature to survive and as a consequence these masses deposit DNA into bodily fluids. One major depot of bodily fluid in which the DNA of diseased cells is found is the plasma of human blood.

In contrast to testing methods that rely on shallow, genome-wide sequence coverage, molecular diagnostics contemplated herein for the genetic state of an individual; genetic diseases; mendelian disorders; genetic mosaicism; fetal testing; paternity testing; predicting response to drug treatment; diagnosing or monitoring a medical condition; pathogen screening; microbiome profiling; and organ transplant monitoring leverage the availability of cfDNA to provide deep sequence coverage of select target genes. In addition, the cfDNA-based cancer diagnostics contemplated herein possess the ability to detect a variety of genetic changes including somatic sequence variations that alter protein function, large-scale chromosomal rearrangements that create chimeric gene fusions, and copy number variation that includes loss or gain of gene copies. Using the contemplated compositions and methods, these changes are detectable and quantifiable in the face of significant dilution, or admixture, of normal sequences within cfDNA that are contributed by the normal turnover processes that happen within healthy tissues. The compositions and methods contemplated herein also successfully address the major challenges associated with detecting rare genetic changes causal of disease; namely, that cfDNA is highly fragmented, that cfDNA levels vary substantially between different individuals, and that the degree of admixture of diseased versus normal sequences is highly variable among patients, even within individuals suffering from the same molecular disease and stage.

In various embodiments, compositions and methods for genetic analysis of comprise interrogating the DNA fraction within biological fluid samples and stool samples. The methods contemplated herein provide a novel comprehensive framework address molecular genetic analysis using cfDNA available from a variety of biological sources. Cloning of purified cfDNA introduces tagged cfDNA sequences that inform downstream analysis and enable amplification of the resulting clone libraries. Hybrid capture with target specific oligonucleotides is used to retrieve specific sequences for subsequent analysis. Independent measurements of the number of genomes present in the library are applied to each sample, and these assays provide a means to estimate the assay's sensitivity. The assays contemplated herein provide reliable, reproducible, and robust methods for the analysis, detection, diagnosis, or monitoring of genetic states, conditions, or disease.

The practice of particular embodiments of the invention will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (*John Wiley and Sons*, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); and Harlow and Lane, *Antibodies*, (Cold Spring Harbor Laboratory Press, Cold Spring Harbor, N.Y., 1998).

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred embodiments of compositions, methods and materials are described herein. For the purposes of the present invention, the following terms are defined below.

The articles "a," "an," and "the" are used herein to refer to one or to more than one (i.e. to at least one) of the grammatical object of the article. By way of example, "an element" means one element or more than one element.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. In particular embodiments, the terms "include," "has," "contains," and "comprise" are used synonymously.

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "isolated" means material that is substantially or essentially free from components that normally accompany it in its native state. In particular embodiments, the term "obtained" or "derived" is used synonymously with isolated.

As used herein, the term "DNA" refers to deoxyribonucleic acid. In various embodiments, the term DNA refers to genomic DNA, recombinant DNA, synthetic DNA, or cDNA. In one embodiment, DNA refers to genomic DNA or cDNA. In particular embodiments, the DNA comprises a "target region." DNA libraries contemplated herein include genomic DNA libraries and cDNA libraries constructed from RNA, e.g., an RNA expression library. In various embodiments, the DNA libraries comprise one or more additional DNA sequences and/or tags.

A "target genetic locus" or "DNA target region" refers to a region of interest within a DNA sequence. In various embodiments, targeted genetic analyses are performed on the target genetic locus. In particular embodiments, the DNA target region is a region of a gene that is associated with a particular genetic state, genetic condition, genetic diseases; fetal testing; genetic mosaicism, paternity testing; predicting response to drug treatment; diagnosing or monitoring a medical condition; microbiome profiling; pathogen screening; or organ transplant monitoring.

As used herein, the terms "circulating DNA," "circulating cell-free DNA" and "cell-free DNA" are often used interchangeably and refer to DNA that is extracellular DNA, DNA that has been extruded from cells, or DNA that has been released from necrotic or apoptotic cells.

A "subject," "individual," or "patient" as used herein, includes any animal that exhibits a symptom of a condition that can be detected or identified with compositions contemplated herein. Suitable subjects include laboratory animals (such as mouse, rat, rabbit, or guinea pig), farm animals (such as horses, cows, sheep, pigs), and domestic animals or pets (such as a cat or dog). In particular embodiments, the subject is a mammal. In certain embodiments, the subject is a non-human primate and, in preferred embodiments, the subject is a human.

C. Methods of Genetic Analysis of Cell Free DNA

In various embodiments, a method for genetic analysis of cfDNA is provided.

In particular embodiments, a method for genetic analysis of cfDNA comprises: generating and amplifying a cfDNA library, determining the number of genome equivalents in the cfDNA library; and performing a quantitative genetic analysis of one or more genomic target loci.

A method for genetic analysis of cfDNA comprises treating cfDNA with one or more end-repair enzymes to generate end-repaired cfDNA and ligating one or more adaptors to each end of the end-repaired cfDNA to generate a cfDNA library; amplifying the cfDNA library to generate cfDNA library clones; determining the number of genome equivalents of cfDNA library clones; and performing a quantitative genetic analysis of one or more target genetic loci in the cfDNA library clones.

1. Generating a cfDNA Library

In particular embodiments, methods of genetic analysis contemplated herein comprise generating a cfDNA library comprising treating cfDNA with one or more end-repair enzymes to generate end-repaired cfDNA and ligating one or more adaptors to each end of the end-repaired cfDNA to generate the cfDNA library.

(a) Cell-Free DNA (cfDNA)

The methods and compositions contemplated herein are designed to efficiently analyze, detect, diagnose, and/or monitor genetic states, genetic conditions, genetic diseases, genetic mosaicism, fetal diagnostics, paternity testing, microbiome profiling, pathogen screening, and organ transplant monitoring using cell-free DNA (cfDNA) as an analyte. The size distribution of cfDNA ranges from about 150 bp to about 180 bp fragments. Fragmentation may be the result of endonucleolytic and/or exonucleolytic activity and presents a formidable challenge to the accurate, reliable, and robust analysis of cfDNA. Another challenge for analyzing cfDNA is its short half-life in the blood stream, on the order of about 15 minutes. Without wishing to be bound to any particular theory, the present invention contemplates, in part, that analysis of cfDNA is like a "liquid biopsy" and is a real-time snapshot of current biological processes.

Moreover, because cfDNA is not found within cells and may be obtained from a number of suitable sources including, but not limited to, biological fluids and stool samples, it is not subject to the existing limitations that plague next generation sequencing analysis, such as direct access to the tissues being analyzed.

Illustrative examples of biological fluids that are suitable sources from which to isolate cfDNA in particular embodiments include, but are not limited to amniotic fluid, blood, plasma, serum, semen, lymphatic fluid, cerebral spinal fluid, ocular fluid, urine, saliva, mucous, and sweat.

In particular embodiments, the biological fluid is blood or blood plasma.

In certain embodiments, commercially available kits and other methods known to the skilled artisan can used to isolate cfDNA directly from the biological fluids of a patient or from a previously obtained and optionally stabilized biological sample, e.g., by freezing and/or addition of enzyme chelating agents including, but not limited to EDTA, EGTA, or other chelating agents specific for divalent cations.

(b) Generating End-Repaired cfDNA

In particular embodiments, generating a cfDNA library comprises the end-repair of isolated cfDNA. The fragmented cfDNA is processed by end-repair enzymes to generate end-repaired cfDNA with blunt ends, 5'-overhangs, or 3'-overhangs. In some embodiments, the end-repair enzymes can yield for example. In some embodiments, the end-repaired cfDNA contains blunt ends. In some embodiments, the end-repaired cfDNA is processed to contain blunt ends. In some embodiments, the blunt ends of the end-repaired cfDNA are further modified to contain a single base pair overhang. In some embodiments, end-repaired cfDNA containing blunt ends can be further processed to contain adenine (A)/thymine (T) overhang. In some embodiments, end-repaired cfDNA containing blunt ends can be further processed to contain adenine (A)/thymine (T) overhang as the single base pair overhang. In some embodiments, the end-repaired cfDNA has non-templated 3' overhangs. In some embodiments, the end-repaired cfDNA is processed to contain 3' overhangs. In some embodiments, the end-repaired cfDNA is processed with terminal transferase (TdT) to contain 3' overhangs. In some embodiments, a G-tail can be added by TdT. In some embodiments, the end-repaired cfDNA is processed to contain overhang ends using partial digestion with any known restriction enzymes (e.g., with the enzyme Sau3A, and the like.

(c) Ligating Adaptor Molecules to End-Repaired cfDNA

In particular embodiments, generating a cfDNA library comprises ligating one or more adaptors to each end of the end-repaired cfDNA. The present invention contemplates, in part, an adaptor module designed to accommodate large numbers of genome equivalents in cfDNA libraries. Adaptor modules are configured to measure the number of genome equivalents present in cfDNA libraries, and, by extension, the sensitivity of sequencing assays used to identify sequence mutations.

As used herein, the term "adaptor module" refers to a polynucleotide comprising at least five elements: (i) a first element comprising a PCR primer binding site for the single-primer library amplification; (ii) a second element comprising a 5 nucleotide read code that acts to uniquely identified each sequencing read; (iii) a third element comprising a 3 nucleotide sample code to identify different samples and enable sample multiplexing within a sequencing run; (iv) a fourth element comprising a 12 nucleotide anchor sequence that enables calibration of proper base calls in sequencing reads and acts as an anchor for hybridization to a partner oligonucleotide; and (v) a fifth element comprising the two 3' terminal nucleotides of Element 4 (FIG. 17 and Tables 12-16). The adaptor module is hybridized to a partner oligonucleotide that is complementary to Element 4 to form an adaptor suitable for ligating to the ends of cfDNA, optionally end-repaired blunt-ended cfDNA.

In particular embodiments, an adaptor module comprises one or more PCR primer sequences, one or more read codes, one or more sample codes, one or more anchor sequences, and two or more 3'nucleotides that are efficient ligation substrates. In additional embodiments, the adaptor module further comprises one or more sequencing primer binding sites.

In particular embodiments, an adaptor module comprises a first element that comprises one or more PCR primer binding sequences for single-primer amplification of a cfDNA library. In one embodiment, the PCR primer binding sequence is about 12 to about 40 nucleotides, about 18 to about 40 nucleotides, about 20 to about 35 nucleotides, or about 20 to about 30 nucleotides. In another embodiment, the PCR primer binding sequence is about 12 nucleotides, about 13 nucleotides, about 14 nucleotides, about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides, about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, or about 40 nucleotides or more.

In one embodiment, the PCR primer binding sequence is about 25 nucleotides.

In particular embodiments, an adaptor module comprises a second element that comprises one or more read code sequences. As used herein, the term "read code" refers to a polynucleotide that is used to identify unique sequencing reads. In one embodiment, the read code is a random sequence of nucleotides. In one embodiment, the read code is about 1 nucleotide, about 2 nucleotides, about 3 nucleotides, about 4 nucleotides, about 5 nucleotides, about 6 nucleotides, about 7 nucleotides, about 8 nucleotides, about 9 nucleotides, about 10 nucleotides, or more.

By way of a non-limiting example, a 5 nucleotide codes consists of 256 possible unique sequences where each code chosen is 2 nucleotides different from every other code in the set. This feature enables unique and distinct reads to be differentiated from reads that appear to be unique owing to a sequencing error in the code region. In particular embodiments, codes that have been empirically determined to interfere with adaptor function, owing to particular sequence combinations, may be excluded from use, e.g., seven codes of the 256 had an overrepresentation of G nucleotides and were excluded.

In other embodiments, each read code of 5, 6, 7, 8, 9, 10 or more nucleotides may differ by 2, 3, 4, or 5 nucleotides from every other read code.

In one embodiment, the read code is about 5 nucleotides and differs from every other read code by 2 nucleotides.

In particular embodiments, an adaptor module comprises a third element that comprises one or more sample code sequences. As used herein, the term "sample code" refers to a polynucleotide that is used to identify the sample. The sample code is also useful in establishing multiplex sequencing reactions because each sample code is unique to the sample and thus, can be used to identify a read from a particular sample within a multiplexed sequencing reaction.

In one embodiment, the sample code comprises sequence that is about 1, about 2 nucleotides, about 3 nucleotides, about 4 nucleotides, or about 5 nucleotides, or more. In another embodiment, each sample code of 2, 3, 4, 5 or more nucleotides may differ from every other sample code by 2, 3, 4, or 5 nucleotides.

In one embodiment, the sample code is about three nucleotides and differs from every other sample code used in other samples by two nucleotides.

In particular embodiments, an adaptor module comprises a fourth element that comprises one or more anchor sequences. As used herein, an "anchor sequence" refers to a nucleotide sequence of at least 8 nucleotides, at least 10 nucleotides, at least 12 nucleotides, at least 14 nucleotides, or at least 16 nucleotides that hybridizes to a partner oligonucleotide and that comprises the following three properties: (1) each anchor sequence is part of a family of four anchor sequences that collectively represent each of the four possible DNA bases at each site within extension; this feature, balanced base representation, is useful to calibrate proper base calling in sequencing reads in particular embodiments; (2) each anchor sequence is composed of only two of four possible bases, and these are specifically chosen to be either and equal number of A +C or an equal number of G+T; an anchor sequence formed from only two bases reduces the possibility that the anchor sequence will participate in secondary structure formation that would preclude proper adaptor function; and (3) because each anchor sequence is composed of equal numbers of A+C or G+T, each anchor sequence shares roughly the same melting temperature and duplex stability as every other anchor sequence in a set of four.

In particular embodiments, an adaptor module comprises a fifth element that is comprised of the two 3' terminal nucleotides of Element 4. These two bases at the 3' end of each anchor are chosen based on an empirical determination that shows that these two nucleotides are efficient substrates for ligation to the cfDNA. In particular embodiments, Element 5 comprises the sequences selected from the group consisting of: AA, CC, TT and GG. In particular embodiments, Element 5 does not comprise the dinucleotide combination CG or TG as the inventors have determined that these combinations are not efficient ligation substrates.

In particular embodiments, a ligation step comprises ligating an adaptor module to the end-repaired cfDNA to generate a "tagged" cfDNA library. In some embodiments, a single adaptor module is employed. In some embodiments, two, three, four or five adaptor modules are employed. In some embodiments, an adaptor module of identical sequence is ligated to each end of the fragmented end-repaired DNA.

In one embodiment, a plurality of adaptor species is ligated to an end-repaired cfDNA library. Each of the plurality of adaptors may comprise one or more primer binding site for amplification of the cfDNA library, one or more read code sequences, one or more sequences for sample multiplexing, and one or more sequences for DNA sequencing.

Ligation of one or more adaptors contemplated herein may be carried out by methods known to those of ordinary skill in the art. In particular embodiments, one or more adaptors contemplated herein are ligated to end-repaired cfDNA that comprises blunt ends. In certain embodiments, one or more adaptors contemplated herein are ligated to end-repaired cfDNA that comprises complementary ends appropriate for the ligation method employed. In certain embodiments, one or more adaptors contemplated herein are ligated to end-repaired cfDNA that comprises a 3' overhang.

2. cfDNA Library Amplification

In particular embodiments, methods of genetic analysis contemplated herein comprise amplification of a cfDNA library to generate a cfDNA clone library or a library of cfDNA clones. Each molecule of the cfDNA library comprises an adaptor ligated to each end of an end-repaired cfDNA, and each adaptor comprises one or more PCR primer binding sites. In one embodiment, different adaptors are ligated to different ends of the end-repaired cfDNA.

In a preferred embodiment, the same adaptor is ligated to both ends of the cfDNA. Ligation of the same adaptor to both ends of end-repaired cfDNA allows for PCR amplification with a single primer sequence. In particular embodiments, a portion of the adaptor ligated-cfDNA library will be amplified using standard PCR techniques with a single primer sequence driving amplification. In one embodiment, the single primer sequence is about 25 nucleotides, optionally with a projected Tm of ≥55° C. under standard ionic strength conditions.

In particular embodiments, picograms of the initial cfDNA library are amplified into micrograms of cfDNA clones, implying a 10,000-fold amplification. The amount of amplified product can be measured using methods known in the art, e.g., quantification on a Qubit 2.0 or Nanodrop instrument.

3. Determining the Number of Genome Equivalents

In various embodiments, a method for genetic analysis of cfDNA comprises determining the number of genome equivalents in the cfDNA clone library. As used herein, the term "genome equivalent" refers to the number of genome copies in each library. An important challenge met by the compositions and methods contemplated herein is achieving sufficient assay sensitivity to detect and analysis rare genetic mutations or differences in genetic sequence. To determine assay sensitivity value on a sample-by-sample basis, the numbers of different and distinct sequences that are present in each sample are measured, by measuring the number of genome equivalents that are present in a sequencing library. To establish sensitivity, the number of genome equivalents must be measured for each sample library.

The number of genome equivalents can be determined by qPCR assay or by using bioinformatics-based counting after sequencing is performed. In the process flow of clinical samples, qPCR measurement of genome equivalents is used as a QC step for cfDNA libraries. It establishes an expectation for assay sensitivity prior to sequence analysis and allows a sample to be excluded from analysis if its corresponding cfDNA clone library lacks the required depth of genome equivalents. Ultimately, the bioinformatics-based counting of genome equivalents is also used to identify the genome equivalents—and hence the assay sensitivity and false negative estimates—for each given cfDNA clone library.

The empirical qPCR assay and statistical counting assays should be well correlated. In cases where sequencing fails to reveal the sequence depth in a cfDNA clone library, reprocessing of the cfDNA clone library and/or additional sequencing may be required.

In one embodiment, the genome equivalents in a cfDNA clone library are determined using a quantitative PCR (qPCR) assay. In a particular embodiment, a standard library of known concentration is used to construct a standard curve and the measurements from the qPCR assay are fit to the resulting standard curve and a value for genome equivalents is derived from the fit. Surprisingly, the present inventors have discovered that a qPCR "repeat-based" assay comprising one primer that specifically hybridizes to a common sequence in the genome, e.g., a repeat sequence, and another primer that binds to the primer binding site in the adaptor, measured an 8-fold increase in genome equivalents compared to methods using just the adaptor specific primer (present on both ends of the cfDNA clone). The number of genome equivalents measured by the repeat-based assays provides a more consistent library-to-library performance and a better alignment between qPCR estimates of genome equivalents and bioinformatically counted tag equivalents in sequencing runs.

Illustrative examples of repeats suitable for use in the repeat-based genome equivalent assays contemplated herein include, but not limited to: short interspersed nuclear elements (SINEs), e.g., Alu repeats; long interspersed nuclear elements (LINEs), e.g., LINE1, LINE2, LINE3; microsatellite repeat elements, e.g., short tandem repeats (STRs), simple sequence repeats (SSRs); and mammalian-wide interspersed repeats (MIRs).

In one embodiment, the repeat is an Alu repeat.

4. Quantitative Genetic Analysis

In various embodiments, a method for genetic analysis of cfDNA comprises quantitative genetic analysis of one or more target genetic loci of the cfDNA library clones. Quantitative genetic analysis comprises one or more of, or all of, the following steps: capturing cfDNA clones comprising a target genetic locus; amplification of the captured targeted genetic locus; sequencing of the amplified captured targeted genetic locus; and bioinformatic analysis of the resulting sequence reads.

(a) Capture of Target Genetic Locus

The present invention contemplates, in part, a capture probe module designed to retain the efficiency and reliability of larger probes but that minimizes uninformative sequence generation in a cfDNA clone library. A "capture probe module" refers to a polynucleotide that comprises a capture probe sequence and a tail sequence. In particular embodiments, the capture probe module sequence or a portion thereof serves as a primer binding site for one or more sequencing primers.

In particular embodiments, a capture probe module comprises a capture probe. As used herein a "capture probe" refers to a region capable of hybridizing to a specific DNA target region. Because the average size of cfDNA is about 150 to about 170 bp and is highly fragmented the compositions and methods contemplated herein comprise the use of high density and relatively short capture probes to interrogate DNA target regions of interest.

One particular concern with using high density capture probes is that generally capture probes are designed using specific "sequence rules." For example, regions of redundant sequence or that exhibit extreme base composition biases are generally excluded in designing capture probes. However, the present inventors have discovered that the lack of flexibility in capture probe design rules does not substantially impact probe performance. In contrast, capture probes chosen strictly by positional constraint provided on-target sequence information; exhibit very little off-target and unmappable read capture; and yield uniform, useful, on-target reads with only few exceptions. Moreover, the high redundancy at close probe spacing more than compensates for occasional poor-performing capture probes.

In particular embodiments, a target region is targeted by a plurality of capture probes, wherein any two or more capture probes are designed to bind to the target region within 10 nucleotides of each other, within 15 nucleotides of each other, within 20 nucleotides of each other, within 25 nucleotides of each other, within 30 nucleotides of each other, within 35 nucleotides of each other, within 40 nucleotides of each other, within 45 nucleotides of each other, or within 50 nucleotides or more of each other, as well as all intervening nucleotide lengths.

In one embodiment, the capture probe is about 25 nucleotides, about 26 nucleotides, about 27 nucleotides, about 28 nucleotides, about 29 nucleotides, about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, about 40 nucleotides, about 41 nucleotides, about 42 nucleotides, about 43 nucleotides, about 44 nucleotides, or about 45 nucleotides.

In one embodiment, the capture probe is about 100 nucleotides, about 200 nucleotides, about 300 nucleotides, about 400 nucleotides, or about 100 nucleotides. In another embodiment, the capture probe is from about 100 nucleotides to about 500 nucleotides, about 200 nucleotides to about 500 nucleotides, about 300 nucleotides to about 500 nucleotides, or about 400 nucleotides to about 500 nucleotides, or any intervening range thereof.

In a particular embodiment, the capture probe is not 60 nucleotides.

In another embodiment, the capture probe is substantially smaller than 60 nucleotides but hybridizes comparably, as well as, or better than a 60 nucleotide capture probe targeting the same DNA target region.

In a certain embodiment, the capture probe is 40 nucleotides.

In certain embodiments, a capture probe module comprises a tail sequence. As used herein, the term "tail sequence" refers to a polynucleotide at the 5' end of the capture probe module, which in particular embodiments can serve as a primer binding site. In particular embodiments, a sequencing primer binds to the primer binding site in the tail region.

In particular embodiments, the tail sequence is about 5 to about 100 nucleotides, about 10 to about 100 nucleotides, about 5 to about 75 nucleotides, about 5 to about 50 nucleotides, about 5 to about 25 nucleotides, or about 5 to about 20 nucleotides. In certain embodiments, the third region is from about 10 to about 50 nucleotides, about 15 to about 40 nucleotides, about 20 to about 30 nucleotides or about 20 nucleotides, or any intervening number of nucleotides.

In particular embodiments, the tail sequence is about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, or about 40 nucleotides.

In various embodiments, the capture probe module comprises a specific member of a binding pair to enable isolation and/or purification of one or more captured fragments of a tagged and or amplified cfDNA library that hybridizes to the capture probe. In particular embodiments, the capture probe module is conjugate to biotin or another suitable hapten, e.g., dinitrophenol, digoxigenin.

In various embodiments, the capture probe module is hybridized to a tagged and optionally amplified cfDNA library to form a complex. In some embodiments, the multifunctional capture probe module substantially hybridizes to a specific genomic target region in the cfDNA library.

Hybridization or hybridizing conditions can include any reaction conditions where two nucleotide sequences form a stable complex; for example, the tagged cfDNA library and capture probe module forming a stable tagged cfDNA library—capture probe module complex. Such reaction conditions are well known in the art and those of skill in the art will appreciated that such conditions can be modified as appropriate, e.g., decreased annealing temperatures with shorter length capture probes, and within the scope of the present invention. Substantial hybridization can occur when the second region of the capture probe complex exhibits 100%, 99%, 98%, 97%, 96%, 95%, 94%, 93%, 92% 91%, 90%, 89%, 88%, 85%, 80%, 75%, or 70% sequence identity, homology or complementarity to a region of the tagged cfDNA library.

In particular embodiments, the capture probe is about 40 nucleotides and has an optimal annealing temperature of about 44° C. o about 47° C.

In certain embodiments, the methods contemplated herein comprise isolating a tagged cfDNA library—capture probe module complex. In particular embodiments, methods for isolating DNA complexes are well known to those skilled in the art and any methods deemed appropriate by one of skill in the art can be employed with the methods of the present invention (Ausubel et al., *Current Protocols in Molecular Biology*, 2007-2012). In particular embodiments, the complexes are isolated using biotin-streptavidin isolation techniques.

In particular embodiments, removal of the single stranded 3'-ends from the isolated tagged cfDNA library-capture probe module complex is contemplated. In certain embodiments, the methods comprise 3'-5' exonuclease enzymatic processing of the isolated tagged DNA library-multifunctional capture probe module complex to remove the single stranded 3' ends.

In certain other embodiments, the methods comprise performing 5'-3' DNA polymerase extension of multifunctional capture probe utilizing the isolated tagged DNA library fragments as template.

In certain other embodiments, the methods comprise creating a hybrid capture probe-isolated tagged cfDNA target molecule through the concerted action of a 5' FLAP endonuclease, DNA polymerization and nick closure by a DNA ligase.

A variety of enzymes can be employed for the 3'-5' exonuclease enzymatic processing of the isolated tagged cfDNA library-multifunctional capture probe module complex. Illustrative examples of suitable enzymes, which exhibit 3'-5' exonuclease enzymatic activity, that can be employed in particular embodiments include, but are not limited to: T4 or Exonucleases I, III, V (see also, Shevelev I V, Hübscher U., "The 3' 5' exonucleases," *Nat Rev Mol Cell Biol.* 3(5):364-76 (2002)). In particular embodiments, the enzyme comprising 3'-5' exonuclease activity is T4 polymerase. In particular embodiments, an enzyme which exhibits 3'-5' exonuclease enzymatic activity and is capable of primer template extension can be employed, including for example T4 or Exonucleases I, III, V. Id.

In some embodiments, the methods contemplated herein comprise performing sequencing and/or PCR on the 3'-5' exonuclease enzymatically processed complex discussed supra and elsewhere herein. In particular embodiments, a tail portion of a capture probe molecule is copied in order to generate a hybrid nucleic acid molecule. In one embodiment, the hybrid nucleic acid molecule generated comprises the target region capable of hybridizing to the capture probe module and the complement of the capture probe module tail sequence.

In a particular embodiment, genetic analysis comprises a) hybridizing one or more capture probe modules to one or more target genetic loci in a plurality of cfDNA library clones to form one or more capture probe module-cfDNA library clone complexes; b) isolating the one or more capture probe module-cfDNA library clone complexes from a); c) enzymatically processing the one or more isolated capture probe module-cfDNA library clone complexes from step b);

d) performing PCR on the enzymatically processed complex from c) wherein the tail portion of the capture probe molecule is copied in order to generate amplified hybrid nucleic acid molecules, wherein the amplified hybrid nucleic acid molecules comprise a target sequence in the target genomic locus capable of hybridizing to the capture probe and the complement of the capture probe module tail sequence; and e) performing quantitative genetic analysis on the amplified hybrid nucleic acid molecules from d).

In a particular embodiment, methods for determining copy number of a specific target genetic locus are contemplated comprising: a) hybridizing one or more capture probe modules to one or more target genetic loci in a plurality of cfDNA library clones to form one or more capture probe module-cfDNA library clone complexes; b) isolating the one or more capture probe module-cfDNA library clone complexes from a); c) enzymatically processing the one or more isolated capture probe module-cfDNA library clone complexes from step b); d) performing PCR on the enzymatically processed complex from c) wherein the tail portion of the capture probe molecule is copied in order to generate amplified hybrid nucleic acid molecules, wherein the amplified hybrid nucleic acid molecules comprise a target sequence in the target genetic locus capable of hybridizing to the capture probe and the complement of the capture probe module tail sequence; e) performing PCR amplification of the amplified hybrid nucleic acid molecules in d); and f) quantitating the PCR reaction in e), wherein the quantitation allows for a determination of copy number of the specific target region.

In one embodiment, the enzymatic processing of step c) comprises performing 3'-5' exonuclease enzymatic processing on the one or more capture probe module-cfDNA library clone complexes from b) using an enzyme with 3'-5' exonuclease activity to remove the single stranded 3' ends; creating one or more hybrid capture probe module-cfDNA library clone molecules through the concerted action of a 5' FLAP endonuclease, DNA polymerization and nick closure by a DNA ligase; or performing 5'-3' DNA polymerase extension of the capture probe using the isolated cfDNA clone in the complex as a template.

In one embodiment, the enzymatic processing of step c) comprises performing 5'-3' DNA polymerase extension of the capture probe using the isolated cfDNA clone in the complex as a template.

In particular embodiments, PCR can be performed using any standard PCR reaction conditions well known to those of skill in the art. In certain embodiments, the PCR reaction in e) employs two PCR primers. In one embodiment, the PCR reaction in e) employs a first PCR primer that hybridizes to a repeat within the target genetic locus. In a particular embodiment, the PCR reaction in e) employs a second PCR primer that hybridizes to the hybrid nucleic acid molecules at the target genetic locus/tail junction. In certain embodiments, the PCR reaction in e) employs a first PCR primer that hybridizes to the target genetic locus and a second PCR primer hybridizes to the amplified hybrid nucleic acid molecules at the target genetic locus/tail junction. In particular embodiments, the second primer hybridizes to the target genetic locus/tail junction such that at least one or more nucleotides of the primer hybridize to the target genetic locus and at least one or more nucleotides of the primer hybridize to the tail sequence.

In certain embodiments, the amplified hybrid nucleic acid molecules obtained from step e) are sequenced and the sequences aligned horizontally, i.e., aligned to one another but not aligned to a reference sequence. In particular embodiments, steps a) through e) are repeated one or more times with one or more capture probe modules. The capture probe modules can be the same or different and designed to target either cfDNA strand of a target genetic locus. In some embodiments, when the capture probes are different, they hybridize at overlapping or adjacent target sequences within a target genetic locus in the tagged cfDNA clone library. In one embodiment, a high density capture probe strategy is used wherein a plurality of capture probes hybridize to a target genetic locus, and wherein each of the plurality of capture probes hybridizes to the target genetic locus within about 5, 10, 15, 20, 25, 30, 35, 40, 45, 50, 100, 200 bp of any other capture probe that hybridizes to the target genetic locus in a tagged cfDNA clone library, including all intervening distances.

In some embodiments, the method can be performed using two capture probe modules per target genetic locus, wherein one hybridizes to the "Watson" strand (non-coding or template strand) upstream of the target region and one hybridizes to the "Crick" strand (coding or non-template strand) downstream of the target region.

In particular embodiments, the methods contemplated herein can further be performed multiple times with any number of capture probe modules, for example 2, 3, 4, 5, 6, 7, 8, 9, or 10 or more capture probe modules per target genetic locus any number of which hybridize to the Watson or Crick strand in any combination. In some embodiments, the sequences obtained can be aligned to one another in order to identify any of a number of differences.

In certain embodiments, a plurality of target genetic loci are interrogated, e.g., 100, 200, 300, 400, 500, 600, 700, 800, 900, 1000, 1500, 2000, 2500, 3000, 3500, 4000, 4500, 5000, 10000, 50000, 100000, 500000 or more in a single reaction, using one or more capture probe modules.

(b) Sequencing

In particular embodiments, the quantitative genetic analysis comprises sequencing a plurality of hybrid nucleic acid molecules, as discussed elsewhere herein, supra, to generate sufficient sequencing depths to obtain a plurality of unique sequencing reads. A unique read is defined as the single consensus read from a "family" of reads that all share the same read code and sequence start point within cfDNA. Each capture probe yields a set of unique reads that are computationally distilled from total reads by grouping into families. The unique reads for a given sample are then computed as the average of all the unique reads observed on a probe-by-probe basis. Cases where there is an obvious copy number change are excluded from the data set used to compute the average. Unique reads are important because each unique read must be derived from a unique cfDNA clone. Each unique read represents the input and analysis of a haploid equivalent of genomic DNA. The sum of unique reads is the sum of haploid genomes analyzed. The number of genomes analyzed, in turn, defines the sensitivity of the sequencing assay. By way of a non-limiting example, if the average unique read count is 100 genome equivalents, then that particular assay has a sensitivity of being able to detect one mutant read in 100, or 1%. Any observation less than this is not defensible.

In particular embodiments, the quantitative genetic analysis comprises multiplex sequencing of hybrid nucleic acid molecules derived from a plurality of samples.

In various embodiments, the quantitative genetic analysis comprises obtaining one or more or a plurality of tagged DNA library clones, each clone comprising a first DNA sequence and a second DNA sequence, wherein the first DNA sequence comprises a sequence in a targeted genetic locus and the second DNA sequence comprises a capture probe sequence; performing a paired end sequencing reaction on the one or more clones and obtaining one or more sequencing reads or performing a sequencing reaction on the one or more clones in which a single long sequencing read of greater than about 100, 200, 300, 400, 500 or more nucleotides is obtained, wherein the read is sufficient to identify both the first DNA sequence and the second DNA sequence; and ordering or clustering the sequencing reads of the one or more clones according to the probe sequences of the sequencing reads.

(c) Bioinformatics Analysis

In various embodiments, the quantitative genetic analysis further comprises bioinformatic analysis of the sequencing reads. Bioinformatic analysis excludes any purely mental analysis performed in the absence of a composition or method for sequencing. In certain embodiments, bioinformatics analysis includes, but is not limited to: sequence alignments; genome equivalents analysis; single nucleotide variant (SNV) analysis; gene copy number variation (CNV) analysis; and detection of genetic lesions. In particular embodiments, bioinformatics analysis is useful to quantify the number of genome equivalents analyzed in the cfDNA clone library; to detect the genetic state of a target genetic locus; to detect genetic lesions in a target genetic locus; and to measure copy number fluctuations within a target genetic locus.

Sequence alignments may be performed between the sequence reads and one or more human reference DNA sequences. In particular embodiments, sequencing alignments can be used to detect genetic lesions in a target genetic locus including, but not limited to detection of a nucleotide transition or transversion, a nucleotide insertion or deletion, a genomic rearrangement, a change in copy number, or a gene fusion. Detection of genetic lesions that are causal or prognostic indicators may be useful in the diagnosis, prognosis, treatment, and/or monitoring of a particular genetic condition or disease.

Also contemplated herein, are methods for sequence alignment analysis that can be performed without the need for alignment to a reference sequence, referred to herein as horizontal sequence analysis. Such analysis can be performed on any sequences generated by the methods contemplated herein or any other methods. In particular embodiments, the sequence analysis comprises performing sequence alignments on the reads obtained by the methods contemplated herein.

In one embodiment, the genome equivalents in a cfDNA clone library are determined using bioinformatics-based counting after sequencing is performed. Each sequencing read is associated with a particular capture probe, and the collection of reads assigned to each capture probe is parsed into groups. Within a group, sets of individual reads share the same read code and the same DNA sequence start position within genomic sequence. These individual reads are grouped into a "family" and a single consensus representative of this family is carried forward as a "unique read." All of the individual reads that constituted a family are derived from a single ligation event and thus, they are amplification-derived "siblings" of one another. Each unique read is considered a unique ligation event and the sum of unique reads is considered equivalent to the number of genome equivalents analyzed.

As the number of unique clones approaches the total number of possible sequence combinations, probability dictates that the same code and start site combinations will be created by independent events and that these independent events will be inappropriately grouped within single families. The net result will be an underestimate of genome equivalents analyzed, and rare mutant reads may be discarded as sequencing errors because they overlap with wild-type reads bearing the same identifiers.

In particular embodiments, to provide an accurate analysis for cfDNA clone libraries, the number of genome equivalents analyzed is about $\frac{1}{10}$, about $\frac{1}{12}$, about $\frac{1}{14}$, about $\frac{1}{16}$, about $\frac{1}{18}$, about $\frac{1}{20}$, about $\frac{1}{25}$ or less the number of possible unique clones. It should be understood that the procedure outlined above is merely illustrative and not limiting.

In some embodiments, the number of genome equivalents to be analyzed may need to be increased. To expand the depth of genome equivalents, at least two solutions are contemplated. The first solution is to use more than one adaptor set per sample. By combining adaptors, it is possible to multiplicatively expand the total number of possible clones and therefore, expand the comfortable limits of genomic input. The second solution is to expand the read code by 1, 2, 3, 4, or 5 or more bases. The number of possible read codes that differ by at least 2 bases from every other read code scales as $4^{(n-1)}$ where n is the number of bases within a read code. Thus, in a non-limiting example, if a read code is 5 nucleotides and $4^{(5-1)}=256$; therefore, the inclusion of additional bases expands the available repertoire by a factor of four for each additional base.

In one embodiment, quantitative genetic analysis comprises bioinformatic analysis of sequencing reads to identify rare single nucleotide variants (SNV).

Next-generation sequencing has an inherent error rate of roughly 0.02-0.02%, meaning that anywhere from $\frac{1}{200}$ to $\frac{1}{500}$ base calls are incorrect. To detect variants and other mutations that occur at frequencies lower than this, for example at frequencies of 1 per 1000 sequences, it is necessary to invoke molecular annotation strategies. By way of a non-limiting example, analysis of 5000 unique molecules using targeted sequence capture technology would generate—at sufficient sequencing depths of >50,000 reads—a collection of 5000 unique reads, with each unique read belonging to a "family" of reads that all possess the same read code. A SNV that occurs within a family is a candidate for being a rare variant. When this same variant is observed in more than one family, it becomes a very strong candidate for being a rare variant that exists within the starting sample. In contrast, variants that occur sporadically within families are likely to be sequencing errors and variants that occur within one and only one family are either rare or the result of a base alteration that occurred ex vivo (e.g., oxidation of a DNA base or PCR-introduced errors).

In one embodiment, the methods of detecting SNVs comprise introducing 10-fold more genomic input (genomes or genome equivalents) as the desired target sensitivity of the assay. In one non-limiting example, if the desired sensitivity is 2% (2 in 100), then the experimental target is an input of 2000 genomes.

In particular embodiments, bioinformatics analysis of sequencing data is used to detect or identify SNV associated with a genetic state, condition or disease, genetic mosaicism, fetal testing, paternity testing, predicting response to drug treatment, diagnosing or monitoring a medical condition, microbiome profiling, pathogen screening, and monitoring organ transplants.

In various embodiments, a method for copy number determination analysis is provided comprising obtaining one or more or a plurality of clones, each clone comprising a first DNA sequence and a second DNA sequence, wherein the first DNA sequence comprises a sequence in a targeted genetic locus and the second DNA sequence comprises a capture probe sequence. In related embodiments, a paired end sequencing reaction on the one or more clones is performed and one or more sequencing reads are obtained. In another embodiment, a sequencing reaction on the one or more clones is performed in which a single long sequencing read of greater than about 100 nucleotides is obtained, wherein the read is sufficient to identify both the first DNA sequence and the second DNA sequence. The sequencing reads of the one or more clones can be ordered or clustered according to the probe sequence of the sequencing reads.

Copy number analyses include, but are not limited to analyses, that examine the number of copies of a particular gene or mutation that occurs in a given genomic DNA sample and can further include quantitative determination of the number of copies of a given gene or sequence differences in a given sample. In particular embodiments, copy number analysis is used to detect or identify gene amplification associated with genetic states, conditions, or diseases, fetal testing, genetic mosaicism, paternity testing, predicting response to drug treatment, diagnosing or monitoring a medical condition, microbiome profiling, pathogen screening, and monitoring organ transplants.

In particular embodiments, bioinformatics analysis of sequencing data is used to detect or identify one or more sequences or genetic lesions in a target locus including, but not limited to detection of a nucleotide transition or transversion, a nucleotide insertion or deletion, a genomic rearrangement, a change in copy number, or a gene fusion. Detection of genetic lesions that are causal or prognostic indicators may be useful in the diagnosis, prognosis, treatment, and/or monitoring of a particular genetic condition or disease. In one embodiment, genetic lesions are associated with genetic states, conditions, or diseases, fetal testing, genetic mosaicism, paternity testing, predicting response to drug treatment, diagnosing or monitoring a medical condition, microbiome profiling, pathogen screening, and monitoring organ transplants.

D. Clinical Applications of Quantitative Genetic Analysis

In various embodiments, the present invention contemplates a method of detecting, identifying, predicting, diagnosing, or monitoring a condition or disease in a subject.

In particular embodiments, a method of detecting, identifying, predicting, diagnosing, or monitoring a genetic state, condition or disease in a subject comprises performing a quantitative genetic analysis of one or more target genetic loci in a cfDNA clone library to detect or identify a change in the sequence at the one or more target genetic loci.

In one embodiment, a method of detecting, identifying, predicting, diagnosing, or monitoring a genetic state, condition or disease comprises isolating or obtaining cfDNA from a biological sample of a subject; treating the cfDNA with one or more end-repair enzymes to generate end-repaired cfDNA; ligating one or more adaptors to each end of the end-repaired cfDNA to generate a cfDNA library; amplifying the cfDNA library to generate a cfDNA clone library; determining the number of genome equivalents in the cfDNA clone library; and performing a quantitative genetic analysis of one or more target genetic loci in a cfDNA clone library to detect or identify a change in the sequence at the one or more target genetic loci.

In particular embodiments, a method of detecting, identifying, predicting, diagnosing, or monitoring a genetic state, or genetic condition or disease selected from the group consisting of: genetic diseases; genetic mosaicism; fetal testing; paternity testing; paternity testing; predicting response to drug treatment; diagnosing or monitoring a medical condition; microbiome profiling; pathogen screening; and organ transplant monitoring comprising isolating or obtaining cfDNA from a biological sample of a subject; treating the cfDNA with one or more end-repair enzymes to generate end-repaired cfDNA; ligating one or more adaptors to each end of the end-repaired cfDNA to generate a cfDNA library; amplifying the cfDNA library to generate a cfDNA clone library; determining the number of genome equivalents in the cfDNA clone library; and performing a quantitative genetic analysis of one or more target genetic loci in a cfDNA clone library to detect or identify a nucleotide transition or transversion, a nucleotide insertion or deletion, a genomic rearrangement, a change in copy number, or a gene fusion in the sequence at the one or more target genetic loci.

Illustrative examples of genetic diseases that can be detected, identified, predicted, diagnosed, or monitored with the compositions and methods contemplated herein include, but are not limited to cancer, Alzheimer's disease (APOE1), Charcot-Marie-Tooth disease, Leber hereditary optic neuropathy (LHON), Angelman syndrome (UBE3A, ubiquitin-protein ligase E3A), Prader-Willi syndrome (region in chromosome 15), β-Thalassaemia (HBB, β-Globin), Gaucher disease (type I) (GBA, Glucocerebrosidase), Cystic fibrosis (CFTR Epithelial chloride channel), Sickle cell disease (HBB, β-Globin), Tay-Sachs disease (HEXA, Hexosaminidase A), Phenylketonuria (PAH, Phenylalanine hydrolyase), Familial hypercholesterolaemia (LDLR, Low density lipoprotein receptor), Adult polycystic kidney disease (PKD1, Polycystin), Huntington disease (HDD, Huntingtin), Neurofibromatosis type I (NF1, NF1 tumour suppressor gene), Myotonic dystrophy (DM, Myotonin), Tuberous sclerosis (TSC1, Tuberin), Achondroplasia (FGFR3, Fibroblast growth factor receptor), Fragile X syndrome (FMR1, RNA-binding protein), Duchenne muscular dystrophy (DMD, Dystrophin), Haemophilia A (F8C, Blood coagulation factor VIII), Lesch-Nyhan syndrome (HPRT1, Hypoxanthine guanine ribosyltransferase 1), and Adrenoleukodystrophy (ABCD1).

Illustrative examples of cancers that can be detected, identified, predicted, diagnosed, or monitored with the compositions and methods contemplated herein include, but are not limited to: B cell cancer, e.g., multiple myeloma, melanomas, breast cancer, lung cancer (such as non-small cell lung carcinoma or NSCLC), bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, adenocarcinomas, inflammatory myofibroblastic tumors, gastrointestinal stromal tumor (GIST), colon cancer, multiple myeloma (MM), myelodysplastic syndrome (MDS), myeloproliferative disorder (MPD), acute lymphocytic leukemia (ALL), acute myelocytic leukemia (AML), chronic myelocytic leukemia (CML), chronic lymphocytic leukemia (CLL), polycythemia Vera, Hodgkin lymphoma, non-Hodgkin lymphoma (NHL), soft-tissue sarcoma, fibrosarcoma, myxosarcoma, liposarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, seminoma, embryonal carcinoma, Wilms' tumor, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, follicular lymphoma, diffuse large B-cell lymphoma, mantle cell lymphoma, hepatocellular carcinoma, thyroid cancer, gastric cancer, head and neck cancer, small cell cancers, essential thrombocythemia, agnogenic myeloid metaplasia, hypereosinophilic syndrome, systemic mastocytosis, familiar hypereosinophilia, chronic eosinophilic leukemia, neuroendocrine cancers, carcinoid tumors, and the like.

In one embodiment, the genetic lesion is a lesion annotated in the Cosmic database (the lesions and sequence data can be downloaded from the Cancer Gene Census section of the Cosmic website) or a lesion annotated in the Cancer Genome Atlas (the lesions and sequence data can be downloaded from The Cancer Genome Atlas website of the National Cancer Institute and National Human Genome Research Institute).

Illustrative examples of genes that harbor one or more genetic lesions associated with cancer that can be detected, identified, predicted, diagnosed, or monitored with the compositions and methods contemplated herein include, but are not limited to ABCB1, ABCC2, ABCC4, ABCG2, ABL1, ABL2, AKT1, AKT2, AKT3, ALDH4A1, ALK, APC, AR, ARAF, ARFRP1, ARID1A, ATM, ATR, AURKA, AURKB, BCL2, BCL2A1, BCL2L1, BCL2L2, BCL6, BRAF, BRCA1, BRCA2, C1orf144, CARD11, CBL, CCND1, CCND2, CCND3, CCNE1, CDH1, CDH2, CDH20, CDH5, CDK4, CDK6, CDK8, CDKN2A, CDKN2B, CDKN2C, CEBPA, CHEK1, CHEK2, CRKL, CRLF2, CTNNB1, CYP1B1, CYP2C19, CYP2C8, CYP2D6, CYP3A4, CYP3A5, DNMT3A, DOT1L, DPYD, EGFR, EPHA3, EPHA5, EPHA6, EPHA7, EPHB1, EPHB4, EPHB6, EPHX1, ERBB2, ERBB3, ERBB4, ERCC2, ERG, ESR1, ESR2, ETV1, ETV4, ETV5, ETV6, EWSR1, EZH2, FANCA, FBXW7, FCGR3A, FGFR1, FGFR2, FGFR3, FGFR4, FLT1, FLT3, FLT4, FOXP4, GATA1, GNA11, GNAQ, GNAS, GPR124, GSTP1, GUCY1A2, HOXA3, HRAS, HSP90AA1, IDH1, IDH2, IGF1R, IGF2R, IKBKE, IKZF1, INHBA, IRS2, ITPA, JAK1, JAK2, JAK3, JUN, KDR, KIT, KRAS, LRP1B, LRP2, LTK, MAN1B1, MAP2K1, MAP2K2, MAP2K4, MCL1, MDM2, MDM4, MEN1, MET, MITF, MLH1, MLL, MPL, MRE11A, MSH2, MSH6, MTHFR, MTOR, MUTYH, MYC, MYCL1, MYCN, NF1, NF2, NKX2-1, NOTCH1, NPM1, NQO1, NRAS, NRP2, NTRK1, NTRK3, PAK3, PAX5, PDGFRA, PDGFRB, PIK3CA, PIK3R1, PKHD1, PLCG1, PRKDC, PTCH1, PTEN, PTPN11, PTPRD, RAF1, RARA, RB1, RET, RICTOR, RPTOR, RUNX1, SLC19A1, SLC22A2, SLCO1B3, SMAD2, SMAD3, SMAD4, SMARCA4, SMARCB1, SMO, SOD2, SOX10, SOX2, SRC, STK11, SULT1A1, TBX22, TET2, TGFBR2, TMPRSS2, TNFRSF14, TOP1, TP53, TPMT, TSC1, TSC2, TYMS, UGT1A1, UMPS, USP9X, VHL, and WT1.

In particular embodiments, the genetic lesion comprises a nucleotide transition or transversion, a nucleotide insertion or deletion, a genomic rearrangement, a change in copy number, or a gene fusion.

In one embodiment, the genetic lesion is a gene fusion that fuses the 3' coding region of the ALK gene to another gene.

In one embodiment, the genetic lesion is a gene fusion that fuses the 3' coding region of the ALK gene to the EML4 gene.

Illustrative examples of conditions suitable for fetal testing that can be detected, identified, predicted, diagnosed, or monitored with the compositions and methods contemplated herein include but are not limited to: Down Syndrome (Trisomy 21), Edwards Syndrome (Trisomy 18), Patau Syndrome (Trisomy 13), Klinefelter's Syndrome (XXY), Triple X syndrome, XYY syndrome, Trisomy 8, Trisomy 16, Turner Syndrome (XO), Robertsonian translocation, DiGeorge Syndrome and Wolf-Hirschhorn Syndrome.

Illustrative examples of alleles suitable for paternity testing that can be detected, identified, predicted, diagnosed, or monitored with the compositions and methods contemplated herein include but are not limited to 16 or more of: D20S1082, D6S474, D12ATA63, D22S1045, D10S1248, D1S1677, D11S4463, D4S2364, D9S1122, D2S1776, D10S1425, D3S3053, D5S2500, D1S1627, D3S4529, D2S441, D17S974, D6S1017, D4S2408, D9S2157, Amelogenin, D17S1301, D1GATA113, D18S853, D20S482, and D14S1434.

Illustrative examples of genes suitable for predicting the response to drug treatment that can be detected, identified, predicted, diagnosed, or monitored with the compositions and methods contemplated herein include, but are not limited to, one or more of the following genes: ABCB1 (ATP-binding cassette, sub-family B (MDR/TAP), member 1), ACE (angiotensin I converting enzyme), ADH1A (alcohol dehydrogenase 1A (class I), alpha polypeptide), ADH1B (alcohol dehydrogenase D3 (class I), beta polypeptide), ADH1C (alcohol dehydrogenase 1C (class I), gamma polypeptide), ADRB1 (adrenergic, beta-1-, receptor), ADRB2 (adrenergic, beta-2-, receptor, surface), AHR (aryl hydrocarbon receptor), ALDH1A1 (aldehyde dehydrogenase 1 family, member A1), ALOX5 (arachidonate 5-lipoxygenase), BRCA1 (breast cancer 1, early onset), COMT (catechol-O-methyltransferase), CYP2A6 (cytochrome P450, family 2, subfamily A, polypeptide 6), CYP2B6 (cytochrome P450, family 2, subfamily B, polypeptide 6), CYP2C9 (cytochrome P450, family 2, subfamily C, polypeptide 9), CYP2C19 (cytochrome P450, family 2, subfamily C, polypeptide 19), CYP2D6 (cytochrome P450, family 2, subfamily D, polypeptide 6), CYP2J2 (cytochrome P450, family 2, subfamily J, polypeptide 2), CYP3A4 (cytochrome P450, family 3, subfamily A, polypeptide 4), CYP3A5 (cytochrome P450, family 3, subfamily A, polypeptide 5), DPYD (dihydropyrimidine dehydrogenase), DRD2 (dopamine receptor D2), F5 (coagulation factor V), GSTP1 (glutathione S-transferase pi), HMGCR (3-hydroxy-3-methylglutaryl-Coenzyme A reductase), KCNH2 (potassium voltage-gated channel, subfamily H (eag-related), member 2), KCNJ11 (potassium inwardly-rectifying channel, subfamily J, member 11), MTHFR (5,10-methylenetetrahydrofolate reductase (NADPH)), NQO1 (NAD(P)H dehydrogenase, quinone 1), P2RY1 (purinergic receptor P2Y, G-protein coupled, 1), P2RY12 (purinergic receptor P2Y, G-protein coupled, 12), PTGIS (prostaglandin I2 (prostacyclin) synthase), SCN5A (sodium channel, voltage-gated, type V, alpha (long QT syndrome 3)), SLC19A1 (solute carrier family 19 (folate transporter), member 1), SLCO1B1 (solute carrier organic anion transporter family, member 1B1), SULT1A1 (sulfotransferase family, cytosolic, 1A, phenol-preferring, member 1), TPMT (thiopurine S-methyltransferase), TYMS (thymidylate synthetase), UGT1A1 (UDP glucuronosyltransferase 1 family, polypeptide A1), VDR (vitamin D (1,25-dihydroxyvitamin D3) receptor), VKORC1 (vitamin K epoxide reductase complex, subunit 1).

Illustrative examples of medical conditions that can be detected, identified, predicted, diagnosed, or monitored with the compositions and methods contemplated herein include, but are not limited to: stroke, transient ischemic attack, traumatic brain injury, heart disease, heart attack, angina, atherosclerosis, and high blood pressure.

Illustrative examples of pathogens that can be screened for with the compositions and methods contemplated herein include, but are not limited to: bacteria fungi, and viruses.

Illustrative examples of bacterial species that can be screened for with the compositions and methods contemplated herein include, but are not limited to: a *Mycobacterium* spp., a *Pneumococcus* spp., an *Escherichia* spp., a *Campylobacter* spp., a *Corynebacterium* spp., a *Clostridium* spp., a *Streptococcus* spp., a *Staphylococcus* spp., a *Pseudomonas* spp., a *Shigella* spp., a *Treponema* spp., or a *Salmonella* spp.

Illustrative examples of fungal species that can be screened for with the compositions and methods contemplated herein include, but are not limited to: an *Aspergillis* spp., a *Blastomyces* spp., a *Candida* spp., a *Coccicioides* spp., a *Cryptococcus* spp., dermatophytes, a *Tinea* spp., a *Trichophyton* spp., a *Microsporum* spp., a *Fusarium* spp., a *Histoplasma* spp., a *Mucoromycotina* spp., a *Pneumocystis* spp., a *Sporothrix* spp., an *Exserophilum* spp., or a *Cladosporium* spp.

Illustrative examples of viruses that can be screened for with the compositions and methods contemplated herein include, but are not limited to: Influenza A such as H1N1, H1N2, H3N2 and H5N1 (bird flu), Influenza B, Influenza C virus, Hepatitis A virus, Hepatitis B virus, Hepatitis C virus, Hepatitis D virus, Hepatitis E virus, Rotavirus, any virus of the Norwalk virus group, enteric adenoviruses, parvovirus, Dengue fever virus, Monkey pox, Mononegavirales, Lyssavirus such as rabies virus, Lagos bat virus, Mokola virus, Duvenhage virus, European bat virus 1 & 2 and Australian bat virus, Ephemerovirus, Vesiculovirus, Vesicular Stomatitis Virus (VSV), Herpesviruses such as Herpes simplex virus types 1 and 2, varicella zoster, cytomegalovirus, Epstein-Bar virus (EBV), human herpesviruses (HHV), human herpesvirus type 6 and 8, Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV), HIV (human immunodeficiency virus; including HIV type 1, and HIV type 2), visna-maedi virus (VMV) virus, the caprine arthritis-encephalitis virus (CAEV), equine infectious anemia virus (EIAV), feline immunodeficiency virus (FIV), bovine immune deficiency virus (BIV), and simian immunodeficiency virus (SIV), papilloma virus, murine gammaherpesvirus, Arenaviruses such as Argentine hemorrhagic fever virus, Bolivian hemorrhagic fever virus, Sabia-associated hemorrhagic fever virus, Venezuelan hemorrhagic fever virus, Lassa fever virus, Machupo virus, Lymphocytic choriomeningitis virus (LCMV), Bunyaviridiae such as Crimean-Congo hemorrhagic fever virus, Hantavirus, hemorrhagic fever with renal syndrome causing virus, Rift Valley fever virus, Filoviridae (filovirus) including Ebola hemorrhagic fever and Marburg hemorrhagic fever, Flaviviridae including Kaysanur Forest disease virus, Omsk hemorrhagic fever virus, Tick-borne encephalitis causing virus and Paramyxoviridae such as Hendra virus and Nipah virus, variola major and variola minor (smallpox), alphaviruses such as Venezuelan equine encephalitis virus, eastern equine encephalitis virus, western equine encephalitis virus, SARS-associated coronavirus (SARS-CoV), West Nile virus, and any encephaliltis causing virus.

Illustrative examples of genes suitable for monitoring an organ transplant in a transplant recipient that can be detected, identified, predicted, diagnosed, or monitored with the compositions and methods contemplated herein include, but are not limited to, one or more of the following genes: HLA-A, HLA-B, HLA-C, HLA-DR, HLA-DP, and HLA-DQ.

In particular embodiments, a bioinformatic analysis is used to quantify the number of genome equivalents analyzed in the cfDNA clone library; detect genetic variants in a target genetic locus; detect mutations within a target genetic locus; detect genetic fusions within a target genetic locus; or measure copy number fluctuations within a target genetic locus.

E. Companion Diagnostics

In various embodiments, a companion diagnostic for a genetic disease is provided, comprising: isolating or obtaining cfDNA from a biological sample of a subject; treating the cfDNA with one or more end-repair enzymes to generate end-repaired cfDNA; ligating one or more adaptors to each end of the end-repaired cfDNA to generate a cfDNA library; amplifying the cfDNA library to generate a cfDNA clone library; determining the number of genome equivalents in the cfDNA clone library; and performing a quantitative genetic analysis of one or more biomarkers associated with the genetic disease in the cfDNA clone library, wherein detection of, or failure to detect, at least one of the one or more biomarkers indicates whether the subject should be treated for the genetic disease.

As used herein, the term "companion diagnostic" refers to a diagnostic test that is linked to a particular anti-cancer therapy. In a particular embodiment, the diagnostic methods comprise detection of genetic lesion in a biomarker associated with in a biological sample, thereby allowing for prompt identification of patients should or should not be treated with the anti-cancer therapy.

Anti-cancer therapy includes, but is not limited to surgery, radiation, chemotherapeutics, anti-cancer drugs, and immunomodulators.

Illustrative examples of anti-cancer drugs include, but are not limited to: alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin and its pegylated formulations, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and doxetaxel (TAXOTERE®., Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on cancers such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

Illustrative examples of immunomodulators include, but are not limited to: cyclosporine, tacrolimus, tresperimus, pimecrolimus, sirolimus, verolimus, laflunimus, laquinimod and imiquimod, as well as analogs, derivatives, salts, ions and complexes thereof.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1: Accurate Detection of Rare Mutations Using Targeted Sequence Capture Technology Purpose The purpose of this experiment was to provide a direct proof-of-principle demonstration of rare variant detection using targeted sequence capture technology.

Background

Target sequence capture technology provides quantitative, sequence-based genetic analysis of nucleic acids and can be exploited to perform a combined mutational and copy number analysis of drug metabolism genes. The present inventors used targeted sequence capture technology and subsequence genetic analysis to detect rare sequence variants.

Genomic DNA inputs play a central role in rare variant detection, but quantitative analysis and control of genomic inputs places bounds on the estimated sensitivity of rare variant analysis. A genomic qPCR assay was used by the present inventors to estimate genomic inputs.

One experimental goal for rare variant analysis is to introduce 10-fold more genomic input as the target sensitivity of the assay. In other words, to measure variants with a sensitivity of 1% (1 in 100), then the experimental target is to input 1000 genomes. Downstream of sequencing, bioinformatics analysis reveals the number of unique reads, and this has the desirable quality of being both an orthogonal and a more direct measure of genomic inputs.

Summary

A cell line (ZR75-30) with known SNVs was admixed with a germ line DNA sample (NA12878) in a dilution series ranging from 1-to-1 through 1-to-1000. Target regions corresponding to known sequence differences were retrieved using targeted sequence capture technology and sequenced. Sequence variants that occur at a frequency of less than 1 per 1000 sequences were detected.

Methods

Capture Probes:

The following table shows a collection of 62 capture probes that were used in this experiment.

TABLE 1

60 base probe sequences used in the admix proof-of-concept study

| Target | SEQ ID NO: | Probe Sequence |
|---|---|---|
| BRAF | 1 | TAAACATTGGAAAGGTTTCTAATTAACCAGGAGATCCAAAAGAAAGCGGTTCAAGTAGCA |
|  | 2 | GATCTCAGTTTTTTTGGTTAACTATGTATTTTGGTATATGAAGCTTCTGGGTTTTGCACA |

TABLE 1-continued 60 base probe sequences used in the admix proof-of-concept study

| Target | SEQ ID NO: | Probe Sequence |
|---|---|---|
| MYCN | 3 | GACAGATAAGCATACATATTAACATGGATATATATGTGAATTTCATTCAAATGGTTCTCA |
|  | 4 | AGCTCTTAGCCTTTGGGGGATGACACTCTTGAGCGGACGTGGGGACGCCTCGCTCTTTA |
| BRAF | 5 | AAGCCCCCACCGCCGCCTCTTTCCAAAATAAACACCAGCCAGCCGCCGAGCCCGGAGTCG |
|  | 6 | GCCTCCCTTCCCCCTCCCCGCCCGACAGCGGCCGCTCGGGCCCCGGCTCTCGGTTATAAG |
| CDH1 | 7 | GGTGTGGCAGCCAGGGGGCGCACTCTGCTCTGGCTGGGCCCCTTCTCCCATGTTTTCTT |
|  | 8 | TTACACAACCTTTGGGCTTGGACAACACTTTGGGGTCCAAAGAACCTAAGAGTCTTTCTG |
| EPHX2 | 9 | TGATGAAACTTGGGCTGGATGGGGCACAGGTAGGGTGCTTGTTGCTTTCAGTCAGATGAA |
|  | 10 | AATGAAAGAAAAGGAGGCCAGATTGCTACTCCTGGTCCCTGCCACACACTAGGTACCCTA |
| BRCA1 | 11 | ATTGACAATACCTACATAAAACTCTTTCCAGAATGTTGTTAAGTCTTAGTCATTAGGGAG |
|  | 12 | GGATTTCCACCAACACTGTATTCATGTACCCATTTTTCTCTTAACCTAACTTTATTGGTC |
| BRCA2 | 13 | CAAAGGGGGAAAACCATCAGGACATTATTTAACAACGGAAATATCTAACTGAAAGGCAAA |
|  | 14 | CAGGCAGACCAACCAAAGTCTTTGTTCCACCTTTTAAAACTAAATCACATTTTCACAGAG |
| MYCN | 15 | CCCCAGCCAGCGGTCCGCAACCCTTGCCGCATCCACGAAACTTTGCCCATAGCAGCGGGC |
| MYC_r1_F1 | 16 | CGACTCATCTCAGCATTAAAGTGATAAAAAAATAAATTAAAAGGCAAGTGGACTTCGGTG |
| MYC_r1_R1 | 17 | CTGTGGCGCGCACTGCGCGCTGCGCCAGGTTTCCGCACCAAGACCCCTTTAACTCAAGAC |
| MYC_r2_F1 | 18 | TTCTACTGCGACGAGGAGGAGAACTTCTACCAGCAGCAGCAGCAGAGCGAGCTGCAGCCC |
| MYC_r2_F2 | 19 | ACCGAGCTGCTGGGAGGAGACATGGTGAACCAGAGTTTCATCTGCGACCCGGACGACGAG |
| MYC_r2_F3 | 20 | GCCGCCGCCTCAGAGTGCATCGACCCCTCGGTGGTCTTCCCCTACCCTCTCAACGACAGC |
| MYC_r2_F4 | 21 | GGCGGCTAGGGGACAGGGGCGGGGTGGGCAGCAGCTCGAATTTCTTCCAGATATCCTCGC |
| MYC_r2_R1 | 22 | AGACGAGCTTGGCGGCGGCCGAGAAGCCGCTCCACATACAGTCCTGGATGATGATGTTTT |
| MYC_r2_R2 | 23 | AGGAGAGCAGAGAATCCGAGGACGGAGAGAAGGCGCTGGAGTCTTGCGAGGCGCAGGACT |
| MYC_r2_R3 | 24 | TAAGAGTGGCCCGTTAAATAAGCTGCCAATGAAAATGGGAAAGGTATCCAGCCGCCCACT |
| MYC_r2_R4 | 25 | TTGTATTTGTACAGCATTAATCTGGTAATTGATTATTTTAATGTAACCTTGCTAAAGGAG |
| MYC_r3_F1 | 26 | GAGGCCACAGCAAACCTCCTCACAGCCCACTGGTCCTCAAGAGGTGCCACGTCTCCACAC |
| MYC_r3_F2 | 27 | AGAGGAGGAACGAGCTAAAACGGAGCTTTTTGCCCTGCGTGACCAGATCCCGGAGTTGG |
| MYC_r3_F3 | 28 | TCCAACTTGACCCTCTTGGCAGCAGGATAGTCCTTCCGAGTGGAGGGAGGCGCTGCGTAG |
| MYC_r3_R1 | 29 | GCTTGGACGGACAGGATGTATGCTGTGGCTTTTTTAAGGATAACTACCTTGGGGGCCTTT |

TABLE 1-continued 60 base probe sequences used in the admix proof-of-concept study

| Target | SEQ ID NO: | Probe Sequence |
|---|---|---|
| MYC_r3_R2 | 30 | GCATTTGATCATGCATTTGAAACAAGTTCATAGGTGATTGCTCAGGACATTTCTGTTAGA |
| MYC_r3_R3 | 31 | CGCCCCGCGCCCTCCCAGCCGGGTCCAGCCGGAGCCATGGGGCCGGAGCCGCAGTGAGCA |
| ERBB2r1r | 32 | CTCTGGCCCCGCCGGCCGCGGGACCTCGGCGGGGCATCCACAGGGCAGGGTCCCGCCGCT |
| ERBB2r2f | 33 | GGCATGACTTGGAGTGAGTTTGGATGGGGTGGCCAGGTCTGAGAAGGTCCCCCGCCAGTG |
| ERBB2r2r | 34 | GCAGGGCACCTTCTTCTGCCACCCACCTGTAAACAGAGGGCTCAGCCCAGCTGGAGGCAG |
| ERBB2r3f | 35 | CCCAAGATCTCCAAGTACTGGGGAACCCCAGGGAGGCCCTGGGGGTGGCAGTGTTCCTA |
| ERBB2r3r | 36 | CTAATGCACACAAAGCCTCCCCCTGGTTAGCAGTGGCCCTGGTCAGCTCTGAATAACCAA |
| ERBB2r4f | 37 | CTGCTCCTCTTTTAGAAGGCAGGAGGGCCCCAAGGGAAGCAGAAGGTGACAGAAGGGGAA |
| ERBB2r4r | 38 | TGGGGCAGTGGCGGGCAGGCACTGGGTTGTAAGTTGGGAGTTTGCGGCTGGGGTCAGGCT |
| ERBB2r5f | 39 | TCTGCTGCTGTTTGTGCCTCTCTCTGTTACTAACCCGTCCTCTCGCTGTTAGACATCTCT |
| ERBB2r5r | 40 | CCCACCCCTCCCATGTCACCTGTATGACACCTGCATTCCACCCGGCCCCAGCCCTCCCCT |
| ERBB2r6f | 41 | TGGGCCAGGTAGTCTCCCTAGAAGGTGATGCTGATGAGGGTCTGGTGCCCAGGGCGCCAC |
| ERBB2r6r | 42 | GGTGCCCACCCCTTGCATCCTGGGGGGTAGAGCACATTGGGCACAAAGCAGAGGCACATA |
| ERBB2r7f | 43 | CACCCTGCCTGGTACTGCCCTATTGCCCCTGGCACACCAGGGCAAAACAGCACAGTGAAA |
| ERBB2r7r | 44 | CCATTTACAGAAACAAACCTCCCCACCAAAATGAGAAAACTGTGTTTCTCCCTGGCACTC |
| ERBB2r8f | 45 | TTATTCTTCTTGTGCCTGGGCACGGTAATGCTGCTCATGGTGGTGCACGAAGGGCCAGGG |
| ERBB2r8r | 46 | GAAGGATAGGACAGGGTGGGCTGGGCCAGGCTGCATGCGCAGAGGGACAGGAACTGCAGC |
| ERBB2r9f | 47 | GGGCCCGGACCCTGATGCTCATGTGGCTGTTGACCTGTCCCGGTATGAAGGCTGAGACGG |
| ERBB2r9r | 48 | TCTGTCTCCTGCCATCCCCAAGAGATGCTGCCACATCTGGATCCTCAGGACTCTGTCTGC |
| TYMSr2f | 49 | TCACGTCCCAGGGCAGTTTTCTTCCCTGAAGAAAGTTGGATGGCATGATCTGTCTTCCCA |
| TYMSr2r | 50 | GTGTTGAGAACAGACTACTGACTTCTAATAGCAGCGACTTCTTTACCTTGATAAACCACA |
| TYMSr3f | 51 | AAAAAAAGGATGGGTTCCATATGGGTGGTGTCAAGTGCCCACCTCCTAGCAAGTCAGCAG |
| TYMSr3r | 52 | CCCTCACAAGGTCAAAGCTATACATCAGCTCCTGTGACATTGACTCATCCCCCAGACCTT |
| TYMSr4f | 53 | AACCCACCGAGATCTGCAAACTTTGCAGGATGCACCAGATGTCTTGTAGCCATGGGTCAA |
| TYMSr4r | 54 | TGCCTCCCTCAGGTGCCTCTGCACAAAACCAGATTGCTTCCCTCTAAGAGTATGGTTAGT |

TABLE 1-continued 60 base probe sequences used in the admix proof-of-concept study

| Target | SEQ ID NO: | Probe Sequence |
|---|---|---|
| TYMSr5f | 55 | GTTTTACTTTGCCTTTAGCTGTGGTCTTTCAAACCACCATCCCTCCTTATCTTCCTCTGC |
| TYMSr5r | 56 | CTCTGCAATTTGTTTTCCCATATTAAAGAACTGAAGAGCTCAGTGTGGTAGGCTGGCAAG |
| TYMSr6f | 57 | TTTTAAATGATGTTTTAAAGAATTGAAACTAACATACTGTTCTGCTTTCTCCCCCGGGTT |
| TYMSr6r | 58 | CCTGCCCACCACTTCTCCCTAAACTGAAGCCCCACATTTGGAGCAGTCATCTTTATCTTG |
| TYMSr7f | 59 | GGTTGCGCTCCAATCATGTTACATAACCTACGGCAAGGTATCGACAGGATCATACTCCTG |
| TYMSr7r | 60 | GCACAGTTACATTTGCCAGTGGCAACATCCTTAAAAATTAATAACTGATAGGTCACGGAC |
| TYMSr1f | 61 | CGTCCCGCCGCGCCACTTGGCCTGCCTCCGTCCCGCCGCGCCACTTCGCCTGCCTCCGTC |
| TYMSr1r | 62 | CTGTAAGGCGAGGAGGACGATGCGTCCCCTCCCTCGCAGGATTGAGGTTAGGACTAAACG |

Capture probe modules were pooled from stock plates, combined with partner oligo #138 (SEQ ID NO: 63) (GT-GAAAACCAGGATCAACTCCCGTGCCAGTCACAT/3BioTEG/) and diluted to a final working concentration of 1 nM.

Genomic Analysis:

Commercially-purchased genomic DNA from germ line sample NA12878 and cell line ZR75-30 was fragmented at a concentration of 10-20 ng/µL to a target fragment size of 500 bp on a Covaris sonication instrument. The DNA was purified with a 1:1 concentration of DNA purification beads and end-repaired using the New England Biolabs (NEB) Quick blunt kit at a final concentration of 15-30 ng/µL. The germ line and cell line DNAs were blended at ratios of 1:1, 10:1, 100:1 and 1000:1, respectively. Libraries were constructed, purified and quantified. The sample codes, library quantitation and inputs used for library construction are shown in Table 2.

TABLE 2

Adaptors and genomic analysis of libraries used as inputs

| Admix | Adaptor code | genomes/µl | # desired genomes | µL into PCR |
|---|---|---|---|---|
| 1:1 | NNNNNNNNNCATGGCCGCAGG (SEQ ID NO: 64) | 55 | 200 | 4 |
| 10:1 | NNNNNNNNNATCTTAGTGGCA (SEQ ID NO: 65) | 66 | 200 | 3 |
| 100:1 | NNNNNNNNNCGGAACTCGGAG (SEQ ID NO: 66) | 64 | 1000 | 16 |
| 1000:1 | NNNNNNNNNGACTCCGATCCC (SEQ ID NO: 67) | 77 | 10000 | 130 |

Genomic libraries were pooled, denatured, combined with probe, hybridized and washed. The washed capture probe-tagged genomic library complexes were amplified with forward and reverse full-length primers, purified, and size-selected for 225-600 bp fragments on a Pippin-prep instrument. Finally, the captured material was sequenced using a 150-V3 Illumina sequencing kit.

Results

The paired capture probes that target BRAF (in two loci), MYCN and CDH1 were used to analyze the SNVs in these loci. The results are shown in Table 3.

TABLE 3

| | | Unique reads by tag and position | | | | | No unique filtering | | | | |
|---|---|---|---|---|---|---|---|---|---|---|---|
| Mutation | Sample NA:ZR | Total # reads | change to A | change to C | change to G | change to T | Total # reads | change to A | change to C | change to G | change to T |
| BRAF-I326T-A-G | 1to1 | 186 | | 0 | 55 | 0 | 34728 | | 6 | 11308 | 10 |
| BRAF-I326T-A-G | 10to1 | 171 | | 0 | 10 | 0 | 46464 | | 6 | 2615 | 2 |
| BRAF-I326T-A-G | 100to1 | 733 | | 0 | 3 | 0 | 51540 | | 10 | 89 | 2 |
| BRAF-I326T-A-G | 1000to1 | 3020 | | 0 | 3 | 0 | 54565 | | 6 | 19 | 7 |
| BRAF-E26D-C-A | 1to1 | 171 | 66 | | 0 | 0 | 29192 | 12388 | | 5 | 2 |
| BRAF-E26D-C-A | 10to1 | 183 | 12 | | 0 | 1 | 38085 | 2573 | | 1 | 4 |
| BRAF-E26D-C-A | 100to1 | 631 | 3 | | 0 | 0 | 38913 | 110 | | 1 | 2 |
| BRAF-E26D-C-A | 1000to1 | 2367 | 1 | | 0 | 0 | 46623 | 13 | | 2 | 2 |
| CDH1-E243*-G-T | 1to1 | 180 | 0 | 0 | | 54 | 23846 | 2 | 1 | | 8556 |
| CDH1-E243*-G-T | 10to1 | 208 | 0 | 0 | | 12 | 42307 | 1 | 2 | | 2658 |
| CDH1-E243*-G-T | 100to1 | 728 | 0 | 0 | | 4 | 42440 | 6 | 0 | | 129 |
| CDH1-E243*-G-T | 1000to1 | 2727 | 0 | 0 | | 0 | 53632 | 5 | 1 | | 7 |
| MYCN-E270Q-G-C | 1to1 | 158 | 0 | 47 | | 0 | 20302 | 0 | 5587 | | 0 |
| MYCN-E270Q-G-C | 10to1 | 186 | 0 | 14 | | 0 | 35733 | 1 | 2663 | | 2 |
| MYCN-E270Q-G-C | 100to1 | 566 | 0 | 3 | | 0 | 35393 | 0 | 247 | | 5 |
| MYCN-E270Q-G-C | 1000to1 | 2101 | 0 | 2 | | 0 | 37223 | 0 | 15 | | 2 |

Figure 2:
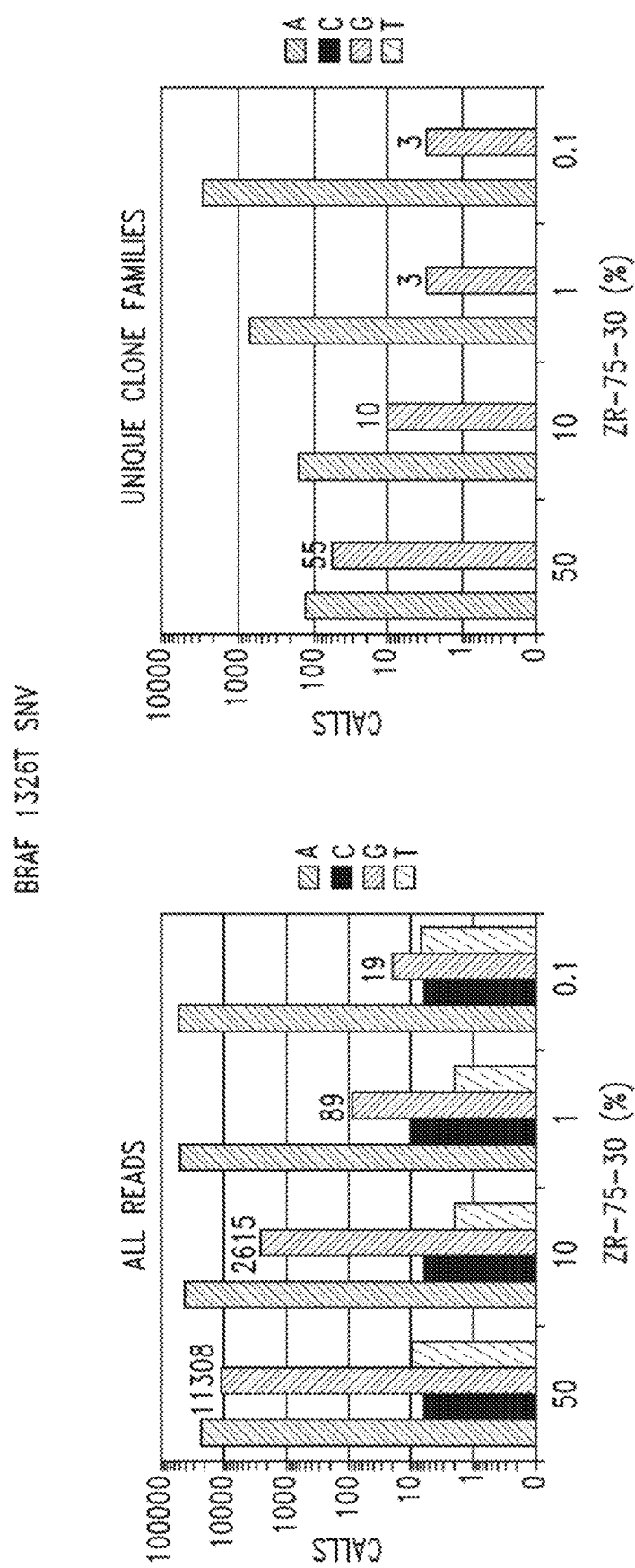
FIG. 2 shows that unique read filtering performed on the data generated in FIG. 1. The left hand panel shows the data from FIG. 1 on the BRAF I326T SNV without unique read filtering. The right hand panel shows that using unique read filtering of the same data increased the assay sensitivity and allowed the discrimination of true signal from error-prone noise.

Column 3 shows the total number unique read counts, which in turn provide bounds on the sensitivity of the assay. The estimated and measured genomic inputs were well within range of one another. The lightly shaded boxes highlight the SNV where the cell line sequence differed from the germ line sequence. In the absence of unique read filtering—shown on the right portion of the table—random base changes at these four selected positions occurred with measurable, non-zero frequencies. FIG. 1. By requiring that changes occur within unique read families, it became possible to sort true signal from error-prone noise. FIG. 2.

Example 2: A Novel Probe Design Effective for Comprehensive Sequencing of Target Regions in Highly Fragmented gDNA Purpose The purpose of these experiments is to develop an assay system to reliably and reproducibly interrogate circulating DNAs.

Background

Analysis of circulating DNA from body fluids represents an exciting, but as yet, unrealized opportunity in molecular diagnostics. Genomic DNA is highly intact. Literature suggest that the average size of circulating DNA is about 150 bp, which correlates well to the size of DNAs wrapped around a single nucleosomal histone complex.

Summary

The technical parameters of targeted sequence capture technology contemplated herein were designed to accommodate highly fragmented DNA and to retain the ability to generate comprehensive sequence coverage of targeted DNA. Capture probe density was increased and the length of capture probe sequences was reduced from 60 nucleotide to 40 nucleotide to minimize uninformative sequence generation in the clone library. The human genome is littered with repetitive sequences and drastic fluctuations in base composition, thus, the suitability of implementing higher capture probe densities and shorter capture probes could not be conceded but required empirical validation of the new assay.

Conditions were established in which the shorter 40 mer capture probe sequences exhibit reliable and robust assay performance. In a first set of experiments, the assays were used to query two large regions—the coding regions for the tumor suppressor gene TP53 and the long, contiguous, intron 19 of the ALK oncogene, both of which are central to cancer diagnostics. In a second set of experiments, several high density pairwise capture probes that possess shorter 40 nucleotide capture probe sequences were used to interrogate known SNVs that reside in the NCI-H69 cell line.

The new high density shorter capture probes were successfully used to query short fragmented DNAs and the results indicated that the assay design is well suited to sequencing of circulating DNAs that are found in the plasma fraction of blood.

Modified 40 Mer Capture Probes:

The capture probe sequences used to empirically validate the performance of the 40 mer capture probes are shown in Table 4.

TABLE 4

Capture probes

| Name | SEQ ID NO: | Sequence |
|---|---|---|
| 60 mer Capture Probes | | |
| PLP1_ex2_F | 68 | ATGTGACTGGCACGGGAGTTGATCCTGGTTTTCACGGGTTTGAGTGGCATGAGCTACCTACTGGATGTGCCTGACTGTTTCCCCTTCTTCTTCCC |
| PLP1_ex2_R | 69 | ATGTGACTGGCACGGGAGTTGATCCTGGTTTTCACCTATCTCCAGGATGGAGAGAGGGAAAAAAAAGATGGGTCTGTGTGGGAGGGCA70GGTACTT |
| PLP1_ex3_F | 70 | ATGTGACTGGCACGGGAGTTGATCCTGGTTTTCACGAAAGAAGCCAGGTCTTCAATTAATAAGATTCCCTGGTCTCGTTTGTCTACCTGTTAATG |
| PLP1_ex3_M | 71 | ATGTGACTGGCACGGGAGTTGATCCTGGTTTTCACCAGACTCGCGCCCAATTTTCCCCCACCCCTTGTTATTGCCACAAAATCCTGAGGATGATC |
| CYP2D6_F | 72 | ATGTGACTGGCACGGGAGTTGATCCTGGTTTTCACAAGCACCTAGCCCCATTCCTGCTGAGCAGGAGGTGGCAGGTACCCCAGACTGGGAGGTAA |
| CYP2D6_R | 73 | ATGTGACTGGCACGGGAGTTGATCCTGGTTTTCACAGTCGGTGGGGCCAGGATGAGGCCCAGTCTGTTCACACATGGCTGCTGCCTCTCAGCTCT |
| chrX_15_F | 74 | ATGTGACTGGCACGGGAGTTGATCCTGGTTTTCACCCTGGCCCTCAGCCAGTACAGAAAGTCATTTGTCAAGGCCTTCAGTTGGCAGACGTGCTC |
| chrX_15_R | 75 | ATGTGACTGGCACGGGAGTTGATCCTGGTTTTCACAGAATTCATTGCCAGCTATAAATCTGTGGAAACGCTGCCACACAATCTTAGCACACAAGA |
| chrX_69_F | 76 | ATGTGACTGGCACGGGAGTTGATCCTGGTTTTCACTTACTTCCCTCCAGTTTTGTTGCTTGCAAAACAACAGAATCTTCTCTCCATGAAATCATG |
| chrX_69_R | 77 | ATGTGACTGGCACGGGAGTTGATCCTGGTTTTCACCAGGGGTATCTATTATCCCCATTTTCTCACAAAGGAAACCAAGATAAAAGGTTTAAATGG |
| KRAS_ex1_F | 78 | ATGTGACTGGCACGGGAGTTGATCCTGGTTTTCACTGTTACCTTTAAAAGACATCTGCTTTCTGCCAAAATTAATGTGCTGAACTTAAACTTACC |
| KRAS_ex1_R | 79 | ATGTGACTGGCACGGGAGTTGATCCTGGTTTTCACTTCCCAGTAAATTACTCTTACCAATGCAACAGACTTTAAAGAAGTTGTGTTTTACAATGC |
| KRAS_ex2_F | 80 | ATGTGACTGGCACGGGAGTTGATCCTGGTTTTCACTAAATGACATAACAGTTATGATTTTGCAGAAAACAGATCTGTATTTATTTCAGTGTTACT |
| KRAS_ex2_R | 81 | ATGTGACTGGCACGGGAGTTGATCCTGGTTTTCACGACAGGTTTTGAAAGATATTTGTGTTACTAATGACTGTGCTATAACTTTTTTTTCTTTCC |
| MYC_r2_F1 | 82 | ATGTGACTGGCACGGGAGTTGATCCTGGTTTTCACCTGTGGCGCGCACTGCGCGCTGCGCCAGGTTTCCGCACCAAGACCCCTTTAACTCAAGAC |
| MYC_r2_R1 | 83 | ATGTGACTGGCACGGGAGTTGATCCTGGTTTTCACGGCGGCTAGGGGACAGGGGCGGGGTGGGCAGCAGCTCGAATTTCTTCCAGATATCCTCGC |
| MYC_r2_F3 | 84 | ATGTGACTGGCACGGGAGTTGATCCTGGTTTTCACACCGAGCTGCTGGGAGGAGACATGGTGAACCAGAGTTTCATCTGCGACCCGGACGACGAG |
| MYC_r2_R3 | 85 | ATGTGACTGGCACGGGAGTTGATCCTGGTTTTCACAGGAGAGCAGAGAATCCGAGGACGGAGAAGGCGCTGGAGTCTTGCGAGGCGCAGGACT |
| SRY_r1_F | 86 | ATGTGACTGGCACGGGAGTTGATCCTGGTTTTCACCTGTAAGTTATCGTAAAAAGGAGCATCTAGGTAGGTCTTTGTAGCCAATGTTACCCGATT |
| SRY_r1_M3 | 87 | ATGTGACTGGCACGGGAGTTGATCCTGGTTTTCACAATGGCCATTCTTCCAGGAGGCACAGAAATTACAGGCCATGCACAGAGAGAAATACCCGA |
| VHL_r3_F | 88 | ATGTGACTGGCACGGGAGTTGATCCTGGTTTTCACCTTGTTCGTTCCTTGTACTGAGACCCTAGTCTGCCACTGAGGATTTGGTTTTTGCCCTTC |
| VHL_r3_R | 89 | ATGTGACTGGCACGGGAGTTGATCCTGGTTTTCACATCAAGACTCATCAGTACCATCAAAAGCTGAGATGAAACAGTGTAAGTTTCAACAGAAAT |
| UGT1A1_r_4F | 90 | ATGTGACTGGCACGGGAGTTGATCCTGGTTTTCACTGTGTCCAGCTGTGAAACTCAGAGATGTAACTGCTGACATCCTCCCTATTTTGCATCTCA |
| UGT1A1_r_4R | 91 | ATGTGACTGGCACGGGAGTTGATCCTGGTTTTCACATTTGAAACAATTTTATCATGAATGCCATGACCAAAGTATTCTTCTGTATCTTCTTTCTT |

TABLE 4-continued

| | | Capture probes |
|---|---|---|
| Name | SEQ ID NO: | Sequence |
| TNFRSF14_r3_F | 92 | ATGTGACTGGCACGGGAGTTGATCCTGGTTTTCACTGATGGGTGGGCTCCCGA<br>AGGGGCCTCCCGCAGACTTGCGAAGTTCCCACTCTCTGGGCG |
| TNFRSF14_r3_R | 93 | ATGTGACTGGCACGGGAGTTGATCCTGGTTTTCACCAGGGTGCGGGGGCATCC<br>AGGCTGCCCAAGCGGAGGCTGGGCCGGCTGTGCTGGCCTCTT |
| RUNX1_r4_F | 94 | ATGTGACTGGCACGGGAGTTGATCCTGGTTTTCACTTTTGAAATGTGGGTTTG<br>TTGCCATGAAACGTGTTTCAAGCATAGTTTTGACAGATAACG |
| RUNX1_r4_R | 95 | ATGTGACTGGCACGGGAGTTGATCCTGGTTTTCACTGCCCTAAAAGTGTATGT<br>ATAACATCCCTGATGTCTGCATTTGTCCTTTGACTGGTGTTT |
| RHD_r5_F | 96 | ATGTGACTGGCACGGGAGTTGATCCTGGTTTTCACAACCCCTCGAGGCTCAGA<br>CCTTTGGAGCAGGAGTGTGATTCTGGCCAACCACCCTCTCTG |
| RHD_r5_R | 97 | ATGTGACTGGCACGGGAGTTGATCCTGGTTTTCACCATAAATATGTGTGCTAG<br>TCCTGTTAGACCCAAGTGCTGCCCAAGGGCAGCGCCCTGCTC |
| PTEN_r5_F | 98 | ATGTGACTGGCACGGGAGTTGATCCTGGTTTTCACTACTTGTTAATTAAAAAT<br>TCAAGAGTTTTTTTTTCTTATTCTGAGGTTATCTTTTTACCA |
| PTEN_r5_R | 99 | ATGTGACTGGCACGGGAGTTGATCCTGGTTTTCACCCAAAATCTGTTTTCCAA<br>TAAATTCTCAGATCCAGGAAGAGGAAAGGAAAAACATCAAAA |
| EP300_r18_F | 100 | ATGTGACTGGCACGGGAGTTGATCCTGGTTTTCACATACTCCATCTCCCGTAA<br>AAATAGTGAGACTTGAGTAATGTTTGATGTCACTTGTCTTTC |
| EP300_r18_R | 101 | ATGTGACTGGCACGGGAGTTGATCCTGGTTTTCACCAGTCACCACTATATTAT<br>TCTAGGTATCCCAGAAAAGTTAAAGTCAAATCTGAAACACAT |
| VHL_r1_F | 102 | ATGTGACTGGCACGGGAGTTGATCCTGGTTTTCACCGCCCCGCGTCCGACCCG<br>CGGATCCCGCGGCGTCCGGCCCGGGTGGTCTGGATCGCGGAG |
| VHL_r1_R | 103 | ATGTGACTGGCACGGGAGTTGATCCTGGTTTTCACCCATACGGGCAGCACGAC<br>GCGCGGACTGCGATTGCAGAAGATGACCTGGGAGGGCTCGCG |
| VHL_r1_M1 | 104 | ATGTGACTGGCACGGGAGTTGATCCTGGTTTTCACTAGAGGGGCTTCAGACCG<br>TGCTATCGTCCCTGCTGGGTCGGGCCTAAGCGCCGGGCCCGT |
| VHL_r1_M2 | 105 | ATGTGACTGGCACGGGAGTTGATCCTGGTTTTCACGGCGCCGAGGAGGAGATG<br>GAGGCCGGGCGGCCGCGGCCCGTGCTGCGCTCGGTGAACTCG |
| VHL_r2_F | 106 | ATGTGACTGGCACGGGAGTTGATCCTGGTTTTCACGGTGTGGGCCACCGTGCC<br>CAGCCACCGGTGTGGCTCTTTAACAACCTTTGCTTGTCCCGA |
| VHL_r2_R | 107 | ATGTGACTGGCACGGGAGTTGATCCTGGTTTTCACAAGTGGTCTATCCTGTAC<br>TTACCACAACAACCTTATCTTTTTAAAAAGTAAAACGTCAGT |
| VHL_r3_F | 108 | ATGTGACTGGCACGGGAGTTGATCCTGGTTTTCACCTTGTTCGTTCCTTGTAC<br>TGAGACCCTAGTCTGCCACTGAGGATTTGGTTTTTGCCCTTC |
| VHL_r3_R | 109 | ATGTGACTGGCACGGGAGTTGATCCTGGTTTTCACATCAAGACTCATCAGTAC<br>CATCAAAAGCTGAGATGAAACAGTGTAAGTTTCAACAGAAAT |
| | | 40 mers |
| PLP1_ex2_F_40 | 110 | ATGTGACTGGCACGGGAGTTGATCCTGGTTTTCACACCTACTGGATGTGCCTG<br>ACTGTTTCCCCTTCTTCTTCCC |
| PLP1_ex2_R_40 | 111 | ATGTGACTGGCACGGGAGTTGATCCTGGTTTTCACGGGAAAAAAAGATGGGT<br>CTGTGTGGGAGGGCAGGTACTT |
| PLP1_ex3_F_40 | 112 | ATGTGACTGGCACGGGAGTTGATCCTGGTTTTCACTTAATAAGATTCCCTGGT<br>CTCGTTTGTCTACCTGTTAATG |
| PLP1_ex3_M_40 | 113 | ATGTGACTGGCACGGGAGTTGATCCTGGTTTTCACCCCCACCCCTTGTTATTG<br>CCACAAAATCCTGAGGATGATC |
| CYP2D6_F_40 | 114 | ATGTGACTGGCACGGGAGTTGATCCTGGTTTTCACGCTGAGCAGGAGGTGGCA<br>GGTACCCCAGACTGGGAGGTAA |

TABLE 4-continued

Capture probes

| Name | SEQ ID NO: | Sequence |
|---|---|---|
| CYP2D6_R_40 | 115 | ATGTGACTGGCACGGGAGTTGATCCTGGTTTTCACGGCCCAGTCTGTTCACAC<br>ATGGCTGCTGCCTCTCAGCTCT |
| chrX_15_F_40 | 116 | ATGTGACTGGCACGGGAGTTGATCCTGGTTTTCACGAAAGTCATTTGTCAAGG<br>CCTTCAGTTGGCAGACGTGCTC |
| chrX_15_R_40 | 117 | ATGTGACTGGCACGGGAGTTGATCCTGGTTTTCACAATCTGTGGAAACGCTGC<br>CACACAATCTTAGCACACAAGA |
| chrX_69_F_40 | 118 | ATGTGACTGGCACGGGAGTTGATCCTGGTTTTCACTGCTTGCAAAACAACAGA<br>ATCTTCTCTCCATGAAATCATG |
| chrX_69_R_40 | 119 | ATGTGACTGGCACGGGAGTTGATCCTGGTTTTCACATTTTCTCACAAAGGAAA<br>CCAAGATAAAAGGTTTAAATGG |
| KRAS_ex1_F_40 | 120 | ATGTGACTGGCACGGGAGTTGATCCTGGTTTTCACTGCTTTCTGCCAAAATTA<br>ATGTGCTGAACTTAAACTTACC |
| KRAS_ex1_R_40 | 121 | ATGTGACTGGCACGGGAGTTGATCCTGGTTTTCACCCAATGCAACAGACTTTA<br>AGAAGTTGTGTTTTACAATGC |
| KRAS_ex2_F_40 | 122 | ATGTGACTGGCACGGGAGTTGATCCTGGTTTTCACATTTTGCAGAAAACAGAT<br>CTGTATTTATTTCAGTGTTACT |
| KRAS_ex2_R_40 | 123 | ATGTGACTGGCACGGGAGTTGATCCTGGTTTTCACTGTGTTACTAATGACTGT<br>GCTATAACTTTTTTTTCTTTCC |
| MYC_r2_F_1_40 | 124 | ATGTGACTGGCACGGGAGTTGATCCTGGTTTTCACTGCGCCAGGTTTCCGCAC<br>CAAGACCCCTTTAACTCAAGAC |
| MYC_r2_R_1_40 | 125 | ATGTGACTGGCACGGGAGTTGATCCTGGTTTTCACGGGGTGGGCAGCAGCTCG<br>AATTTCTTCCAGATATCCTCGC |
| MYC_r2_F_3_40 | 126 | ATGTGACTGGCACGGGAGTTGATCCTGGTTTTCACCATGGTGAACCAGAGTTT<br>CATCTGCGACCCGGACGACGAG |
| MYC_r2_R_3_40 | 127 | ATGTGACTGGCACGGGAGTTGATCCTGGTTTTCACGACGGAGAGAAGGCGCTG<br>GAGTCTTGCGAGGCGCAGGACT |
| SRY_r1_F40 | 128 | ATGTGACTGGCACGGGAGTTGATCCTGGTTTTCACGAGCATCTAGGTAGGTCT<br>TTGTAGCCAATGTTACCCGATT |
| SRY_r1_M3_40 | 129 | ATGTGACTGGCACGGGAGTTGATCCTGGTTTTCACGCACAGAAATTACAGGCC<br>ATGCACAGAGAGAAATACCCGA |
| VHL_r3_F_40 | 130 | ATGTGACTGGCACGGGAGTTGATCCTGGTTTTCACAGACCCTAGTCTGCCACT<br>GAGGATTTGGTTTTTGCCCTTC |
| VHL_r3_R_40 | 131 | ATGTGACTGGCACGGGAGTTGATCCTGGTTTTCACTCAAAAGCTGAGATGAAA<br>CAGTGTAAGTTTCAACAGAAAT |
| UGT1A1_r_4F_40 | 132 | ATGTGACTGGCACGGGAGTTGATCCTGGTTTTCACAGAGATGTAACTGCTGAC<br>ATCCTCCCTATTTTGCATCTCA |
| UGT1A1_r_4R_40 | 133 | ATGTGACTGGCACGGGAGTTGATCCTGGTTTTCACGAATGCCATGACCAAAGT<br>ATTCTTCTGTATCTTCTTTCTT |
| TNFRSF14_r3_F_40 | 134 | ATGTGACTGGCACGGGAGTTGATCCTGGTTTTCACGGGCCTCCCGCAGACTTG<br>CGAAGTTCCCACTCTCTGGGCG |
| TNFRSF14_r3_R_40 | 135 | ATGTGACTGGCACGGGAGTTGATCCTGGTTTTCACGCTGCCCAAGCGGAGGCT<br>GGGCCGGCTGTGCTGGCCTCTT |
| RUNX1_r4_F_40 | 136 | ATGTGACTGGCACGGGAGTTGATCCTGGTTTTCACGCCATGAAACGTGTTTCA<br>AGCATAGTTTTGACAGATAACG |
| RUNX1_r4_R_40 | 137 | ATGTGACTGGCACGGGAGTTGATCCTGGTTTTCACAACATCCCTGATGTCTGC<br>ATTTGTCCTTTGACTGGTGTTT |
| RHD_r5_F_40 | 138 | ATGTGACTGGCACGGGAGTTGATCCTGGTTTTCACTTTGGAGCAGGAGTGTGA<br>TTCTGGCCAACCACCCTCTCTG |
| RHD_r5_R_40 | 139 | ATGTGACTGGCACGGGAGTTGATCCTGGTTTTCACCTGTTAGACCCAAGTGCT<br>GCCCAAGGGCAGCGCCCTGCTC |

TABLE 4-continued

Capture probes

| Name | SEQ ID NO: | Sequence |
|---|---|---|
| PTEN_r5_F_40 | 140 | ATGTGACTGGCACGGGAGTTGATCCTGGTTTTCACAAGAGTTTTTTTTCTTATTCTGAGGTTATCTTTTTACCA |
| PTEN_r5_R_40 | 141 | ATGTGACTGGCACGGGAGTTGATCCTGGTTTTCACAATTCTCAGATCCAGGAAGAGGAAAGGAAAAACATCAAAA |
| EP300_r18_F_40 | 142 | ATGTGACTGGCACGGGAGTTGATCCTGGTTTTCACATAGTGAGACTTGAGTAATGTTTGATGTCACTTGTCTTTC |
| EP300_r18_R_40 | 143 | ATGTGACTGGCACGGGAGTTGATCCTGGTTTTCACTAGGTATCCCAGAAAAGTTAAAGTCAAATCTGAAACACAT |
| VHL_r1_F_40 | 144 | ATGTGACTGGCACGGGAGTTGATCCTGGTTTTCACGATCCCGCGGCGTCCGGCCCGGGTGGTCTGGATCGCGGAG |
| VHL_r1_R_40 | 145 | ATGTGACTGGCACGGGAGTTGATCCTGGTTTTCACGCGGACTGCGATTGCAGAAGATGACCTGGGAGGGCTCGCG |
| VHL_r1_M1_40 | 146 | ATGTGACTGGCACGGGAGTTGATCCTGGTTTTCACCTATCGTCCCTGCTGGGTCGGGCCTAAGCGCCGGGCCCGT |
| VHL_r1_M2_40 | 147 | ATGTGACTGGCACGGGAGTTGATCCTGGTTTTCACGGCCGGGCGGCCGCGGCCCGTGCTGCGCTCGGTGAACTCG |
| VHL_r2_F_40 | 148 | ATGTGACTGGCACGGGAGTTGATCCTGGTTTTCACGCCACCGGTGTGGCTCTTTAACAACCTTTGCTTGTCCCGA |
| VHL_r2_R_40 | 149 | ATGTGACTGGCACGGGAGTTGATCCTGGTTTTCACACCACAACAACCTTATCTTTTTAAAAAGTAAAACGTCAGT |
| VHL_r3_F_40 | 150 | ATGTGACTGGCACGGGAGTTGATCCTGGTTTTCACAGACCCTAGTCTGCCACTGAGGATTTGGTTTTTGCCCTTC |
| VHL_r3_R_40 | 151 | ATGTGACTGGCACGGGAGTTGATCCTGGTTTTCACTCAAAAGCTGAGATGAAACAGTGTAAGTTTCAACAGAAAT |

The performance of 40 mer capture probes was compared to that of 60 mer capture probes. The 40 mer was designed from the 60 mer by removing 20 nucleotides from the 5' end of the 60 mer. Although the 3' end of both capture probe sets are identical with respect to the sequences that are copied from captured genomic clones, the probe sequence signature (Read 2 of the paired end read) is different between the 60 mer and 40 mer probe sets. This design is useful because it allows the capture probes to be multiplexed during sequencing and their performance subsequently analyzed during downstream bioinformatics deconvolution.

Genomic Samples:

A pool of 12 genomic DNA samples (chosen from a Coriell human panel of 112 human genomic DNAs) was used as the target DNA. The 12 samples were broken into four sets of four samples each, as shown in detail in Table 5.

TABLE 5

Sample Summary

| Capture probes | Wash temp. | Sample Code | | | Samples | |
|---|---|---|---|---|---|---|
| 60 mer | 50 C. | AAT | GM20291 | M | Americas | AFRICAN ANCESTRY IN SOUTHWEST USA |
| | | CTA | GM19373 | M | WAfrican | LUHYA IN WEBUYE, KENYA |
| | | GGG | HG00428 | F | AsianE | HAN CHINESE SOUTH |
| | | TCC | HG01624 | M | Euro | IBERIAN POPULATIONS IN SPAIN |
| 40 mer | 50 C. | AAT | GM20291 | M | Americas | AFRICAN ANCESTRY IN SOUTHWEST USA |
| | | CTA | GM19373 | M | WAfrican | LUHYA IN WEBUYE, KENYA |
| | | GGG | HG00428 | F | AsianE | HAN CHINESE SOUTH |
| | | TCC | HG01624 | M | Euro | IBERIAN POPULATIONS IN SPAIN |
| 60 mer | 47 C. | AGA | HG02489 | M | Americas | AFRICAN CARIBBEAN IN BARBADOS |
| | | CCT | HG01108 | F | Americas | PUERTO RICAN IN PUERTO RICO |
| | | GAC | GM19011 | F | AsianE | JAPANESE IN TOKYO, JAPAN |
| | | TTG | GM18946 | F | AsianE | JAPANESE IN TOKYO, JAPAN |

TABLE 5-continued

Sample Summary

| Capture probes | Wash temp. | Sample Code | | | Samples |
|---|---|---|---|---|---|
| 40 mer | 47 C. | AGA | HG02489 | M Americas | AFRICAN CARIBBEAN IN BARBADOS |
| | | CCT | HG01108 | F Americas | PUERTO RICAN IN PUERTO RICO |
| | | GAC | GM19011 | F AsianE | JAPANESE IN TOKYO, JAPAN |
| | | TTG | GM18946 | F AsianE | JAPANESE IN TOKYO, JAPAN |
| 60 mer | 44 C. | ATC | NA13783 | F NA13783 | GM13783 |
| | | CAG | HG03700 | F AsianS | PUNJABI IN LAHORE, PAKISTAN |
| | | GCA | HG03367 | M WAfrican | ESAN FROM NIGERIA |
| | | TGT | NA22991 | F NA22991 | GM22991 |
| 40 mer | 44 C. | ATC | NA13783 | F NA13783 | GM13783 |
| | | CAG | HG03700 | F AsianS | PUNJABI IN LAHORE, PAKISTAN |
| | | GCA | HG03367 | M WAfrican | ESAN FROM NIGERIA |
| | | TGT | NA22991 | F NA22991 | GM22991 |

Hybridization, Washing and Sequencing:

Six different hybridization conditions were used to hybridize the 60 mer and 40 mer probes to the genomic target DNA:

1) 60 mer probes washed at 50° C.
2) 40 mer probes washed at 50° C.
3) 60 mer probes washed at 47° C.
4) 40 mer probes washed at 47° C.
5) 60 mer probes washed at 44° C.
6) 40 mer probes washed at 44° C.

For each experiment, the capture probe oligos were combined with partner oligo; the final concentration of duplex capture probe was 1 nM for each capture probe.

Each hybridization reaction had ~2.5 µg of genomic library in 40 µL total volume. Each sample was heated to 98° C. for 2 min then cooled on ice. 20 µL of capture probe and 90 µL of hybridization buffer were added and the hybridization mix was incubated for 24 hours starting at 80° C. and decreasing one degree every 48 minutes to 50° C. The complexes were bound to 20 µL of streptavidin beads in 1 mL total volume of TEzero buffer+0.05% Tween20 (TT). The beads were washed 3 times, 5 min each with 200 µL of TT, and once at 45° C. for 5 min in wash buffer. The beads were then washed with TEzero and each reaction was resuspended in 20 µL TEzero. The complexes were then PCR amplified with full length forward (ACA2_FLFP; SEQ ID NO: 152; AATGATACGGCGACCACCGAGATCTA-CACGTCATGCAGGACCAGAGAATTCGAATA CA) and full length reverse (CAC3_FLRP; SEQ ID NO: 153; CAAGCAGAAGACGGCAT-ACGAGATGTGACTGGCACGGGAGTT-GATCCTGGTTTTCA C) primers.

Following amplification and purification, the resulting product masses were measured and equal masses were pooled for sequencing.

Results—Modified 40Mer Primers

Figure 3:
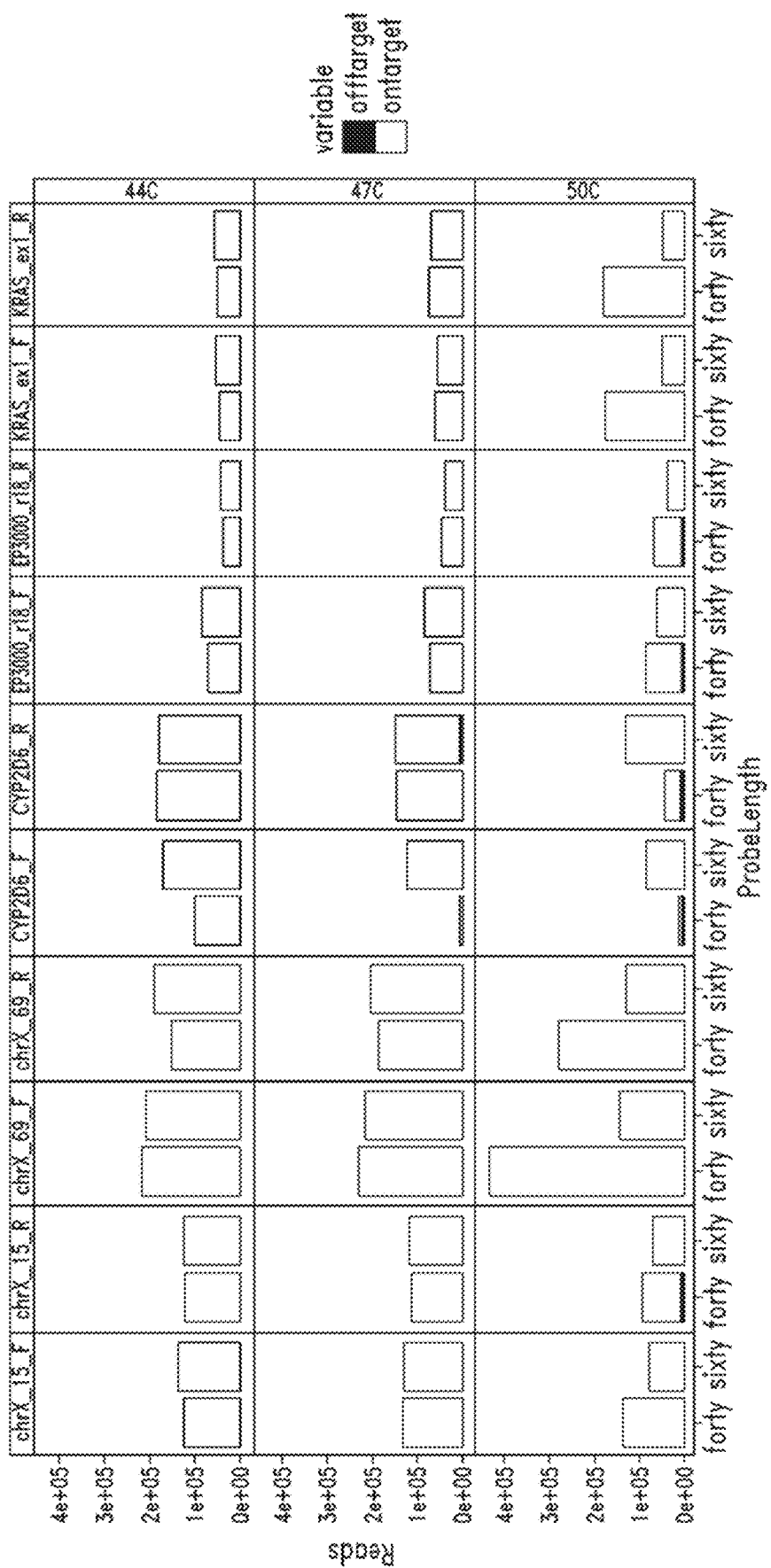
FIG. 3 shows capture probe performance as a function of length and wash temperature. The y-axis shows the total number of reads associated with each capture probe. The bars in the bar chart are broken into two categories, where open bars correspond to on-target reads that align to the intended capture probe targets and solid bars show off-target reads that are associated with a capture probe but that map to unintended regions of the genome. Overall, the 40-mer and 60-mer capture probes perform substantially the same with 44° C. and 47° C. washes. With the 50° C. wash, the 40-mer capture probes perform erratically. These data validate the use of 40-mer capture probes at wash temperatures in the range of about 44° C. to about 47° C.

The capture probe performance as a function of length and wash temperature is shown graphically in FIG. 3. Overall, the 40 mer capture probes performed as well as the 60 mer capture probes with 44° C. and 47° C. washes. With the 50° C. wash, the 40 mer capture probes exhibit sporadic behavior. These data empirically validate the use of 40 mer capture probes and wash temperatures in the 44° C. to 47° C. range when using these reagents.

Methods—High Density 40 Mers
High Density 40 Mers:

In general, sequence capture probes are designed using specific "rules." For example, regions of redundant sequence or that exhibit extreme base composition biases are generally avoided. One key implication of the requirement for high probe density and close spacing of probes along target regions is that there is little or no latitude to move probes in order to accommodate any such probe design rules. In this study, probes were designed based solely on their position relative to one another with no consideration of probe binding sequences; thus, use of this high density approach required empirically validating that the hybridization and processing methods would accommodate such a collection of probes.

Figure 4:
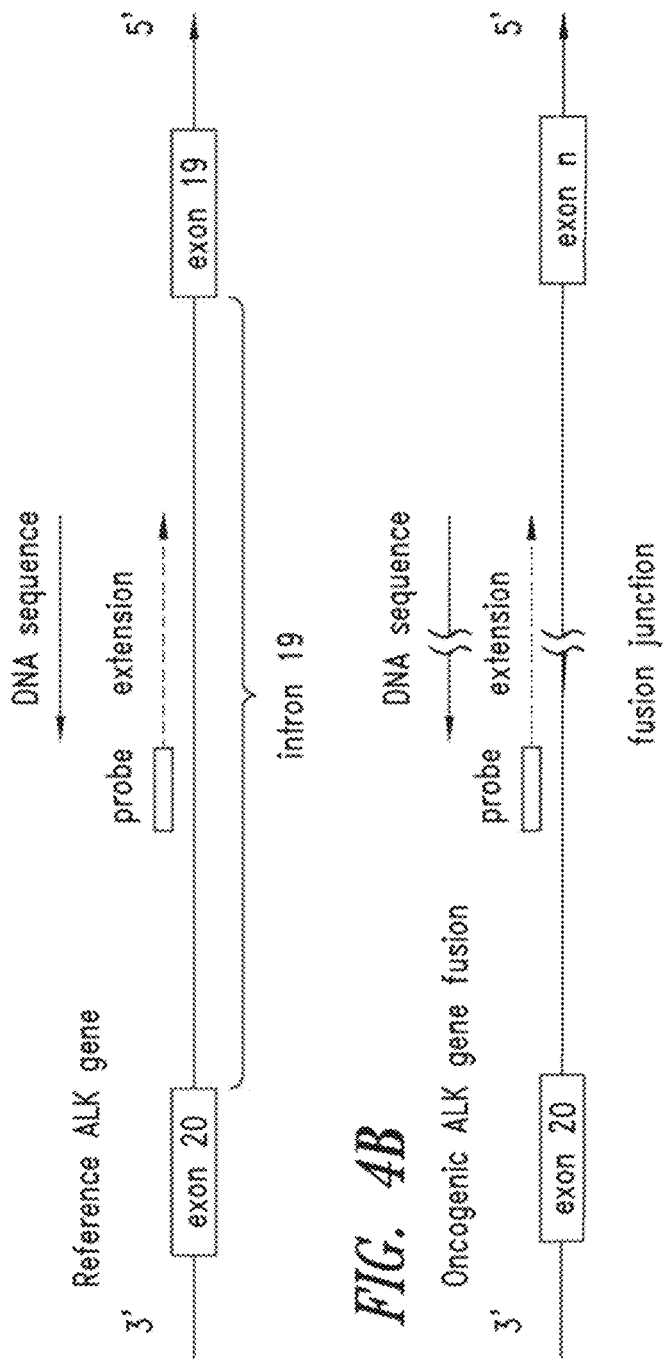
FIG. 4A-FIG. 4B shows a schematic for the targeted and oriented sequencing of intron 19 of the ALK gene. In the "wild-type" reference sequence, antisense-oriented ALK capture probes identify sequences from intron 19 (FIG. 4A). In the case of pathogenic fusion genes, some ALK capture probes will identify junction sequences associated with the gene fusion event (FIG. 4B).

The human ALK gene encodes a protein kinase important in early development, but normal ALK gene expression is essentially undetectable in normal adults. Oncogenic ALK fusions are created when intron 19 of ALK undergoes illegitimate recombination to fuse the kinase encoding portion of ALK to the 5' end of another gene. Such gene fusions often cause ectopic expression of the ALK kinase, which in turn is important in driving the inappropriate cell proliferation observed in pulmonary tumors. In lung cancer, this "other gene" is often EML4, but other fusion partners have also been detected. To create an assay that can detect any possible ALK gene fusion event, 40 nucleotide probes were designed that were placed at 80 nucleotide intervals in intron 19 of ALK. These probes were oriented such that they are antisense relative to the gene (FIG. 4). This means that their 3' terminus extends and copies genic regions that are 5' to their hybridization site. When fusion genes are present, probe extension from probes positioned near the fusion junction copy junction sequences. The DNA sequences resulting from these junction clones have fusion partner sequences at their 5' end, the fusion junction sequence, and ALK intron 19 sequences at their 3' ends (FIG. 4B).

Figure 5:
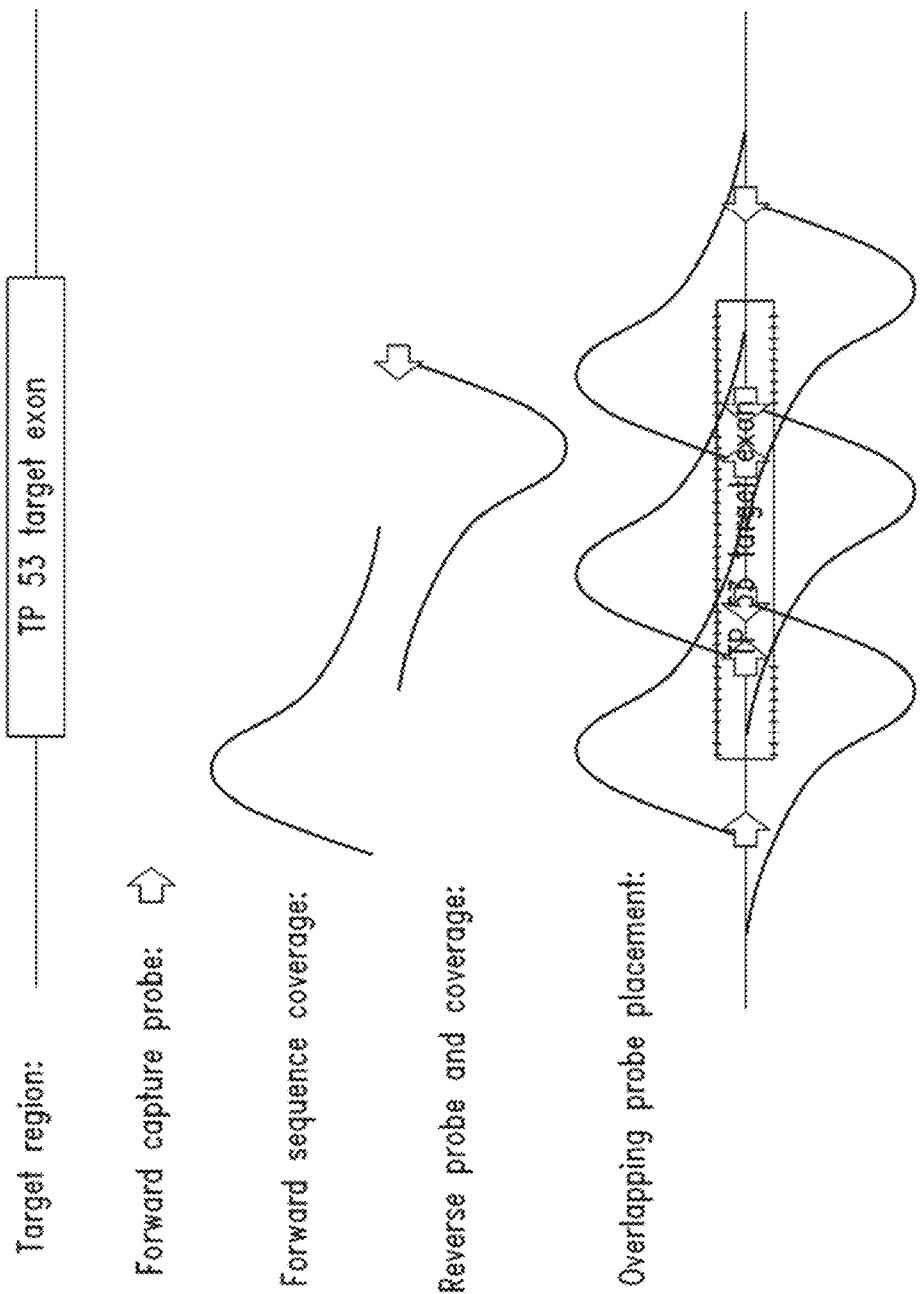
FIG. 5 shows a schematic for high density capture probe placement for complete sequencing of target regions. Each capture probe captures a collection of sequences that provide cumulative coverage at each base position. Here, coverage is represented by a line, and the amplitude of the line denotes depth of coverage derived from a particular capture probe. Overlapping coverage from adjacent capture probes provides complete sequencing of target regions in both possible directions. In addition, the head-to-head placement of opposite strand capture probes ensures that all capture probe binding sites are sequenced.

Another important diagnostic target in cancer is the TP53 gene. It encodes a tumor suppressor, and it is often inactivated by mutations in cancers. Mutations that can inactivate gene function are scattered throughout the gene, and hence conclusive sequence-based assays for TP53 inactivating mutations must address the entire coding region and untranslated regions (UTRs) of the gene. Because circulating DNA fragments are short, high density probes were used to interrogate all target regions of the TP53 gene. Unlike ALK, probes for TP53 are placed in both possible orientations (FIG. 5). At high probe densities, the cumulative coverage from multiple probes provides uniform deep sequencing coverage of target regions.

The collection of 105 probes used in this study is shown in Table 6. In addition to probes that target the fusion-prone region of ALK and the coding regions of TP53, probes that cover known SNVs in the cell line DNA were also included.

TABLE 6

| Name_target region | SEQ ID NO: | Probe sequence |
|---|---|---|
| ALK_chr2:29446208_fusion_f | 154 | ATGTGACTGGCACGGGAGTTGATCCTGGTTTTCACCGAATGAGGGTGATGTTTTTCCGCGGCACCTCCTTCAGGT |
| ALK_chr2:29446288_fusion_f | 155 | ATGTGACTGGCACGGGAGTTGATCCTGGTTTTCACGTTGTAGTCGGTCATGATGGTCGAGGTGCGGAGCTTGCTC |
| ALK_chr2:29446368_fusion_f | 156 | ATGTGACTGGCACGGGAGTTGATCCTGGTTTTCACGCAGCTCCTGGTGCTTCCGGCGGTACACTGCAGGTGGGTG |
| ALK_chr2:29446448_fusion_f | 157 | ATGTGACTGGCACGGGAGTTGATCCTGGTTTTCACCTACACAGGCCACTTCCTACAGGAAGCCTCCCTGGATCTC |
| ALK_chr2:29446528_fusion_f | 158 | ATGTGACTGGCACGGGAGTTGATCCTGGTTTTCACGAAATACTAATAAAATGATTAAAGAAGGTGTGTCTTTAAT |
| ALK_chr2:29446608_fusion_f | 159 | ATGTGACTGGCACGGGAGTTGATCCTGGTTTTCACTATATGGAAAATAATTATTTGTATTATATAGGGCAGAGTC |
| ALK_chr2:29446688_fusion_f | 160 | ATGTGACTGGCACGGGAGTTGATCCTGGTTTTCACATTAGACCCAATATGGTCTGCAGATTTTATTAGAAGAAAT |
| ALK_chr2:29446768_fusion_f | 161 | ATGTGACTGGCACGGGAGTTGATCCTGGTTTTCACGTGAACCAGCAGACTGTGTTGCAAGTATAACCCCACGTGA |
| ALK_chr2:29446848_fusion_f | 162 | ATGTGACTGGCACGGGAGTTGATCCTGGTTTTCACGCCATGGAGCCTAAGGAAGTTTCAGCAAGGCCCTAAGGGG |
| ALK_chr2:29446928_fusion_f | 163 | ATGTGACTGGCACGGGAGTTGATCCTGGTTTTCACCCCAGGAATTGGCCTGCCTTAGTATTTCTGCTGTGCTCAG |
| ALK_chr2:29447008_fusion_f | 164 | ATGTGACTGGCACGGGAGTTGATCCTGGTTTTCACTTTGAGGGTGCAGCTGGGATCTTGGTCAGTTGTGTTTCCT |
| ALK_chr2:29447088_fusion_f | 165 | ATGTGACTGGCACGGGAGTTGATCCTGGTTTTCACCACATCATGAAAAGATCTCTGAATTGGTGTCTGGGGATCT |
| ALK_chr2:29447168_fusion_f | 166 | ATGTGACTGGCACGGGAGTTGATCCTGGTTTTCACTGAGGACCAGGTCACAGGACCTCTTTGGACTGCAGTTTCC |
| ALK_chr2:29447248_fusion_f | 167 | ATGTGACTGGCACGGGAGTTGATCCTGGTTTTCACTAACCACTGCCACTCCCCACCCTCTAGGGTTGTCAATGAA |
| ALK_chr2:29447328_fusion_f | 168 | ATGTGACTGGCACGGGAGTTGATCCTGGTTTTCACGAGCTCTACCAATGTGAGTGACCATTATCACTCCTACATG |
| ALK_chr2:29447408_fusion_f | 169 | ATGTGACTGGCACGGGAGTTGATCCTGGTTTTCACAAAATTGTGATTCAGTGGGTAGATTCTGTGTGTAAAGCCC |
| ALK_chr2:29447488_fusion_f | 170 | ATGTGACTGGCACGGGAGTTGATCCTGGTTTTCACTATGTGCTCAGTTCCCTCCTCTATGCAATGGACCGACCGT |
| ALK_chr2:29447568_fusion_f | 171 | ATGTGACTGGCACGGGAGTTGATCCTGGTTTTCACGTGTAAATTGCCGAGCACGTAGTAACCATGCAACAAGTGT |

TABLE 6-continued

| Name_target region | SEQ ID NO: | Probe sequence |
|---|---|---|
| ALK_chr2:29447648_fusion_f | 172 | ATGTGACTGGCACGGGAGTTGATCCTGGTTTTCA CTGGGGACACAGTGTGTGCTGCCATCTCCCTTCT ACCGGCA |
| ALK_chr2:29447728_fusion_f | 173 | ATGTGACTGGCACGGGAGTTGATCCTGGTTTTCA CAAGAGCCTTTCCCTCTGCCCTTTTCAAGCCTCT GCCCATC |
| ALK_chr2:29447808_fusion_f | 174 | ATGTGACTGGCACGGGAGTTGATCCTGGTTTTCA CGACCACACTGAGTTCTCTGTGACCTGCAGGTCA GCTCACC |
| ALK_chr2:29447888_fusion_f | 175 | ATGTGACTGGCACGGGAGTTGATCCTGGTTTTCA CTTTCCTATCTCTCTGCCTGGAGGGTGGTGGAGG GCTGGTT |
| ALK_chr2:29447968_fusion_f | 176 | ATGTGACTGGCACGGGAGTTGATCCTGGTTTTCA CAAACAGGAGCTGCGCCGGTGGAAGCATGTGGGA GCTAGAA |
| ALK_chr2:29448048_fusion_f | 177 | ATGTGACTGGCACGGGAGTTGATCCTGGTTTTCA CGGACACTGAAGGAGCTCCCCACCCCCTGATCAG CCAGGAG |
| ALK_chr2:29448128_fusion_f | 178 | ATGTGACTGGCACGGGAGTTGATCCTGGTTTTCA CGGGAACTGCAGCTGCTCTGGTGGGGGGAAGGTT GGGAGCT |
| ALK_chr2:29448208_fusion_f | 179 | ATGTGACTGGCACGGGAGTTGATCCTGGTTTTCA CACCCAATTCCAGGGACTAGCATAACGAAGTGAC ACCTTGG |
| ALK_chr2:29448288_fusion_f | 180 | ATGTGACTGGCACGGGAGTTGATCCTGGTTTTCA CCCTGCCCCCTTGGGAGTCCCTGGGGCTCTGTGC ACTCACC |
| MYCNr1f_40 | 181 | ATGTGACTGGCACGGGAGTTGATCCTGGTTTTCA CGGAAGCACCCCCGGTATTAAAACGAACGGGGCG GAAAGAA |
| MYCNr1r_40 | 182 | ATGTGACTGGCACGGGAGTTGATCCTGGTTTTCA CCTAACAAAGGGGACGCGACCCGGGGTCCAGTGC CCCAGGG |
| MYCNr1f2_40 | 183 | ATGTGACTGGCACGGGAGTTGATCCTGGTTTTCA CCCTGGGGGGACTGGGTGGCCTCACCCCCAACCC GGTCATC |
| MYCNr1r2_40 | 184 | ATGTGACTGGCACGGGAGTTGATCCTGGTTTTCA CCGCGCTCCAGCTTCTCGCGGGCGGAGAAGCCGC TCCACAT |
| MYCNr1f3_40 | 185 | ATGTGACTGGCACGGGAGTTGATCCTGGTTTTCA CCCCACCCGGCCGCCGAGTGCGTGGATCCCGCCG TGGTCTT |
| MYCNr1r3_40 | 186 | ATGTGACTGGCACGGGAGTTGATCCTGGTTTTCA CGGGCACGGGCGCTGGCTCGCGCTTGTTCACGGG AAAGGGG |
| MYCNr2f_40 | 187 | ATGTGACTGGCACGGGAGTTGATCCTGGTTTTCA CAACATGGATATATATGTGAATTTCATTCAAATG GTTCTCA |
| MYCNr2r_40 | 188 | ATGTGACTGGCACGGGAGTTGATCCTGGTTTTCA CTAAACCAACATTCTTAATGTCAACACAATGTTT GTTTAAA |
| MYCNr2f2_40 | 189 | ATGTGACTGGCACGGGAGTTGATCCTGGTTTTCA CCCCTACGTGGAGAGTGAGGATGCACCCCCACAG AAGAAGA |
| MYCNr2r2_40 | 190 | ATGTGACTGGCACGGGAGTTGATCCTGGTTTTCA CATGACACTCTTGAGCGGACGTGGGGACGCCTCG CTCTTTA |

TABLE 6-continued

| Name_target region | SEQ ID NO: | Probe sequence |
|---|---|---|
| MYCNr2f3_40 | 191 | ATGTGACTGGCACGGGAGTTGATCCTGGTTTTCACTCTCACGCTCAGGGACCACGTGCCGGAGTTGGTAAAGAAT |
| MYCNr2r3_40 | 192 | ATGTGACTGGCACGGGAGTTGATCCTGGTTTTCACCAGTGGCCTTTTTCAAAATGACCACCTTGGCGGCCTTCTC |
| TP53_chr17:7579779:region_1:75nt:-59:-20:f | 193 | ATGTGACTGGCACGGGAGTTGATCCTGGTTTTCACGCTAGGGGCTGGGGTTGGGGTGGGGGTGGTGGGCCTGCC |
| TP53_chr17:7579838:region_1:75nt:1:40:f | 194 | ATGTGACTGGCACGGGAGTTGATCCTGGTTTTCACCAGTTTCCATAGGTCTGAAAATGTTTCCTGACTCAGAGGG |
| TP53_chr17:7579878:region_1:75nt:41:+5:r | 195 | ATGTGACTGGCACGGGAGTTGATCCTGGTTTTCACCTGCCATGGAGGAGCCGCAGTCAGATCCTAGCGTCGAGCC |
| TP53_chr17:7579932:region_1:75nt:+20:+59:r | 196 | ATGTGACTGGCACGGGAGTTGATCCTGGTTTTCACTCATGCTGGATCCCCACTTTTCCTCTTGCAGCAGCCAGAC |
| TP53_chr17:7579640:region_2:23nt:-59:-20:f | 197 | ATGTGACTGGCACGGGAGTTGATCCTGGTTTTCACAGCCCCCCAGCCCTCCAGGTCCCCAGCCCTCCAGGTCCCC |
| TP53_chr17:7579741:region_2:23nt:+20:+59:r | 198 | ATGTGACTGGCACGGGAGTTGATCCTGGTTTTCACGCAGAGACCTGTGGGAAGCGAAAATTCCATGGGACTGACT |
| TP53_chr17:7579252:region_3:280nt:-59:-20:f | 199 | ATGTGACTGGCACGGGAGTTGATCCTGGTTTTCACGCAGGGGGATACGGCCAGGCATTGAAGTCTCATGGAAGCC |
| TP53_chr17:7579311:region_3:280nt:1:40:f | 200 | ATGTGACTGGCACGGGAGTTGATCCTGGTTTTCACCCGTGCAAGTCACAGACTTGGCTGTCCCAGAATGCAAGAA |
| TP53_chr17:7579351:region_3:280nt:41:80:r | 201 | ATGTGACTGGCACGGGAGTTGATCCTGGTTTTCACCCAGAAAACCTACCAGGGCAGCTACGGTTTCCGTCTGGGC |
| TP53_chr17:7579391:region_3:280nt:81:120:f | 202 | ATGTGACTGGCACGGGAGTTGATCCTGGTTTTCACGAAGGGACAGAAGATGACAGGGGCCAGGAGGGGGCTGGTG |
| TP53_chr17:7579431:region_3:280nt:121:160:r | 203 | ATGTGACTGGCACGGAGTTGATCCTGGTTTTCACGTGGCCCCTGCACCAGCAGCTCCTACACCGGCGGCCCCTG |
| TP53_chr17:7579471:region_3:280nt:161:200:f | 204 | ATGTGACTGGCACGGAGTTGATCCTGGTTTTCACGGGGGGAGCAGCCTCTGGCATTCTGGGAGCTTCATCTGGA |
| TP53_chr17:7579511:region_3:280nt:201:240:r | 205 | ATGTGACTGGCACGGGAGTTGATCCTGGTTTTCACCCCCGGACGATATTGAACAATGGTTCACTGAAGACCCAGG |
| TP53_chr17:7579610:region_3:280nt:+20:+59:r | 206 | ATGTGACTGGCACGGAGTTGATCCTGGTTTTCACCTGGGGGGCTGGGGGGCTGAGGACCTGGTCCTCTGACTGC |
| TP53_chr17:7578327:region_4:185nt:-43:-4:f | 207 | ATGTGACTGGCACGGGAGTTGATCCTGGTTTTCACCCTGGGCAACCAGCCCTGTCGTCTCTCCAGCCCCAGCTGC |
| TP53_chr17:7578370:region_4:185nt:1:40:f | 208 | ATGTGACTGGCACGGGAGTTGATCCTGGTTTTCACCCATCGCTATCTGAGCAGCGCTCATGGTGGGGGCAGCGCC |
| TP53_chr17:7578410:region_4:185nt:41:80:r | 209 | ATGTGACTGGCACGGGAGTTGATCCTGGTTTTCACGCCATCTACAAGCAGTCACAGCACATGACGGAGGTTGTGA |

TABLE 6-continued

| Name_target region | SEQ ID NO: | Probe sequence |
|---|---|---|
| TP53_chr17:7578450:region_4:185nt:81:120:f | 210 | ATGTGACTGGCACGGGAGTTGATCCTGGTTTTCACCATGGCGCGGACGCGGGTGCCGGGCGGGGTGTGGAATCA |
| TP53_chr17:7578490:region_4:185nt:121:160:r | 211 | ATGTGACTGGCACGGGAGTTGATCCTGGTTTTCACTTTGCCAACTGGCCAAGACCTGCCCTGTGCAGCTGTGGGT |
| TP53_chr17:7578574:region_4:185nt:+20:+59:r | 212 | ATGTGACTGGCACGGGAGTTGATCCTGGTTTTCACTGCTTTATCTGTTCACTTGTGCCCTGACTTTCAACTCTGT |
| TP53_chr17:7578117:region_5:114nt:-59:-20:f | 213 | ATGTGACTGGCACGGGAGTTGATCCTGGTTTTCACGAGGGCCACTGACAACCACCCTTAACCCCTCCTCCCAGAG |
| TP53_chr17:7578176:region_5:114nt:1:40:f | 214 | ATGTGACTGGCACGGGAGTTGATCCTGGTTTTCACCCTCAGGCGGCTCATAGGGCACCACCACACTATGTCGAAA |
| TP53_chr17:7578216:region_5:114nt:41:80:r | 215 | ATGTGACTGGCACGGGAGTTGATCCTGGTTTTCACAGGAAATTTGCGTGTGGAGTATTTGGATGACAGAAACACT |
| TP53_chr17:7578292:region_5:114nt:+3:+42:r | 216 | ATGTGACTGGCACGGGAGTTGATCCTGGTTTTCACCCAGGGTCCCCAGGCCTCTGATTCCTCACTGATTGCTCTT |
| TP53_chr17:7577439:region_6:111nt:-59:-20:f | 217 | ATGTGACTGGCACGGGAGTTGATCCTGGTTTTCACGAGGCAAGCAGAGGCTGGGGCACAGCAGGCCAGTGTGCAG |
| TP53_chr17:7577498:region_6:111nt:1:40:f | 218 | ATGTGACTGGCACGGGAGTTGATCCTGGTTTTCACCCTGGAGTCTTCCAGTGTGATGATGGTGAGGATGGGCCTC |
| TP53_chr17:7577538:region_6:111nt:41:80:r | 219 | ATGTGACTGGCACGGGAGTTGATCCTGGTTTTCACACTACATGTGTAACAGTTCCTGCATGGGCGGCATGAACCG |
| TP53_chr17:7577628:region_6:111nt:+20:+59:r | 220 | ATGTGACTGGCACGGGAGTTGATCCTGGTTTTCACCTTGCCACAGGTCTCCCCAAGGCGCACTGGCCTCATCTTG |
| TP53_chr17:7576974:region_7:138nt:-44:-5:f | 221 | ATGTGACTGGCACGGGAGTTGATCCTGGTTTTCACCTGCACCCTTGGTCTCCTCCACCGCTTCTTGTCCTGCTTG |
| TP53_chr17:7577018:region_7:138nt:1:40:f | 222 | ATGTGACTGGCACGGGAGTTGATCCTGGTTTTCACCCTCGCTTAGTGCTCCCTGGGGGCAGCTCGTGGTGAGGCT |
| TP53_chr17:7577058:region_7:138nt:41:80:r | 223 | ATGTGACTGGCACGGGAGTTGATCCTGGTTTTCACGACCGGCGCACAGAGGAAGAGAATCTCCGCAAGAAAGGGG |
| TP53_chr17:7577098:region_7:138nt:81:120:f | 224 | ATGTGACTGGCACGGGAGTTGATCCTGGTTTTCACTCTCCCAGGACAGGCACAAACACGCACCTCAAAGCTGTTC |
| TP53_chr17:7577138:region_7:138nt:121:+22:r | 225 | ATGTGACTGGCACGGGAGTTGATCCTGGTTTTCACTCTCTTTTCCTATCCTGAGTAGTGGTAATCTACTGGGACG |
| TP53_chr17:7577175:region_7:138nt:+20:+59:r | 226 | ATGTGACTGGCACGGGAGTTGATCCTGGTTTTCACGGACAGGTAGGACCTGATTTCCTTACTGCCTCTTGCTTCT |
| TP53_chr17:7576793:region_8:75nt:-59:-20:f | 227 | ATGTGACTGGCACGGGAGTTGATCCTGGTTTTCACGGCATTTTGAGTGTTAGACTGGAAACTTTCCACTTGATAA |
| TP53_chr17:7576852:region_8:75nt:1:40:f | 228 | ATGTGACTGGCACGGGAGTTGATCCTGGTTTTCACCCTGAAGGGTGAAATATTCTCCATCCAGTGGTTTCTTCTT |

TABLE 6-continued

| Name_target region | SEQ ID NO: | Probe sequence |
|---|---|---|
| TP53_chr17:7576892:region_8:75nt: 41:+5:r | 229 | ATGTGACTGGCACGGGAGTTGATCCTGGTTTTCA CCCTAGCACTGCCCAACAACACCAGCTCCTCTCC CCAGCCA |
| TP53_chr17:7576931:region_8:75nt: +5:+44:r | 230 | ATGTGACTGGCACGGGAGTTGATCCTGGTTTTCA CTGCCTCAGATTCACTTTTATCACCTTTCCTTGC CTCTTTC |
| TP53_chr17:7573867:region_9:108nt: -59:-20:f | 231 | ATGTGACTGGCACGGGAGTTGATCCTGGTTTTCA CATGGCTTTCCAACCTAGGAAGGCAGGGGAGTAG GGCCAGG |
| TP53_chr17:7573926:region_9:108nt: 1:40:f | 232 | ATGTGACTGGCACGGGAGTTGATCCTGGTTTTCA CCCTGGAGTGAGCCCTGCTCCCCCCTGGCTCCTT CCCAGCC |
| TP53_chr17:7573966:region_9:108nt: 41:80:r | 233 | ATGTGACTGGCACGGGAGTTGATCCTGGTTTTCA CTCCGAGAGCTGAATGAGGCCTTGGAACTCAAGG ATGCCCA |
| TP53_chr17:7574053:region_9:108nt: +20:+59:r | 234 | ATGTGACTGGCACGGGAGTTGATCCTGGTTTTCA CCATCTTTTAACTCAGGTACTGTGTATATACTTA CTTCTCC |
| TP53_chr17:7572867:region_10:83nt: -59:-20:f | 235 | ATGTGACTGGCACGGGAGTTGATCCTGGTTTTCA CGGCAGGGGAGGGAGAGATGGGGGTGGGAGGCTG TCAGTGG |
| TP53_chr17:7572926:region_10:83nt: 1:40:f | 236 | ATGTGACTGGCACGGGAGTTGATCCTGGTTTTCA CGTCAGTCTGAGTCAGGCCCTTCTGTCTTGAACA TGAGTTT |
| TP53_chr17:7572966:region_10:83nt: 41:80:r | 237 | ATGTGACTGGCACGGGAGTTGATCCTGGTTTTCA CCCTGAAGTCCAAAAAGGGTCAGTCTACCTCCCG CCATAAA |
| TP53_chr17:7573028:region_10:83nt: +20:+59:r | 238 | ATGTGACTGGCACGGGAGTTGATCCTGGTTTTCA CGGCACAGACCCTCTCACTCATGTGATGTCATCT CTCCTCC |
| ALDH4A1_chr1:19199369_rs61757683: G:T:f | 239 | ATGTGACTGGCACGGGAGTTGATCCTGGTTTTCA CCAGGGGCTTATGTGTCTCCTTGATGACCTGCGG CGACGTC |
| ALDH4A1_chr1:19199488_rs61757683: G:T:r | 240 | ATGTGACTGGCACGGGAGTTGATCCTGGTTTTCA CCCATCATCTCCTCCCTTCCCCTTCTGCCCAGGC TGTTGCA |
| BRCA1_chr17:41223015_rs1799966: T:A,C:f | 241 | ATGTGACTGGCACGGAGTTGATCCTGGTTTTCA CAATTCTGGCTTCTCCCTGCTCACACTTTCTTCC ATTGCAT |
| BRCA1_chr17:41223134_rs1799966: T:A,C:r | 242 | ATGTGACTGGCACGGAGTTGATCCTGGTTTTCA CGTCAGCTCGTGTTGGCAACATACCATCTTCAAC CTCTGCA |
| BRCA1_chr17:41243921_rs16942:T: C:f | 243 | ATGTGACTGGCACGGGAGTTGATCCTGGTTTTCA CTAATTTCTTGGCCCCTCTTCGGTAACCCTGAGC CAAATGT |
| BRCA1_chr17:41244040_rs16942:T: C:r | 244 | ATGTGACTGGCACGGGAGTTGATCCTGGTTTTCA CGGTGAAATAAAGGAAGATACTAGTTTTGCTGAA AATGACA |
| BRCA2_chr13:32906670_rs144848: A:C:f | 245 | ATGTGACTGGCACGGGAGTTGATCCTGGTTTTCA CACTCATTTGTATCTGAAGTGGAACCAAATGATA CTGATCC |
| BRCA2_chr13:32906769_rs144848: A:C:r | 246 | ATGTGACTGGCACGGGAGTTGATCCTGGTTTTCA CAGTTGAGACCATTCACAGGCCAAAGACGGTACA ACTTCCT |
| CDKN2A_chr9:21970837_rs3731249: C:T:f | 247 | ATGTGACTGGCACGGGAGTTGATCCTGGTTTTCA CGAAAATGAATGCTCTGAGCTTTGGAAGCTCTCA GGGTACA |

TABLE 6-continued

| Name_target region | SEQ ID NO: | Probe sequence |
|---|---|---|
| CDKN2A_chr9:21970956_rs3731249:C:T:r | 248 | ATGTGACTGGCACGGGAGTTGATCCTGGTTTTCACGGGCCATCGCGATGTCGCACGGTACCTGCGCGCGGCTGCG |
| DPYD_chr1:97981316_rs1801159:T:C:f | 249 | ATGTGACTGGCACGGGAGTTGATCCTGGTTTTCACCCCCATCCAGCTTCAAAAGCTCTTCGAATCATTGATGTGC |
| DPYD_chr1:97981435_rs1801159:T:C:r | 250 | ATGTGACTGGCACGGGAGTTGATCCTGGTTTTCACTGCCAAGCCTGAACTACCCCTCTTTTACACTCCTATTGAT |
| EPHX1_chr1:226026327_rs2234922:A:G:f | 251 | ATGTGACTGGCACGGGAGTTGATCCTGGTTTTCACCCACCCTGACTGTGCTCTGTCCCCCCAGGGCTGGACATCC |
| EPHX1_chr1:226026446_rs2234922:A:G:r | 252 | ATGTGACTGGCACGGGAGTTGATCCTGGTTTTCACAGTCAGGAGTGGGATGATCTTATAAAACTCGTAGAAAGAG |
| MYC_chr8:128750752_G123E:f | 253 | ATGTGACTGGCACGGGAGTTGATCCTGGTTTTCACCTTCGGGGAGACAACGACGGCGGTGGCGGGAGCTTCTCCA |
| MYC_chr8:128750871_G123E:r | 254 | ATGTGACTGGCACGGGAGTTGATCCTGGTTTTCACCATACAGTCCTGGATGATGATGTTTTTGATGAAGGTCTCG |
| RB1_chr13:49039115_rs121913297:G:T:f | 255 | ATGTGACTGGCACGGGAGTTGATCCTGGTTTTCACTTTTACTGTTCTTCCTCAGACATTCAAACGTGTTTTGATC |
| RB1_chr13:49039204_rs121913297:G:T:r | 256 | ATGTGACTGGCACGGGAGTTGATCCTGGTTTTCACGTGGAAGCATACTGCAAAATATTTGTTTTCAGTCTCTGCA |
| TNFRSF14_chr1:2491227_rs2234163:G:A:f | 257 | ATGTGACTGGCACGGGAGTTGATCCTGGTTTTCACACGTACCCCTCTCAGCCCCTCCTCTTGGACTCCAGCCATG |
| TNFRSF14_chr1:2491346_rs2234163:G:A:r | 258 | ATGTGACTGGCACGGGAGTTGATCCTGGTTTTCACGTGGCGTAAGCGCGGCACGCGGCGCAGTGGTCCCCGTCCT |

Genomic Samples:

Three samples of genomic DNA were analyzed:
1) Germline sample NA 06994—a normal human sample obtained from the Coriell repository;
2) Cancer cell line NCI-H69—a cell line known to harbor a mutation in TP53, an amplification of the MYCN locus, and SNVs in ALDH4A1, BRCA1, BRCA2, CDKN2A, DPYD, EPHX1, MYC, RB1 and TNFRSF14 that were included in the target probe set;
3) Cancer cell line ZR-75-1, which was reported to harbor an EML4-ALK fusion gene (Lin et al., Mol. Cancer Res. 7(9):1466, 2009).

Figure 6:
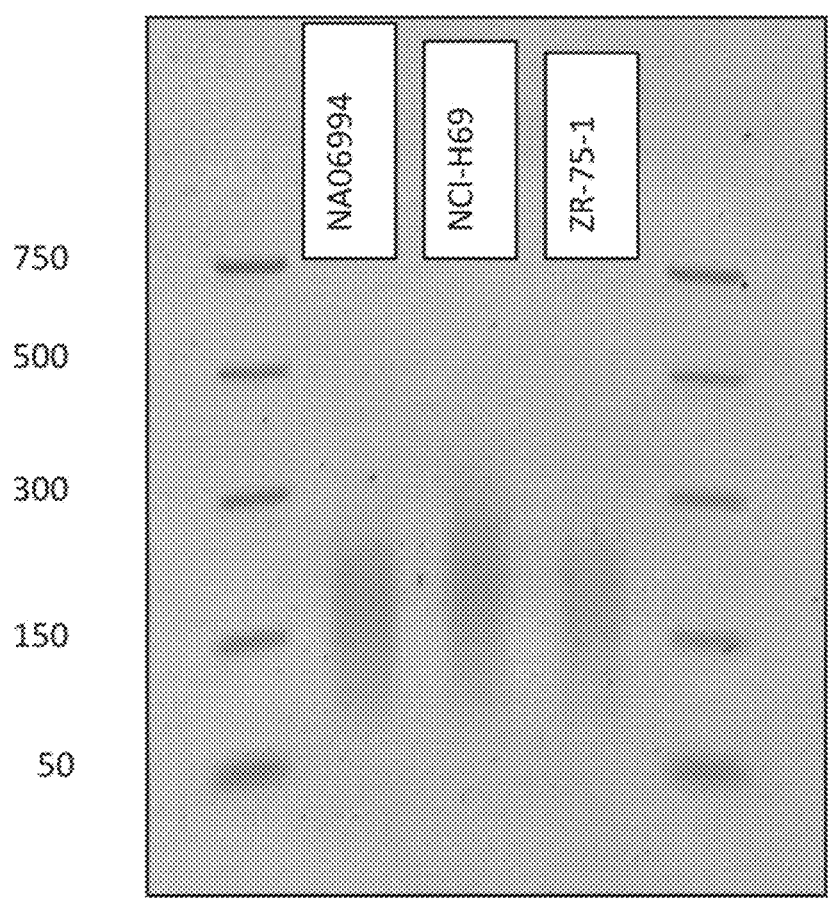
FIG. 6 shows a representative example of the size distribution of fragmented DNA used in library construction.

DNA sequencing libraries are generally constructed from sheared DNA fragments. Acoustic disruption was used to generate DNA fragments that ranged in size from 200 to >500 bp. Enzymatic fragmentation of the acoustically fragmented DNA was performed in an effort to emulate circulating DNA, which is reputed to be composed of nucleosomal, ~150 bp fragments. Briefly, DNA at 20-40 ng/μL was sonicated on the 200 bp setting, which yields fragments that range in size from 150 bp to 400 bp in a broad smear. The DNA was further fragmented by the addition of 0.01 and 0.02 μL of DNAse enzyme (New England Biolabs recombinant bovine DNAse) to 50 μl aliquots of DNA in DNAse buffer (10 mM Tris pH 8.0, 2.5 mM MnCl$_2$, 0.5 mM CaCl$_2$). The DNAse reaction was incubated at 37° C. for 10 min and stopped with the addition of 0.5 M EDTA to a final concentration of 25 mM. DNA with an average size of 150 bp was purified by "two-sided" bead selection by first adding 0.9 volumes of beads to 1 volume of DNA. The beads bind unwanted larger fragments and are discarded, and an additional 1.6 volumes of beads are added to the supernatant. The bound material is then purified and quantified. An agarose gel of the resulting, highly fragmented, short DNA used for library construction is shown in FIG. 6.

Fragmented DNA was end-repaired using the Quick Blunt kit form NEB and blended in the ratios shown in Table 7. Ten nanograms of blended DNA were then ligated to adaptors with the sequences shown in Table 7. For mixes 9 and 15, two ligation reactions with 10 ng each were performed and subsequently pooled. For mix 16, four reactions were done. An estimate of genomic inputs into each library using a qPCR assay is also shown in Table 7.

TABLE 7

Samples and admixture ratios

| | Sample | Admix ratio | Code | SEQ ID NO: | Genomic inputs |
|---|---|---|---|---|---|
| 1) | NA06994 = GL | pure | NNNNNAAGATCTTAGTGGCAC | 259 | 202 |
| 2) | NCI-H69 = N | pure | NNNNNCGACAGAACTATTGCC | 260 | 149 |
| 3) | ZR-75-1 = Z | pure | NNNNNACTATCTTAGTGGCAC | 261 | 242 |
| 4) | GL:N | 1:1 | NNNNNCTCCAGAACTATTGCC | 262 | 200 |
| 5) | GL:N | 2:1 | NNNNNAGCATCTTAGTGGCAC | 263 | 83 |
| 6) | GL:N | 4:1 | NNNNNCATCAGAACTATTGCC | 264 | 186 |
| 7) | GL:N | 10:1 | NNNNNATAATCTTAGTGGCAC | 265 | 264 |
| 8) | GL:N | 20:1 | NNNNNAAGAAGGTAGACCCTC | 266 | 203 |
| 9) | GL:N | 100:1 | NNNNNTTTCTCTACTCGTGAC | 267 | 436 |
| 10) | GL:Z | 1:1 | NNNNNACTAAGGTAGACCCTC | 268 | 297 |
| 11) | GL:Z | 2:1 | NNNNNGAAGCTACGAGTATCC | 269 | 224 |
| 12) | GL:Z | 4:1 | NNNNNAGCAAGGTAGACCCTC | 270 | 73 |
| 13) | GL:Z | 10:1 | NNNNNCATTGACGTCTAGAGC | 271 | 181 |
| 14) | GL:Z | 20:1 | NNNNNTCACTCTACTCGTGAC | 272 | 224 |
| 15) | GL:Z | 100:1 | NNNNNATAAAGGTAGACCCTC | 273 | 580 |
| 16) | GL:N:Z | 500:1:1 | NNNNNTACCTCTACTCGTGAC | 274 | 1324 |

Targeted Sequencing:

One microgram of each of the sixteen DNA libraries shown in Table 7 were pooled and adjusted to a final volume of 160 μL. Eight identical 20 μL aliquots were denatured at 98° C., cooled on ice, and 20 μL of probes (Table 6) at 1 nM/probe and 50 μL of CF hyb buffer were added. The samples were annealed for 24 hours from 80° C. to 50° C., washed, and amplified. Following amplification of the resulting captured and processed fragments, the final sequencing library was size selected using the Pippin Prep™ instrument with a size selection of 175-400 bp. The library was sequenced on an Illumina MiSeq using a 150 read V3 kit.

Results

Figure 7:
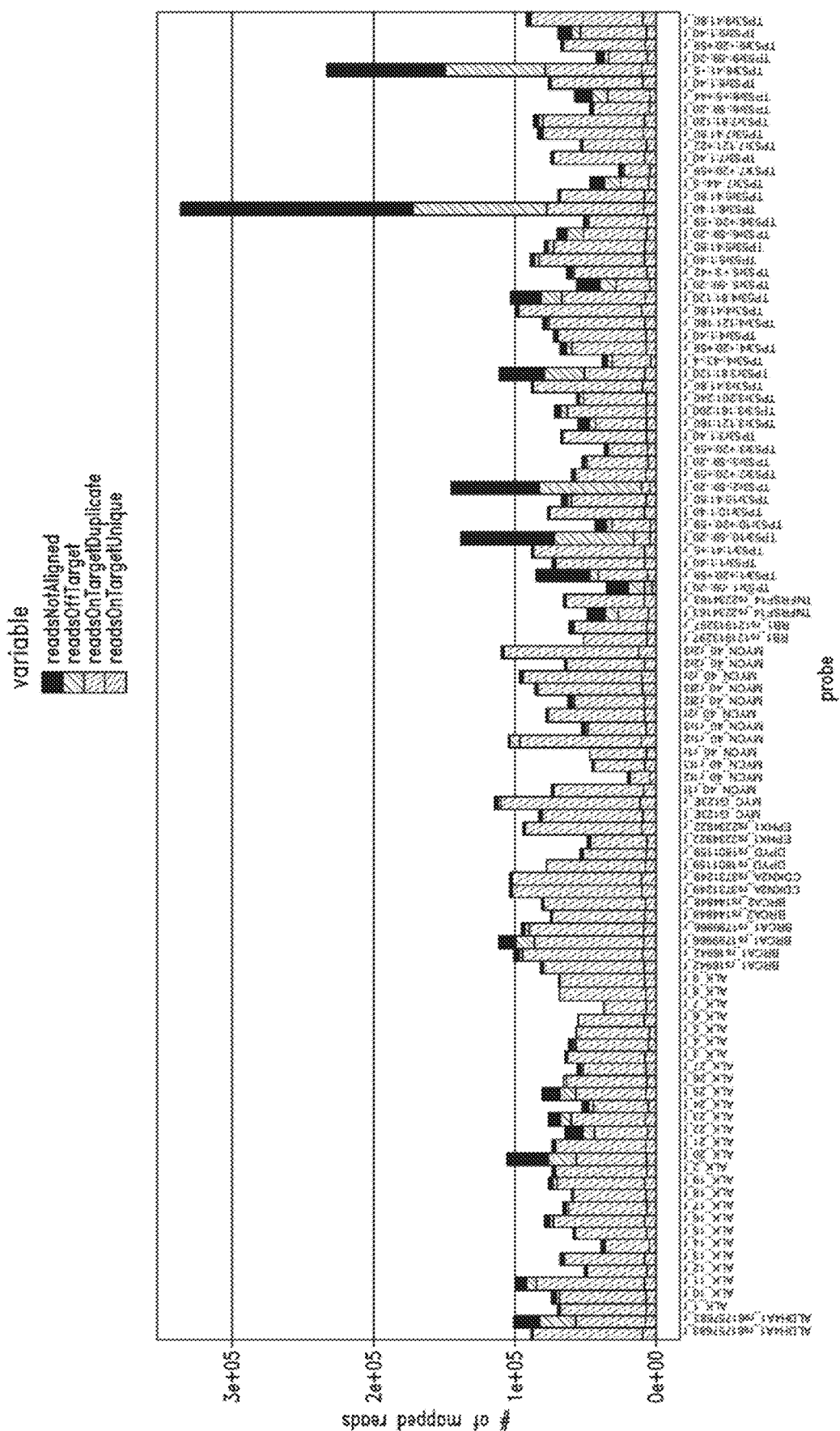
FIG. 7 shows the performance of high-density 40-mer capture probes in a representative experiment. The y-axis shows the total number of reads, which are broken out as on-target reads, off-target reads, and unmappable reads. The x-axis enumerates each of the 105 capture probes used in this experiment for sequence capture.

Capture probe performance of high density capture probes that were chosen based on their position with target sequences were monitored. A graphical display of the performance of each capture probe is shown in FIG. 7. These data demonstrate that:

1) all capture probes chosen strictly by positional constraint provided on-target sequence information;
2) most capture probes exhibit very little off-target and unmappable read capture; and
3) the yield of useful, on-target reads was substantially uniform.

Figure 8:
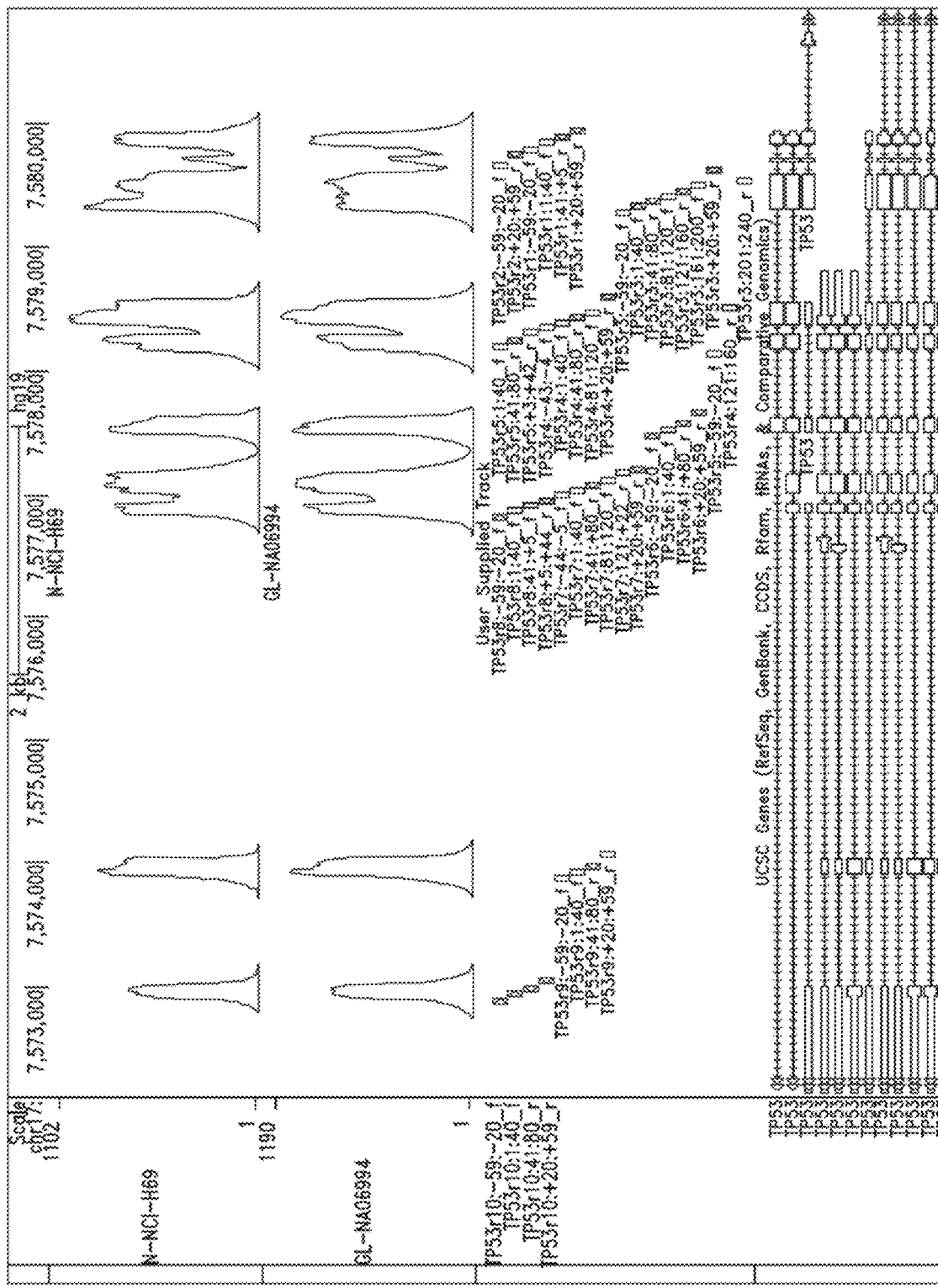
FIG. 8 shows a representative example of the cumulative coverage of a target region using high density 40-mer capture probes. Shown here is the cumulative coverage of TP53 coding exons.

Capture probes that captured a high proportion of off-target and unmappable reads were analyzed further. These capture probes were generally positioned in regions of low sequence complexity/high sequence redundancy. Here, however, such capture probes had no significant detrimental impact on the sequencing depth because the high level of probe redundancy (high density probes) means that all regions are covered by reads derived from several probes. The net effect was excellent uniformity of coverage. See, e.g., FIG. 8, probe coverage for the TP53 gene using the 40 mer capture probes.

Conclusion

Taken together, these data demonstrate that capture probe length can be reduced from 60 nucleotides to 40 nucleotides with little or no discernible loss of probe performance (once capture wash temperatures are adjusted). They also show that probe design can follow positional constraints and can generally ignore sequence context or composition. Even though this methodology produces the occasional poor-performing probe, the high redundancy at close probe spacing more than compensates for individual probe deficiencies.

Example 3: Genetic Analysis of Circulating DNA

Purpose

The purpose of this example was to benchmark the genetic analysis of cfDNA using an efficient cloning procedure for cfDNA and target retrieval system.

Background

While there is tremendous enthusiasm in the scientific and health-care community for "liquid biopsies"—analysis of circulating DNA (cfDNA) for markers associated with potential disease states, there is remarkably little practical information about this potential analyte.

Summary

Plasma samples collected from healthy donors and individuals suffering from either ovarian or colon cancers were used to perform the genetic analysis of circulating DNA. The amount and the overall character of circulating cfDNA can vary widely from individual to individual. Surprisingly, the present inventors found that cfDNA is readily clonable with an efficiency indistinguishable from highly purified and fragmented genomic DNA; that the fragment size was remarkably consistent, with an average clone insert size of 170±10 bp (in ⅞ samples); and that the genome representation from such samples was uniform and comparable to experiments performed using purified gDNA. It was further established that by counting unique reads, the depth of representation in each library provided an estimate of minor allele frequency for tumor markers present in the cfDNA of diseased patients. This study established that construction and target retrieval systems contemplated herein were effectively applied to the quantitative genetic analysis of cfDNA.

Methods

DNA Purification:

Eight sets of plasma samples were purchased from Proteogenex, Inc., Culver City, CA (Table 8). Circulating DNA was extracted from the samples (on two separate occasions) using the Circulating Nucleic Acid Purification kit from Qiagen. Samples were passed through DNA mini-columns using centrifugation. The specimen IDs and yield of DNA are shown in Table 8.

TABLE 8

Plasma samples and cfDNA yields

| Sample ID | Patient diagnosis | Specimen type | Volume | DNA yield (ng per mL of input) |
|---|---|---|---|---|
| D5930P | Healthy donor | plasma | 4 mL | 11 |
| D5942P | Healthy donor | plasma | 4 mL | 68 |
| 023407P | Colorectal cancer | plasma | 4 mL | 10 |
| 023406P | Colorectal cancer | plasma | 4 mL | 63 |
| 023185P | Colorectal cancer | plasma | 4 mL | 171 |
| 023149P | Colorectal cancer | plasma | 4 mL | 36 |
| 032667P | Ovarian cancer | plasma | 4 mL | 24 |
| 032676P | Ovarian cancer | plasma | 4 mL | 13 |

Library Construction:

Purified DNA from 4 mL of plasma was collected in 100 μL elution buffer. For the four samples collected from colon cancer patients (CRC), the DNA was split in half and one 50 μL aliquot from each patient was sonicated to 200 bp. One 50 aliquot of untreated cfDNA and one 50 μL fragmented cfDNA from each patient (the entire sample from each patient) was end repaired by adding (per sample):

6 μL of 10× quick blunt buffer (New England Biolabs (NEB))
  0.6 μL of 10 mM dNTPs
  2.4 μL of quick blunt enzyme mix
  1.2 μL of PreCR enzyme mix.

Samples were incubated at 20° C. for 30 min and at 70° C. for 10 min. Ligations with adaptors (Table 2) were performed by combining:

60 μL end-repaired cfDNA
  12 μL adaptor duplex (10 μM)
  10 μL 10× ligase buffer (NEB)
  15 μL 50% PEG$_{8000}$
  3 μL HC T4 DNA ligase

TABLE 9

Samples and codes used for four CRC plasma samples

| Progenex ID | Sample # | Pre-treatment | Adapter | SEQ ID NO: |
|---|---|---|---|---|
| 23149 | 1 | none | NNNNNTTTTGTGTGTGTGTG | 275 |
| 23407 | 2 | none | NNNNNACTACACACACACAC | 276 |

TABLE 9-continued

Samples and codes used for four CRC plasma samples

| Progenex ID | Sample # | Pre-treatment | Adapter | SEQ ID NO: |
|---|---|---|---|---|
| 23406 | 3 | none | NNNNNCTCGTGTGTGTGTGT | 277 |
| 23185 | 4 | none | NNNNNGAACACACACACACA | 278 |
| 23149 | 5 | frag | NNNNNCATGTGTGTGTGTGT | 279 |
| 23407 | 6 | frag | NNNNNGTGCACACACACACA | 280 |
| 23406 | 7 | frag | NNNNNATAACACACACACAC | 281 |
| 23185 | 8 | frag | NNNNNTACTGTGTGTGTGTG | 282 |

Reactions were incubated at 22° C. for one hour and 65° C. for 10 min. Ligation products were purified by the addition of 100 μL beads, washing, and elution in 40 μL TEzero. All 40 μL of ligation product was amplified by PCR with primer ACA2 (SEQ ID NO: 283) and the samples were combined in equal mass for targeted capture.

Targeted Sequence Capture and Sequencing:

The four unfragmented and four fragmented colon plasma samples (FIG. 9C) were hybridized with our high-density, 40 nucleotide probe set that targets TP53, ALK, among others. The capture complexes were processed as described above in Example 2.

Results

Figure 9A:
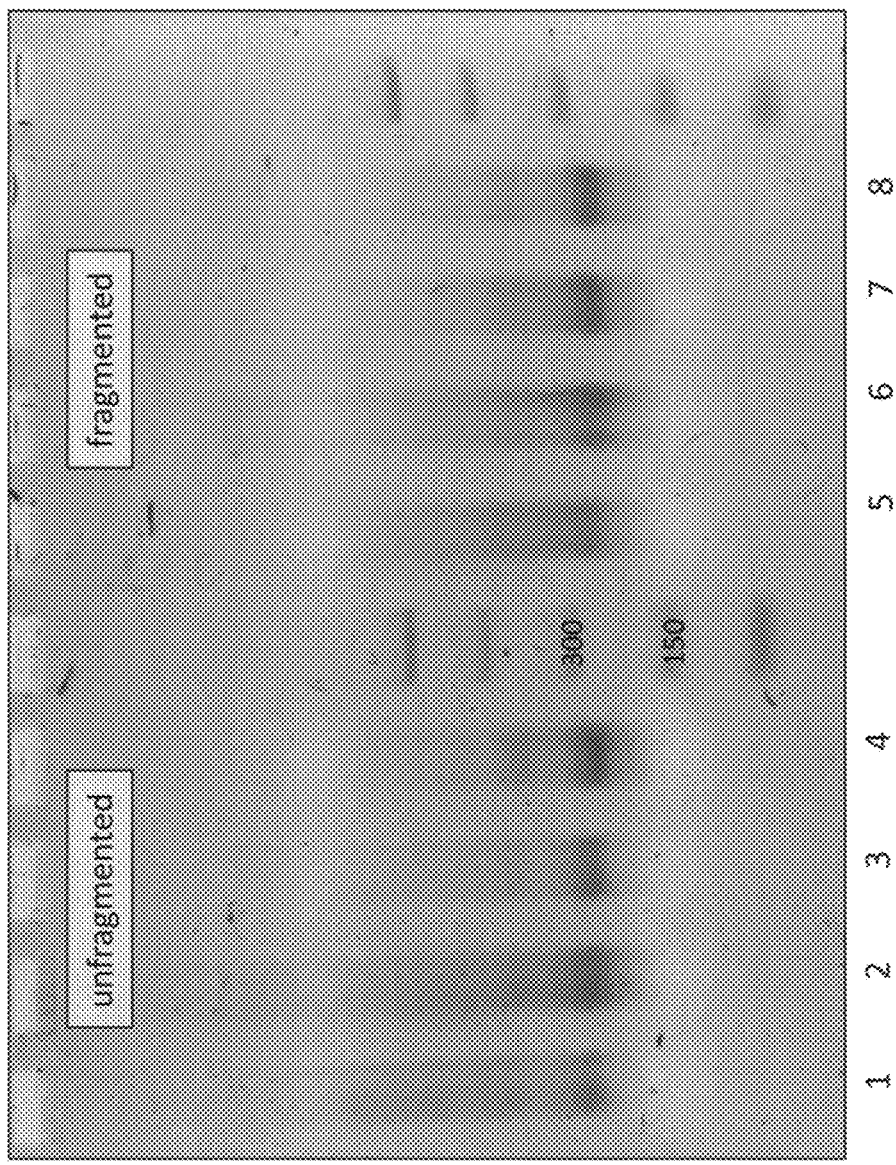
FIG. 9A-FIG. 9C show representative examples of cfDNA libraries.
Figure 9B:
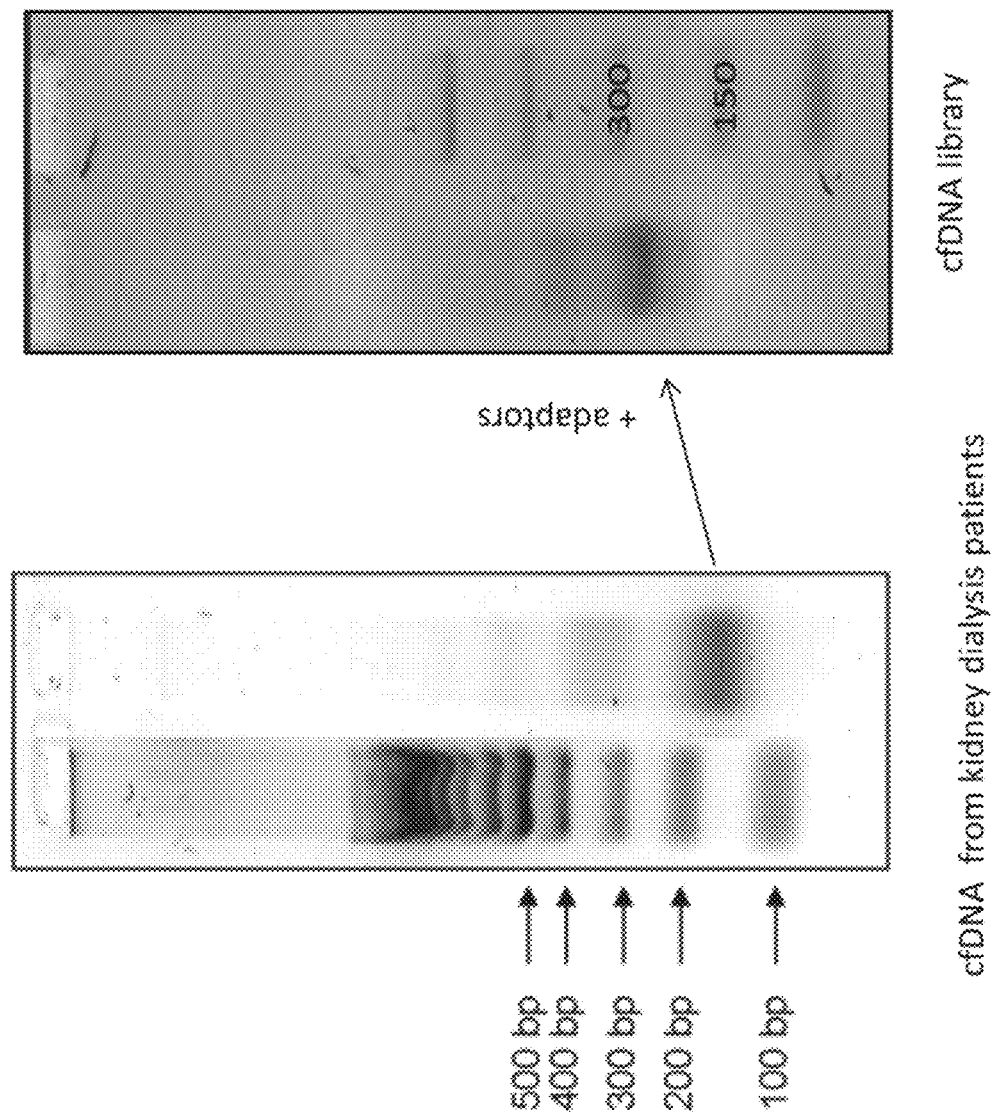

Library Appearance:

A false-color picture of a 2% agarose gel loaded with 50 ng of each library is shown in FIG. 9A. The average fragment size was in a tight range of 260±20 bp. These data indicated that the clonable fraction of cfDNA is present predominantly as nucleosomal fragments. In addition, the size of the cfDNA libraries had the same basic superficial appearance as cfDNA in kidney dialysis patients (Atamaniuk et al., *Clinical Chemistry* 52(3):pp. 523-26 (2006)) except that the cfDNA libraries were shifted to higher mass by the addition of adaptor sequences (FIG. 9B). In contrast, the cfDNA libraries differed dramatically from sonicated gDNA libraries, which appear as broad smears.

Figure 9C:
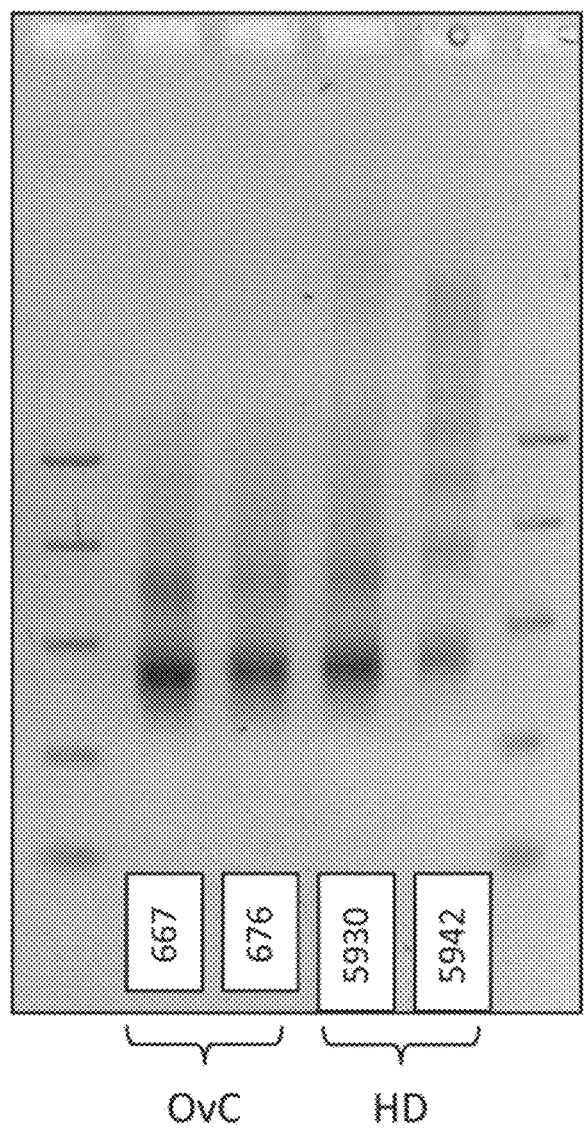

Four additional sets of cfDNA libraries were constructed from the two ovarian cancer patient plasma samples and two plasma samples from healthy volunteers. 38 μL aliquots of cfDNA were end-repaired in 50 μL total volume. Ligations included 40 μL of end-repaired fragment, 16 μL of adaptor (10 μM) 8 μl of 10× ligase buffer, 16 μL of 50% PEG and 4 μL of HC T4 DNA ligase in a total volume of 80 μL. The ligation reaction was incubated at 20° C. for 1 hour and 65° C. for 10 min. For purification, 20 μL of TEzero and 150 μL of beads were added. The purified ligation products were resuspended in 40 μL, all of which was used in a subsequent 200 μL library amplification by PCR. The resulting amplified libraries are shown in FIG. 9C.

Figure 10:
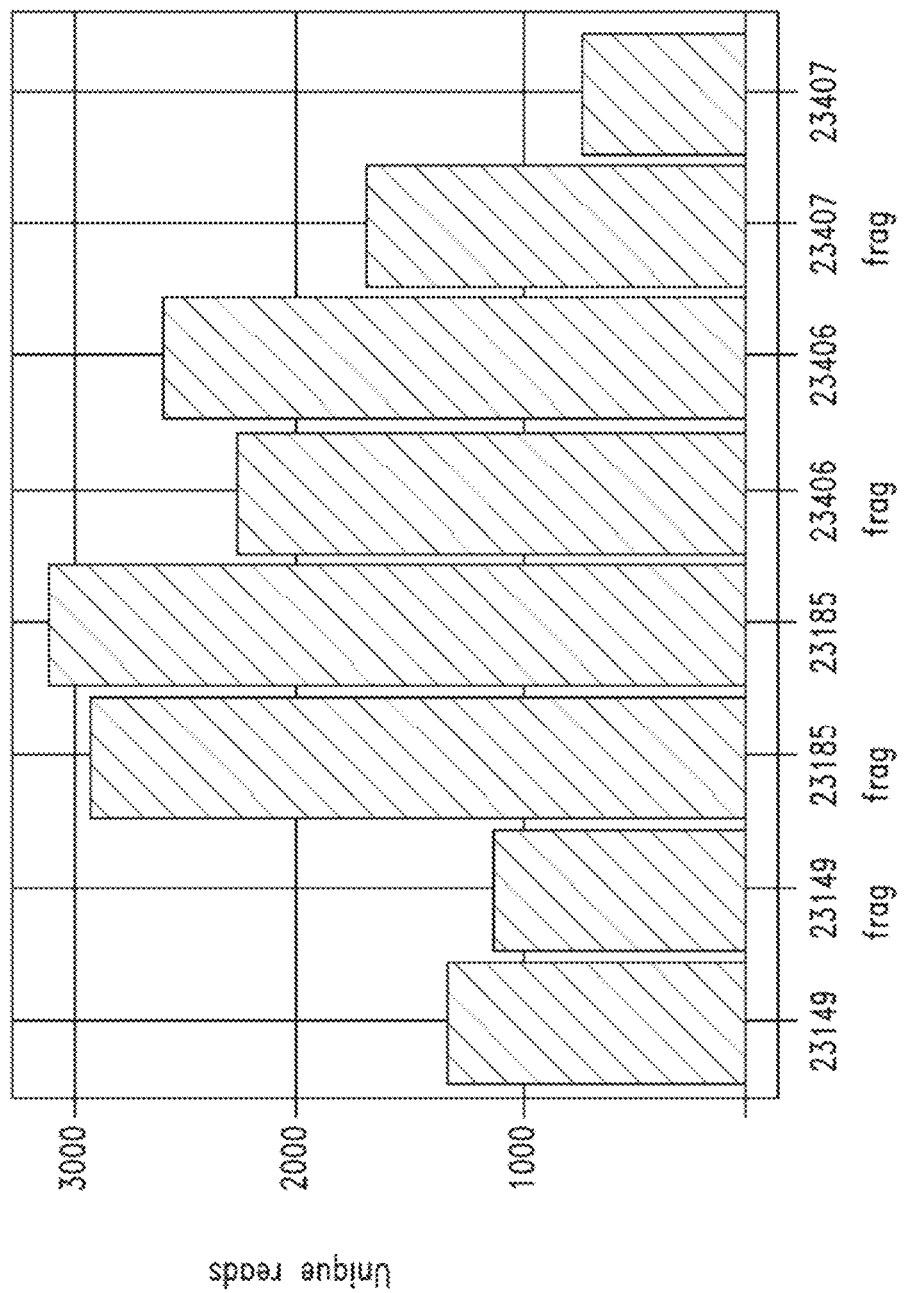
FIG. 10 shows the unique read counts across eight cfDNA libraries derived from four plasma samples. Fragmentation (frag) prior to library construction with this sample 23407 increased the library yield by more than two-fold.

Sequencing Data Analysis:

The average unique read count observed in each of the eight libraries ranges from ~700 unique reads to >3000 unique reads, defining a range of sensitivities from ~0.15% to ~0.03%. FIG. 10. A rare mutant read will likely be observed more than once, meaning minimum sensitivities are less than those calculated above. In preferred embodiments, unique reads provide the lower bound on statistically defensible observation frequencies.

cfDNA Cloning Efficiency:

Sample 23407 was used as a benchmark. 10 ng/mL of cfDNA was recovered from the plasma sample and 20 ng of the isolated cfDNA was used in each of two library construction efforts. The unique read counts indicated that we recovered an average of 700 unique reads (genome equivalents) from unfragmented DNA ("23407" in FIG. 10). Given that each genome contains 0.003 ng of gDNA, 2.1 ng of input DNA in this library (10% cloning efficiency) was recovered.

Fragmentation prior to library construction with this sample increased the library yield by more than two-fold ("23407 frag" in FIG. 10). This indicates that much of the DNA present in the 23407 sample was high molecular weight DNA that required fragmentation in order to be clonable. Thus, the library cloning efficiency was likely far greater than 10% and was likely in the range of 20% for input cfDNA. This cloning efficiency is comparable to highly purified genomic DNA and indicates that cfDNA was not likely modified in any way that is deleterious to downstream cloning efforts.

Figure 11:
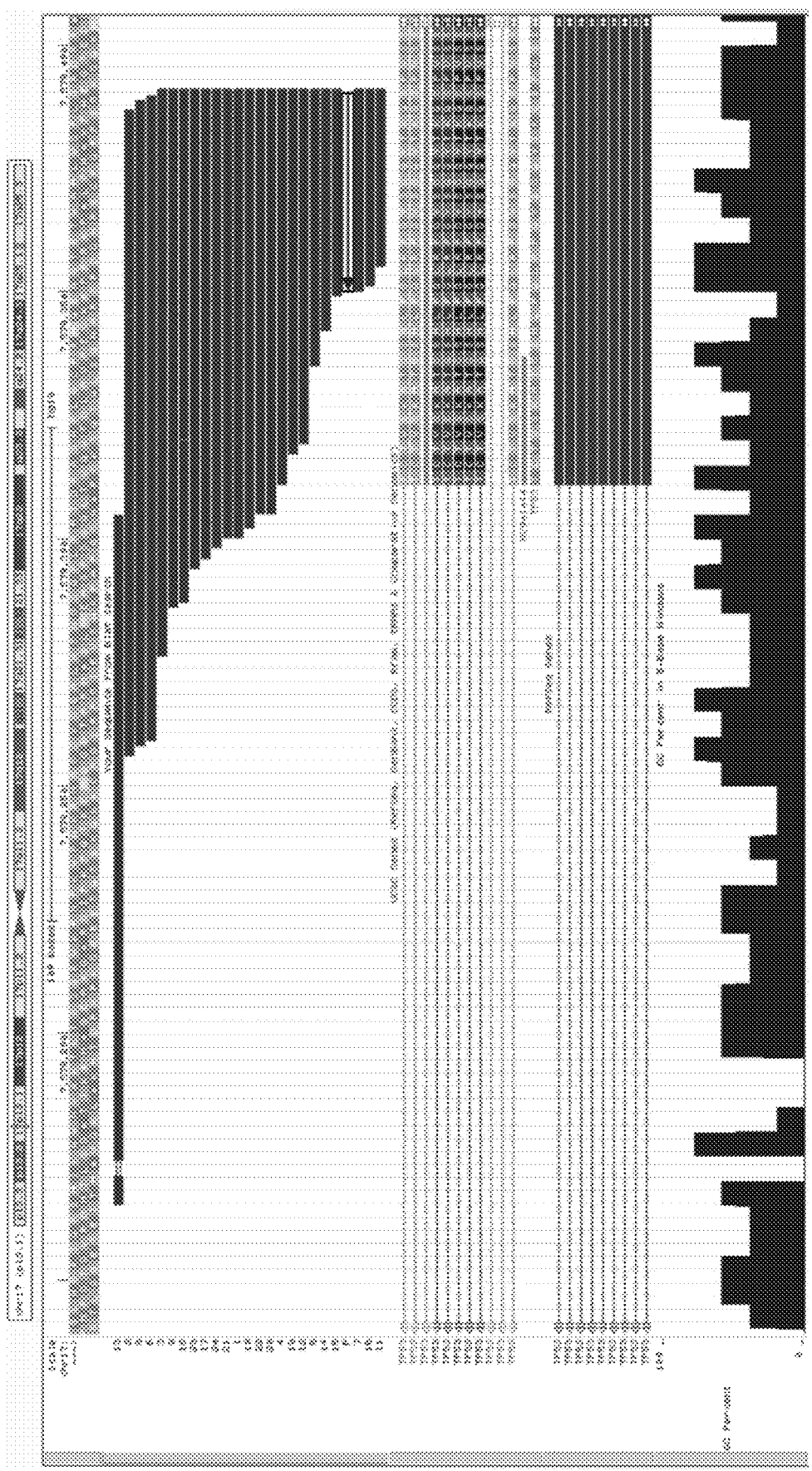
FIG. 11 shows the representative read coverage of cfDNA across a region of the TP53 gene. Twenty four 131 bp reads captured by the "TP53_NM_000546_chr17:7579351:region_3:280nt:41:80:r" capture probe (SEQ ID NO: 201) were chosen at random and aligned using the BLAT algorithm within the UCSC genome browser. Twenty one reads map to the target region, and they do so in a pattern of overlapping coverage. The probe used to capture these reads is marked with an arrow.

Library Coverage:

The cfDNA libraries resembled a set of discrete bands with random coverage of target regions. FIG. 11 shows a random sampling of sequence data. A random set of reads from sample 23407 that was not fragmented prior to cloning (see FIG. 10), and that were captured by the TP53 probe "chr17:7579351:region_3:280nt:41:80:r" (SEQ ID NO: 201) were aligned using BLAT. Given the way that the sample was prepared, these are likely a reflection of cfDNA fragments in general because the left hand portion of these reads (the read start sites) are randomly distributed across the target region. This random distribution indicates the random breakage of genomic DNA, and it demonstrates that despite the band-like appearance of cfDNA libraries, the sequencing output was a random coverage of the target region. The random distribution is important for effective genetic analysis using technology contemplated herein.

Figure 12:
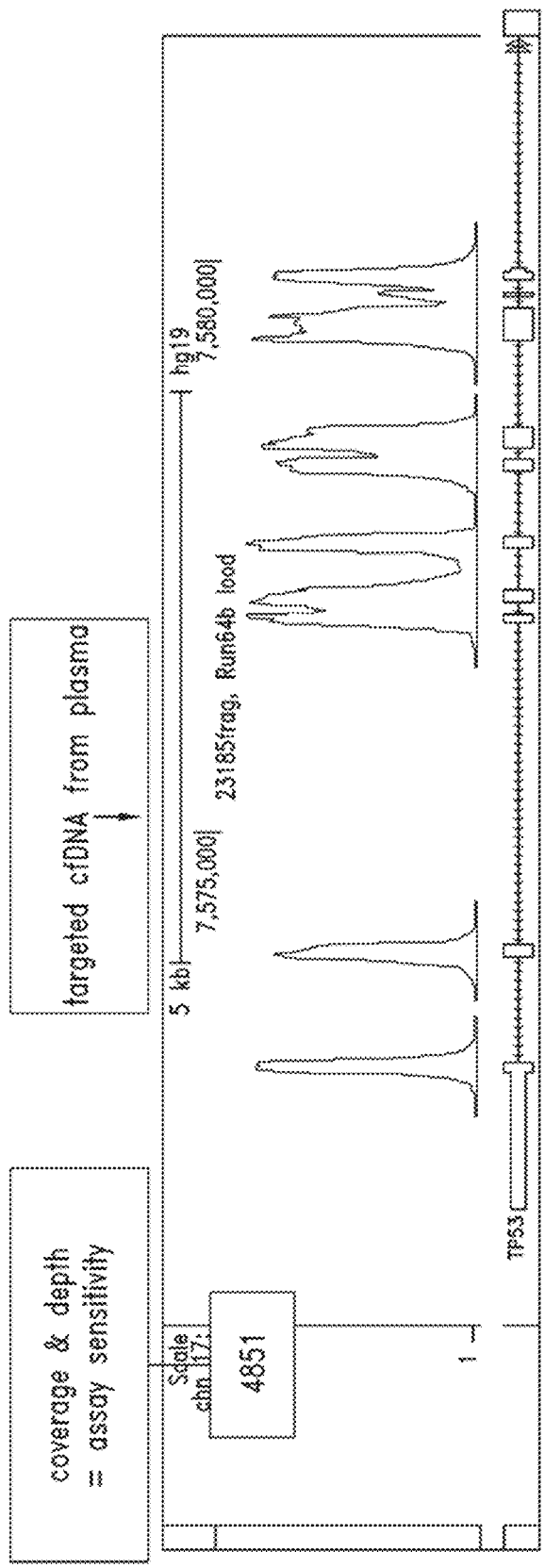
FIG. 12 shows an overview of targeted DNA sequencing of the coding regions of the TP53 gene from a cfDNA genomic library. The coverage (horizontal axis) extends across all 10 coding regions and includes intronic regions involved in mRNA splicing. The sequencing depth (vertical axis) reaches a maximum of 4851 and is uniform across all coding exons.

FIG. 12 provides a more high resolution overview of TP53 coding region sequencing for a typical cfDNA library. The elements of targeted sequencing—coverage across all target regions and uniform depth at each sequenced base—are readily apparent. At this depth of >4000 unique reads per base, and with a requirement that legitimate candidate base changes must be encountered at least twice, it is possible to estimate that the mutation detection sensitivity for this particular library was about 1 mutation in 2000 sequences, or 0.05%. This level of sensitivity represents a surprising and unexpected outstanding technical achievement.

Conclusion cfDNA was isolated and cloned from plasma clones with an efficiency comparable to highly purified gDNA isolated from cell lines (the gold standard). The cfDNA libraries resembled circulating nucleosomal-sized DNA fragments+ adaptors and the ends possessed sufficiently random character, which enabled efficient genetic analysis. In addition, the highly uniform size characteristic of plasma cfDNA libraries allows designing capture strategies and underlying probe sequences to maximize reliable coverage of targets as far as 120 bp (=160-40) from the ends of probes.

Example 4: Measurement of Genome Equivalents in Circulating DNA Libraries

Purpose and Background

One of the major challenges in the analysis of circulating, cell-free DNA is achieving sufficient assay sensitivity. If sufficient sensitivity is not achieved then analysis of the cfDNA libraries is confounded: if a sample is sequenced and no mutational events are detected, that result could be interpreted to mean that no mutations are present, or that significant events were missed because the sampling depth was too small. The sensitivity of an assay is defined in statistical terms as the false negative rate. In the context of sequencing circulating, cell-free DNA, a significant obstacle is the detection of a rare sequence that is blended in a large excess of reference sequence.

One method for determining assay sensitivity is to measure the occurrences of mutant sequence in a set of samples where mutant sequence is progressively diluted into non-mutant, reference sequence. The dilution at which mutant sequences are no longer detected defines assay sensitivity. This method is adequate if both the identity of the mutant sequence and the extent of dilution are known. Unfortunately, clinical samples do not generally provide either parameter. Often the identity of the mutant sequence is not known, and the extent of dilution varies from sample to sample. In this context, assay sensitivity is established on a sample-by-sample basis.

To assign a sensitivity value on a sample-by-sample basis, the numbers of different and distinct sequences that are present in each sample are measured, by measuring the number of genome equivalents that are present in a sequencing library. By way of a non-limiting example, if a DNA sequencing library is known to contain 3 ng (3000 pg) of human genomic DNA and each human genome has a mass of 3 pg, then the library possesses 3000÷3=1000 genome equivalents of DNA. If a mutant DNA sequence must be detected twice to be statistically significant, then an estimate of the best possible sensitivity of detection for this particular library is 2 mutant sequences÷1000 total sequences=0.002=0.2%. To establish sensitivity, the number of genome equivalents must be measured for each sample library.

Summary

Two methods were used to measure genome equivalents. The first method is based on quantitative PCR (qPCR). A genomic library was constructed using ligation of adaptors to genomic fragments and a pair of PCR primers, one that is specific to a common genomic sequence (e.g., Alu I repeat) and one that is specific to the adaptor. The abundance of ligated adaptor: fragment sequences of these cfDNA libraries was measured. A standard library of known concentration was used to construct a standard curve and the measurements were fit to the resulting standard curve and a value for genome equivalents was derived from the fit.

The second method to measure genome equivalents used bioinformatics counting after sequencing was performed. Each unique sequence in a library was identified by its random sequence label and the starting nucleotide of the genomic sequence. Moreover, each unique sequence must be derived from an independent genome. Therefore, the sum of unique sequences present in sequence data established a precise quantitative measurement of the number of genome equivalents present in a sample.

Figure 13:
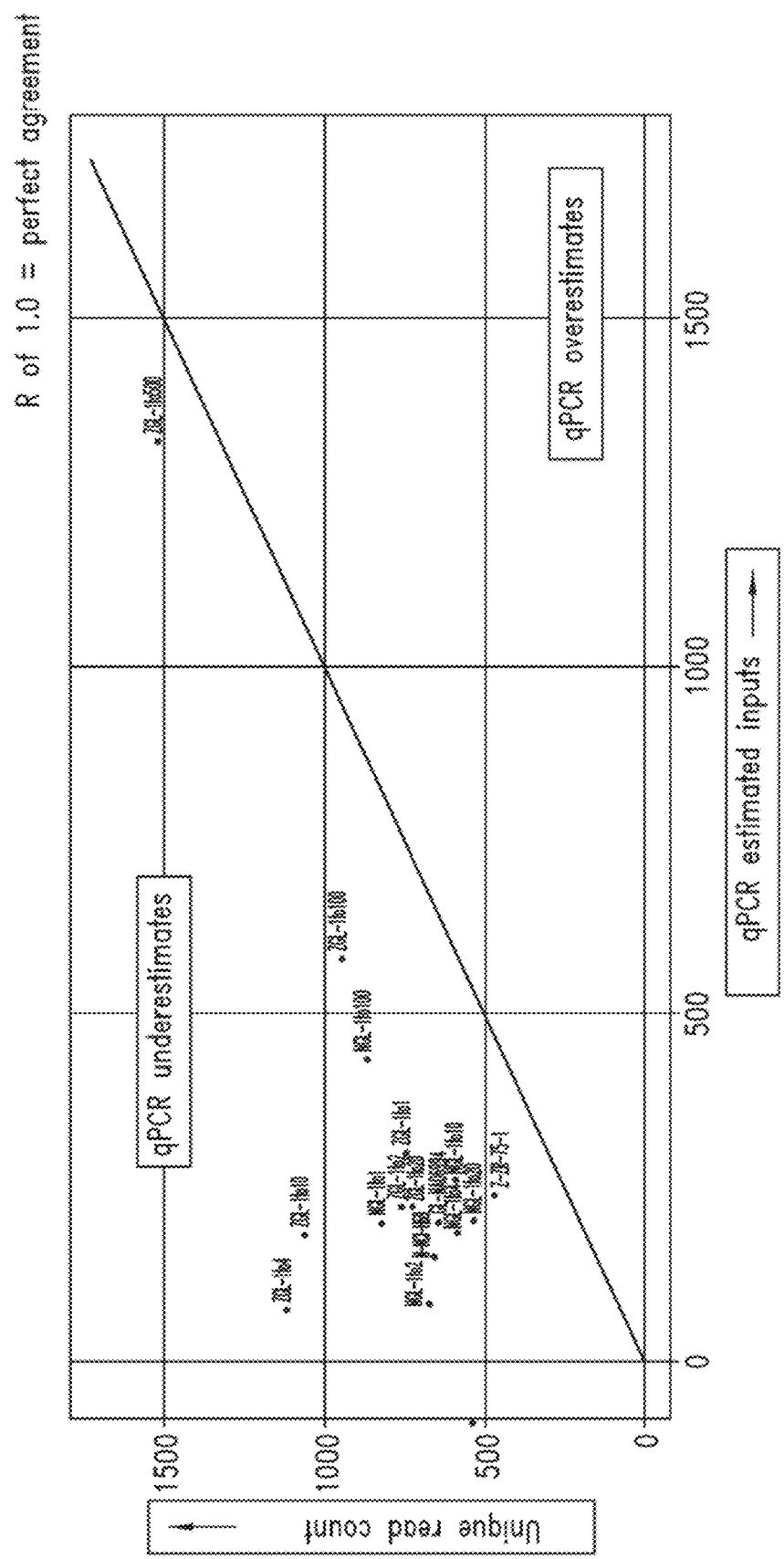
FIG. 13 shows a plot of unique read counts versus qPCR estimated genome equivalents in an ACA2-based assay. qPCR measurements are shown on the X-axis versus read counts on the Y-axis. Perfect agreement between these measurements is shown as the diagonal. There is very poor, if any, correlation between measurements, especially at lower genomic inputs. These data show that the ACA2-based qPCR assay chronically underestimates library complexity and is inadequate for measuring genome equivalents.

Methods and Results qPCR Assay Development:

The first version of a qPCR-based genome equivalence assay used the ACA2 primer (Table 10), but this assay chronically under-reports the number of genome equivalents that are present in a cfDNA library (FIG. 13).

TABLE 10

PCR primers used in the development of the genome equivalent qPCR assay

| Name | SEQ ID NO: | Sequence |
|---|---|---|
| ACA2 | 283 | TGCAGGACCAGAGAATTCGAATACA |
| ACA2_FLFP | 284 | AATGATACGGCGACCACCGAGATCTACACGTCAT GCAGGACCAGAGAATTCGAATACA |
| Alu_F1 | 285 | CGGTGGCTCACGCCTGTA |
| Alu_R1 | 286 | GCCTCGGCCTCCCAAAGT |
| Alu_F2 | 287 | GAGGCTGAGGCAGGAGAATCG |
| Alu_R2 | 288 | GTCGCCCAGGCTGGAGTG |

The improved version of the assay was based on endogenous repeats (e.g., Alu repeats) that are found at very high frequency throughout the human genome. By coupling an Alu-specific primer with an adaptor-specific primer, the frequency with which adaptors are joined to genomic fragments was reliably measured. Standard curves using libraries of known genome equivalents were generated, and the number of genome equivalents in cloned libraries was measure by fitting to the curve.

The PCR primers used to develop an Alu+adaptor-based qPCR assay are shown in Table 10. The PCR primers for Alu amplification were designed from consensus a consensus human Alu sequence (Batzer & Deininger, *Nat Rev Genet.* 3(5):370-9 (2002)) using PRIMER3 (Alu_F1 & Alu_R1, SEQ ID NOs: 285 and 286, respectively). The remaining two Alu primers (Alu_F2 and Alu_R2, SEQ ID NOs: 287 and 288, respectively) were reported in the literature (Marullo et al., *Genome Biology* 11:R9 (2010)).

A schematic of the assay design is provided in FIG. 14. Because a single PCR primer can used to amplify the genomic DNA libraries (FIG. 14A), a primer that recognizes the adaptor sequence but that cannot amplify genomic clones was used. The 58 nucleotide ACA2-FLFP primer (henceforth abbreviated AF, SEQ ID NO: 284) fills these criteria because its length induces strong stem-loop PCR suppression (FIG. 14B). Additionally, a functional pair of Alu primers were used (FIG. 14C). Moreover, a primer pair consisting of one Alu primer and the long ACA2 primer that did not amplify genomic DNA used (FIG. 14D). These same primers also amplified genomic library clones (FIG. 14E).

Figure 15B:
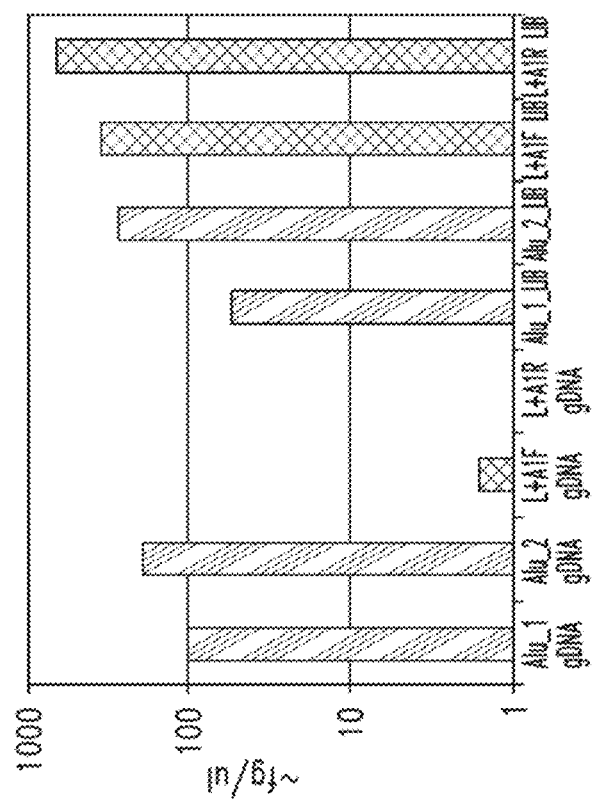
FIG. 15A-FIG. 15B show proof-of-concept data for an Alu plus adaptor-based qPCR assay of genome equivalents.
Figure 15A:
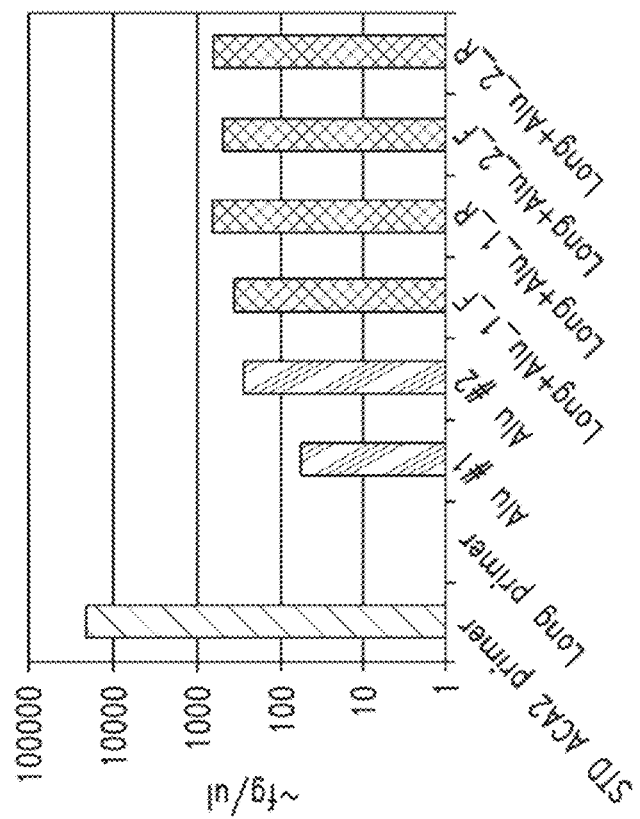

All of the required elements for a functional Alu-based assay were validated. FIG. 15. Specifically, the long primer alone was inert, both sets of Alu primer pairs recognized human genomic DNA, and any combination of one Alu primer and the long ACA2 primer amplified genomic library clones (FIG. 15A). Finally, the ability of Alu primer plus long ACA2 primer pair to discriminate between genomic DNA and genomic library clones is shown in FIG. 15B. The combination of Alu_R1 and AF primers were used for measuring genome equivalents in the newly constructed libraries.

Figure 16:
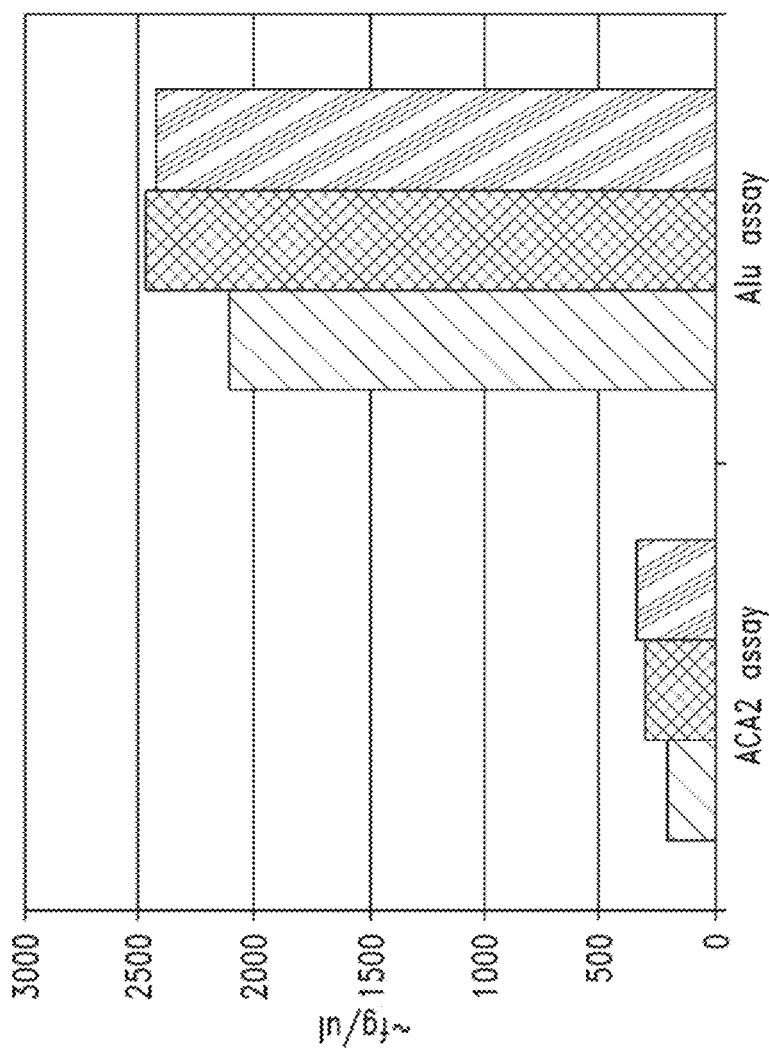
FIG. 16 shows a direct comparison of ACA2 primer qPCR assay with the Alu-ACA2 long-primer qPCR assay. The Alu ACA2 long-primer qPCR assay shows an 8-fold increase in detectable genome equivalents, which is more consistent with unique read counts derived from sequencing data.

A direct comparison between the ACA2-based and the Alu-based qPCR assays is shown in FIG. 16. An 8-fold difference in genome equivalents was found. In addition the Alu-based assays provided a more consistent performance library-to-library and a better alignment between qPCR derived equivalents and bioinformatically counted tag equivalents in sequencing runs (Table 11).

TABLE 11 qPCR vs counted sequencing tags

| Sample | Alu-based qPCR | counted tags |
|---|---|---|
| Run_68 50to1 | 6962 | 3459 |
| Run_68 1000to1 | 10937 | 4641 |

High-Sensitivity Library Adaptors for Sequence-Based Counting of Genome Equivalents:

As discussed above, the reality of disease surveillance using cfDNA is that mutant sequences may be rare constituents in an otherwise vast excess of "normal" (meaning germline) DNA sequences. Thus, highly sensitive and quantifiable sequencing assays are needed. Assay sensitivity could be made by counting the number of unique sequences present in a sequencing library. However, such counting would lead to a false underestimate of sensitivity because cfDNA fragments are rather short (~165 bp) and may lead to identical reads that were actually derived from independent cloning events. One solution to this problem is to mark each independent sequencing clone during library construction by including, for example, a set of DNA tags in the adaptors used to construct libraries.

A set of such library construction adaptors was specifically designed to measure the number of genome equivalents present in cfDNA libraries, and, by extension, the sensitivity of sequencing assays used to monitor mutant sequences.

The architecture of high-sensitivity library adaptors that were configured to accommodate large numbers of genome equivalents in cfDNA libraries is shown in FIG. 17. There is a substantial amount of molecular engineering within the 45 nucleotide ligation strand, which is the strand that becomes attached to end repaired cfDNA fragments. The adaptors comprise at least five elements.

Element 1 is a PCR primer binding site for the single-primer library amplification primer ACA2 (Table 12).

TABLE 12

Element 1 Summary

| Element | Function | Number of sequences | Sequences (5' -> 3') | SEQ ID NO: |
|---|---|---|---|---|
| Element 1 | PCR primer binding site | 1 | TGCAGGACCAGAGAATTCGAATACA | 289 |

Element 2 is a 5 nucleotide read code. The combination of this code with the genomic DNA sequence constitutes the DNA tag that was used to uniquely identify each read. The 5 nucleotide codes consist of 256 possible unique sequences that were chosen to be 2 base changes different from every other code in the set. This feature enabled unique and distinct reads to be differentiated from reads that appeared to be unique owing to a sequencing error in the code region. Seven codes in which G residues are over-represented and that were shown empirically to interfere with adaptor function were removed, leaving 249 random codes. Table 13.

TABLE 13

Element 2 Summary

| Element | Function | Number of sequences |
|---|---|---|
| Element 2 | Distinct sequence labels | 249 |

| Sequences (5' -> 3') | SEQ ID NO: |
|---|---|
| CGGGT | 290 |
| CGGTG | 291 |
| CGTGG | 292 |
| GCGGT | 293 |
| GCGTG | 294 |
| GCTGG | 295 |
| GGCGT | 296 |
| GGCTG | 297 |
| GGGCT | 298 |
| TTAAA | 299 |
| TTACC | 300 |
| TTATT | 301 |
| TTCAC | 302 |
| TTCCA | 303 |
| TTTAT | 304 |
| TTTTA | 305 |
| GCACG | 306 |
| GCAGC | 307 |
| GCCAG | 308 |
| GCCGA | 309 |
| GCGAC | 310 |
| GCGCA | 311 |
| GGAAA | 312 |
| GGACC | 313 |
| GGATT | 314 |
| GGCAC | 315 |
| GGCCA | 316 |
| GGTAT | 317 |
| GGTTA | 318 |
| GTAGT | 319 |
| GTATG | 320 |
| GTGAT | 321 |

TABLE 13-continued

Element 2 Summary

| CCGTC | 322 |
|---|---|
| CCTCG | 323 |
| CCTGC | 324 |
| CGAAT | 325 |
| CGATA | 326 |
| CGCCT | 327 |
| CGCTC | 328 |
| CGTAA | 329 |
| CGTCC | 330 |
| CGTTT | 331 |
| CTAAG | 332 |
| CTAGA | 333 |
| CTCCG | 334 |
| CTCGC | 335 |
| CTGAA | 336 |
| CTGCC | 337 |
| TTGTC | 338 |
| TTTCG | 339 |
| TTTGC | 340 |
| AAAAA | 341 |
| AAACC | 342 |
| AAATT | 343 |
| AACAC | 344 |
| AACCA | 345 |
| AATAT | 346 |
| AATTA | 347 |
| ACAAC | 348 |
| ACACA | 349 |
| ACCAA | 350 |
| ACCCC | 351 |
| ACCTT | 352 |
| ACTCT | 353 |
| GGGTC | 354 |
| GGTCG | 355 |
| GGTGC | 356 |
| GTCGG | 357 |
| GTGCG | 358 |
| GTGGC | 359 |
| TGCGG | 360 |

TABLE 13-continued

Element 2 Summary

| | |
|---|---|
| TGGCG | 361 |
| TGGGC | 362 |
| AAAGG | 363 |
| AAGAG | 364 |
| AAGGA | 365 |
| ACCGG | 366 |
| ACGCG | 367 |
| ACGGC | 368 |
| AGAAG | 369 |
| GTGTA | 370 |
| GTTAG | 371 |
| GTTGA | 372 |
| TAGGT | 373 |
| TAGTG | 374 |
| TATGG | 375 |
| TGAGT | 376 |
| TGATG | 377 |
| TGGAT | 378 |
| TGGTA | 379 |
| TGTAG | 380 |
| TGTGA | 381 |
| TTAGG | 382 |
| TTGAG | 383 |
| TTGGA | 384 |
| AACGT | 385 |
| CTGTT | 386 |
| CTTGT | 387 |
| CTTTG | 388 |
| GAACT | 389 |
| GAATC | 390 |
| GACAT | 391 |
| GACTA | 392 |
| GATAC | 393 |
| GATCA | 394 |
| GCAAT | 395 |
| GCATA | 396 |
| GCCCT | 397 |
| GCCTC | 398 |
| GCTAA | 399 |
| GCTCC | 400 |
| GCTTT | 401 |
| ACTTC | 402 |
| ATAAT | 403 |
| ATATA | 404 |
| ATCCT | 405 |
| ATCTC | 406 |
| ATTAA | 407 |
| ATTCC | 408 |
| ATTTT | 409 |
| CAAAC | 410 |
| CAACA | 411 |
| CACAA | 412 |
| CACCC | 413 |
| CACTT | 414 |
| CATCT | 415 |
| CATTC | 416 |
| CCAAA | 417 |
| AGAGA | 418 |
| AGCCG | 419 |
| AGCGC | 420 |
| AGGAA | 421 |
| AGGCC | 422 |
| AGGTT | 423 |
| AGTGT | 424 |
| AGTTG | 425 |
| ATGGT | 426 |
| ATGTG | 427 |
| ATTGG | 428 |
| CACGG | 429 |
| CAGCG | 430 |
| CAGGC | 431 |
| CCAGG | 432 |
| CCGAG | 433 |
| AACTG | 434 |
| AAGCT | 435 |
| AAGTC | 436 |
| AATCG | 437 |
| AATGC | 438 |

TABLE 13-continued

Element 2 Summary

| | |
|---|---|
| ACAGT | 439 |
| ACATG | 440 |
| ACGAT | 441 |
| ACGTA | 442 |
| ACTAG | 443 |
| ACTGA | 444 |
| AGACT | 445 |
| AGATC | 446 |
| AGCAT | 447 |
| AGCTA | 448 |
| AGTAC | 449 |
| GTAAC | 450 |
| GTACA | 451 |
| GTCAA | 452 |
| GTCCC | 453 |
| GTCTT | 454 |
| GTTCT | 455 |
| GTTTC | 456 |
| TAACG | 457 |
| TAAGC | 458 |
| TACAG | 459 |
| TACGA | 460 |
| TAGAC | 461 |
| TAGCA | 462 |
| TCAAG | 463 |
| TCAGA | 464 |
| TCCCG | 465 |
| CCACC | 466 |
| CCATT | 467 |
| CCCAC | 468 |
| CCCCA | 469 |
| CCTAT | 470 |
| CCTTA | 471 |
| CTACT | 472 |
| CTATC | 473 |
| CTCAT | 474 |
| CTCTA | 475 |
| CTTAC | 476 |
| CTTCA | 477 |
| TAAAT | 478 |
| TAATA | 479 |
| TACCT | 480 |
| TACTC | 481 |
| CCGGA | 482 |
| CGACG | 483 |
| CGAGC | 484 |
| CGCAG | 485 |
| CGCGA | 486 |
| CGGAC | 487 |
| CGGCA | 488 |
| GAAAG | 489 |
| GAAGA | 490 |
| GACCG | 491 |
| GACGC | 492 |
| GAGAA | 493 |
| GAGCC | 494 |
| GAGTT | 495 |
| GATGT | 496 |
| GATTG | 497 |
| AGTCA | 498 |
| ATACG | 499 |
| ATAGC | 500 |
| ATCAG | 501 |
| ATCGA | 502 |
| ATGAC | 503 |
| ATGCA | 504 |
| CAAGT | 505 |
| CAATG | 506 |
| CAGAT | 507 |
| CAGTA | 508 |
| CATAG | 509 |
| CATGA | 510 |
| CCCGT | 511 |
| CCCTG | 512 |
| CCGCT | 513 |

TABLE 13-continued

Element 2 Summary

| | |
|---|---|
| TCCGC | 514 |
| TCGAA | 515 |
| TCGCC | 516 |
| TCGTT | 517 |
| TCTGT | 518 |
| TCTTG | 519 |
| TGAAC | 520 |
| TGACA | 521 |
| TGCAA | 522 |
| TGCCC | 523 |
| TGCTT | 524 |
| TGTCT | 525 |
| TGTTC | 526 |
| TTCGT | 527 |
| TTCTG | 528 |
| TTGCT | 529 |
| TATAA | 530 |
| TATCC | 531 |
| TATTT | 532 |
| TCACT | 533 |
| TCATC | 534 |
| TCCAT | 535 |
| TCCTA | 536 |
| TCTAC | 537 |
| TCTCA | 538 |

Element 3 is a 3 nucleotide sample code that differ by at least two base changes. This element was used to identify different samples and enabled sample multiplexing within a sequencing run. Table 14.

TABLE 14

Element 3 Summary

| Element | Function | Number of sequences | Sequences (5' -> 3') | SEQ ID NO: |
|---|---|---|---|---|
| Element 3 | Distinct sample labels; sample multiplexing | 16 | AAG | 539 |
| | | | CTC | 540 |
| | | | GGT | 541 |
| | | | TCA | 542 |
| | | | ACT | 543 |
| | | | CGA | 544 |
| | | | GTG | 545 |
| | | | TAC | 546 |
| | | | AGC | 547 |
| | | | CCG | 548 |
| | | | GAA | 549 |
| | | | TTT | 550 |
| | | | ATA | 551 |
| | | | CAT | 552 |
| | | | GCC | 553 |
| | | | TGG | 554 |

Element 4 is a 12 nucleotide anchor sequence with three important characteristics with respect to library construction and downstream sequencing. Table 15. These are A) each 12 base extension is part of a family of four 12 base extensions that collectively represent each of the four possible DNA bases at each site within extension. This feature, balanced base representation, is required by the Illumina sequencing instrument in order to calibrate proper base calling in sequencing reads. B) Each extension is composed of only two of four possible bases, and these are specifically chosen to be either 6 A's+6 C's or 6 G's+6 T's. This extension formed from only two bases greatly reduces the possibility that the extension sequence will participate in secondary structure formation that would preclude proper adaptor function. C) Because each extension is composed of equal numbers of A+C or G+T, each extension shares roughly the same melting temperature and duplex stability as every other extension in a set of four.

TABLE 15

Element 4 Summary

| Element | Function | Number of sequences | Sequences (5' -> 3') | SEQ ID NO: |
|---|---|---|---|---|
| Element 4 | 12 nucleotide extension that provides a duplexing site for the partner oligonucleotide | 4 | ACCCACACCAAA | 555 |
| | | | CAAACACAACCC | 556 |
| | | | GTGTGGGTTGTT | 557 |
| | | | TGTGTTTGGTGG | 558 |

Element 5 is the two base sequence found at the 3' end of Element 4. The particular two base extensions were chosen based on empirical data that shows that these two base sequences are efficient substrates for ligation. Table 15.

The adaptor module is hybridized to a partner oligonucleotide. Table 16. The hybridization takes place between the sequence within Element 4 and the partner oligonucleotide. The double-stranded adaptor was ligated to end-repaired cfDNA.

TABLE 16

Element 4 Summary

| Element | Function | Number of sequences | Sequences (5' -> 3') | SEQ ID NO: |
|---|---|---|---|---|
| Element 4 | 12 nucleotide extension that provides a duplexing site for the partner oligonucleotide | 4 | TTTGGTGTGGGT | 559 |
| | | | GGGTTGTGTTTG | 560 |
| | | | AACAACCCACAC | 561 |
| | | | CCACCAAACACA | 562 |

Figures 17A, 17B, 17C:
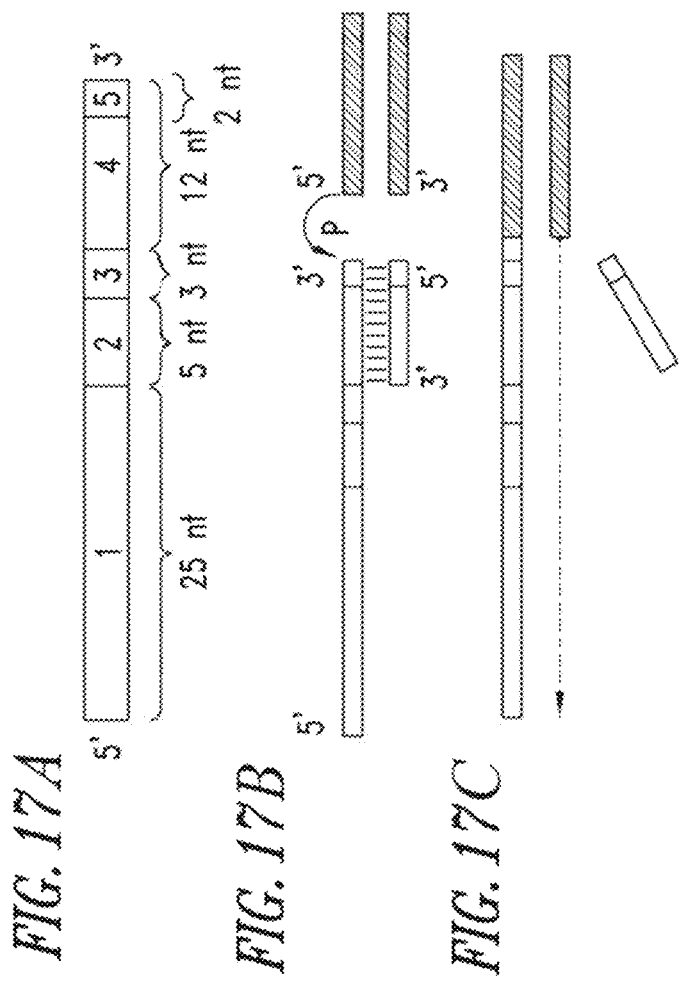
FIG. 17A-FIG. 17C show a representative example of adaptor structure and function for high sensitivity, quantitative genetic assays that provide accurate determinations of genome equivalents analyzed.

To convert a set of 256 independently synthesized and pooled ligation strands (each of which shares a common sample code and therefore constitutes a single sample adaptor set) to duplexes suitable for ligation, the 45 nucleotide ligation strand was combined with the appropriate complementary 12 nucleotide partner strand, heated to 95° C., cooled to 65° C. for 5 min, then cooled to room temperature. This duplex formed a blunt end ligation substrate as shown in FIG. 17B. Following ligation and DNA purification, a DNA polymerase-mediated step that occurs prior to PCR amplification displaced the partner strand and copied the ligation strand to form a double-strand adaptor that was suitable for exponential amplification by single-primer PCR.

The quantitative analysis of genome equivalents derived from targeted sequencing data was then performed. Each unique read was considered a unique ligation event and the sum of unique reads was considered equivalent to the number of genome equivalents analyzed.

A rough, "back-of-the-envelope", "rule-of-thumb" calculation was performed to determine the number of genome equivalents that could be analyzed. Each cfDNA clone was approximately 150 base pairs, 50 base pairs of which were required for binding to capture probes. This left roughly 100 possible sequence start sites within any captured cfDNA clone. The attachment of 249 random codes to each of the 100 possible start sites created a total repertoire of ~249,000 possible unique clones. As the number of unique clones approaches the total number of possible sequence combinations, probability dictates that the same code and start site combinations will be created by independent events and that these independent events will be inappropriately grouped within single families. The net result will be an underestimate of genome equivalents analyzed, and rare mutant reads may be discarded as sequencing errors because they overlap with wild-type reads bearing the same identifiers. To avoid this, efforts were made using the qPCR assay to constrain genomic inputs to one tenth or less the number of possible unique clones. For example, a single adaptor has 24,900 possible clones and thus, has a reliable capacity to provide accurate analysis for libraries consisting of 2500 or fewer genome equivalents.

The procedure that is outlined is provided as an example and the methods contemplated herein are not meant to be bound by this example. In some cases, the number of genome equivalents to be analyzed may well exceed the 2500 limit illustrated in the preceding paragraph. To expand the depth of genome equivalents, two solutions to this problem are readily available. The first solution is to use more than one adaptor set per sample. By combining adaptors, it is possible to expand the total number of possible clones and therefore, expand the comfortable limits of genomic input. As a non-limiting example, the combination of four adaptor sets used for one sample would expand the analysis to 24,900×4=99,600 possible sequences and ~10,000 reasonably analyzed genome equivalents. The second solution is to expand the code in Element 2 of FIG. 17A to 6, 7, or more bases. The number of possible codes that differ by at least 2 bases from every other code scales as $4^{(n-1)}$ where n is the number of bases within Element 2. Thus, in the non-limiting example presented here, n=5 and $4^{(5-1)}$=256; therefore, the inclusion of additional bases expands the available repertoire by a factor of four for each additional base.

Conclusion

The results from this example showed that two independent methods for the determination of genome equivalents have utility in sample processing workflow. The first method, qPCR, was implemented during the library construction phase of cfDNA analysis and it was used as a quality control step to ensure that adequate numbers of genome equivalents are moved through library amplification, targeted sequence capture, and DNA sequencing. The other method use explicit counting of unique reads as a more direct measure of the actual number of genome equivalents that fell under informatics consideration.

Example 5: Quantitative Genetic Analysis

Purpose

The purpose of this example was to apply quantitative genetic analysis to normal DNA admixed cancer genomes and to uncharacterized cfDNA isolated from the plasma of cancer patients.

Background

Three types of genomic events are prevalent in human cancers. These are somatic mutations that alter the function of the affected gene and its expressed protein product(s); genomic rearrangements that create chimeric gene fusions and therefore expressed fusion proteins with novel biological properties; and changes in gene copy number that lead to gene loss and under expression of gene product(s), or, conversely, amplification of genes and over-representation of the corresponding gene product(s). In the circulating DNA of a cancer patient, these aberrant loci, many of which have critical significance in guiding patient care, are admixed (blended) with the patient's normal, germline DNA.

Summary

In the previous examples, technology has been described that was configured for the analysis of circulating, cell-free DNA (cfDNA), with an aim toward cancer surveillance. However, the technology is widely applicable to any analytical, diagnostic and monitoring paradigm including, but not limited to r genetic diseases; fetal testing; mendelian disorders; pathogen screening; and organ transplant monitoring in which circulating DNA is a potential analyte. In this example, the technical features highlighted in previous examples are applied to the analysis of admixed cancer samples. In the first phase of this validation, cancer-derived cell lines were admixed with normal human DNA at defined dilutions, and quantitative genetic analysis was performed. In the second phase of this study, uncharacterized cfDNA was isolated from the plasma of cancer patients and subsequently examined using quantitative genetic analysis.

Methods

Admixtures of Cell Line Genomic DNA with Normal Human DNA:

The following DNA samples were used:
NA06994—normal human genomic DNA (Coriell repository);
NCI-H2228—non-small cell lung cancer cell line (ATCC), harbors mutation in TP53 (Q331*) and EML4-ALK gene fusion (breakpoint unknown); and
NCI-H69—small cell lung cancer cell line (ATCC), harbors amplification of the MYCN gene (~100 copies).

Figure 18:
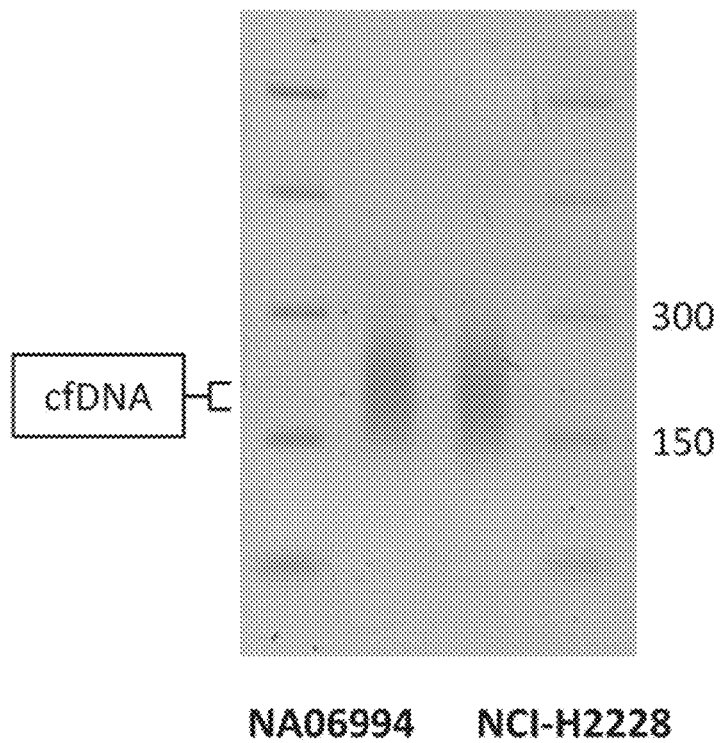
FIG. 18 shows a representative example of the size distribution of two DNA samples (NA06994 & NCI-H2228) processed to mimic cfDNA.

Library Preparation:

Genomic DNA isolated from cell lines (all three above) is high molecular weight material that is dissimilar to the small size of cfDNA. To mimic cfDNA in these validation experiments, genomic DNAs were first fragmented on the "150 bp" setting using a Covaris Acoustic Sonicator. The sonication generally produces a broad smear, and the DNA was further processed using "two sided" bead selection. A dilute solution of DNA purification beads were added to the sample and the higher molecular mass fragments that adhere to the beads were discarded (the size of purified DNA is proportional to the amount of beads added). An additional aliquot of beads are added to the remaining supernatant and in this second round, DNA that adheres to the beads that (in a higher overall concentration of binding buffer) are purified. This "two-sided" purification produces a narrow size distribution that is a reasonable proxy for cfDNA (FIG. 18).

Fragmented genomic DNA was end repaired, quantified, and mixed in the various ratios shown in Table 17 and described in the results section below.

TABLE 17

Samples and admixtures used for validation studies

| Sample, Admixture | genome equivalents (qPCR) |
| --- | --- |
| Pure H2228 | 2248 |
| NA06994:H2228 4:1 | 2616 |
| NA06994:H2228 10:1 | 2600 |
| NA06994:H2228 20:1 | 2968 |
| NA06994:H2228 50:1 | 5000 |
| NA06994:H2228 1000:1 | 10000 |
| Pure H69 | 2472 |
| NA06994:H69 4:1 | 2768 |
| NA06994:H69 10:1 | 3088 |
| NA06994:H69 20:1 | 2944 |
| NA06994:H69 40:1 | 1616 |
| NA06994:H69 100:1 | 1920 |
| NA06994:H69 200:1 | 2920 |
| NA06994:H69 500:1 | 17520 | cfDNA libraries may have limited DNA inputs. The amount of cfDNA obtained per mL of patient plasma is widely variable, but the lower limits (e.g., Example 3) are generally ~10 ng/mL, which is equivalent to 3300 human genomes. To guard against limited cfDNA quantities, the admixture experiments were modeled to reflect the lower limits of cfDNA that were routinely collected from patients. This constraint was applied to all but the most extreme admixtures. In these latter admixtures, libraries were made to mimic inputs from 4 mLs (NA06994:H2228 1000:1) or 8 mLs (NA06994:H69 500:1) of low yield patient cfDNA. Admixed samples were then ligated to the adaptor sets described in Example 4. Measurement of the genome equivalents in each purified library using qPCR (Example 4) is also shown in Table 17. Libraries were amplified, quantified, and equivalent masses of each library were pooled (500 ng of each). The pooled sample was hybridized with the proof-of-concept, high-density 40 mer capture probes listed in Table 6 of Example 2. The resulting complexes were captured on streptavidin-coated beads, washed, processed, amplified, purified and size-selected as described in previous examples. The resulting library was analyzed using an Illumina 150 bp-V3 Miseq sequencing kit on the Illumina MiSeq instrument.

For bioinformatics analysis, a rare somatic variant caller was used to detect mutations, a split read aligner was used to detect fusion genes, and in-house analysis that quantifies and statistically fits tags was used to call copy number variation (CNV).

Figure 19:
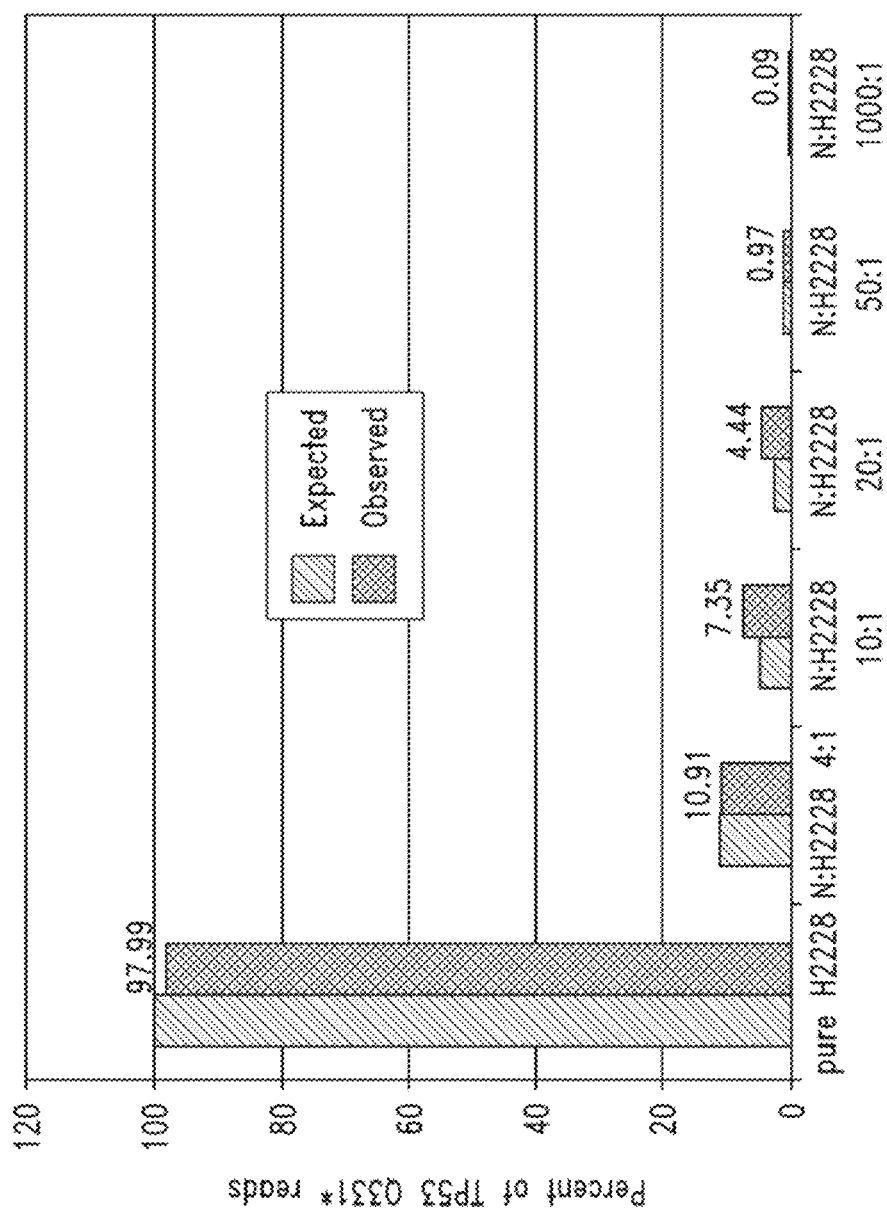
FIG. 19 shows a representative example of the sensitivity of detection of the TP53 point mutation Q331* in tumor sample DNA (H2228) admixed with normal genomic DNA (N). The most sensitive detection corresponds to ~1 mutant copy of TP53 among 1000 normal copies of the gene.

The detection of an admixed point mutation in the TP53 gene is shown in FIG. 19. The "expected" frequency deviates from the admix ratio because it is known that TP53 is hemizygous in the NCI-H2228 cell line. Automated software was able to call the mutant allele in the 50:1 admixture. Manual curation was required to call the mutant event at 1000:1. With respect to specificity, the tag filtering described in Example 1 was applied to the analysis, and no other mutation calls in TP53 were detected after applying this tag filter.

Figure 20:
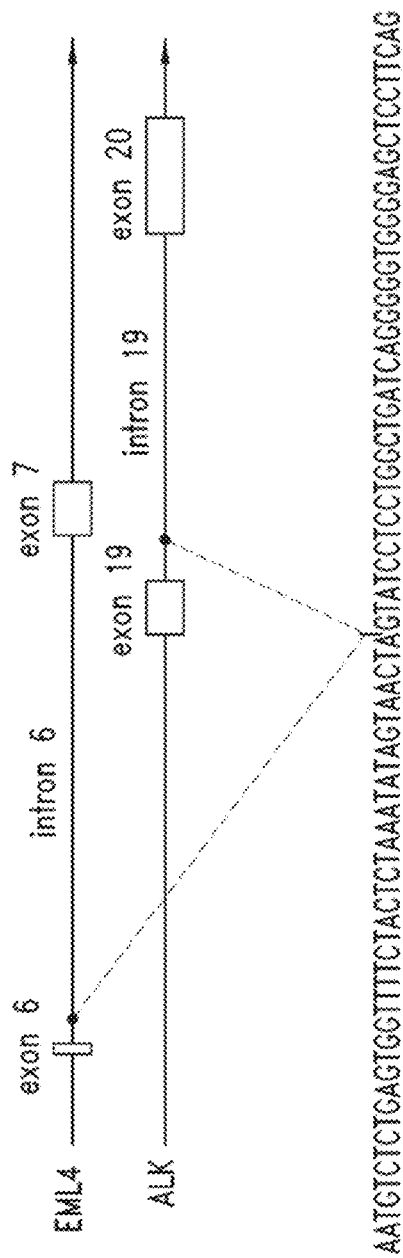
FIG. 20 shows the precise determination of the junction sequence for the EML4-ALK fusion gene harbored in cell line NCI-H2228 using the compositions and methods contemplated herein.

Cell line NCI-H2228 is known to harbor a fusion gene between EML4 and ALK; the cell line serves as a positive control in both fluorescence in situ hybridization assays and in detection of fusion gene transcripts using RT-PCR. There are no published reports of the exact location of the gene fusion junction. Using dense probe coverage of the intron 19 region of ALK, sequence analysis revealed precise location and sequence of the junction formed when the two genes fused (FIG. 20). The frequency of normal reads versus junction reads in the NCI-H2228 cell line (378 vs 249, respectively) suggests that the fusion gene is heterozygous with a normal copy of ALK.

Figure 21:
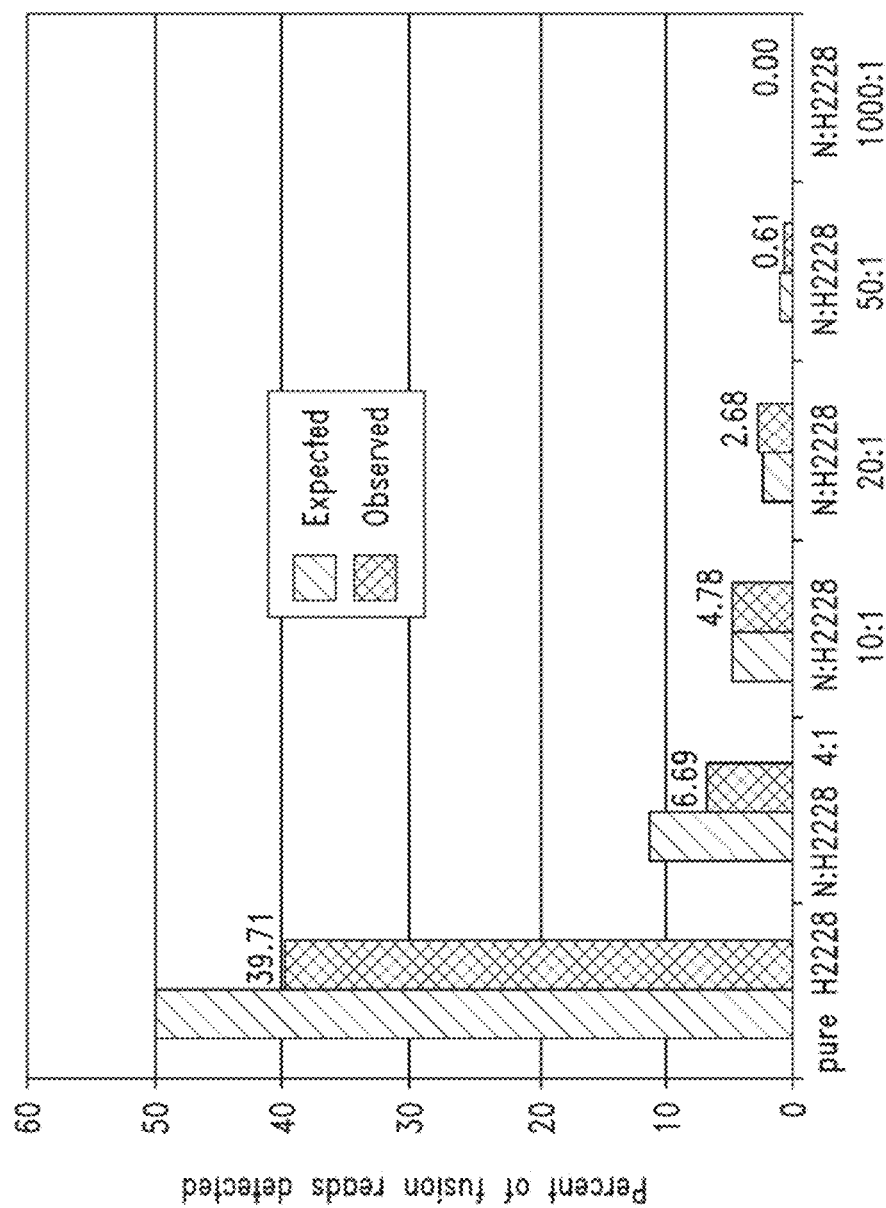
FIG. 21 shows the detection of the EML4-ALK fusion gene tumor sample DNA (H2228) admixed with normal genomic DNA (N). Because the fusion is present as a heterozygote in the NCI-H2228 cell line, the most sensitive detection corresponds to one gene fusion among ~100 normal chromosomal copies of the ALK gene (50 genome equivalents).

Detection of junction reads as a function of admixture is shown in FIG. 21. As with point mutation detection, the expected values were adjusted to reflect the fact that the mutant allele is found in one copy per diploid genome. No fusion reads were detected in the 1000:1 admixed sample.

Figure 22:
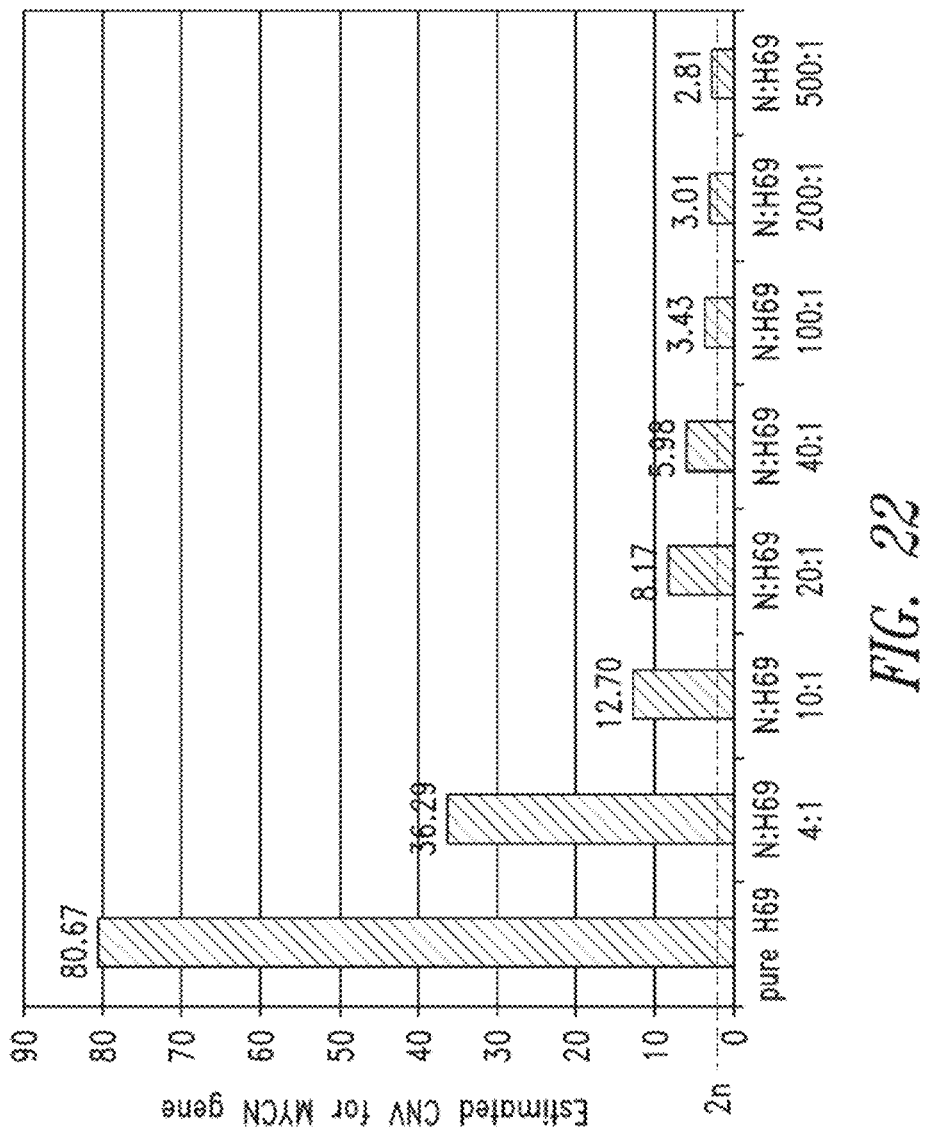
FIG. 22 shows the detection of the MYCN gene amplification in admixtures of cell line NCI-H69 (H69) diluted into normal human DNA (N). The threshold value of two normal diploid copies is shown as a dashed red line.

FIG. 22 shows the results of CNV determination for the MYCN gene as a function of admixture. The NCI-H69 cell line harbors a highly amplified MYCN gene. MYCN is normally found as a single copy gene, two per diploid genome, and thus the expected result for progressively more dilute admixtures is that the tag-calculated CNV should asymptotically approach 2 copies (the asymptote is highlighted in the figure). The validation experiment shown here indicated that the assay system described in this invention is robustly sensitive to highly amplified genes.

Variant Discovery in cfDNA from Cancer Patients:

The most rigorous validation of the technology contemplated herein is to apply it to cfDNA samples in which the spectrum of mutations is unknown. An analysis was performed by sequencing matched cfDNA, tumor and normal adjacent tissue (NAT) samples from two ovarian cancer patients. In addition, two cfDNA samples from colorectal cancer (CRC) patients and two cfDNA samples from healthy volunteers were analyzed. In no case, were mutations, fusions or abnormal CNV detected in the healthy volunteer samples.

Figure 23:
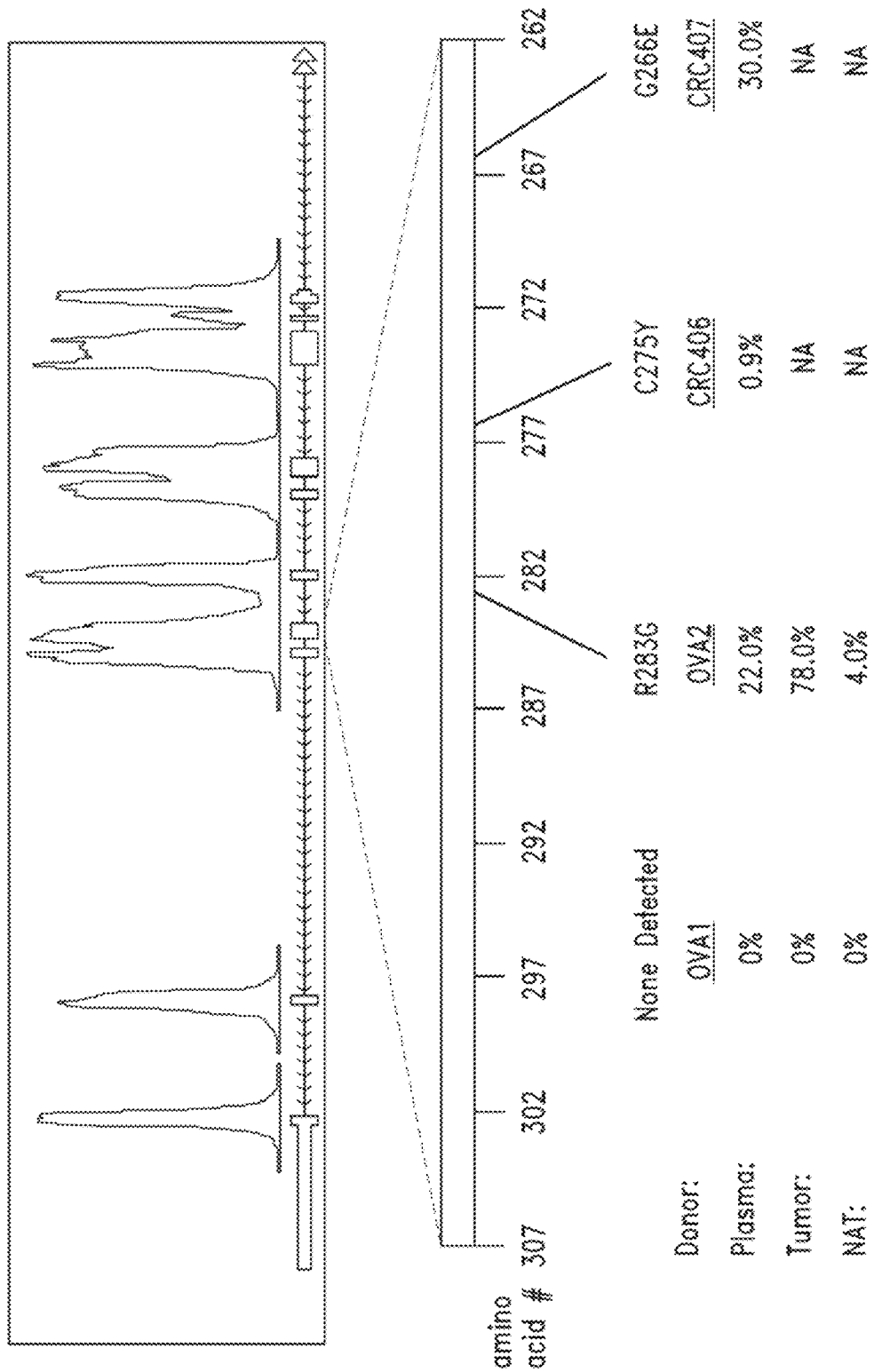
FIG. 23 shows the DNA mutations detected in the TP53 gene of three different cancer patients. The canonical gene model is shown at the top of the figure. The peaks represent DNA sequence coverage (X-axis) and depth (Y-axis). Sequencing depth was >4000 genome equivalents for all sample analyzed. An expanded view of exon 7 below the gene model shows where all detected mutations were localized. The frequency of mutant detection in cfDNA (plasma), tumor tissue, and normal adjacent tissue is shown, where available (NA—not available). OVA1 and OVA2 are ovarian cancer patients; CRC406 and CRC407 are colorectal cancer patients. No mutations in TP53 were found in any of the OVA1 samples.

Libraries of cfDNA from the four cancer patients were initially screened using the targeted probes described in Table 6 of Example 2. These probes were primarily configured to detect point mutations in the TP53 gene, gene fusions with ALK and amplifications of the MYCN. The results of this initial sequencing screen are shown in FIG. 23. A point mutation occurring at the same base position was found in the cfDNA, tumor, and NAT of one ovarian patient. No TP53 mutations were found in the other set of ovarian cancer patient matched samples. Point mutations were also detected in the two CRC cfDNA libraries for which matching tissues were unavailable. All of these point mutations have been previously identified in tumors and all are known to be causal drivers of tumorogenesis. The mutant sequence detection in cfDNA library CRC406 of 0.9% was well within the scope of assay sensitivity. Sensitivity is defined by the presence of multiple families of tagged reads, all of which possess the mutant sequence. These data highlight the clinical utility of the system contemplated herein.

To further explore the detection of cancer-related changes in cfDNA libraries and associated tissues, the same libraries were hybridized to a set of 679 probes that are directed to a total of 20 different cancer-related genes (Table 18). In this probe set, all of the coding regions of 14 genes were targeted while select loci were targeted in the remaining 6 genes.

TABLE 18

| Cancer genes targeted | |
|---|---|
| Genes: coding region targeted | Genes: select regions targeted |
| BRCA1 | ALK |
| BRCA2 | DPYD |
| BRAF | EPHX1 |
| CDH1 | MYC |
| ERBB2 | TNFRSF14 |
| JAK2 | ALDH4A1 |
| NF2 | |
| PIK3CA | |
| RB1 | |
| CDKN2A | |
| KRAS | |
| MYCN | |
| PTEN | |
| TP53 | |

Figure 24:
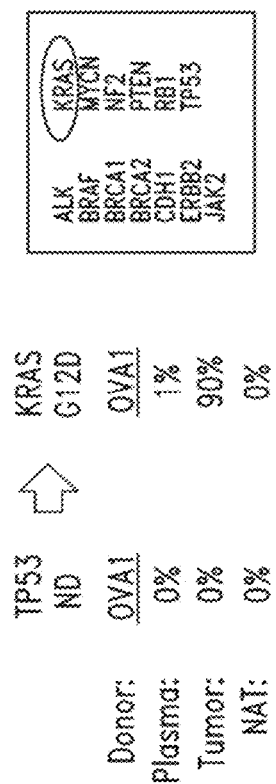
FIG. 24 shows the DNA sequencing of a larger, thirteen gene panel (boxed). The sequencing identified a KRAS mutation in cfDNA and tumor from ovarian cancer patient OVA1.

As shown in FIG. 24, the OVA1 sample, which lacked any detectable changes in TP53, carried a mutation in KRAS that was found in both cfDNA and in the corresponding tumor. This observation highlights a significant feature of the assay system described here. Libraries created from cfDNA can be interrogated with hundreds (as in this example), and even thousands, of targeting probes. The sequencing of the resulting targeted libraries revealed somatic mutations that reside within the tumor and not within the germline of the affected individual. These tumor-associated somatic markers can also be used to quantify the amount of circulating DNA that is shed from the tumor (as opposed to cfDNA that has germline sequence). Thus, the discovery of mutations, regardless of their biological significance, also provides an estimate of tumor content in admixed cfDNA.

Many targeted therapies are most successful in the presence of normal genes (e.g., EGFR inhibitors work only in the presence of wild-type KRAS). A quantitative assessment of circulating tumor DNA levels becomes especially significant in these cases where mutations in genes are not found. In other words, the demonstrable presence of circulating tumor DNA coupled with a wild-type sequencing result at a particular target gene suggests that the target gene is normal within the tumor, and such results can have a significant influence in guiding the choice of therapies. Such is the case with the OVA1 sample highlighted in FIG. 24. The presence of the KRAS mutation in the cfDNA library suggested that this patient's tumor harbors a wild-type TP53 gene(s).

Figure 25:
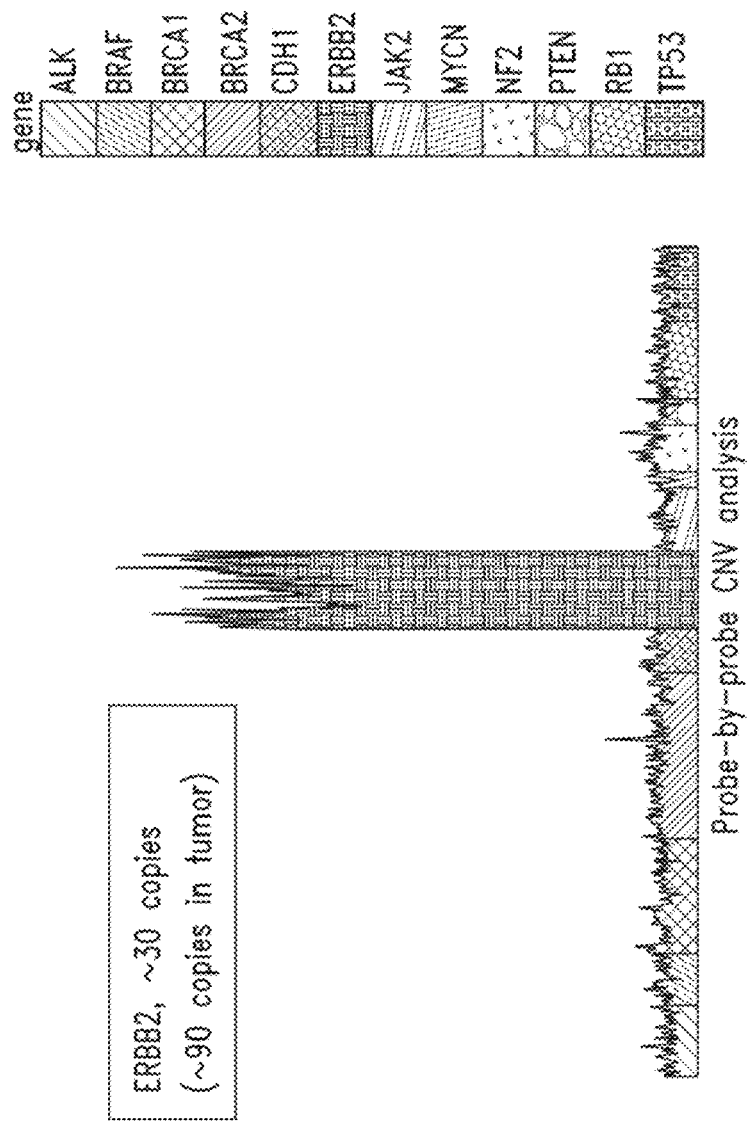
FIG. 25 shows the DNA sequencing of a larger, twelve gene panel. The sequencing identified an ERBB2 gene amplification in the plasma of colorectal cancer patient CRC407.

Another example of aberrant gene discovery is shown in FIG. 25. The targeted quantitative genetic analysis system revealed the presence of a significant amplification in the ERBB2 gene, otherwise referred to as HER-2/neu. While this type of amplification has been much publicized in breast cancer, it is occasionally identified in colorectal carcinomas as well.

Conclusion

Validation experiments with cell line DNA revealed the thresholds of detection of three types of genetic variation that are central to driving neoplastic growth in cancers. Characterization of cfDNA derived from cancer patients revealed tumor-associated genetic changes that were well above the thresholds set by reconstruction experiments in all four samples analyzed. These data indicated that the quantitative analysis system contemplated herein may have significant clinical utility, especially in settings where liquid biopsies are most appropriate.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for targeted genetic analysis of circulating cell-free DNA (cfDNA), said method comprising:
   (a) hybridizing one or more capture probe modules to a target genetic locus in a tagged cfDNA library to form one or more tagged cfDNA-capture probe module complexes,
   wherein each capture probe module comprises a capture probe sequence at a 3' end of the capture probe module and a tail sequence at a 5' end of the capture probe module,
   wherein the capture probe sequence is less than 60 nucleotides in length and hybridizes to a specific DNA target region,
   wherein the one or more capture probe modules is not immobilized to a surface,
   wherein the tail sequence comprises a primer binding site that is hybridized to a partner oligonucleotide comprising at its 3' end a first member of a binding pair to allow for isolation and/or purification of a tagged cfDNA-capture probe module complex, and
   wherein the tagged cfDNA library comprises cfDNA molecules ligated at each end to an adaptor;
   (b) isolating the one or more tagged cfDNA capture probe module complexes from (a) to form one or more isolated tagged cfDNA-capture probe module complexes, wherein the isolating comprises binding the first member of the binding pair of a partner oligonucleotide hybridized to a tagged cfDNA-capture probe module complex to a second member of the binding pair, and each isolated tagged cfDNA capture probe module complex comprises a tagged cfDNA molecule and a capture probe module;
   (c) enzymatically processing the one or more isolated tagged cfDNA-capture probe module complexes from (b) to generate one or more tagged hybrid nucleic acid molecules, wherein the enzymatic processing of each isolated tagged cfDNA-capture probe module complex comprises performing 5' to 3' DNA polymerase extension of the capture probe module using the tagged cfDNA molecule as a template,
wherein each tagged hybrid nucleic acid molecule comprises the capture probe module and a complement of the tagged cfDNA molecule, and wherein the complement of the tagged cfDNA molecule comprises the complement of the adaptor;

(d) amplifying the one or more tagged hybrid nucleic acid molecules of (c) to generate amplified tagged hybrid nucleic acid molecules; and (e) performing a quantitative genetic analysis of the amplified tagged hybrid nucleic acid molecules.

2. The method of claim 1, wherein the primer binding site is a first primer binding site, and the adaptor comprises:
(a) a second primer binding site,
(b) a unique read code that identifies each unique sequencing read,
(c) one or more sequences for DNA sequencing; and, optionally,
(d) one or more sample codes for sample multiplexing.

3. The method of claim 1, wherein the targeted genetic analysis is performed on a plurality of target genetic loci.

4. The method of claim 1, wherein the capture probe sequences are about 25 nucleotides to about 45 nucleotides in length.

5. The method of claim 1, wherein the capture probe sequences are 40 nucleotides in length.

6. The method of claim 1, further comprising determining a number of genome equivalents in the tagged cfDNA library.

7. The method of claim 1, wherein the tagged cfDNA library comprises cfDNA isolated from a biological sample of a subject selected from the group consisting of amniotic fluid, blood, plasma, serum, semen, lymphatic fluid, cerebral spinal fluid, ocular fluid, urine, saliva, stool, mucous, and sweat.

8. The method of claim 1, wherein the quantitative genetic analysis comprises sequencing of the amplified tagged hybrid nucleic acid molecules to generate a plurality of sequencing reads and performing bioinformatics analysis on the plurality of sequencing reads.

9. The method of claim 8, wherein the bioinformatics analysis is used to detect one or more genetic lesions with the target genetic locus.

10. The method of claim 9, wherein the one or more genetic lesions comprise a nucleotide transition or transversion, a nucleotide insertion or deletion, a genomic rearrangement, or a change in copy number.

11. The method of claim 1, wherein the quantitative genetic analysis is used to identify or detect one or more genetic lesions that cause or are associated with a genetic disease.

12. The method of claim 11, wherein the genetic disease is cancer.

13. The method of claim 12, wherein the one or more genetic lesions are chromosomal rearrangements.

14. The method of claim 11, wherein the one or more genetic lesions comprise a genomic rearrangement that fuses a 3' coding region of an ALK gene to another gene.

15. The method of claim 14, wherein the 3' coding region of the ALK gene is fused to an EML4 gene.

16. The method of claim 1, wherein the first member of the binding pair comprises biotin.

17. The method of claim 1, wherein a plurality of capture probe modules hybridize to the target genetic locus.

18. The method of claim 17, wherein each of the plurality of capture probe modules hybridizes to the target genetic locus within about 200 bp of any other capture probe module.

* * * * *

```
                              SEQUENCE LISTING

<160> NUMBER OF SEQ ID NOS: 562

<210> SEQ ID NO 1
<211> LENGTH: 60
<212> TYPE: DNA
<213> ORGANISM: Artificial Sequence
<220> FEATURE:
<223> OTHER INFORMATION: Probe

<400> SEQUENCE: 1
taaacattgg aaaggtttct aattaaccag gagatccaaa agaaagcggt tcaagtagca    60

<210> SEQ ID NO 2
<211> LENGTH: 60
<212> TYPE: DNA
<213> ORGANISM: Artificial Sequence
<220> FEATURE:
<223> OTHER INFORMATION: Probe

<400> SEQUENCE: 2
gatctcagtt ttttttggtta actatgtatt ttggtatatg aagcttctgg gttttgcaca    60

<210> SEQ ID NO 3
<211> LENGTH: 60
<212> TYPE: DNA
<213> ORGANISM: Artificial Sequence
<220> FEATURE:
<223> OTHER INFORMATION: Probe

<400> SEQUENCE: 3
gacagataag catacatatt aacatggata tatatgtgaa tttcattcaa atggttctca    60

<210> SEQ ID NO 4
<211> LENGTH: 60
<212> TYPE: DNA
<213> ORGANISM: Artificial Sequence
<220> FEATURE:
<223> OTHER INFORMATION: Probe

<400> SEQUENCE: 4
agctcttagc ctttgggggg atgacactct tgagcggacg tggggacgcc tcgctcttta    60

<210> SEQ ID NO 5
<211> LENGTH: 60
<212> TYPE: DNA
<213> ORGANISM: Artificial Sequence
<220> FEATURE:
<223> OTHER INFORMATION: Probe

<400> SEQUENCE: 5
aagcccccac cgccgcctct ttccaaaata aacaccagcc agccgccgag cccggagtcg    60

<210> SEQ ID NO 6
<211> LENGTH: 60
<212> TYPE: DNA
<213> ORGANISM: Artificial Sequence
<220> FEATURE:
<223> OTHER INFORMATION: Probe

<400> SEQUENCE: 6
gcctcccttc ccctcccg cccgacagcg gccgctcggg cccggctct cggttataag    60
```

<210> SEQ ID NO 7
<211> LENGTH: 60
<212> TYPE: DNA
<213> ORGANISM: Artificial Sequence
<220> FEATURE:
<223> OTHER INFORMATION: Probe

<400> SEQUENCE: 7
ggtgtggcag ccaggggggc gcactctgct ctggctgggc cccttctccc atgttttctt    60

<210> SEQ ID NO 8
<211> LENGTH: 60
<212> TYPE: DNA
<213> ORGANISM: Artificial Sequence
<220> FEATURE:
<223> OTHER INFORMATION: Probe

<400> SEQUENCE: 8
ttacacaacc tttgggcttg gacaacactt tggggtccaa agaacctaag agtctttctg    60

<210> SEQ ID NO 9
<211> LENGTH: 60
<212> TYPE: DNA
<213> ORGANISM: Artificial Sequence
<220> FEATURE:
<223> OTHER INFORMATION: Probe

<400> SEQUENCE: 9
tgatgaaact tgggctggat ggggcacagg tagggtgctt gttgctttca gtcagatgaa    60

<210> SEQ ID NO 10
<211> LENGTH: 60
<212> TYPE: DNA
<213> ORGANISM: Artificial Sequence
<220> FEATURE:
<223> OTHER INFORMATION: Probe

<400> SEQUENCE: 10
aatgaaagaa aaggaggcca gattgctact cctggtccct gccacacact aggtacccta    60

<210> SEQ ID NO 11
<211> LENGTH: 60
<212> TYPE: DNA
<213> ORGANISM: Artificial Sequence
<220> FEATURE:
<223> OTHER INFORMATION: Probe

<400> SEQUENCE: 11
attgacaata cctacataaa actctttcca gaatgttgtt aagtcttagt cattagggag    60

<210> SEQ ID NO 12
<211> LENGTH: 60
<212> TYPE: DNA
<213> ORGANISM: Artificial Sequence
<220> FEATURE:
<223> OTHER INFORMATION: Probe

<400> SEQUENCE: 12
ggatttccac caacactgta ttcatgtacc cattttctc ttaacctaac tttattggtc    60

<210> SEQ ID NO 13
<211> LENGTH: 60
<212> TYPE: DNA
<213> ORGANISM: Artificial Sequence
<220> FEATURE:

<223> OTHER INFORMATION: Probe

<400> SEQUENCE: 13
caaaggggga aaaccatcag gacattattt aacaacggaa atatctaact gaaaggcaaa        60

<210> SEQ ID NO 14
<211> LENGTH: 60
<212> TYPE: DNA
<213> ORGANISM: Artificial Sequence
<220> FEATURE:
<223> OTHER INFORMATION: Probe

<400> SEQUENCE: 14
caggcagacc aaccaaagtc tttgttccac cttttaaaac taaatcacat tttcacagag        60

<210> SEQ ID NO 15
<211> LENGTH: 60
<212> TYPE: DNA
<213> ORGANISM: Artificial Sequence
<220> FEATURE:
<223> OTHER INFORMATION: Probe

<400> SEQUENCE: 15
ccccagccag cggtccgcaa cccttgccgc atccacgaaa ctttgcccat agcagcgggc        60

<210> SEQ ID NO 16
<211> LENGTH: 60
<212> TYPE: DNA
<213> ORGANISM: Artificial Sequence
<220> FEATURE:
<223> OTHER INFORMATION: Probe

<400> SEQUENCE: 16
cgactcatct cagcattaaa gtgataaaaa aataaattaa aaggcaagtg gacttcggtg        60

<210> SEQ ID NO 17
<211> LENGTH: 60
<212> TYPE: DNA
<213> ORGANISM: Artificial Sequence
<220> FEATURE:
<223> OTHER INFORMATION: Probe

<400> SEQUENCE: 17
ctgtggcgcg cactgcgcgc tgcgccaggt ttccgcacca agaccccttt aactcaagac        60

<210> SEQ ID NO 18
<211> LENGTH: 60
<212> TYPE: DNA
<213> ORGANISM: Artificial Sequence
<220> FEATURE:
<223> OTHER INFORMATION: Probe

<400> SEQUENCE: 18
ttctactgcg acgaggagga gaacttctac cagcagcagc agcagagcga gctgcagccc        60

<210> SEQ ID NO 19
<211> LENGTH: 60
<212> TYPE: DNA
<213> ORGANISM: Artificial Sequence
<220> FEATURE:
<223> OTHER INFORMATION: Probe

<400> SEQUENCE: 19
accgagctgc tgggaggaga catggtgaac cagagtttca tctgcgaccc ggacgacgag        60

```
<210> SEQ ID NO 20
<211> LENGTH: 60
<212> TYPE: DNA
<213> ORGANISM: Artificial Sequence
<220> FEATURE:
<223> OTHER INFORMATION: Probe

<400> SEQUENCE: 20
gccgccgcct cagagtgcat cgacccctcg gtggtcttcc cctaccctct caacgacagc    60

<210> SEQ ID NO 21
<211> LENGTH: 60
<212> TYPE: DNA
<213> ORGANISM: Artificial Sequence
<220> FEATURE:
<223> OTHER INFORMATION: Probe

<400> SEQUENCE: 21
ggcggctagg ggacaggggc ggggtgggca gcagctcgaa tttcttccag atatcctcgc    60

<210> SEQ ID NO 22
<211> LENGTH: 60
<212> TYPE: DNA
<213> ORGANISM: Artificial Sequence
<220> FEATURE:
<223> OTHER INFORMATION: Probe

<400> SEQUENCE: 22
agacgagctt ggcggcggcc gagaagccgc tccacataca gtcctggatg atgatgtttt    60

<210> SEQ ID NO 23
<211> LENGTH: 60
<212> TYPE: DNA
<213> ORGANISM: Artificial Sequence
<220> FEATURE:
<223> OTHER INFORMATION: Probe

<400> SEQUENCE: 23
aggagagcag agaatccgag gacggagaga aggcgctgga gtcttgcgag gcgcaggact    60

<210> SEQ ID NO 24
<211> LENGTH: 60
<212> TYPE: DNA
<213> ORGANISM: Artificial Sequence
<220> FEATURE:
<223> OTHER INFORMATION: Probe

<400> SEQUENCE: 24
taagagtggc ccgttaaata agctgccaat gaaaatggga aggtatcca gccgcccact    60

<210> SEQ ID NO 25
<211> LENGTH: 60
<212> TYPE: DNA
<213> ORGANISM: Artificial Sequence
<220> FEATURE:
<223> OTHER INFORMATION: Probe

<400> SEQUENCE: 25
ttgtatttgt acagcattaa tctggtaatt gattatttta atgtaacctt gctaaaggag    60

<210> SEQ ID NO 26
<211> LENGTH: 60
<212> TYPE: DNA
<213> ORGANISM: Artificial Sequence
<220> FEATURE:
<223> OTHER INFORMATION: Probe
```

```
<400> SEQUENCE: 26
gaggccacag caaacctcct cacagcccac tggtcctcaa gaggtgccac gtctccacac       60

<210> SEQ ID NO 27
<211> LENGTH: 60
<212> TYPE: DNA
<213> ORGANISM: Artificial Sequence
<220> FEATURE:
<223> OTHER INFORMATION: Probe

<400> SEQUENCE: 27
agaggaggaa cgagctaaaa cggagctttt ttgccctgcg tgaccagatc ccggagttgg       60

<210> SEQ ID NO 28
<211> LENGTH: 60
<212> TYPE: DNA
<213> ORGANISM: Artificial Sequence
<220> FEATURE:
<223> OTHER INFORMATION: Probe

<400> SEQUENCE: 28
tccaacttga ccctcttggc agcaggatag tccttccgag tggagggagg cgctgcgtag       60

<210> SEQ ID NO 29
<211> LENGTH: 60
<212> TYPE: DNA
<213> ORGANISM: Artificial Sequence
<220> FEATURE:
<223> OTHER INFORMATION: Probe

<400> SEQUENCE: 29
gcttggacgg acaggatgta tgctgtggct tttttaagga taactacctt gggggccttt       60

<210> SEQ ID NO 30
<211> LENGTH: 60
<212> TYPE: DNA
<213> ORGANISM: Artificial Sequence
<220> FEATURE:
<223> OTHER INFORMATION: Probe

<400> SEQUENCE: 30
gcatttgatc atgcatttga aacaagttca taggtgattg ctcaggacat ttctgttaga       60

<210> SEQ ID NO 31
<211> LENGTH: 60
<212> TYPE: DNA
<213> ORGANISM: Artificial Sequence
<220> FEATURE:
<223> OTHER INFORMATION: Probe

<400> SEQUENCE: 31
cgccccgcgc cctcccagcc gggtccagcc ggagccatgg ggccggagcc gcagtgagca       60

<210> SEQ ID NO 32
<211> LENGTH: 60
<212> TYPE: DNA
<213> ORGANISM: Artificial Sequence
<220> FEATURE:
<223> OTHER INFORMATION: Probe

<400> SEQUENCE: 32
ctctggcccc gccggccgcg ggacctcggc ggggcatcca cagggcaggg tcccgccgct       60

<210> SEQ ID NO 33
<211> LENGTH: 60
```

```
<212> TYPE: DNA
<213> ORGANISM: Artificial Sequence
<220> FEATURE:
<223> OTHER INFORMATION: Probe

<400> SEQUENCE: 33
ggcatgactt ggagtgagtt tggatggggt ggccaggtct gagaaggtcc cccgccagtg    60

<210> SEQ ID NO 34
<211> LENGTH: 60
<212> TYPE: DNA
<213> ORGANISM: Artificial Sequence
<220> FEATURE:
<223> OTHER INFORMATION: Probe

<400> SEQUENCE: 34
gcagggcacc ttcttctgcc acccacctgt aaacagaggg ctcagcccag ctggaggcag    60

<210> SEQ ID NO 35
<211> LENGTH: 60
<212> TYPE: DNA
<213> ORGANISM: Artificial Sequence
<220> FEATURE:
<223> OTHER INFORMATION: Probe

<400> SEQUENCE: 35
cccaagatct ccaagtactg gggaacccca gggaggccct gggggtggc agtgttccta    60

<210> SEQ ID NO 36
<211> LENGTH: 60
<212> TYPE: DNA
<213> ORGANISM: Artificial Sequence
<220> FEATURE:
<223> OTHER INFORMATION: Probe

<400> SEQUENCE: 36
ctaatgcaca caaagcctcc ccctggttag cagtggccct ggtcagctct gaataaccaa    60

<210> SEQ ID NO 37
<211> LENGTH: 60
<212> TYPE: DNA
<213> ORGANISM: Artificial Sequence
<220> FEATURE:
<223> OTHER INFORMATION: Probe

<400> SEQUENCE: 37
ctgctcctct tttagaaggc aggagggccc caagggaagc agaaggtgac agaagggaa     60

<210> SEQ ID NO 38
<211> LENGTH: 60
<212> TYPE: DNA
<213> ORGANISM: Artificial Sequence
<220> FEATURE:
<223> OTHER INFORMATION: Probe

<400> SEQUENCE: 38
tggggcagtg gcgggcaggc actgggttgt aagttgggag tttgcggctg gggtcaggct    60

<210> SEQ ID NO 39
<211> LENGTH: 60
<212> TYPE: DNA
<213> ORGANISM: Artificial Sequence
<220> FEATURE:
<223> OTHER INFORMATION: Probe

<400> SEQUENCE: 39
```
tctgctgctg tttgtgcctc tctctgttac taacccgtcc tctcgctgtt agacatctct    60

<210> SEQ ID NO 40
<211> LENGTH: 60
<212> TYPE: DNA
<213> ORGANISM: Artificial Sequence
<220> FEATURE:
<223> OTHER INFORMATION: Probe

<400> SEQUENCE: 40
cccacccctc ccatgtcacc tgtatgacac ctgcattcca cccggcccca gccctcccct    60

<210> SEQ ID NO 41
<211> LENGTH: 60
<212> TYPE: DNA
<213> ORGANISM: Artificial Sequence
<220> FEATURE:
<223> OTHER INFORMATION: Probe

<400> SEQUENCE: 41
tgggccaggt agtctcccta gaaggtgatg ctgatgaggg tctggtgccc agggcgccac    60

<210> SEQ ID NO 42
<211> LENGTH: 60
<212> TYPE: DNA
<213> ORGANISM: Artificial Sequence
<220> FEATURE:
<223> OTHER INFORMATION: Probe

<400> SEQUENCE: 42
ggtgcccacc ccttgcatcc tgggggtag agcacattgg gcacaaagca gaggcacata    60

<210> SEQ ID NO 43
<211> LENGTH: 60
<212> TYPE: DNA
<213> ORGANISM: Artificial Sequence
<220> FEATURE:
<223> OTHER INFORMATION: Probe

<400> SEQUENCE: 43
caccctgcct ggtactgccc tattgcccct ggcacaccag ggcaaaacag cacagtgaaa    60

<210> SEQ ID NO 44
<211> LENGTH: 60
<212> TYPE: DNA
<213> ORGANISM: Artificial Sequence
<220> FEATURE:
<223> OTHER INFORMATION: Probe

<400> SEQUENCE: 44
ccatttacag aaacaaacct ccccaccaaa atgagaaaac tgtgtttctc cctggcactc    60

<210> SEQ ID NO 45
<211> LENGTH: 60
<212> TYPE: DNA
<213> ORGANISM: Artificial Sequence
<220> FEATURE:
<223> OTHER INFORMATION: Probe

<400> SEQUENCE: 45
ttattcttct tgtgcctggg cacggtaatg ctgctcatgg tggtgcacga agggccaggg    60

<210> SEQ ID NO 46
<211> LENGTH: 60
<212> TYPE: DNA
<213> ORGANISM: Artificial Sequence

```
<220> FEATURE:
<223> OTHER INFORMATION: Probe

<400> SEQUENCE: 46
gaaggatagg acagggtggg ctgggccagg ctgcatgcgc agagggacag gaactgcagc    60

<210> SEQ ID NO 47
<211> LENGTH: 60
<212> TYPE: DNA
<213> ORGANISM: Artificial Sequence
<220> FEATURE:
<223> OTHER INFORMATION: Probe

<400> SEQUENCE: 47
gggcccggac cctgatgctc atgtggctgt tgacctgtcc cggtatgaag gctgagacgg    60

<210> SEQ ID NO 48
<211> LENGTH: 60
<212> TYPE: DNA
<213> ORGANISM: Artificial Sequence
<220> FEATURE:
<223> OTHER INFORMATION: Probe

<400> SEQUENCE: 48
tctgtctcct gccatcccca agagatgctg ccacatctgg atcctcagga ctctgtctgc    60

<210> SEQ ID NO 49
<211> LENGTH: 60
<212> TYPE: DNA
<213> ORGANISM: Artificial Sequence
<220> FEATURE:
<223> OTHER INFORMATION: Probe

<400> SEQUENCE: 49
tcacgtccca gggcagtttt cttccctgaa gaaagttgga tggcatgatc tgtcttccca    60

<210> SEQ ID NO 50
<211> LENGTH: 60
<212> TYPE: DNA
<213> ORGANISM: Artificial Sequence
<220> FEATURE:
<223> OTHER INFORMATION: Probe

<400> SEQUENCE: 50
gtgttgagaa cagactactg acttctaata gcagcgactt ctttaccttg ataaaccaca    60

<210> SEQ ID NO 51
<211> LENGTH: 60
<212> TYPE: DNA
<213> ORGANISM: Artificial Sequence
<220> FEATURE:
<223> OTHER INFORMATION: Probe

<400> SEQUENCE: 51
aaaaaaagga tgggttccat atgggtggtg tcaagtgccc acctcctagc aagtcagcag    60

<210> SEQ ID NO 52
<211> LENGTH: 60
<212> TYPE: DNA
<213> ORGANISM: Artificial Sequence
<220> FEATURE:
<223> OTHER INFORMATION: Probe

<400> SEQUENCE: 52
ccctcacaag gtcaaagcta tacatcagct cctgtgacat tgactcatcc cccagacctt    60
```

<210> SEQ ID NO 53
<211> LENGTH: 60
<212> TYPE: DNA
<213> ORGANISM: Artificial Sequence
<220> FEATURE:
<223> OTHER INFORMATION: Probe

<400> SEQUENCE: 53
aacccaccga gatctgcaaa ctttgcagga tgcaccagat gtcttgtagc catgggtcaa    60

<210> SEQ ID NO 54
<211> LENGTH: 60
<212> TYPE: DNA
<213> ORGANISM: Artificial Sequence
<220> FEATURE:
<223> OTHER INFORMATION: TYMSr4r probe

<400> SEQUENCE: 54
tgcctccctc aggtgcctct gcacaaaacc agattgcttc cctctaagag tatggttagt    60

<210> SEQ ID NO 55
<211> LENGTH: 60
<212> TYPE: DNA
<213> ORGANISM: Artificial Sequence
<220> FEATURE:
<223> OTHER INFORMATION: Probe

<400> SEQUENCE: 55
gttttacttt gcctttagct gtggtctttc aaaccaccat ccctccttat cttcctctgc    60

<210> SEQ ID NO 56
<211> LENGTH: 60
<212> TYPE: DNA
<213> ORGANISM: Artificial Sequence
<220> FEATURE:
<223> OTHER INFORMATION: Probe

<400> SEQUENCE: 56
ctctgcaatt tgttttccca tattaaagaa ctgaagagct cagtgtggta ggctggcaag    60

<210> SEQ ID NO 57
<211> LENGTH: 60
<212> TYPE: DNA
<213> ORGANISM: Artificial Sequence
<220> FEATURE:
<223> OTHER INFORMATION: Probe

<400> SEQUENCE: 57
ttttaaatga tgttttaaag aattgaaact aacatactgt tctgctttct ccccgggtt    60

<210> SEQ ID NO 58
<211> LENGTH: 60
<212> TYPE: DNA
<213> ORGANISM: Artificial Sequence
<220> FEATURE:
<223> OTHER INFORMATION: Probe

<400> SEQUENCE: 58
cctgcccacc acttctccct aaactgaagc cccacatttg gagcagtcat ctttatcttg    60

<210> SEQ ID NO 59
<211> LENGTH: 60
<212> TYPE: DNA
<213> ORGANISM: Artificial Sequence
<220> FEATURE:
<223> OTHER INFORMATION: Probe

```
<400> SEQUENCE: 59
ggttgcgctc caatcatgtt acataaccta cggcaaggta tcgacaggat catactcctg       60

<210> SEQ ID NO 60
<211> LENGTH: 60
<212> TYPE: DNA
<213> ORGANISM: Artificial Sequence
<220> FEATURE:
<223> OTHER INFORMATION: Probe

<400> SEQUENCE: 60
gcacagttac atttgccagt ggcaacatcc ttaaaaatta ataactgata ggtcacggac       60

<210> SEQ ID NO 61
<211> LENGTH: 60
<212> TYPE: DNA
<213> ORGANISM: Artificial Sequence
<220> FEATURE:
<223> OTHER INFORMATION: Probe

<400> SEQUENCE: 61
cgtcccgccg cgccacttgg cctgcctccg tcccgccgcg ccacttcgcc tgcctccgtc       60

<210> SEQ ID NO 62
<211> LENGTH: 60
<212> TYPE: DNA
<213> ORGANISM: Artificial Sequence
<220> FEATURE:
<223> OTHER INFORMATION: Probe

<400> SEQUENCE: 62
ctgtaaggcg aggaggacga tgcgtcccct ccctcgcagg attgaggtta ggactaaacg       60

<210> SEQ ID NO 63
<211> LENGTH: 35
<212> TYPE: DNA
<213> ORGANISM: Artificial Sequence
<220> FEATURE:
<223> OTHER INFORMATION: Partner Oligo #138

<400> SEQUENCE: 63
gtgaaaacca ggatcaactc ccgtgccagt cacat                                 35

<210> SEQ ID NO 64
<211> LENGTH: 20
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(8)
<223> OTHER INFORMATION: n is a, c, g, or t

<400> SEQUENCE: 64
nnnnnnnnca tggccgcagg                                                  20

<210> SEQ ID NO 65
<211> LENGTH: 20
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(8)
```

<223> OTHER INFORMATION: n is a, c, g, or t

<400> SEQUENCE: 65
nnnnnnnnat cttagtggca                                              20

<210> SEQ ID NO 66
<211> LENGTH: 20
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(8)
<223> OTHER INFORMATION: n is a, c, g, or t

<400> SEQUENCE: 66
nnnnnnnncg gaactcggag                                              20

<210> SEQ ID NO 67
<211> LENGTH: 20
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(8)
<223> OTHER INFORMATION: n is a, c, g, or t

<400> SEQUENCE: 67
nnnnnnnnga ctccgatccc                                              20

<210> SEQ ID NO 68
<211> LENGTH: 95
<212> TYPE: DNA
<213> ORGANISM: Artificial Sequence
<220> FEATURE:
<223> OTHER INFORMATION: Probe

<400> SEQUENCE: 68
atgtgactgg cacgggagtt gatcctggtt ttcacgggtt tgagtggcat gagctaccta    60
ctggatgtgc ctgactgttt ccccttcttc ttccc                               95

<210> SEQ ID NO 69
<211> LENGTH: 95
<212> TYPE: DNA
<213> ORGANISM: Artificial Sequence
<220> FEATURE:
<223> OTHER INFORMATION: Probe

<400> SEQUENCE: 69
atgtgactgg cacgggagtt gatcctggtt ttcacctatc tccaggatgg agagagggaa    60
aaaaaagatg ggtctgtgtg ggagggcagg tactt                               95

<210> SEQ ID NO 70
<211> LENGTH: 95
<212> TYPE: DNA
<213> ORGANISM: Artificial Sequence
<220> FEATURE:
<223> OTHER INFORMATION: Probe

<400> SEQUENCE: 70
atgtgactgg cacgggagtt gatcctggtt ttcacgaaag aagccaggtc ttcaattaat    60
aagattccct ggtctcgttt gtctacctgt taatg                               95

<210> SEQ ID NO 71
<211> LENGTH: 95
<212> TYPE: DNA
<213> ORGANISM: Artificial Sequence
<220> FEATURE:
<223> OTHER INFORMATION: Probe

<400> SEQUENCE: 71
atgtgactgg cacgggagtt gatcctggtt ttcaccagac tcgcgcccaa ttttccccca    60 cccttgtta ttgccacaaa atcctgagga tgatc                                95

<210> SEQ ID NO 72
<211> LENGTH: 95
<212> TYPE: DNA
<213> ORGANISM: Artificial Sequence
<220> FEATURE:
<223> OTHER INFORMATION: Probe

<400> SEQUENCE: 72
atgtgactgg cacgggagtt gatcctggtt ttcacaagca cctagcccca ttcctgctga    60
gcaggaggtg gcaggtaccc cagactggga ggtaa                               95

<210> SEQ ID NO 73
<211> LENGTH: 95
<212> TYPE: DNA
<213> ORGANISM: Artificial Sequence
<220> FEATURE:
<223> OTHER INFORMATION: Probe

<400> SEQUENCE: 73
atgtgactgg cacgggagtt gatcctggtt ttcacagtcg gtggggccag gatgaggccc    60
agtctgttca cacatggctg ctgcctctca gctct                               95

<210> SEQ ID NO 74
<211> LENGTH: 95
<212> TYPE: DNA
<213> ORGANISM: Artificial Sequence
<220> FEATURE:
<223> OTHER INFORMATION: Probe

<400> SEQUENCE: 74
atgtgactgg cacgggagtt gatcctggtt ttcaccctgg ccctcagcca gtacagaaag    60
tcatttgtca aggccttcag ttggcagacg tgctc                               95

<210> SEQ ID NO 75
<211> LENGTH: 95
<212> TYPE: DNA
<213> ORGANISM: Artificial Sequence
<220> FEATURE:
<223> OTHER INFORMATION: Probe

<400> SEQUENCE: 75
atgtgactgg cacgggagtt gatcctggtt ttcacagaat tcattgccag ctataaatct    60
gtggaaacgc tgccacacaa tcttagcaca caaga                               95

<210> SEQ ID NO 76
<211> LENGTH: 95
<212> TYPE: DNA
<213> ORGANISM: Artificial Sequence
<220> FEATURE:
<223> OTHER INFORMATION: Probe

```
<400> SEQUENCE: 76
atgtgactgg cacgggagtt gatcctggtt ttcacttact tccctccagt tttgttgctt    60 gcaaacaac agaatcttct ctccatgaaa tcatg                                95

<210> SEQ ID NO 77
<211> LENGTH: 95
<212> TYPE: DNA
<213> ORGANISM: Artificial Sequence
<220> FEATURE:
<223> OTHER INFORMATION: Probe

<400> SEQUENCE: 77
atgtgactgg cacgggagtt gatcctggtt ttcaccaggg gtatctatta tccccatttt    60
ctcacaaagg aaaccaagat aaaaggttta aatgg                               95

<210> SEQ ID NO 78
<211> LENGTH: 95
<212> TYPE: DNA
<213> ORGANISM: Artificial Sequence
<220> FEATURE:
<223> OTHER INFORMATION: Probe

<400> SEQUENCE: 78
atgtgactgg cacgggagtt gatcctggtt ttcactgtta cctttaaaag acatctgctt    60
tctgccaaaa ttaatgtgct gaacttaaac ttacc                               95

<210> SEQ ID NO 79
<211> LENGTH: 95
<212> TYPE: DNA
<213> ORGANISM: Artificial Sequence
<220> FEATURE:
<223> OTHER INFORMATION: Probe

<400> SEQUENCE: 79
atgtgactgg cacgggagtt gatcctggtt ttcacttccc agtaaattac tcttaccaat    60
gcaacagact ttaagaagt tgtgttttac aatgc                                95

<210> SEQ ID NO 80
<211> LENGTH: 95
<212> TYPE: DNA
<213> ORGANISM: Artificial Sequence
<220> FEATURE:
<223> OTHER INFORMATION: Probe

<400> SEQUENCE: 80
atgtgactgg cacgggagtt gatcctggtt ttcactaaat gacataacag ttatgatttt    60
gcagaaaaca gatctgtatt tatttcagtg ttact                               95

<210> SEQ ID NO 81
<211> LENGTH: 95
<212> TYPE: DNA
<213> ORGANISM: Artificial Sequence
<220> FEATURE:
<223> OTHER INFORMATION: Probe

<400> SEQUENCE: 81
atgtgactgg cacgggagtt gatcctggtt ttcacgacag gttttgaaag atatttgtgt    60
tactaatgac tgtgctataa ctttttttc tttcc                                95

<210> SEQ ID NO 82
<211> LENGTH: 95
```

-continued

```
<212> TYPE: DNA
<213> ORGANISM: Artificial Sequence
<220> FEATURE:
<223> OTHER INFORMATION: Probe

<400> SEQUENCE: 82
atgtgactgg cacgggagtt gatcctggtt ttcacctgtg gcgcgcactg cgcgctgcgc    60
caggtttccg caccaagacc cctttaactc aagac                               95

<210> SEQ ID NO 83
<211> LENGTH: 95
<212> TYPE: DNA
<213> ORGANISM: Artificial Sequence
<220> FEATURE:
<223> OTHER INFORMATION: Probe

<400> SEQUENCE: 83
atgtgactgg cacgggagtt gatcctggtt ttcacggcgg ctaggggaca ggggcggggt    60
gggcagcagc tcgaatttct tccagatatc ctcgc                               95

<210> SEQ ID NO 84
<211> LENGTH: 95
<212> TYPE: DNA
<213> ORGANISM: Artificial Sequence
<220> FEATURE:
<223> OTHER INFORMATION: Probe

<400> SEQUENCE: 84
atgtgactgg cacgggagtt gatcctggtt ttcacaccga gctgctggga ggagacatgg    60
tgaaccagag tttcatctgc gacccggacg acgag                               95

<210> SEQ ID NO 85
<211> LENGTH: 95
<212> TYPE: DNA
<213> ORGANISM: Artificial Sequence
<220> FEATURE:
<223> OTHER INFORMATION: Probe

<400> SEQUENCE: 85
atgtgactgg cacgggagtt gatcctggtt ttcacaggag agcagagaat ccgaggacgg    60
agagaaggcg ctggagtctt gcgaggcgca ggact                               95

<210> SEQ ID NO 86
<211> LENGTH: 95
<212> TYPE: DNA
<213> ORGANISM: Artificial Sequence
<220> FEATURE:
<223> OTHER INFORMATION: Probe

<400> SEQUENCE: 86
atgtgactgg cacgggagtt gatcctggtt ttcacctgta agttatcgta aaaaggagca    60
tctaggtagg tctttgtagc caatgttacc cgatt                               95

<210> SEQ ID NO 87
<211> LENGTH: 95
<212> TYPE: DNA
<213> ORGANISM: Artificial Sequence
<220> FEATURE:
<223> OTHER INFORMATION: Probe

<400> SEQUENCE: 87
atgtgactgg cacgggagtt gatcctggtt ttcacaatgg ccattcttcc aggaggcaca    60
```
gaaattacag gccatgcaca gagagaaata cccga    95

<210> SEQ ID NO 88
<211> LENGTH: 95
<212> TYPE: DNA
<213> ORGANISM: Artificial Sequence
<220> FEATURE:
<223> OTHER INFORMATION: Probe

<400> SEQUENCE: 88
atgtgactgg cacgggagtt gatcctggtt ttcaccttgt tcgttccttg tactgagacc    60
ctagtctgcc actgaggatt tggtttttgc ccttc    95

<210> SEQ ID NO 89
<211> LENGTH: 95
<212> TYPE: DNA
<213> ORGANISM: Artificial Sequence
<220> FEATURE:
<223> OTHER INFORMATION: Probe

<400> SEQUENCE: 89
atgtgactgg cacgggagtt gatcctggtt ttcacatcaa gactcatcag taccatcaaa    60
agctgagatg aaacagtgta agtttcaaca gaaat    95

<210> SEQ ID NO 90
<211> LENGTH: 95
<212> TYPE: DNA
<213> ORGANISM: Artificial Sequence
<220> FEATURE:
<223> OTHER INFORMATION: Probe

<400> SEQUENCE: 90
atgtgactgg cacgggagtt gatcctggtt ttcactgtgt ccagctgtga aactcagaga    60
tgtaactgct gacatcctcc ctattttgca tctca    95

<210> SEQ ID NO 91
<211> LENGTH: 95
<212> TYPE: DNA
<213> ORGANISM: Artificial Sequence
<220> FEATURE:
<223> OTHER INFORMATION: Probe

<400> SEQUENCE: 91
atgtgactgg cacgggagtt gatcctggtt ttcacatttg aaacaatttt atcatgaatg    60
ccatgaccaa agtattcttc tgtatcttct ttctt    95

<210> SEQ ID NO 92
<211> LENGTH: 95
<212> TYPE: DNA
<213> ORGANISM: Artificial Sequence
<220> FEATURE:
<223> OTHER INFORMATION: Probe

<400> SEQUENCE: 92
atgtgactgg cacgggagtt gatcctggtt ttcactgatg ggtgggctcc cgaaggggcc    60
tcccgcagac ttgcgaagtt cccactctct gggcg    95

<210> SEQ ID NO 93
<211> LENGTH: 95
<212> TYPE: DNA
<213> ORGANISM: Artificial Sequence
<220> FEATURE:
<223> OTHER INFORMATION: Probe

<400> SEQUENCE: 93
atgtgactgg cacgggagtt gatcctggtt ttcaccaggg tgcgggggca tccaggctgc  60
ccaagcggag gctgggccgg ctgtgctggc ctctt  95

<210> SEQ ID NO 94
<211> LENGTH: 95
<212> TYPE: DNA
<213> ORGANISM: Artificial Sequence
<220> FEATURE:
<223> OTHER INFORMATION: Probe

<400> SEQUENCE: 94
atgtgactgg cacgggagtt gatcctggtt ttcacttttg aaatgtgggt ttgttgccat  60
gaaacgtgtt tcaagcatag ttttgacaga taacg  95

<210> SEQ ID NO 95
<211> LENGTH: 95
<212> TYPE: DNA
<213> ORGANISM: Artificial Sequence
<220> FEATURE:
<223> OTHER INFORMATION: Probe

<400> SEQUENCE: 95
atgtgactgg cacgggagtt gatcctggtt ttcactgccc taaaagtgta tgtataacat  60
ccctgatgtc tgcatttgtc ctttgactgg tgttt  95

<210> SEQ ID NO 96
<211> LENGTH: 95
<212> TYPE: DNA
<213> ORGANISM: Artificial Sequence
<220> FEATURE:
<223> OTHER INFORMATION: Probe

<400> SEQUENCE: 96
atgtgactgg cacgggagtt gatcctggtt ttcacaaccc ctcgaggctc agacctttgg  60
agcaggagtg tgattctggc caaccaccct ctctg  95

<210> SEQ ID NO 97
<211> LENGTH: 95
<212> TYPE: DNA
<213> ORGANISM: Artificial Sequence
<220> FEATURE:
<223> OTHER INFORMATION: Probe

<400> SEQUENCE: 97
atgtgactgg cacgggagtt gatcctggtt ttcaccataa atatgtgtgc tagtcctgtt  60
agacccaagt gctgcccaag ggcagcgccc tgctc  95

<210> SEQ ID NO 98
<211> LENGTH: 95
<212> TYPE: DNA
<213> ORGANISM: Artificial Sequence
<220> FEATURE:
<223> OTHER INFORMATION: Probe

<400> SEQUENCE: 98
atgtgactgg cacgggagtt gatcctggtt ttcactactt gttaattaaa aattcaagag  60 ttttttttc ttattctgag gttatctttt tacca  95

<210> SEQ ID NO 99

```
<211> LENGTH: 95
<212> TYPE: DNA
<213> ORGANISM: Artificial Sequence
<220> FEATURE:
<223> OTHER INFORMATION: Probe

<400> SEQUENCE: 99
atgtgactgg cacgggagtt gatcctggtt ttcacccaaa atctgttttc caataaattc      60
tcagatccag gaagaggaaa ggaaaaacat caaaa                                 95

<210> SEQ ID NO 100
<211> LENGTH: 95
<212> TYPE: DNA
<213> ORGANISM: Artificial Sequence
<220> FEATURE:
<223> OTHER INFORMATION: Probe

<400> SEQUENCE: 100
atgtgactgg cacgggagtt gatcctggtt ttcacatact ccatctcccg taaaaatagt      60
gagacttgag taatgtttga tgtcacttgt ctttc                                 95

<210> SEQ ID NO 101
<211> LENGTH: 95
<212> TYPE: DNA
<213> ORGANISM: Artificial Sequence
<220> FEATURE:
<223> OTHER INFORMATION: Probe

<400> SEQUENCE: 101
atgtgactgg cacgggagtt gatcctggtt ttcaccagtc accactatat tattctaggt      60
atcccagaaa agttaaagtc aaatctgaaa cacat                                 95

<210> SEQ ID NO 102
<211> LENGTH: 95
<212> TYPE: DNA
<213> ORGANISM: Artificial Sequence
<220> FEATURE:
<223> OTHER INFORMATION: Probe

<400> SEQUENCE: 102
atgtgactgg cacgggagtt gatcctggtt ttcaccgccc cgcgtccgac ccgcggatcc      60
cgcggcgtcc ggcccgggtg gtctggatcg cggag                                 95

<210> SEQ ID NO 103
<211> LENGTH: 95
<212> TYPE: DNA
<213> ORGANISM: Artificial Sequence
<220> FEATURE:
<223> OTHER INFORMATION: Probe

<400> SEQUENCE: 103
atgtgactgg cacgggagtt gatcctggtt ttcacccata cgggcagcac gacgcgcgga      60
ctgcgattgc agaagatgac ctgggagggc tcgcg                                 95

<210> SEQ ID NO 104
<211> LENGTH: 95
<212> TYPE: DNA
<213> ORGANISM: Artificial Sequence
<220> FEATURE:
<223> OTHER INFORMATION: Probe

<400> SEQUENCE: 104
atgtgactgg cacgggagtt gatcctggtt ttcactagag gggcttcaga ccgtgctatc      60
```

```
gtccctgctg ggtcgggcct aagcgccggg cccgt                                  95
```

<210> SEQ ID NO 105
<211> LENGTH: 95
<212> TYPE: DNA
<213> ORGANISM: Artificial Sequence
<220> FEATURE:
<223> OTHER INFORMATION: Probe

<400> SEQUENCE: 105

```
atgtgactgg cacgggagtt gatcctggtt ttcacggcgc cgaggaggag atggaggccg       60
ggcggccgcg gcccgtgctg cgctcggtga actcg                                  95
```

<210> SEQ ID NO 106
<211> LENGTH: 95
<212> TYPE: DNA
<213> ORGANISM: Artificial Sequence
<220> FEATURE:
<223> OTHER INFORMATION: Probe

<400> SEQUENCE: 106

```
atgtgactgg cacgggagtt gatcctggtt ttcacggtgt gggccaccgt gcccagccac       60
cggtgtggct ctttaacaac ctttgcttgt cccga                                  95
```

<210> SEQ ID NO 107
<211> LENGTH: 95
<212> TYPE: DNA
<213> ORGANISM: Artificial Sequence
<220> FEATURE:
<223> OTHER INFORMATION: Probe

<400> SEQUENCE: 107

```
atgtgactgg cacgggagtt gatcctggtt ttcacaagtg gtctatcctg tacttaccac       60
aacaacctta tcttttttaaa aagtaaaacg tcagt                                 95
```

<210> SEQ ID NO 108
<211> LENGTH: 95
<212> TYPE: DNA
<213> ORGANISM: Artificial Sequence
<220> FEATURE:
<223> OTHER INFORMATION: Probe

<400> SEQUENCE: 108

```
atgtgactgg cacgggagtt gatcctggtt ttcaccttgt tcgttccttg tactgagacc       60
ctagtctgcc actgaggatt tggtttttgc ccttc                                  95
```

<210> SEQ ID NO 109
<211> LENGTH: 95
<212> TYPE: DNA
<213> ORGANISM: Artificial Sequence
<220> FEATURE:
<223> OTHER INFORMATION: Probe

<400> SEQUENCE: 109

```
atgtgactgg cacgggagtt gatcctggtt ttcacatcaa gactcatcag taccatcaaa       60
agctgagatg aaacagtgta agtttcaaca gaaat                                  95
```

<210> SEQ ID NO 110
<211> LENGTH: 75
<212> TYPE: DNA
<213> ORGANISM: Artificial Sequence
<220> FEATURE:

<223> OTHER INFORMATION: Probe

<400> SEQUENCE: 110
atgtgactgg cacgggagtt gatcctggtt ttcacaccta ctggatgtgc ctgactgttt    60 cccttcttc ttccc    75

<210> SEQ ID NO 111
<211> LENGTH: 75
<212> TYPE: DNA
<213> ORGANISM: Artificial Sequence
<220> FEATURE:
<223> OTHER INFORMATION: Probe

<400> SEQUENCE: 111
atgtgactgg cacgggagtt gatcctggtt ttcacgggaa aaaaaagatg ggtctgtgtg    60
ggagggcagg tactt    75

<210> SEQ ID NO 112
<211> LENGTH: 75
<212> TYPE: DNA
<213> ORGANISM: Artificial Sequence
<220> FEATURE:
<223> OTHER INFORMATION: Probe

<400> SEQUENCE: 112
atgtgactgg cacgggagtt gatcctggtt ttcacttaat aagattccct ggtctcgttt    60
gtctacctgt taatg    75

<210> SEQ ID NO 113
<211> LENGTH: 75
<212> TYPE: DNA
<213> ORGANISM: Artificial Sequence
<220> FEATURE:
<223> OTHER INFORMATION: Probe

<400> SEQUENCE: 113
atgtgactgg cacgggagtt gatcctggtt ttcaccccca cccttgtta ttgccacaaa    60 atcctgagga tgatc    75

<210> SEQ ID NO 114
<211> LENGTH: 75
<212> TYPE: DNA
<213> ORGANISM: Artificial Sequence
<220> FEATURE:
<223> OTHER INFORMATION: Probe

<400> SEQUENCE: 114
atgtgactgg cacgggagtt gatcctggtt ttcacgctga gcaggaggtg gcaggtaccc    60
cagactggga ggtaa    75

<210> SEQ ID NO 115
<211> LENGTH: 75
<212> TYPE: DNA
<213> ORGANISM: Artificial Sequence
<220> FEATURE:
<223> OTHER INFORMATION: Probe

<400> SEQUENCE: 115
atgtgactgg cacgggagtt gatcctggtt ttcacggccc agtctgttca cacatggctg    60
ctgcctctca gctct    75

```
<210> SEQ ID NO 116
<211> LENGTH: 75
<212> TYPE: DNA
<213> ORGANISM: Artificial Sequence
<220> FEATURE:
<223> OTHER INFORMATION: Probe

<400> SEQUENCE: 116
atgtgactgg cacgggagtt gatcctggtt ttcacgaaag tcatttgtca aggccttcag    60
ttggcagacg tgctc                                                    75

<210> SEQ ID NO 117
<211> LENGTH: 75
<212> TYPE: DNA
<213> ORGANISM: Artificial Sequence
<220> FEATURE:
<223> OTHER INFORMATION: Probe

<400> SEQUENCE: 117
atgtgactgg cacgggagtt gatcctggtt ttcacaatct gtggaaacgc tgccacacaa    60
tcttagcaca caaga                                                    75

<210> SEQ ID NO 118
<211> LENGTH: 75
<212> TYPE: DNA
<213> ORGANISM: Artificial Sequence
<220> FEATURE:
<223> OTHER INFORMATION: Probe

<400> SEQUENCE: 118
atgtgactgg cacgggagtt gatcctggtt ttcactgctt gcaaacaac agaatcttct    60 ctccatgaaa tcatg                                                    75

<210> SEQ ID NO 119
<211> LENGTH: 75
<212> TYPE: DNA
<213> ORGANISM: Artificial Sequence
<220> FEATURE:
<223> OTHER INFORMATION: Probe

<400> SEQUENCE: 119
atgtgactgg cacgggagtt gatcctggtt ttcacatttt ctcacaaagg aaaccaagat    60
aaaaggttta aatgg                                                    75

<210> SEQ ID NO 120
<211> LENGTH: 75
<212> TYPE: DNA
<213> ORGANISM: Artificial Sequence
<220> FEATURE:
<223> OTHER INFORMATION: Probe

<400> SEQUENCE: 120
atgtgactgg cacgggagtt gatcctggtt ttcactgctt tctgccaaaa ttaatgtgct    60
gaacttaaac ttacc                                                    75

<210> SEQ ID NO 121
<211> LENGTH: 75
<212> TYPE: DNA
<213> ORGANISM: Artificial Sequence
<220> FEATURE:
<223> OTHER INFORMATION: Probe

<400> SEQUENCE: 121
```

```
atgtgactgg cacgggagtt gatcctggtt ttcacccaat gcaacagact ttaaagaagt    60
tgtgttttac aatgc                                                     75

<210> SEQ ID NO 122
<211> LENGTH: 75
<212> TYPE: DNA
<213> ORGANISM: Artificial Sequence
<220> FEATURE:
<223> OTHER INFORMATION: Probe

<400> SEQUENCE: 122
atgtgactgg cacgggagtt gatcctggtt ttcacatttt gcagaaaaca gatctgtatt    60
tatttcagtg ttact                                                     75

<210> SEQ ID NO 123
<211> LENGTH: 75
<212> TYPE: DNA
<213> ORGANISM: Artificial Sequence
<220> FEATURE:
<223> OTHER INFORMATION: Probe

<400> SEQUENCE: 123
atgtgactgg cacgggagtt gatcctggtt ttcactgtgt tactaatgac tgtgctataa    60
cttttttttc tttcc                                                     75

<210> SEQ ID NO 124
<211> LENGTH: 75
<212> TYPE: DNA
<213> ORGANISM: Artificial Sequence
<220> FEATURE:
<223> OTHER INFORMATION: Probe

<400> SEQUENCE: 124
atgtgactgg cacgggagtt gatcctggtt ttcactgcgc caggtttccg caccaagacc    60
cctttaactc aagac                                                     75

<210> SEQ ID NO 125
<211> LENGTH: 75
<212> TYPE: DNA
<213> ORGANISM: Artificial Sequence
<220> FEATURE:
<223> OTHER INFORMATION: Probe

<400> SEQUENCE: 125
atgtgactgg cacgggagtt gatcctggtt ttcacggggt gggcagcagc tcgaatttct    60
tccagatatc ctcgc                                                     75

<210> SEQ ID NO 126
<211> LENGTH: 75
<212> TYPE: DNA
<213> ORGANISM: Artificial Sequence
<220> FEATURE:
<223> OTHER INFORMATION: Probe

<400> SEQUENCE: 126
atgtgactgg cacgggagtt gatcctggtt ttcaccatgg tgaaccagag tttcatctgc    60
gacccggacg acgag                                                     75

<210> SEQ ID NO 127
<211> LENGTH: 75
<212> TYPE: DNA
<213> ORGANISM: Artificial Sequence
```

```
<220> FEATURE:
<223> OTHER INFORMATION: Probe

<400> SEQUENCE: 127
atgtgactgg cacgggagtt gatcctggtt ttcacgacgg agagaaggcg ctggagtctt    60
gcgaggcgca ggact                                                    75

<210> SEQ ID NO 128
<211> LENGTH: 75
<212> TYPE: DNA
<213> ORGANISM: Artificial Sequence
<220> FEATURE:
<223> OTHER INFORMATION: Probe

<400> SEQUENCE: 128
atgtgactgg cacgggagtt gatcctggtt ttcacgagca tctaggtagg tctttgtagc    60
caatgttacc cgatt                                                    75

<210> SEQ ID NO 129
<211> LENGTH: 75
<212> TYPE: DNA
<213> ORGANISM: Artificial Sequence
<220> FEATURE:
<223> OTHER INFORMATION: Probe

<400> SEQUENCE: 129
atgtgactgg cacgggagtt gatcctggtt ttcacgcaca gaaattacag gccatgcaca    60
gagagaaata cccga                                                    75

<210> SEQ ID NO 130
<211> LENGTH: 75
<212> TYPE: DNA
<213> ORGANISM: Artificial Sequence
<220> FEATURE:
<223> OTHER INFORMATION: Probe

<400> SEQUENCE: 130
atgtgactgg cacgggagtt gatcctggtt ttcacagacc ctagtctgcc actgaggatt    60
tggtttttgc ccttc                                                    75

<210> SEQ ID NO 131
<211> LENGTH: 75
<212> TYPE: DNA
<213> ORGANISM: Artificial Sequence
<220> FEATURE:
<223> OTHER INFORMATION: Probe

<400> SEQUENCE: 131
atgtgactgg cacgggagtt gatcctggtt ttcactcaaa agctgagatg aaacagtgta    60
agtttcaaca gaaat                                                    75

<210> SEQ ID NO 132
<211> LENGTH: 75
<212> TYPE: DNA
<213> ORGANISM: Artificial Sequence
<220> FEATURE:
<223> OTHER INFORMATION: Probe

<400> SEQUENCE: 132
atgtgactgg cacgggagtt gatcctggtt ttcacagaga tgtaactgct gacatcctcc    60
ctattttgca tctca                                                    75
```

<210> SEQ ID NO 133
<211> LENGTH: 75
<212> TYPE: DNA
<213> ORGANISM: Artificial Sequence
<220> FEATURE:
<223> OTHER INFORMATION: Probe

<400> SEQUENCE: 133
atgtgactgg cacgggagtt gatcctggtt ttcacgaatg ccatgaccaa agtattcttc    60
tgtatcttct ttctt                                                    75

<210> SEQ ID NO 134
<211> LENGTH: 75
<212> TYPE: DNA
<213> ORGANISM: Artificial Sequence
<220> FEATURE:
<223> OTHER INFORMATION: Probe

<400> SEQUENCE: 134
atgtgactgg cacgggagtt gatcctggtt ttcacgggcc tcccgcagac ttgcgaagtt    60
cccactctct gggcg                                                    75

<210> SEQ ID NO 135
<211> LENGTH: 75
<212> TYPE: DNA
<213> ORGANISM: Artificial Sequence
<220> FEATURE:
<223> OTHER INFORMATION: Probe

<400> SEQUENCE: 135
atgtgactgg cacgggagtt gatcctggtt ttcacgctgc ccaagcggag gctgggccgg    60
ctgtgctggc ctctt                                                    75

<210> SEQ ID NO 136
<211> LENGTH: 75
<212> TYPE: DNA
<213> ORGANISM: Artificial Sequence
<220> FEATURE:
<223> OTHER INFORMATION: Probe

<400> SEQUENCE: 136
atgtgactgg cacgggagtt gatcctggtt ttcacgccat gaaacgtgtt tcaagcatag    60
ttttgacaga taacg                                                    75

<210> SEQ ID NO 137
<211> LENGTH: 75
<212> TYPE: DNA
<213> ORGANISM: Artificial Sequence
<220> FEATURE:
<223> OTHER INFORMATION: Probe

<400> SEQUENCE: 137
atgtgactgg cacgggagtt gatcctggtt ttcacaacat ccctgatgtc tgcatttgtc    60
ctttgactgg tgttt                                                    75

<210> SEQ ID NO 138
<211> LENGTH: 75
<212> TYPE: DNA
<213> ORGANISM: Artificial Sequence
<220> FEATURE:
<223> OTHER INFORMATION: Probe

<400> SEQUENCE: 138

```
atgtgactgg cacgggagtt gatcctggtt ttcactttgg agcaggagtg tgattctggc    60
caaccaccct ctctg                                                     75

<210> SEQ ID NO 139
<211> LENGTH: 75
<212> TYPE: DNA
<213> ORGANISM: Artificial Sequence
<220> FEATURE:
<223> OTHER INFORMATION: Probe

<400> SEQUENCE: 139
atgtgactgg cacgggagtt gatcctggtt ttcacctgtt agacccaagt gctgcccaag    60
ggcagcgccc tgctc                                                     75

<210> SEQ ID NO 140
<211> LENGTH: 75
<212> TYPE: DNA
<213> ORGANISM: Artificial Sequence
<220> FEATURE:
<223> OTHER INFORMATION: Probe

<400> SEQUENCE: 140
atgtgactgg cacgggagtt gatcctggtt ttcacaagag ttttttttc ttattctgag     60 gttatctttt tacca                                                     75

<210> SEQ ID NO 141
<211> LENGTH: 75
<212> TYPE: DNA
<213> ORGANISM: Artificial Sequence
<220> FEATURE:
<223> OTHER INFORMATION: Probe

<400> SEQUENCE: 141
atgtgactgg cacgggagtt gatcctggtt ttcacaattc tcagatccag gaagaggaaa    60
ggaaaaacat caaaa                                                     75

<210> SEQ ID NO 142
<211> LENGTH: 75
<212> TYPE: DNA
<213> ORGANISM: Artificial Sequence
<220> FEATURE:
<223> OTHER INFORMATION: Probe

<400> SEQUENCE: 142
atgtgactgg cacgggagtt gatcctggtt ttcacatagt gagacttgag taatgtttga    60
tgtcacttgt ctttc                                                     75

<210> SEQ ID NO 143
<211> LENGTH: 75
<212> TYPE: DNA
<213> ORGANISM: Artificial Sequence
<220> FEATURE:
<223> OTHER INFORMATION: Probe

<400> SEQUENCE: 143
atgtgactgg cacgggagtt gatcctggtt ttcactaggt atcccagaaa agttaaagtc    60
aaatctgaaa cacat                                                     75

<210> SEQ ID NO 144
<211> LENGTH: 75
<212> TYPE: DNA
```

```
<213> ORGANISM: Artificial Sequence
<220> FEATURE:
<223> OTHER INFORMATION: Probe

<400> SEQUENCE: 144
atgtgactgg cacgggagtt gatcctggtt ttcacgatcc cgcggcgtcc ggcccgggtg    60
gtctggatcg cggag                                                    75

<210> SEQ ID NO 145
<211> LENGTH: 75
<212> TYPE: DNA
<213> ORGANISM: Artificial Sequence
<220> FEATURE:
<223> OTHER INFORMATION: Probe

<400> SEQUENCE: 145
atgtgactgg cacgggagtt gatcctggtt ttcacgcgga ctgcgattgc agaagatgac    60
ctgggagggc tcgcg                                                    75

<210> SEQ ID NO 146
<211> LENGTH: 75
<212> TYPE: DNA
<213> ORGANISM: Artificial Sequence
<220> FEATURE:
<223> OTHER INFORMATION: Probe

<400> SEQUENCE: 146
atgtgactgg cacgggagtt gatcctggtt ttcacctatc gtccctgctg ggtcgggcct    60
aagcgccggg cccgt                                                    75

<210> SEQ ID NO 147
<211> LENGTH: 75
<212> TYPE: DNA
<213> ORGANISM: Artificial Sequence
<220> FEATURE:
<223> OTHER INFORMATION: Probe

<400> SEQUENCE: 147
atgtgactgg cacgggagtt gatcctggtt ttcacggccg ggcggccgcg gcccgtgctg    60
cgctcggtga actcg                                                    75

<210> SEQ ID NO 148
<211> LENGTH: 75
<212> TYPE: DNA
<213> ORGANISM: Artificial Sequence
<220> FEATURE:
<223> OTHER INFORMATION: Probe

<400> SEQUENCE: 148
atgtgactgg cacgggagtt gatcctggtt ttcacgccac cggtgtggct ctttaacaac    60
ctttgcttgt cccga                                                    75

<210> SEQ ID NO 149
<211> LENGTH: 75
<212> TYPE: DNA
<213> ORGANISM: Artificial Sequence
<220> FEATURE:
<223> OTHER INFORMATION: Probe

<400> SEQUENCE: 149
atgtgactgg cacgggagtt gatcctggtt ttcacaccac aacaaccttta tcttttttaaa   60 aagtaaaacg tcagt                                                    75
```

```
<210> SEQ ID NO 150
<211> LENGTH: 75
<212> TYPE: DNA
<213> ORGANISM: Artificial Sequence
<220> FEATURE:
<223> OTHER INFORMATION: Probe

<400> SEQUENCE: 150
atgtgactgg cacgggagtt gatcctggtt ttcacagacc ctagtctgcc actgaggatt      60
tggtttttgc ccttc                                                      75

<210> SEQ ID NO 151
<211> LENGTH: 75
<212> TYPE: DNA
<213> ORGANISM: Artificial Sequence
<220> FEATURE:
<223> OTHER INFORMATION: Probe

<400> SEQUENCE: 151
atgtgactgg cacgggagtt gatcctggtt ttcactcaaa agctgagatg aaacagtgta      60
agtttcaaca gaaat                                                      75

<210> SEQ ID NO 152
<211> LENGTH: 58
<212> TYPE: DNA
<213> ORGANISM: Artificial Sequence
<220> FEATURE:
<223> OTHER INFORMATION: ACA2_FLFP primer

<400> SEQUENCE: 152
aatgatacgg cgaccaccga gatctacacg tcatgcagga ccagagaatt cgaataca       58

<210> SEQ ID NO 153
<211> LENGTH: 57
<212> TYPE: DNA
<213> ORGANISM: Artificial Sequence
<220> FEATURE:
<223> OTHER INFORMATION: CAC3_FLRP primer

<400> SEQUENCE: 153
caagcagaag acggcatacg agatgtgact ggcacgggag ttgatcctgg ttttcac        57

<210> SEQ ID NO 154
<211> LENGTH: 75
<212> TYPE: DNA
<213> ORGANISM: Artificial Sequence
<220> FEATURE:
<223> OTHER INFORMATION: Probe

<400> SEQUENCE: 154
atgtgactgg cacgggagtt gatcctggtt ttcaccgaat gagggtgatg tttttccgcg      60
gcacctcctt caggt                                                      75

<210> SEQ ID NO 155
<211> LENGTH: 75
<212> TYPE: DNA
<213> ORGANISM: Artificial Sequence
<220> FEATURE:
<223> OTHER INFORMATION: Probe

<400> SEQUENCE: 155
atgtgactgg cacgggagtt gatcctggtt ttcacgttgt agtcggtcat gatggtcgag      60
```

```
gtgcggagct tgctc                                              75

<210> SEQ ID NO 156
<211> LENGTH: 75
<212> TYPE: DNA
<213> ORGANISM: Artificial Sequence
<220> FEATURE:
<223> OTHER INFORMATION: Probe

<400> SEQUENCE: 156
atgtgactgg cacgggagtt gatcctggtt ttcacgcagc tcctggtgct tccggcggta   60
cactgcaggt gggtg                                              75

<210> SEQ ID NO 157
<211> LENGTH: 75
<212> TYPE: DNA
<213> ORGANISM: Artificial Sequence
<220> FEATURE:
<223> OTHER INFORMATION: Probe

<400> SEQUENCE: 157
atgtgactgg cacgggagtt gatcctggtt ttcacctaca caggccactt cctacaggaa   60
gcctccctgg atctc                                              75

<210> SEQ ID NO 158
<211> LENGTH: 75
<212> TYPE: DNA
<213> ORGANISM: Artificial Sequence
<220> FEATURE:
<223> OTHER INFORMATION: Probe

<400> SEQUENCE: 158
atgtgactgg cacgggagtt gatcctggtt ttcacgaaat actaataaaa tgattaaaga   60
aggtgtgtct ttaat                                              75

<210> SEQ ID NO 159
<211> LENGTH: 75
<212> TYPE: DNA
<213> ORGANISM: Artificial Sequence
<220> FEATURE:
<223> OTHER INFORMATION: Probe

<400> SEQUENCE: 159
atgtgactgg cacgggagtt gatcctggtt ttcactatat ggaaaataat tatttgtatt   60
atatagggca gagtc                                              75

<210> SEQ ID NO 160
<211> LENGTH: 75
<212> TYPE: DNA
<213> ORGANISM: Artificial Sequence
<220> FEATURE:
<223> OTHER INFORMATION: Probe

<400> SEQUENCE: 160
atgtgactgg cacgggagtt gatcctggtt ttcacattag acccaatatg gtctgcagat   60
tttattagaa gaaat                                              75

<210> SEQ ID NO 161
<211> LENGTH: 75
<212> TYPE: DNA
<213> ORGANISM: Artificial Sequence
<220> FEATURE:
<223> OTHER INFORMATION: Probe
```

```
<400> SEQUENCE: 161
atgtgactgg cacgggagtt gatcctggtt ttcacgtgaa ccagcagact gtgttgcaag    60
tataacccca cgtga                                                     75

<210> SEQ ID NO 162
<211> LENGTH: 75
<212> TYPE: DNA
<213> ORGANISM: Artificial Sequence
<220> FEATURE:
<223> OTHER INFORMATION: Probe

<400> SEQUENCE: 162
atgtgactgg cacgggagtt gatcctggtt ttcacgccat ggagcctaag gaagtttcag    60
caaggcccta agggg                                                     75

<210> SEQ ID NO 163
<211> LENGTH: 75
<212> TYPE: DNA
<213> ORGANISM: Artificial Sequence
<220> FEATURE:
<223> OTHER INFORMATION: Probe

<400> SEQUENCE: 163
atgtgactgg cacgggagtt gatcctggtt ttcaccccag gaattggcct gccttagtat    60
ttctgctgtg ctcag                                                     75

<210> SEQ ID NO 164
<211> LENGTH: 75
<212> TYPE: DNA
<213> ORGANISM: Artificial Sequence
<220> FEATURE:
<223> OTHER INFORMATION: Probe

<400> SEQUENCE: 164
atgtgactgg cacgggagtt gatcctggtt ttcactttga gggtgcagct gggatcttgg    60
tcagttgtgt ttcct                                                     75

<210> SEQ ID NO 165
<211> LENGTH: 75
<212> TYPE: DNA
<213> ORGANISM: Artificial Sequence
<220> FEATURE:
<223> OTHER INFORMATION: Probe

<400> SEQUENCE: 165
atgtgactgg cacgggagtt gatcctggtt ttcaccacat catgaaaaga tctctgaatt    60
ggtgtctggg gatct                                                     75

<210> SEQ ID NO 166
<211> LENGTH: 75
<212> TYPE: DNA
<213> ORGANISM: Artificial Sequence
<220> FEATURE:
<223> OTHER INFORMATION: Probe

<400> SEQUENCE: 166
atgtgactgg cacgggagtt gatcctggtt ttcactgagg accaggtcac aggacctctt    60
tggactgcag tttcc                                                     75

<210> SEQ ID NO 167
```

```
<211> LENGTH: 75
<212> TYPE: DNA
<213> ORGANISM: Artificial Sequence
<220> FEATURE:
<223> OTHER INFORMATION: Probe

<400> SEQUENCE: 167
atgtgactgg cacgggagtt gatcctggtt ttcactaacc actgccactc cccaccctct    60
agggttgtca atgaa                                                     75

<210> SEQ ID NO 168
<211> LENGTH: 75
<212> TYPE: DNA
<213> ORGANISM: Artificial Sequence
<220> FEATURE:
<223> OTHER INFORMATION: Probe

<400> SEQUENCE: 168
atgtgactgg cacgggagtt gatcctggtt ttcacgagct ctaccaatgt gagtgaccat    60
tatcactcct acatg                                                     75

<210> SEQ ID NO 169
<211> LENGTH: 75
<212> TYPE: DNA
<213> ORGANISM: Artificial Sequence
<220> FEATURE:
<223> OTHER INFORMATION: Probe

<400> SEQUENCE: 169
atgtgactgg cacgggagtt gatcctggtt ttcacaaaat tgtgattcag tgggtagatt    60
ctgtgtgtaa agccc                                                     75

<210> SEQ ID NO 170
<211> LENGTH: 75
<212> TYPE: DNA
<213> ORGANISM: Artificial Sequence
<220> FEATURE:
<223> OTHER INFORMATION: Probe

<400> SEQUENCE: 170
atgtgactgg cacgggagtt gatcctggtt ttcactatgt gctcagttcc ctcctctatg    60
caatggaccg accgt                                                     75

<210> SEQ ID NO 171
<211> LENGTH: 75
<212> TYPE: DNA
<213> ORGANISM: Artificial Sequence
<220> FEATURE:
<223> OTHER INFORMATION: Probe

<400> SEQUENCE: 171
atgtgactgg cacgggagtt gatcctggtt ttcacgtgta aattgccgag cacgtagtaa    60
ccatgcaaca agtgt                                                     75

<210> SEQ ID NO 172
<211> LENGTH: 75
<212> TYPE: DNA
<213> ORGANISM: Artificial Sequence
<220> FEATURE:
<223> OTHER INFORMATION: Probe

<400> SEQUENCE: 172
atgtgactgg cacgggagtt gatcctggtt ttcactgggg acacagtgtg tgctgccatc    60
```

```
tcccttctac cggca                                                    75

<210> SEQ ID NO 173
<211> LENGTH: 75
<212> TYPE: DNA
<213> ORGANISM: Artificial Sequence
<220> FEATURE:
<223> OTHER INFORMATION: Probe

<400> SEQUENCE: 173
atgtgactgg cacgggagtt gatcctggtt ttcacaagag cctttccctc tgcccttttc    60
aagcctctgc ccatc                                                    75

<210> SEQ ID NO 174
<211> LENGTH: 75
<212> TYPE: DNA
<213> ORGANISM: Artificial Sequence
<220> FEATURE:
<223> OTHER INFORMATION: Probe

<400> SEQUENCE: 174
atgtgactgg cacgggagtt gatcctggtt ttcacgacca cactgagttc tctgtgacct    60
gcaggtcagc tcacc                                                    75

<210> SEQ ID NO 175
<211> LENGTH: 75
<212> TYPE: DNA
<213> ORGANISM: Artificial Sequence
<220> FEATURE:
<223> OTHER INFORMATION: Probe

<400> SEQUENCE: 175
atgtgactgg cacgggagtt gatcctggtt ttcactttcc tatctctctg cctggagggt    60
ggtggagggc tggtt                                                    75

<210> SEQ ID NO 176
<211> LENGTH: 75
<212> TYPE: DNA
<213> ORGANISM: Artificial Sequence
<220> FEATURE:
<223> OTHER INFORMATION: Probe

<400> SEQUENCE: 176
atgtgactgg cacgggagtt gatcctggtt ttcacaaaca ggagctgcgc cggtggaagc    60
atgtgggagc tagaa                                                    75

<210> SEQ ID NO 177
<211> LENGTH: 75
<212> TYPE: DNA
<213> ORGANISM: Artificial Sequence
<220> FEATURE:
<223> OTHER INFORMATION: Probe

<400> SEQUENCE: 177
atgtgactgg cacgggagtt gatcctggtt ttcacggaca ctgaaggagc tccccacccc    60
ctgatcagcc aggag                                                    75

<210> SEQ ID NO 178
<211> LENGTH: 75
<212> TYPE: DNA
<213> ORGANISM: Artificial Sequence
<220> FEATURE:
```

<223> OTHER INFORMATION: Probe

<400> SEQUENCE: 178
atgtgactgg cacgggagtt gatcctggtt ttcacgggaa ctgcagctgc tctggtgggg    60
ggaaggttgg gagct    75

<210> SEQ ID NO 179
<211> LENGTH: 75
<212> TYPE: DNA
<213> ORGANISM: Artificial Sequence
<220> FEATURE:
<223> OTHER INFORMATION: Probe

<400> SEQUENCE: 179
atgtgactgg cacgggagtt gatcctggtt ttcacaccca attccaggga ctagcataac    60
gaagtgacac cttgg    75

<210> SEQ ID NO 180
<211> LENGTH: 75
<212> TYPE: DNA
<213> ORGANISM: Artificial Sequence
<220> FEATURE:
<223> OTHER INFORMATION: Probe

<400> SEQUENCE: 180
atgtgactgg cacgggagtt gatcctggtt ttcaccctgc cccttggga gtccctgggg    60 ctctgtgcac tcacc    75

<210> SEQ ID NO 181
<211> LENGTH: 75
<212> TYPE: DNA
<213> ORGANISM: Artificial Sequence
<220> FEATURE:
<223> OTHER INFORMATION: Probe

<400> SEQUENCE: 181
atgtgactgg cacgggagtt gatcctggtt ttcacggaag cacccccggt attaaaacga    60
acggggcgga aagaa    75

<210> SEQ ID NO 182
<211> LENGTH: 75
<212> TYPE: DNA
<213> ORGANISM: Artificial Sequence
<220> FEATURE:
<223> OTHER INFORMATION: Probe

<400> SEQUENCE: 182
atgtgactgg cacgggagtt gatcctggtt ttcacctaac aaagggacg cgacccgggg    60 tccagtgccc caggg    75

<210> SEQ ID NO 183
<211> LENGTH: 75
<212> TYPE: DNA
<213> ORGANISM: Artificial Sequence
<220> FEATURE:
<223> OTHER INFORMATION: Probe

<400> SEQUENCE: 183
atgtgactgg cacgggagtt gatcctggtt ttcaccctgg ggggactggg tggcctcacc    60 cccaaccccgg tcatc    75

-continued

```
<210> SEQ ID NO 184
<211> LENGTH: 75
<212> TYPE: DNA
<213> ORGANISM: Artificial Sequence
<220> FEATURE:
<223> OTHER INFORMATION: Probe

<400> SEQUENCE: 184
atgtgactgg cacgggagtt gatcctggtt ttcaccgcgc tccagcttct cgcgggcgga    60
gaagccgctc cacat                                                    75

<210> SEQ ID NO 185
<211> LENGTH: 75
<212> TYPE: DNA
<213> ORGANISM: Artificial Sequence
<220> FEATURE:
<223> OTHER INFORMATION: Probe

<400> SEQUENCE: 185
atgtgactgg cacgggagtt gatcctggtt ttcaccccac ccggccgccg agtgcgtgga    60
tcccgccgtg gtctt                                                    75

<210> SEQ ID NO 186
<211> LENGTH: 75
<212> TYPE: DNA
<213> ORGANISM: Artificial Sequence
<220> FEATURE:
<223> OTHER INFORMATION: Probe

<400> SEQUENCE: 186
atgtgactgg cacgggagtt gatcctggtt ttcacgggca cgggcgctgg ctcgcgcttg    60
ttcacgggaa agggg                                                    75

<210> SEQ ID NO 187
<211> LENGTH: 75
<212> TYPE: DNA
<213> ORGANISM: Artificial Sequence
<220> FEATURE:
<223> OTHER INFORMATION: Probe

<400> SEQUENCE: 187
atgtgactgg cacgggagtt gatcctggtt ttcacaacat ggatatatat gtgaatttca    60
ttcaaatggt tctca                                                    75

<210> SEQ ID NO 188
<211> LENGTH: 75
<212> TYPE: DNA
<213> ORGANISM: Artificial Sequence
<220> FEATURE:
<223> OTHER INFORMATION: Probe

<400> SEQUENCE: 188
atgtgactgg cacgggagtt gatcctggtt ttcactaaac caacattctt aatgtcaaca    60
caatgtttgt ttaaa                                                    75

<210> SEQ ID NO 189
<211> LENGTH: 75
<212> TYPE: DNA
<213> ORGANISM: Artificial Sequence
<220> FEATURE:
<223> OTHER INFORMATION: Probe

<400> SEQUENCE: 189
```

```
atgtgactgg cacgggagtt gatcctggtt ttcaccccta cgtggagagt gaggatgcac      60
ccccacagaa gaaga                                                      75

<210> SEQ ID NO 190
<211> LENGTH: 75
<212> TYPE: DNA
<213> ORGANISM: Artificial Sequence
<220> FEATURE:
<223> OTHER INFORMATION: Probe

<400> SEQUENCE: 190
atgtgactgg cacgggagtt gatcctggtt ttcacatgac actcttgagc ggacgtgggg      60
acgcctcgct cttta                                                      75

<210> SEQ ID NO 191
<211> LENGTH: 75
<212> TYPE: DNA
<213> ORGANISM: Artificial Sequence
<220> FEATURE:
<223> OTHER INFORMATION: Probe

<400> SEQUENCE: 191
atgtgactgg cacgggagtt gatcctggtt ttcactctca cgctcaggga ccacgtgccg      60
gagttggtaa agaat                                                      75

<210> SEQ ID NO 192
<211> LENGTH: 75
<212> TYPE: DNA
<213> ORGANISM: Artificial Sequence
<220> FEATURE:
<223> OTHER INFORMATION: Probe

<400> SEQUENCE: 192
atgtgactgg cacgggagtt gatcctggtt ttcaccagtg gccttttttca aaatgaccac     60 cttggcggcc ttctc                                                      75

<210> SEQ ID NO 193
<211> LENGTH: 75
<212> TYPE: DNA
<213> ORGANISM: Artificial Sequence
<220> FEATURE:
<223> OTHER INFORMATION: Probe

<400> SEQUENCE: 193
atgtgactgg cacgggagtt gatcctggtt ttcacgctag ggggctgggg ttggggtggg      60
ggtggtgggc ctgcc                                                      75

<210> SEQ ID NO 194
<211> LENGTH: 75
<212> TYPE: DNA
<213> ORGANISM: Artificial Sequence
<220> FEATURE:
<223> OTHER INFORMATION: Probe

<400> SEQUENCE: 194
atgtgactgg cacgggagtt gatcctggtt ttcaccagtt tccataggtc tgaaaatgtt      60
tcctgactca gaggg                                                      75

<210> SEQ ID NO 195
<211> LENGTH: 75
<212> TYPE: DNA
<213> ORGANISM: Artificial Sequence
```

```
<220> FEATURE:
<223> OTHER INFORMATION: Probe

<400> SEQUENCE: 195
atgtgactgg cacgggagtt gatcctggtt ttcacctgcc atggaggagc cgcagtcaga    60
tcctagcgtc gagcc                                                     75

<210> SEQ ID NO 196
<211> LENGTH: 75
<212> TYPE: DNA
<213> ORGANISM: Artificial Sequence
<220> FEATURE:
<223> OTHER INFORMATION: Probe

<400> SEQUENCE: 196
atgtgactgg cacgggagtt gatcctggtt ttcactcatg ctggatcccc acttttcctc    60
ttgcagcagc cagac                                                     75

<210> SEQ ID NO 197
<211> LENGTH: 75
<212> TYPE: DNA
<213> ORGANISM: Artificial Sequence
<220> FEATURE:
<223> OTHER INFORMATION: Probe

<400> SEQUENCE: 197
atgtgactgg cacgggagtt gatcctggtt ttcacagccc ccagccctc caggtcccca     60 gccctccagg tcccc                                                     75

<210> SEQ ID NO 198
<211> LENGTH: 75
<212> TYPE: DNA
<213> ORGANISM: Artificial Sequence
<220> FEATURE:
<223> OTHER INFORMATION: Probe

<400> SEQUENCE: 198
atgtgactgg cacgggagtt gatcctggtt ttcacgcaga gacctgtggg aagcgaaaat    60
tccatgggac tgact                                                     75

<210> SEQ ID NO 199
<211> LENGTH: 75
<212> TYPE: DNA
<213> ORGANISM: Artificial Sequence
<220> FEATURE:
<223> OTHER INFORMATION: Probe

<400> SEQUENCE: 199
atgtgactgg cacgggagtt gatcctggtt ttcacgcagg gggatacggc caggcattga    60
agtctcatgg aagcc                                                     75

<210> SEQ ID NO 200
<211> LENGTH: 75
<212> TYPE: DNA
<213> ORGANISM: Artificial Sequence
<220> FEATURE:
<223> OTHER INFORMATION: Probe

<400> SEQUENCE: 200
atgtgactgg cacgggagtt gatcctggtt ttcacccgtg caagtcacag acttggctgt    60
cccagaatgc aagaa                                                     75
```

```
<210> SEQ ID NO 201
<211> LENGTH: 75
<212> TYPE: DNA
<213> ORGANISM: Artificial Sequence
<220> FEATURE:
<223> OTHER INFORMATION: Probe

<400> SEQUENCE: 201
atgtgactgg cacgggagtt gatcctggtt ttcacccaga aaacctacca gggcagctac    60
ggtttccgtc tgggc                                                    75

<210> SEQ ID NO 202
<211> LENGTH: 75
<212> TYPE: DNA
<213> ORGANISM: Artificial Sequence
<220> FEATURE:
<223> OTHER INFORMATION: Probe

<400> SEQUENCE: 202
atgtgactgg cacgggagtt gatcctggtt ttcacgaagg acagaagat gacaggggcc     60 aggaggggc tggtg                                                     75

<210> SEQ ID NO 203
<211> LENGTH: 75
<212> TYPE: DNA
<213> ORGANISM: Artificial Sequence
<220> FEATURE:
<223> OTHER INFORMATION: Probe

<400> SEQUENCE: 203
atgtgactgg cacgggagtt gatcctggtt ttcacgtggc ccctgcacca gcagctccta    60
caccggcggc ccctg                                                    75

<210> SEQ ID NO 204
<211> LENGTH: 75
<212> TYPE: DNA
<213> ORGANISM: Artificial Sequence
<220> FEATURE:
<223> OTHER INFORMATION: Probe

<400> SEQUENCE: 204
atgtgactgg cacgggagtt gatcctggtt ttcacggggg gagcagcctc tggcattctg    60
ggagcttcat ctgga                                                    75

<210> SEQ ID NO 205
<211> LENGTH: 75
<212> TYPE: DNA
<213> ORGANISM: Artificial Sequence
<220> FEATURE:
<223> OTHER INFORMATION: Probe

<400> SEQUENCE: 205
atgtgactgg cacgggagtt gatcctggtt ttcaccccg gacgatattg aacaatggtt     60
cactgaagac ccagg                                                    75

<210> SEQ ID NO 206
<211> LENGTH: 75
<212> TYPE: DNA
<213> ORGANISM: Artificial Sequence
<220> FEATURE:
<223> OTHER INFORMATION: Probe

<400> SEQUENCE: 206
```

```
atgtgactgg cacgggagtt gatcctggtt ttcacctggg gggctggggg gctgaggacc    60
tggtcctctg actgc                                                    75

<210> SEQ ID NO 207
<211> LENGTH: 75
<212> TYPE: DNA
<213> ORGANISM: Artificial Sequence
<220> FEATURE:
<223> OTHER INFORMATION: Probe

<400> SEQUENCE: 207
atgtgactgg cacgggagtt gatcctggtt ttcaccctgg gcaaccagcc ctgtcgtctc    60
tccagcccca gctgc                                                    75

<210> SEQ ID NO 208
<211> LENGTH: 75
<212> TYPE: DNA
<213> ORGANISM: Artificial Sequence
<220> FEATURE:
<223> OTHER INFORMATION: Probe

<400> SEQUENCE: 208
atgtgactgg cacgggagtt gatcctggtt ttcacccatc gctatctgag cagcgctcat    60
ggtgggggca gcgcc                                                    75

<210> SEQ ID NO 209
<211> LENGTH: 75
<212> TYPE: DNA
<213> ORGANISM: Artificial Sequence
<220> FEATURE:
<223> OTHER INFORMATION: Probe

<400> SEQUENCE: 209
atgtgactgg cacgggagtt gatcctggtt ttcacgccat ctacaagcag tcacagcaca    60
tgacggaggt tgtga                                                    75

<210> SEQ ID NO 210
<211> LENGTH: 75
<212> TYPE: DNA
<213> ORGANISM: Artificial Sequence
<220> FEATURE:
<223> OTHER INFORMATION: Probe

<400> SEQUENCE: 210
atgtgactgg cacgggagtt gatcctggtt ttcaccatgg cgcggacgcg ggtgccgggc    60
gggggtgtgg aatca                                                    75

<210> SEQ ID NO 211
<211> LENGTH: 75
<212> TYPE: DNA
<213> ORGANISM: Artificial Sequence
<220> FEATURE:
<223> OTHER INFORMATION: Probe

<400> SEQUENCE: 211
atgtgactgg cacgggagtt gatcctggtt ttcactttgc caactggcca agacctgccc    60
tgtgcagctg tgggt                                                    75

<210> SEQ ID NO 212
<211> LENGTH: 75
<212> TYPE: DNA
```

```
<213> ORGANISM: Artificial Sequence
<220> FEATURE:
<223> OTHER INFORMATION: Probe

<400> SEQUENCE: 212
atgtgactgg cacgggagtt gatcctggtt ttcactgctt tatctgttca cttgtgccct    60
gactttcaac tctgt                                                    75

<210> SEQ ID NO 213
<211> LENGTH: 75
<212> TYPE: DNA
<213> ORGANISM: Artificial Sequence
<220> FEATURE:
<223> OTHER INFORMATION: Probe

<400> SEQUENCE: 213
atgtgactgg cacgggagtt gatcctggtt ttcacgaggg ccactgacaa ccacccttaa    60
cccctcctcc cagag                                                   75

<210> SEQ ID NO 214
<211> LENGTH: 75
<212> TYPE: DNA
<213> ORGANISM: Artificial Sequence
<220> FEATURE:
<223> OTHER INFORMATION: Probe

<400> SEQUENCE: 214
atgtgactgg cacgggagtt gatcctggtt ttcaccctca ggcggctcat agggcaccac    60
cacactatgt cgaaa                                                    75

<210> SEQ ID NO 215
<211> LENGTH: 75
<212> TYPE: DNA
<213> ORGANISM: Artificial Sequence
<220> FEATURE:
<223> OTHER INFORMATION: Probe

<400> SEQUENCE: 215
atgtgactgg cacgggagtt gatcctggtt ttcacaggaa atttgcgtgt ggagtatttg    60
gatgacagaa acact                                                    75

<210> SEQ ID NO 216
<211> LENGTH: 75
<212> TYPE: DNA
<213> ORGANISM: Artificial Sequence
<220> FEATURE:
<223> OTHER INFORMATION: Probe

<400> SEQUENCE: 216
atgtgactgg cacgggagtt gatcctggtt ttcacccagg gtccccaggc ctctgattcc    60
tcactgattg ctctt                                                    75

<210> SEQ ID NO 217
<211> LENGTH: 75
<212> TYPE: DNA
<213> ORGANISM: Artificial Sequence
<220> FEATURE:
<223> OTHER INFORMATION: Probe

<400> SEQUENCE: 217
atgtgactgg cacgggagtt gatcctggtt ttcacgaggc aagcagaggc tggggcacag    60
caggccagtg tgcag                                                    75
```

<210> SEQ ID NO 218
<211> LENGTH: 75
<212> TYPE: DNA
<213> ORGANISM: Artificial Sequence
<220> FEATURE:
<223> OTHER INFORMATION: Probe

<400> SEQUENCE: 218
atgtgactgg cacgggagtt gatcctggtt ttcaccctgg agtcttccag tgtgatgatg    60
gtgaggatgg gcctc                                                    75

<210> SEQ ID NO 219
<211> LENGTH: 75
<212> TYPE: DNA
<213> ORGANISM: Artificial Sequence
<220> FEATURE:
<223> OTHER INFORMATION: Probe

<400> SEQUENCE: 219
atgtgactgg cacgggagtt gatcctggtt ttcacactac atgtgtaaca gttcctgcat    60
gggcggcatg aaccg                                                    75

<210> SEQ ID NO 220
<211> LENGTH: 75
<212> TYPE: DNA
<213> ORGANISM: Artificial Sequence
<220> FEATURE:
<223> OTHER INFORMATION: Probe

<400> SEQUENCE: 220
atgtgactgg cacgggagtt gatcctggtt ttcaccttgc cacaggtctc cccaaggcgc    60
actggcctca tcttg                                                    75

<210> SEQ ID NO 221
<211> LENGTH: 75
<212> TYPE: DNA
<213> ORGANISM: Artificial Sequence
<220> FEATURE:
<223> OTHER INFORMATION: Probe

<400> SEQUENCE: 221
atgtgactgg cacgggagtt gatcctggtt ttcacctgca cccttggtct cctccaccgc    60
ttcttgtcct gcttg                                                    75

<210> SEQ ID NO 222
<211> LENGTH: 75
<212> TYPE: DNA
<213> ORGANISM: Artificial Sequence
<220> FEATURE:
<223> OTHER INFORMATION: Probe

<400> SEQUENCE: 222
atgtgactgg cacgggagtt gatcctggtt ttcaccctcg cttagtgctc cctgggggca    60
gctcgtggtg aggct                                                    75

<210> SEQ ID NO 223
<211> LENGTH: 75
<212> TYPE: DNA
<213> ORGANISM: Artificial Sequence
<220> FEATURE:
<223> OTHER INFORMATION: Probe -continued

<400> SEQUENCE: 223
atgtgactgg cacgggagtt gatcctggtt ttcacgaccg gcgcacagag gaagagaatc    60
tccgcaagaa agggg                                                    75

<210> SEQ ID NO 224
<211> LENGTH: 75
<212> TYPE: DNA
<213> ORGANISM: Artificial Sequence
<220> FEATURE:
<223> OTHER INFORMATION: Probe

<400> SEQUENCE: 224
atgtgactgg cacgggagtt gatcctggtt ttcactctcc caggacaggc acaaacacgc    60
acctcaaagc tgttc                                                    75

<210> SEQ ID NO 225
<211> LENGTH: 75
<212> TYPE: DNA
<213> ORGANISM: Artificial Sequence
<220> FEATURE:
<223> OTHER INFORMATION: Probe

<400> SEQUENCE: 225
atgtgactgg cacgggagtt gatcctggtt ttcactctct tttcctatcc tgagtagtgg    60
taatctactg ggacg                                                    75

<210> SEQ ID NO 226
<211> LENGTH: 75
<212> TYPE: DNA
<213> ORGANISM: Artificial Sequence
<220> FEATURE:
<223> OTHER INFORMATION: Probe

<400> SEQUENCE: 226
atgtgactgg cacgggagtt gatcctggtt ttcacggaca ggtaggacct gatttcctta    60
ctgcctcttg cttct                                                    75

<210> SEQ ID NO 227
<211> LENGTH: 75
<212> TYPE: DNA
<213> ORGANISM: Artificial Sequence
<220> FEATURE:
<223> OTHER INFORMATION: Probe

<400> SEQUENCE: 227
atgtgactgg cacgggagtt gatcctggtt ttcacggcat tttgagtgtt agactggaaa    60
ctttccactt gataa                                                    75

<210> SEQ ID NO 228
<211> LENGTH: 75
<212> TYPE: DNA
<213> ORGANISM: Artificial Sequence
<220> FEATURE:
<223> OTHER INFORMATION: Probe

<400> SEQUENCE: 228
atgtgactgg cacgggagtt gatcctggtt ttcaccctga agggtgaaat attctccatc    60
cagtggtttc ttctt                                                    75

<210> SEQ ID NO 229
<211> LENGTH: 75

```
<212> TYPE: DNA
<213> ORGANISM: Artificial Sequence
<220> FEATURE:
<223> OTHER INFORMATION: Probe

<400> SEQUENCE: 229
atgtgactgg cacgggagtt gatcctggtt ttcaccctag cactgcccaa caacaccagc    60
tcctctcccc agcca                                                    75

<210> SEQ ID NO 230
<211> LENGTH: 75
<212> TYPE: DNA
<213> ORGANISM: Artificial Sequence
<220> FEATURE:
<223> OTHER INFORMATION: Probe

<400> SEQUENCE: 230
atgtgactgg cacgggagtt gatcctggtt ttcactgcct cagattcact tttatcacct    60
ttccttgcct ctttc                                                    75

<210> SEQ ID NO 231
<211> LENGTH: 75
<212> TYPE: DNA
<213> ORGANISM: Artificial Sequence
<220> FEATURE:
<223> OTHER INFORMATION: Probe

<400> SEQUENCE: 231
atgtgactgg cacgggagtt gatcctggtt ttcacatggc tttccaacct aggaaggcag    60
gggagtaggg ccagg                                                    75

<210> SEQ ID NO 232
<211> LENGTH: 75
<212> TYPE: DNA
<213> ORGANISM: Artificial Sequence
<220> FEATURE:
<223> OTHER INFORMATION: Probe

<400> SEQUENCE: 232
atgtgactgg cacgggagtt gatcctggtt ttcaccctgg agtgagccct gctcccccct    60
ggctccttcc cagcc                                                    75

<210> SEQ ID NO 233
<211> LENGTH: 75
<212> TYPE: DNA
<213> ORGANISM: Artificial Sequence
<220> FEATURE:
<223> OTHER INFORMATION: Probe

<400> SEQUENCE: 233
atgtgactgg cacgggagtt gatcctggtt ttcactccga gagctgaatg aggccttgga    60
actcaaggat gccca                                                    75

<210> SEQ ID NO 234
<211> LENGTH: 75
<212> TYPE: DNA
<213> ORGANISM: Artificial Sequence
<220> FEATURE:
<223> OTHER INFORMATION: Probe

<400> SEQUENCE: 234
atgtgactgg cacgggagtt gatcctggtt ttcaccatct tttaactcag gtactgtgta    60
```

```
tatacttact tctcc                                                          75

<210> SEQ ID NO 235
<211> LENGTH: 75
<212> TYPE: DNA
<213> ORGANISM: Artificial Sequence
<220> FEATURE:
<223> OTHER INFORMATION: Probe

<400> SEQUENCE: 235
atgtgactgg cacgggagtt gatcctggtt ttcacggcag gggagggaga gatggggtg        60 ggaggctgtc agtgg                                                          75

<210> SEQ ID NO 236
<211> LENGTH: 75
<212> TYPE: DNA
<213> ORGANISM: Artificial Sequence
<220> FEATURE:
<223> OTHER INFORMATION: Probe

<400> SEQUENCE: 236
atgtgactgg cacgggagtt gatcctggtt ttcacgtcag tctgagtcag gcccttctgt        60
cttgaacatg agttt                                                          75

<210> SEQ ID NO 237
<211> LENGTH: 75
<212> TYPE: DNA
<213> ORGANISM: Artificial Sequence
<220> FEATURE:
<223> OTHER INFORMATION: Probe

<400> SEQUENCE: 237
atgtgactgg cacgggagtt gatcctggtt ttcaccctga agtccaaaaa gggtcagtct        60
acctcccgcc ataaa                                                          75

<210> SEQ ID NO 238
<211> LENGTH: 75
<212> TYPE: DNA
<213> ORGANISM: Artificial Sequence
<220> FEATURE:
<223> OTHER INFORMATION: Probe

<400> SEQUENCE: 238
atgtgactgg cacgggagtt gatcctggtt ttcacggcac agaccctctc actcatgtga        60
tgtcatctct cctcc                                                          75

<210> SEQ ID NO 239
<211> LENGTH: 75
<212> TYPE: DNA
<213> ORGANISM: Artificial Sequence
<220> FEATURE:
<223> OTHER INFORMATION: Probe

<400> SEQUENCE: 239
atgtgactgg cacgggagtt gatcctggtt ttcaccaggg gcttatgtgt ctccttgatg        60
acctgcggcg acgtc                                                          75

<210> SEQ ID NO 240
<211> LENGTH: 75
<212> TYPE: DNA
<213> ORGANISM: Artificial Sequence
<220> FEATURE:
<223> OTHER INFORMATION: Probe
```

<400> SEQUENCE: 240
atgtgactgg cacgggagtt gatcctggtt ttcacccatc atctcctccc ttcccttct    60 gcccaggctg ttgca    75

<210> SEQ ID NO 241
<211> LENGTH: 75
<212> TYPE: DNA
<213> ORGANISM: Artificial Sequence
<220> FEATURE:
<223> OTHER INFORMATION: Probe

<400> SEQUENCE: 241
atgtgactgg cacgggagtt gatcctggtt ttcacaattc tggcttctcc ctgctcacac    60
tttcttccat tgcat    75

<210> SEQ ID NO 242
<211> LENGTH: 75
<212> TYPE: DNA
<213> ORGANISM: Artificial Sequence
<220> FEATURE:
<223> OTHER INFORMATION: Probe

<400> SEQUENCE: 242
atgtgactgg cacgggagtt gatcctggtt ttcacgtcag ctcgtgttgg caacatacca    60
tcttcaacct ctgca    75

<210> SEQ ID NO 243
<211> LENGTH: 75
<212> TYPE: DNA
<213> ORGANISM: Artificial Sequence
<220> FEATURE:
<223> OTHER INFORMATION: Probe

<400> SEQUENCE: 243
atgtgactgg cacgggagtt gatcctggtt ttcactaatt tcttggcccc tcttcggtaa    60
ccctgagcca aatgt    75

<210> SEQ ID NO 244
<211> LENGTH: 75
<212> TYPE: DNA
<213> ORGANISM: Artificial Sequence
<220> FEATURE:
<223> OTHER INFORMATION: Probe

<400> SEQUENCE: 244
atgtgactgg cacgggagtt gatcctggtt ttcacggtga aataaaggaa gatactagtt    60
ttgctgaaaa tgaca    75

<210> SEQ ID NO 245
<211> LENGTH: 75
<212> TYPE: DNA
<213> ORGANISM: Artificial Sequence
<220> FEATURE:
<223> OTHER INFORMATION: Probe

<400> SEQUENCE: 245
atgtgactgg cacgggagtt gatcctggtt ttcacactca tttgtatctg aagtggaacc    60
aaatgatact gatcc    75

<210> SEQ ID NO 246

```
<211> LENGTH: 75
<212> TYPE: DNA
<213> ORGANISM: Artificial Sequence
<220> FEATURE:
<223> OTHER INFORMATION: Probe

<400> SEQUENCE: 246
atgtgactgg cacgggagtt gatcctggtt ttcacagttg agaccattca caggccaaag    60
acggtacaac ttcct                                                     75

<210> SEQ ID NO 247
<211> LENGTH: 75
<212> TYPE: DNA
<213> ORGANISM: Artificial Sequence
<220> FEATURE:
<223> OTHER INFORMATION: Probe

<400> SEQUENCE: 247
atgtgactgg cacgggagtt gatcctggtt ttcacgaaaa tgaatgctct gagctttgga    60
agctctcagg gtaca                                                     75

<210> SEQ ID NO 248
<211> LENGTH: 75
<212> TYPE: DNA
<213> ORGANISM: Artificial Sequence
<220> FEATURE:
<223> OTHER INFORMATION: Probe

<400> SEQUENCE: 248
atgtgactgg cacgggagtt gatcctggtt ttcacgggcc atcgcgatgt cgcacggtac    60
ctgcgcgcgg ctgcg                                                     75

<210> SEQ ID NO 249
<211> LENGTH: 75
<212> TYPE: DNA
<213> ORGANISM: Artificial Sequence
<220> FEATURE:
<223> OTHER INFORMATION: Probe

<400> SEQUENCE: 249
atgtgactgg cacgggagtt gatcctggtt ttcaccccca tccagcttca aaagctcttc    60
gaatcattga tgtgc                                                     75

<210> SEQ ID NO 250
<211> LENGTH: 75
<212> TYPE: DNA
<213> ORGANISM: Artificial Sequence
<220> FEATURE:
<223> OTHER INFORMATION: Probe

<400> SEQUENCE: 250
atgtgactgg cacgggagtt gatcctggtt ttcactgcca agcctgaact acccctcttt    60
tacactccta ttgat                                                     75

<210> SEQ ID NO 251
<211> LENGTH: 75
<212> TYPE: DNA
<213> ORGANISM: Artificial Sequence
<220> FEATURE:
<223> OTHER INFORMATION: Probe

<400> SEQUENCE: 251
atgtgactgg cacgggagtt gatcctggtt ttcacccacc ctgactgtgc tctgtccccc    60
```
cagggctgga catcc 75

<210> SEQ ID NO 252
<211> LENGTH: 75
<212> TYPE: DNA
<213> ORGANISM: Artificial Sequence
<220> FEATURE:
<223> OTHER INFORMATION: Probe

<400> SEQUENCE: 252
atgtgactgg cacgggagtt gatcctggtt ttcacagtca ggagtgggat gatcttataa 60
aactcgtaga aagag 75

<210> SEQ ID NO 253
<211> LENGTH: 75
<212> TYPE: DNA
<213> ORGANISM: Artificial Sequence
<220> FEATURE:
<223> OTHER INFORMATION: Probe

<400> SEQUENCE: 253
atgtgactgg cacgggagtt gatcctggtt ttcaccttcg gggagacaac gacggcggtg 60
gcgggagctt ctcca 75

<210> SEQ ID NO 254
<211> LENGTH: 75
<212> TYPE: DNA
<213> ORGANISM: Artificial Sequence
<220> FEATURE:
<223> OTHER INFORMATION: Probe

<400> SEQUENCE: 254
atgtgactgg cacgggagtt gatcctggtt ttcaccatac agtcctggat gatgatgttt 60
ttgatgaagg tctcg 75

<210> SEQ ID NO 255
<211> LENGTH: 75
<212> TYPE: DNA
<213> ORGANISM: Artificial Sequence
<220> FEATURE:
<223> OTHER INFORMATION: Probe

<400> SEQUENCE: 255
atgtgactgg cacgggagtt gatcctggtt ttcacttttta ctgttcttcc tcagacattc 60
aaacgtgttt tgatc 75

<210> SEQ ID NO 256
<211> LENGTH: 75
<212> TYPE: DNA
<213> ORGANISM: Artificial Sequence
<220> FEATURE:
<223> OTHER INFORMATION: Probe

<400> SEQUENCE: 256
atgtgactgg cacgggagtt gatcctggtt ttcacgtgga agcatactgc aaaatatttg 60
ttttcagtct ctgca 75

<210> SEQ ID NO 257
<211> LENGTH: 75
<212> TYPE: DNA
<213> ORGANISM: Artificial Sequence
<220> FEATURE:

```
<223> OTHER INFORMATION: Probe

<400> SEQUENCE: 257
atgtgactgg cacgggagtt gatcctggtt ttcacacgta cccctctcag cccctcctct    60
tggactccag ccatg                                                     75

<210> SEQ ID NO 258
<211> LENGTH: 75
<212> TYPE: DNA
<213> ORGANISM: Artificial Sequence
<220> FEATURE:
<223> OTHER INFORMATION: Probe

<400> SEQUENCE: 258
atgtgactgg cacgggagtt gatcctggtt ttcacgtggc gtaagcgcgg cacgcggcgc    60
agtggtcccc gtcct                                                     75

<210> SEQ ID NO 259
<211> LENGTH: 21
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 259
nnnnnaagat cttagtggca c                                              21

<210> SEQ ID NO 260
<211> LENGTH: 21
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 260
nnnnncgaca gaactattgc c                                              21

<210> SEQ ID NO 261
<211> LENGTH: 21
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<223> OTHER INFORMATION: n is a, c, g, or t
<220> FEATURE:
<221> NAME/KEY: misc_feature
<222> LOCATION: (1)..(5)
<223> OTHER INFORMATION: n is a, c, g, or t

<400> SEQUENCE: 261
nnnnnactat cttagtggca c                                              21

<210> SEQ ID NO 262
<211> LENGTH: 21
<212> TYPE: DNA
<213> ORGANISM: Artificial Sequence
<220> FEATURE:
```

```
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 262
nnnnnctcca gaactattgc c                                              21

<210> SEQ ID NO 263
<211> LENGTH: 21
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 263
nnnnnagcat cttagtggca c                                              21

<210> SEQ ID NO 264
<211> LENGTH: 21
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 264
nnnnncatca gaactattgc c                                              21

<210> SEQ ID NO 265
<211> LENGTH: 21
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 265
nnnnnataat cttagtggca c                                              21

<210> SEQ ID NO 266
<211> LENGTH: 21
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 266
nnnnnaagaa ggtagaccct c                                              21

<210> SEQ ID NO 267
<211> LENGTH: 21
<212> TYPE: DNA
<213> ORGANISM: Artificial Sequence
```

```
<220> FEATURE:
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 267
nnnnntttct ctactcgtga c                                              21

<210> SEQ ID NO 268
<211> LENGTH: 21
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 268
nnnnnactaa ggtagaccct c                                              21

<210> SEQ ID NO 269
<211> LENGTH: 21
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 269
nnnnngaagc tacgagtatc c                                              21

<210> SEQ ID NO 270
<211> LENGTH: 21
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 270
nnnnnagcaa ggtagaccct c                                              21

<210> SEQ ID NO 271
<211> LENGTH: 21
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 271
nnnnncattg acgtctagag c                                              21

<210> SEQ ID NO 272
<211> LENGTH: 21
<212> TYPE: DNA
```

```
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 272
nnnnntcact ctactcgtga c                                              21

<210> SEQ ID NO 273
<211> LENGTH: 21
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 273
nnnnnataaa ggtagaccct c                                              21

<210> SEQ ID NO 274
<211> LENGTH: 21
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 274
nnnnntacct ctactcgtga c                                              21

<210> SEQ ID NO 275
<211> LENGTH: 20
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 275
nnnnnttttg tgtgtgtgtg                                                20

<210> SEQ ID NO 276
<211> LENGTH: 20
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 276
nnnnnactac acacacacac                                                20

<210> SEQ ID NO 277
<211> LENGTH: 20
```

```
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 277
nnnnnctcgt gtgtgtgtgt                                              20

<210> SEQ ID NO 278
<211> LENGTH: 20
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 278
nnnnngaaca cacacacaca                                              20

<210> SEQ ID NO 279
<211> LENGTH: 20
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 279
nnnnncatgt gtgtgtgtgt                                              20

<210> SEQ ID NO 280
<211> LENGTH: 20
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 280
nnnnngtgca cacacacaca                                              20

<210> SEQ ID NO 281
<211> LENGTH: 20
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 281
nnnnnataac acacacacac                                              20

<210> SEQ ID NO 282
```

```
<211> LENGTH: 20
<212> TYPE: DNA
<213> ORGANISM: Artificial Sequence
<220> FEATURE:
<223> OTHER INFORMATION: Adaptor
<220> FEATURE:
<221> NAME/KEY: misc_feature
<222> LOCATION: (1)..(5)
<223> OTHER INFORMATION: n is a, c, g, or t

<400> SEQUENCE: 282
nnnnntactg tgtgtgtgtg                                              20

<210> SEQ ID NO 283
<211> LENGTH: 25
<212> TYPE: DNA
<213> ORGANISM: Artificial Sequence
<220> FEATURE:
<223> OTHER INFORMATION: Primer

<400> SEQUENCE: 283
tgcaggacca gagaattcga ataca                                        25

<210> SEQ ID NO 284
<211> LENGTH: 58
<212> TYPE: DNA
<213> ORGANISM: Artificial Sequence
<220> FEATURE:
<223> OTHER INFORMATION: Primer

<400> SEQUENCE: 284
aatgatacgg cgaccaccga gatctacacg tcatgcagga ccagagaatt cgaataca    58

<210> SEQ ID NO 285
<211> LENGTH: 18
<212> TYPE: DNA
<213> ORGANISM: Artificial Sequence
<220> FEATURE:
<223> OTHER INFORMATION: Primer

<400> SEQUENCE: 285
cggtggctca cgcctgta                                                18

<210> SEQ ID NO 286
<211> LENGTH: 18
<212> TYPE: DNA
<213> ORGANISM: Artificial Sequence
<220> FEATURE:
<223> OTHER INFORMATION: Primer

<400> SEQUENCE: 286
gcctcggcct cccaaagt                                                18

<210> SEQ ID NO 287
<211> LENGTH: 21
<212> TYPE: DNA
<213> ORGANISM: Artificial Sequence
<220> FEATURE:
<223> OTHER INFORMATION: Primer

<400> SEQUENCE: 287
gaggctgagg caggagaatc g                                            21

<210> SEQ ID NO 288
<211> LENGTH: 18
<212> TYPE: DNA
<213> ORGANISM: Artificial Sequence
```

```
<220> FEATURE:
<223> OTHER INFORMATION: Primer

<400> SEQUENCE: 288
gtcgcccagg ctggagtg                                                 18

<210> SEQ ID NO 289
<211> LENGTH: 25
<212> TYPE: DNA
<213> ORGANISM: Artificial Sequence
<220> FEATURE:
<223> OTHER INFORMATION: Element 1

<400> SEQUENCE: 289
tgcaggacca gagaattcga ataca                                         25

<210> SEQ ID NO 290
<211> LENGTH: 5
<212> TYPE: DNA
<213> ORGANISM: Artificial Sequence
<220> FEATURE:
<223> OTHER INFORMATION: Element 2

<400> SEQUENCE: 290 cgggt                                                                5

<210> SEQ ID NO 291
<211> LENGTH: 5
<212> TYPE: DNA
<213> ORGANISM: Artificial Sequence
<220> FEATURE:
<223> OTHER INFORMATION: Element 2

<400> SEQUENCE: 291 cggtg                                                                5

<210> SEQ ID NO 292
<211> LENGTH: 5
<212> TYPE: DNA
<213> ORGANISM: Artificial Sequence
<220> FEATURE:
<223> OTHER INFORMATION: Element 2

<400> SEQUENCE: 292 cgtgg                                                                5

<210> SEQ ID NO 293
<211> LENGTH: 5
<212> TYPE: DNA
<213> ORGANISM: Artificial Sequence
<220> FEATURE:
<223> OTHER INFORMATION: Element 2

<400> SEQUENCE: 293 gcggt                                                                5

<210> SEQ ID NO 294
<211> LENGTH: 5
<212> TYPE: DNA
<213> ORGANISM: Artificial Sequence
<220> FEATURE:
<223> OTHER INFORMATION: Element 2

<400> SEQUENCE: 294 gcgtg                                                                5
```

```
<210> SEQ ID NO 295
<211> LENGTH: 5
<212> TYPE: DNA
<213> ORGANISM: Artificial Sequence
<220> FEATURE:
<223> OTHER INFORMATION: Element 2

<400> SEQUENCE: 295 gctgg                                                                    5

<210> SEQ ID NO 296
<211> LENGTH: 5
<212> TYPE: DNA
<213> ORGANISM: Artificial Sequence
<220> FEATURE:
<223> OTHER INFORMATION: Element 2

<400> SEQUENCE: 296 ggcgt                                                                    5

<210> SEQ ID NO 297
<211> LENGTH: 5
<212> TYPE: DNA
<213> ORGANISM: Artificial Sequence
<220> FEATURE:
<223> OTHER INFORMATION: Element 2

<400> SEQUENCE: 297 ggctg                                                                    5

<210> SEQ ID NO 298
<211> LENGTH: 5
<212> TYPE: DNA
<213> ORGANISM: Artificial Sequence
<220> FEATURE:
<223> OTHER INFORMATION: Element 2

<400> SEQUENCE: 298 gggct                                                                    5

<210> SEQ ID NO 299
<211> LENGTH: 5
<212> TYPE: DNA
<213> ORGANISM: Artificial Sequence
<220> FEATURE:
<223> OTHER INFORMATION: Element 2

<400> SEQUENCE: 299 ttaaa                                                                    5

<210> SEQ ID NO 300
<211> LENGTH: 5
<212> TYPE: DNA
<213> ORGANISM: Artificial Sequence
<220> FEATURE:
<223> OTHER INFORMATION: Element 2

<400> SEQUENCE: 300 ttacc                                                                    5

<210> SEQ ID NO 301
<211> LENGTH: 5
<212> TYPE: DNA
<213> ORGANISM: Artificial Sequence
<220> FEATURE:
<223> OTHER INFORMATION: Element 2
```

```
<400> SEQUENCE: 301 ttatt                                                                 5

<210> SEQ ID NO 302
<211> LENGTH: 5
<212> TYPE: DNA
<213> ORGANISM: Artificial Sequence
<220> FEATURE:
<223> OTHER INFORMATION: Element 2

<400> SEQUENCE: 302 ttcac                                                                 5

<210> SEQ ID NO 303
<211> LENGTH: 5
<212> TYPE: DNA
<213> ORGANISM: Artificial Sequence
<220> FEATURE:
<223> OTHER INFORMATION: Element 2

<400> SEQUENCE: 303 ttcca                                                                 5

<210> SEQ ID NO 304
<211> LENGTH: 5
<212> TYPE: DNA
<213> ORGANISM: Artificial Sequence
<220> FEATURE:
<223> OTHER INFORMATION: Element 2

<400> SEQUENCE: 304 tttat                                                                 5

<210> SEQ ID NO 305
<211> LENGTH: 5
<212> TYPE: DNA
<213> ORGANISM: Artificial Sequence
<220> FEATURE:
<223> OTHER INFORMATION: Element 2

<400> SEQUENCE: 305 tttta                                                                 5

<210> SEQ ID NO 306
<211> LENGTH: 5
<212> TYPE: DNA
<213> ORGANISM: Artificial Sequence
<220> FEATURE:
<223> OTHER INFORMATION: Element 2

<400> SEQUENCE: 306 gcacg                                                                 5

<210> SEQ ID NO 307
<211> LENGTH: 5
<212> TYPE: DNA
<213> ORGANISM: Artificial Sequence
<220> FEATURE:
<223> OTHER INFORMATION: Element 2

<400> SEQUENCE: 307 gcagc                                                                 5

<210> SEQ ID NO 308
```

```
<211> LENGTH: 5
<212> TYPE: DNA
<213> ORGANISM: Artificial Sequence
<220> FEATURE:
<223> OTHER INFORMATION: Element 2

<400> SEQUENCE: 308 gccag                                                                    5

<210> SEQ ID NO 309
<211> LENGTH: 5
<212> TYPE: DNA
<213> ORGANISM: Artificial Sequence
<220> FEATURE:
<223> OTHER INFORMATION: Element 2

<400> SEQUENCE: 309 gccga                                                                    5

<210> SEQ ID NO 310
<211> LENGTH: 5
<212> TYPE: DNA
<213> ORGANISM: Artificial Sequence
<220> FEATURE:
<223> OTHER INFORMATION: Element 2

<400> SEQUENCE: 310 gcgac                                                                    5

<210> SEQ ID NO 311
<211> LENGTH: 5
<212> TYPE: DNA
<213> ORGANISM: Artificial Sequence
<220> FEATURE:
<223> OTHER INFORMATION: Element 2

<400> SEQUENCE: 311 gcgca                                                                    5

<210> SEQ ID NO 312
<211> LENGTH: 5
<212> TYPE: DNA
<213> ORGANISM: Artificial Sequence
<220> FEATURE:
<223> OTHER INFORMATION: Element 2

<400> SEQUENCE: 312 ggaaa                                                                    5

<210> SEQ ID NO 313
<211> LENGTH: 5
<212> TYPE: DNA
<213> ORGANISM: Artificial Sequence
<220> FEATURE:
<223> OTHER INFORMATION: Element 2

<400> SEQUENCE: 313 ggacc                                                                    5

<210> SEQ ID NO 314
<211> LENGTH: 5
<212> TYPE: DNA
<213> ORGANISM: Artificial Sequence
<220> FEATURE:
<223> OTHER INFORMATION: Element 2

<400> SEQUENCE: 314
``` ggatt                                                            5

<210> SEQ ID NO 315
<211> LENGTH: 5
<212> TYPE: DNA
<213> ORGANISM: Artificial Sequence
<220> FEATURE:
<223> OTHER INFORMATION: Element 2

<400> SEQUENCE: 315 ggcac                                                            5

<210> SEQ ID NO 316
<211> LENGTH: 5
<212> TYPE: DNA
<213> ORGANISM: Artificial Sequence
<220> FEATURE:
<223> OTHER INFORMATION: Element 2

<400> SEQUENCE: 316 ggcca                                                            5

<210> SEQ ID NO 317
<211> LENGTH: 5
<212> TYPE: DNA
<213> ORGANISM: Artificial Sequence
<220> FEATURE:
<223> OTHER INFORMATION: Element 2

<400> SEQUENCE: 317 ggtat                                                            5

<210> SEQ ID NO 318
<211> LENGTH: 5
<212> TYPE: DNA
<213> ORGANISM: Artificial Sequence
<220> FEATURE:
<223> OTHER INFORMATION: Element 2

<400> SEQUENCE: 318 ggtta                                                            5

<210> SEQ ID NO 319
<211> LENGTH: 5
<212> TYPE: DNA
<213> ORGANISM: Artificial Sequence
<220> FEATURE:
<223> OTHER INFORMATION: Element 2

<400> SEQUENCE: 319 gtagt                                                            5

<210> SEQ ID NO 320
<211> LENGTH: 5
<212> TYPE: DNA
<213> ORGANISM: Artificial Sequence
<220> FEATURE:
<223> OTHER INFORMATION: Element 2

<400> SEQUENCE: 320 gtatg                                                            5

<210> SEQ ID NO 321
<211> LENGTH: 5
<212> TYPE: DNA

```
<213> ORGANISM: Artificial Sequence
<220> FEATURE:
<223> OTHER INFORMATION: Element 2

<400> SEQUENCE: 321 gtgat                                                                    5

<210> SEQ ID NO 322
<211> LENGTH: 5
<212> TYPE: DNA
<213> ORGANISM: Artificial Sequence
<220> FEATURE:
<223> OTHER INFORMATION: Element 2

<400> SEQUENCE: 322 ccgtc                                                                    5

<210> SEQ ID NO 323
<211> LENGTH: 5
<212> TYPE: DNA
<213> ORGANISM: Artificial Sequence
<220> FEATURE:
<223> OTHER INFORMATION: Element 2

<400> SEQUENCE: 323 cctcg                                                                    5

<210> SEQ ID NO 324
<211> LENGTH: 5
<212> TYPE: DNA
<213> ORGANISM: Artificial Sequence
<220> FEATURE:
<223> OTHER INFORMATION: Element 2

<400> SEQUENCE: 324 cctgc                                                                    5

<210> SEQ ID NO 325
<211> LENGTH: 5
<212> TYPE: DNA
<213> ORGANISM: Artificial Sequence
<220> FEATURE:
<223> OTHER INFORMATION: Element 2

<400> SEQUENCE: 325 cgaat                                                                    5

<210> SEQ ID NO 326
<211> LENGTH: 5
<212> TYPE: DNA
<213> ORGANISM: Artificial Sequence
<220> FEATURE:
<223> OTHER INFORMATION: Element 2

<400> SEQUENCE: 326 cgata                                                                    5

<210> SEQ ID NO 327
<211> LENGTH: 5
<212> TYPE: DNA
<213> ORGANISM: Artificial Sequence
<220> FEATURE:
<223> OTHER INFORMATION: Element 2

<400> SEQUENCE: 327 cgcct                                                                    5
```

```
<210> SEQ ID NO 328
<211> LENGTH: 5
<212> TYPE: DNA
<213> ORGANISM: Artificial Sequence
<220> FEATURE:
<223> OTHER INFORMATION: Element 2

<400> SEQUENCE: 328 cgctc                                                                    5

<210> SEQ ID NO 329
<211> LENGTH: 5
<212> TYPE: DNA
<213> ORGANISM: Artificial Sequence
<220> FEATURE:
<223> OTHER INFORMATION: Element 2

<400> SEQUENCE: 329 cgtaa                                                                    5

<210> SEQ ID NO 330
<211> LENGTH: 5
<212> TYPE: DNA
<213> ORGANISM: Artificial Sequence
<220> FEATURE:
<223> OTHER INFORMATION: Element 2

<400> SEQUENCE: 330 cgtcc                                                                    5

<210> SEQ ID NO 331
<211> LENGTH: 5
<212> TYPE: DNA
<213> ORGANISM: Artificial Sequence
<220> FEATURE:
<223> OTHER INFORMATION: Element 2

<400> SEQUENCE: 331 cgttt                                                                    5

<210> SEQ ID NO 332
<211> LENGTH: 5
<212> TYPE: DNA
<213> ORGANISM: Artificial Sequence
<220> FEATURE:
<223> OTHER INFORMATION: Element 2

<400> SEQUENCE: 332 ctaag                                                                    5

<210> SEQ ID NO 333
<211> LENGTH: 5
<212> TYPE: DNA
<213> ORGANISM: Artificial Sequence
<220> FEATURE:
<223> OTHER INFORMATION: Element 2

<400> SEQUENCE: 333 ctaga                                                                    5

<210> SEQ ID NO 334
<211> LENGTH: 5
<212> TYPE: DNA
<213> ORGANISM: Artificial Sequence
<220> FEATURE:
```

```
<223> OTHER INFORMATION: Element 2

<400> SEQUENCE: 334 ctccg                                                                    5

<210> SEQ ID NO 335
<211> LENGTH: 5
<212> TYPE: DNA
<213> ORGANISM: Artificial Sequence
<220> FEATURE:
<223> OTHER INFORMATION: Element 2

<400> SEQUENCE: 335 ctcgc                                                                    5

<210> SEQ ID NO 336
<211> LENGTH: 5
<212> TYPE: DNA
<213> ORGANISM: Artificial Sequence
<220> FEATURE:
<223> OTHER INFORMATION: Element 2

<400> SEQUENCE: 336 ctgaa                                                                    5

<210> SEQ ID NO 337
<211> LENGTH: 5
<212> TYPE: DNA
<213> ORGANISM: Artificial Sequence
<220> FEATURE:
<223> OTHER INFORMATION: Element 2

<400> SEQUENCE: 337 ctgcc                                                                    5

<210> SEQ ID NO 338
<211> LENGTH: 5
<212> TYPE: DNA
<213> ORGANISM: Artificial Sequence
<220> FEATURE:
<223> OTHER INFORMATION: Element 2

<400> SEQUENCE: 338 ttgtc                                                                    5

<210> SEQ ID NO 339
<211> LENGTH: 5
<212> TYPE: DNA
<213> ORGANISM: Artificial Sequence
<220> FEATURE:
<223> OTHER INFORMATION: Element 2

<400> SEQUENCE: 339 tttcg                                                                    5

<210> SEQ ID NO 340
<211> LENGTH: 5
<212> TYPE: DNA
<213> ORGANISM: Artificial Sequence
<220> FEATURE:
<223> OTHER INFORMATION: Element 2

<400> SEQUENCE: 340 tttgc                                                                    5
```

```
<210> SEQ ID NO 341
<211> LENGTH: 5
<212> TYPE: DNA
<213> ORGANISM: Artificial Sequence
<220> FEATURE:
<223> OTHER INFORMATION: Element 2

<400> SEQUENCE: 341 aaaaa                                                                    5

<210> SEQ ID NO 342
<211> LENGTH: 5
<212> TYPE: DNA
<213> ORGANISM: Artificial Sequence
<220> FEATURE:
<223> OTHER INFORMATION: Element 2

<400> SEQUENCE: 342 aaacc                                                                    5

<210> SEQ ID NO 343
<211> LENGTH: 5
<212> TYPE: DNA
<213> ORGANISM: Artificial Sequence
<220> FEATURE:
<223> OTHER INFORMATION: Element 2

<400> SEQUENCE: 343 aaatt                                                                    5

<210> SEQ ID NO 344
<211> LENGTH: 5
<212> TYPE: DNA
<213> ORGANISM: Artificial Sequence
<220> FEATURE:
<223> OTHER INFORMATION: Element 2

<400> SEQUENCE: 344 aacac                                                                    5

<210> SEQ ID NO 345
<211> LENGTH: 5
<212> TYPE: DNA
<213> ORGANISM: Artificial Sequence
<220> FEATURE:
<223> OTHER INFORMATION: Element 2

<400> SEQUENCE: 345 aacca                                                                    5

<210> SEQ ID NO 346
<211> LENGTH: 5
<212> TYPE: DNA
<213> ORGANISM: Artificial Sequence
<220> FEATURE:
<223> OTHER INFORMATION: Element 2

<400> SEQUENCE: 346 aatat                                                                    5

<210> SEQ ID NO 347
<211> LENGTH: 5
<212> TYPE: DNA
<213> ORGANISM: Artificial Sequence
<220> FEATURE:
<223> OTHER INFORMATION: Element 2
```

```
<400> SEQUENCE: 347 aatta                                                              5

<210> SEQ ID NO 348
<211> LENGTH: 5
<212> TYPE: DNA
<213> ORGANISM: Artificial Sequence
<220> FEATURE:
<223> OTHER INFORMATION: Element 2

<400> SEQUENCE: 348 acaac                                                              5

<210> SEQ ID NO 349
<211> LENGTH: 5
<212> TYPE: DNA
<213> ORGANISM: Artificial Sequence
<220> FEATURE:
<223> OTHER INFORMATION: Element 2

<400> SEQUENCE: 349 acaca                                                              5

<210> SEQ ID NO 350
<211> LENGTH: 5
<212> TYPE: DNA
<213> ORGANISM: Artificial Sequence
<220> FEATURE:
<223> OTHER INFORMATION: Element 2

<400> SEQUENCE: 350 accaa                                                              5

<210> SEQ ID NO 351
<211> LENGTH: 5
<212> TYPE: DNA
<213> ORGANISM: Artificial Sequence
<220> FEATURE:
<223> OTHER INFORMATION: Element 2

<400> SEQUENCE: 351 acccc                                                              5

<210> SEQ ID NO 352
<211> LENGTH: 5
<212> TYPE: DNA
<213> ORGANISM: Artificial Sequence
<220> FEATURE:
<223> OTHER INFORMATION: Element 2

<400> SEQUENCE: 352 acctt                                                              5

<210> SEQ ID NO 353
<211> LENGTH: 5
<212> TYPE: DNA
<213> ORGANISM: Artificial Sequence
<220> FEATURE:
<223> OTHER INFORMATION: Element 2

<400> SEQUENCE: 353 actct                                                              5

<210> SEQ ID NO 354
<211> LENGTH: 5
```

```
<212> TYPE: DNA
<213> ORGANISM: Artificial Sequence
<220> FEATURE:
<223> OTHER INFORMATION: Element 2

<400> SEQUENCE: 354 gggtc                                                                    5

<210> SEQ ID NO 355
<211> LENGTH: 5
<212> TYPE: DNA
<213> ORGANISM: Artificial Sequence
<220> FEATURE:
<223> OTHER INFORMATION: Element 2

<400> SEQUENCE: 355 ggtcg                                                                    5

<210> SEQ ID NO 356
<211> LENGTH: 5
<212> TYPE: DNA
<213> ORGANISM: Artificial Sequence
<220> FEATURE:
<223> OTHER INFORMATION: Element 2

<400> SEQUENCE: 356 ggtgc                                                                    5

<210> SEQ ID NO 357
<211> LENGTH: 5
<212> TYPE: DNA
<213> ORGANISM: Artificial Sequence
<220> FEATURE:
<223> OTHER INFORMATION: Element 2

<400> SEQUENCE: 357 gtcgg                                                                    5

<210> SEQ ID NO 358
<211> LENGTH: 5
<212> TYPE: DNA
<213> ORGANISM: Artificial Sequence
<220> FEATURE:
<223> OTHER INFORMATION: Element 2

<400> SEQUENCE: 358 gtgcg                                                                    5

<210> SEQ ID NO 359
<211> LENGTH: 5
<212> TYPE: DNA
<213> ORGANISM: Artificial Sequence
<220> FEATURE:
<223> OTHER INFORMATION: Element 2

<400> SEQUENCE: 359 gtggc                                                                    5

<210> SEQ ID NO 360
<211> LENGTH: 5
<212> TYPE: DNA
<213> ORGANISM: Artificial Sequence
<220> FEATURE:
<223> OTHER INFORMATION: Element 2

<400> SEQUENCE: 360
``` tgcgg                                                                 5

<210> SEQ ID NO 361
<211> LENGTH: 5
<212> TYPE: DNA
<213> ORGANISM: Artificial Sequence
<220> FEATURE:
<223> OTHER INFORMATION: Element 2

<400> SEQUENCE: 361 tggcg                                                                 5

<210> SEQ ID NO 362
<211> LENGTH: 5
<212> TYPE: DNA
<213> ORGANISM: Artificial Sequence
<220> FEATURE:
<223> OTHER INFORMATION: Element 2

<400> SEQUENCE: 362 tgggc                                                                 5

<210> SEQ ID NO 363
<211> LENGTH: 5
<212> TYPE: DNA
<213> ORGANISM: Artificial Sequence
<220> FEATURE:
<223> OTHER INFORMATION: Element 2

<400> SEQUENCE: 363 aaagg                                                                 5

<210> SEQ ID NO 364
<211> LENGTH: 5
<212> TYPE: DNA
<213> ORGANISM: Artificial Sequence
<220> FEATURE:
<223> OTHER INFORMATION: Element 2

<400> SEQUENCE: 364 aagag                                                                 5

<210> SEQ ID NO 365
<211> LENGTH: 5
<212> TYPE: DNA
<213> ORGANISM: Artificial Sequence
<220> FEATURE:
<223> OTHER INFORMATION: Element 2

<400> SEQUENCE: 365 aagga                                                                 5

<210> SEQ ID NO 366
<211> LENGTH: 5
<212> TYPE: DNA
<213> ORGANISM: Artificial Sequence
<220> FEATURE:
<223> OTHER INFORMATION: Element 2

<400> SEQUENCE: 366 accgg                                                                 5

<210> SEQ ID NO 367
<211> LENGTH: 5
<212> TYPE: DNA
<213> ORGANISM: Artificial Sequence

```
<220> FEATURE:
<223> OTHER INFORMATION: Element 2

<400> SEQUENCE: 367 acgcg                                                                        5

<210> SEQ ID NO 368
<211> LENGTH: 5
<212> TYPE: DNA
<213> ORGANISM: Artificial Sequence
<220> FEATURE:
<223> OTHER INFORMATION: Element 2

<400> SEQUENCE: 368 acggc                                                                        5

<210> SEQ ID NO 369
<211> LENGTH: 5
<212> TYPE: DNA
<213> ORGANISM: Artificial Sequence
<220> FEATURE:
<223> OTHER INFORMATION: Element 2

<400> SEQUENCE: 369 agaag                                                                        5

<210> SEQ ID NO 370
<211> LENGTH: 5
<212> TYPE: DNA
<213> ORGANISM: Artificial Sequence
<220> FEATURE:
<223> OTHER INFORMATION: Element 2

<400> SEQUENCE: 370 gtgta                                                                        5

<210> SEQ ID NO 371
<211> LENGTH: 5
<212> TYPE: DNA
<213> ORGANISM: Artificial Sequence
<220> FEATURE:
<223> OTHER INFORMATION: Element 2

<400> SEQUENCE: 371 gttag                                                                        5

<210> SEQ ID NO 372
<211> LENGTH: 5
<212> TYPE: DNA
<213> ORGANISM: Artificial Sequence
<220> FEATURE:
<223> OTHER INFORMATION: Element 2

<400> SEQUENCE: 372 gttga                                                                        5

<210> SEQ ID NO 373
<211> LENGTH: 5
<212> TYPE: DNA
<213> ORGANISM: Artificial Sequence
<220> FEATURE:
<223> OTHER INFORMATION: Element 2

<400> SEQUENCE: 373 taggt                                                                        5
```

```
<210> SEQ ID NO 374
<211> LENGTH: 5
<212> TYPE: DNA
<213> ORGANISM: Artificial Sequence
<220> FEATURE:
<223> OTHER INFORMATION: Element 2

<400> SEQUENCE: 374 tagtg                                                                    5

<210> SEQ ID NO 375
<211> LENGTH: 5
<212> TYPE: DNA
<213> ORGANISM: Artificial Sequence
<220> FEATURE:
<223> OTHER INFORMATION: Element 2

<400> SEQUENCE: 375 tatgg                                                                    5

<210> SEQ ID NO 376
<211> LENGTH: 5
<212> TYPE: DNA
<213> ORGANISM: Artificial Sequence
<220> FEATURE:
<223> OTHER INFORMATION: Element 2

<400> SEQUENCE: 376 tgagt                                                                    5

<210> SEQ ID NO 377
<211> LENGTH: 5
<212> TYPE: DNA
<213> ORGANISM: Artificial Sequence
<220> FEATURE:
<223> OTHER INFORMATION: Element 2

<400> SEQUENCE: 377 tgatg                                                                    5

<210> SEQ ID NO 378
<211> LENGTH: 5
<212> TYPE: DNA
<213> ORGANISM: Artificial Sequence
<220> FEATURE:
<223> OTHER INFORMATION: Element 2

<400> SEQUENCE: 378 tggat                                                                    5

<210> SEQ ID NO 379
<211> LENGTH: 5
<212> TYPE: DNA
<213> ORGANISM: Artificial Sequence
<220> FEATURE:
<223> OTHER INFORMATION: Element 2

<400> SEQUENCE: 379 tggta                                                                    5

<210> SEQ ID NO 380
<211> LENGTH: 5
<212> TYPE: DNA
<213> ORGANISM: Artificial Sequence
<220> FEATURE:
<223> OTHER INFORMATION: Element 2
```

```
<400> SEQUENCE: 380 tgtag                                                               5

<210> SEQ ID NO 381
<211> LENGTH: 5
<212> TYPE: DNA
<213> ORGANISM: Artificial Sequence
<220> FEATURE:
<223> OTHER INFORMATION: Element 2

<400> SEQUENCE: 381 tgtga                                                               5

<210> SEQ ID NO 382
<211> LENGTH: 5
<212> TYPE: DNA
<213> ORGANISM: Artificial Sequence
<220> FEATURE:
<223> OTHER INFORMATION: Element 2

<400> SEQUENCE: 382 ttagg                                                               5

<210> SEQ ID NO 383
<211> LENGTH: 5
<212> TYPE: DNA
<213> ORGANISM: Artificial Sequence
<220> FEATURE:
<223> OTHER INFORMATION: Element 2

<400> SEQUENCE: 383 ttgag                                                               5

<210> SEQ ID NO 384
<211> LENGTH: 5
<212> TYPE: DNA
<213> ORGANISM: Artificial Sequence
<220> FEATURE:
<223> OTHER INFORMATION: Element 2

<400> SEQUENCE: 384 ttgga                                                               5

<210> SEQ ID NO 385
<211> LENGTH: 5
<212> TYPE: DNA
<213> ORGANISM: Artificial Sequence
<220> FEATURE:
<223> OTHER INFORMATION: Element 2

<400> SEQUENCE: 385 aacgt                                                               5

<210> SEQ ID NO 386
<211> LENGTH: 5
<212> TYPE: DNA
<213> ORGANISM: Artificial Sequence
<220> FEATURE:
<223> OTHER INFORMATION: Element 2

<400> SEQUENCE: 386 ctgtt                                                               5

<210> SEQ ID NO 387
```

```
<211> LENGTH: 5
<212> TYPE: DNA
<213> ORGANISM: Artificial Sequence
<220> FEATURE:
<223> OTHER INFORMATION: Element 2

<400> SEQUENCE: 387 cttgt                                                                    5

<210> SEQ ID NO 388
<211> LENGTH: 5
<212> TYPE: DNA
<213> ORGANISM: Artificial Sequence
<220> FEATURE:
<223> OTHER INFORMATION: Element 2

<400> SEQUENCE: 388 ctttg                                                                    5

<210> SEQ ID NO 389
<211> LENGTH: 5
<212> TYPE: DNA
<213> ORGANISM: Artificial Sequence
<220> FEATURE:
<223> OTHER INFORMATION: Element 2

<400> SEQUENCE: 389 gaact                                                                    5

<210> SEQ ID NO 390
<211> LENGTH: 5
<212> TYPE: DNA
<213> ORGANISM: Artificial Sequence
<220> FEATURE:
<223> OTHER INFORMATION: Element 2

<400> SEQUENCE: 390 gaatc                                                                    5

<210> SEQ ID NO 391
<211> LENGTH: 5
<212> TYPE: DNA
<213> ORGANISM: Artificial Sequence
<220> FEATURE:
<223> OTHER INFORMATION: Element 2

<400> SEQUENCE: 391 gacat                                                                    5

<210> SEQ ID NO 392
<211> LENGTH: 5
<212> TYPE: DNA
<213> ORGANISM: Artificial Sequence
<220> FEATURE:
<223> OTHER INFORMATION: Element 2

<400> SEQUENCE: 392 gacta                                                                    5

<210> SEQ ID NO 393
<211> LENGTH: 5
<212> TYPE: DNA
<213> ORGANISM: Artificial Sequence
<220> FEATURE:
<223> OTHER INFORMATION: Element 2

<400> SEQUENCE: 393
``` gatac                                                          5

<210> SEQ ID NO 394
<211> LENGTH: 5
<212> TYPE: DNA
<213> ORGANISM: Artificial Sequence
<220> FEATURE:
<223> OTHER INFORMATION: Element 2

<400> SEQUENCE: 394 gatca                                                          5

<210> SEQ ID NO 395
<211> LENGTH: 5
<212> TYPE: DNA
<213> ORGANISM: Artificial Sequence
<220> FEATURE:
<223> OTHER INFORMATION: Element 2

<400> SEQUENCE: 395 gcaat                                                          5

<210> SEQ ID NO 396
<211> LENGTH: 5
<212> TYPE: DNA
<213> ORGANISM: Artificial Sequence
<220> FEATURE:
<223> OTHER INFORMATION: Element 2

<400> SEQUENCE: 396 gcata                                                          5

<210> SEQ ID NO 397
<211> LENGTH: 5
<212> TYPE: DNA
<213> ORGANISM: Artificial Sequence
<220> FEATURE:
<223> OTHER INFORMATION: Element 2

<400> SEQUENCE: 397 gccct                                                          5

<210> SEQ ID NO 398
<211> LENGTH: 5
<212> TYPE: DNA
<213> ORGANISM: Artificial Sequence
<220> FEATURE:
<223> OTHER INFORMATION: Element 2

<400> SEQUENCE: 398 gcctc                                                          5

<210> SEQ ID NO 399
<211> LENGTH: 5
<212> TYPE: DNA
<213> ORGANISM: Artificial Sequence
<220> FEATURE:
<223> OTHER INFORMATION: Element 2

<400> SEQUENCE: 399 gctaa                                                          5

<210> SEQ ID NO 400
<211> LENGTH: 5
<212> TYPE: DNA

-continued

```
<213> ORGANISM: Artificial Sequence
<220> FEATURE:
<223> OTHER INFORMATION: Element 2

<400> SEQUENCE: 400 gctcc                                                                    5

<210> SEQ ID NO 401
<211> LENGTH: 5
<212> TYPE: DNA
<213> ORGANISM: Artificial Sequence
<220> FEATURE:
<223> OTHER INFORMATION: Element 2

<400> SEQUENCE: 401 gcttt                                                                    5

<210> SEQ ID NO 402
<211> LENGTH: 5
<212> TYPE: DNA
<213> ORGANISM: Artificial Sequence
<220> FEATURE:
<223> OTHER INFORMATION: Element 2

<400> SEQUENCE: 402 acttc                                                                    5

<210> SEQ ID NO 403
<211> LENGTH: 5
<212> TYPE: DNA
<213> ORGANISM: Artificial Sequence
<220> FEATURE:
<223> OTHER INFORMATION: Element 2

<400> SEQUENCE: 403 ataat                                                                    5

<210> SEQ ID NO 404
<211> LENGTH: 5
<212> TYPE: DNA
<213> ORGANISM: Artificial Sequence
<220> FEATURE:
<223> OTHER INFORMATION: Element 2

<400> SEQUENCE: 404 atata                                                                    5

<210> SEQ ID NO 405
<211> LENGTH: 5
<212> TYPE: DNA
<213> ORGANISM: Artificial Sequence
<220> FEATURE:
<223> OTHER INFORMATION: Element 2

<400> SEQUENCE: 405 atcct                                                                    5

<210> SEQ ID NO 406
<211> LENGTH: 5
<212> TYPE: DNA
<213> ORGANISM: Artificial Sequence
<220> FEATURE:
<223> OTHER INFORMATION: Element 2

<400> SEQUENCE: 406 atctc                                                                    5
```

```
<210> SEQ ID NO 407
<211> LENGTH: 5
<212> TYPE: DNA
<213> ORGANISM: Artificial Sequence
<220> FEATURE:
<223> OTHER INFORMATION: Element 2

<400> SEQUENCE: 407 attaa                                                                     5

<210> SEQ ID NO 408
<211> LENGTH: 5
<212> TYPE: DNA
<213> ORGANISM: Artificial Sequence
<220> FEATURE:
<223> OTHER INFORMATION: Element 2

<400> SEQUENCE: 408 attcc                                                                     5

<210> SEQ ID NO 409
<211> LENGTH: 5
<212> TYPE: DNA
<213> ORGANISM: Artificial Sequence
<220> FEATURE:
<223> OTHER INFORMATION: Element 2

<400> SEQUENCE: 409 atttt                                                                     5

<210> SEQ ID NO 410
<211> LENGTH: 5
<212> TYPE: DNA
<213> ORGANISM: Artificial Sequence
<220> FEATURE:
<223> OTHER INFORMATION: Element 2

<400> SEQUENCE: 410 caaac                                                                     5

<210> SEQ ID NO 411
<211> LENGTH: 5
<212> TYPE: DNA
<213> ORGANISM: Artificial Sequence
<220> FEATURE:
<223> OTHER INFORMATION: Element 2

<400> SEQUENCE: 411 caaca                                                                     5

<210> SEQ ID NO 412
<211> LENGTH: 5
<212> TYPE: DNA
<213> ORGANISM: Artificial Sequence
<220> FEATURE:
<223> OTHER INFORMATION: Element 2

<400> SEQUENCE: 412 cacaa                                                                     5

<210> SEQ ID NO 413
<211> LENGTH: 5
<212> TYPE: DNA
<213> ORGANISM: Artificial Sequence
<220> FEATURE:
```

```
<223> OTHER INFORMATION: Element 2

<400> SEQUENCE: 413 caccc                                                                    5

<210> SEQ ID NO 414
<211> LENGTH: 5
<212> TYPE: DNA
<213> ORGANISM: Artificial Sequence
<220> FEATURE:
<223> OTHER INFORMATION: Element 2

<400> SEQUENCE: 414 cactt                                                                    5

<210> SEQ ID NO 415
<211> LENGTH: 5
<212> TYPE: DNA
<213> ORGANISM: Artificial Sequence
<220> FEATURE:
<223> OTHER INFORMATION: Element 2

<400> SEQUENCE: 415 catct                                                                    5

<210> SEQ ID NO 416
<211> LENGTH: 5
<212> TYPE: DNA
<213> ORGANISM: Artificial Sequence
<220> FEATURE:
<223> OTHER INFORMATION: Element 2

<400> SEQUENCE: 416 cattc                                                                    5

<210> SEQ ID NO 417
<211> LENGTH: 5
<212> TYPE: DNA
<213> ORGANISM: Artificial Sequence
<220> FEATURE:
<223> OTHER INFORMATION: Element 2

<400> SEQUENCE: 417 ccaaa                                                                    5

<210> SEQ ID NO 418
<211> LENGTH: 5
<212> TYPE: DNA
<213> ORGANISM: Artificial Sequence
<220> FEATURE:
<223> OTHER INFORMATION: Element 2

<400> SEQUENCE: 418 agaga                                                                    5

<210> SEQ ID NO 419
<211> LENGTH: 5
<212> TYPE: DNA
<213> ORGANISM: Artificial Sequence
<220> FEATURE:
<223> OTHER INFORMATION: Element 2

<400> SEQUENCE: 419 agccg                                                                    5
```

```
<210> SEQ ID NO 420
<211> LENGTH: 5
<212> TYPE: DNA
<213> ORGANISM: Artificial Sequence
<220> FEATURE:
<223> OTHER INFORMATION: Element 2

<400> SEQUENCE: 420 agcgc                                                                    5

<210> SEQ ID NO 421
<211> LENGTH: 5
<212> TYPE: DNA
<213> ORGANISM: Artificial Sequence
<220> FEATURE:
<223> OTHER INFORMATION: Element 2

<400> SEQUENCE: 421 aggaa                                                                    5

<210> SEQ ID NO 422
<211> LENGTH: 5
<212> TYPE: DNA
<213> ORGANISM: Artificial Sequence
<220> FEATURE:
<223> OTHER INFORMATION: Element 2

<400> SEQUENCE: 422 aggcc                                                                    5

<210> SEQ ID NO 423
<211> LENGTH: 5
<212> TYPE: DNA
<213> ORGANISM: Artificial Sequence
<220> FEATURE:
<223> OTHER INFORMATION: Element 2

<400> SEQUENCE: 423 aggtt                                                                    5

<210> SEQ ID NO 424
<211> LENGTH: 5
<212> TYPE: DNA
<213> ORGANISM: Artificial Sequence
<220> FEATURE:
<223> OTHER INFORMATION: Element 2

<400> SEQUENCE: 424 agtgt                                                                    5

<210> SEQ ID NO 425
<211> LENGTH: 5
<212> TYPE: DNA
<213> ORGANISM: Artificial Sequence
<220> FEATURE:
<223> OTHER INFORMATION: Element 2

<400> SEQUENCE: 425 agttg                                                                    5

<210> SEQ ID NO 426
<211> LENGTH: 5
<212> TYPE: DNA
<213> ORGANISM: Artificial Sequence
<220> FEATURE:
<223> OTHER INFORMATION: Element 2
```

```
<400> SEQUENCE: 426 atggt                                                              5

<210> SEQ ID NO 427
<211> LENGTH: 5
<212> TYPE: DNA
<213> ORGANISM: Artificial Sequence
<220> FEATURE:
<223> OTHER INFORMATION: Element 2

<400> SEQUENCE: 427 atgtg                                                              5

<210> SEQ ID NO 428
<211> LENGTH: 5
<212> TYPE: DNA
<213> ORGANISM: Artificial Sequence
<220> FEATURE:
<223> OTHER INFORMATION: Element 2

<400> SEQUENCE: 428 attgg                                                              5

<210> SEQ ID NO 429
<211> LENGTH: 5
<212> TYPE: DNA
<213> ORGANISM: Artificial Sequence
<220> FEATURE:
<223> OTHER INFORMATION: Element 2

<400> SEQUENCE: 429 cacgg                                                              5

<210> SEQ ID NO 430
<211> LENGTH: 5
<212> TYPE: DNA
<213> ORGANISM: Artificial Sequence
<220> FEATURE:
<223> OTHER INFORMATION: Element 2

<400> SEQUENCE: 430 cagcg                                                              5

<210> SEQ ID NO 431
<211> LENGTH: 5
<212> TYPE: DNA
<213> ORGANISM: Artificial Sequence
<220> FEATURE:
<223> OTHER INFORMATION: Element 2

<400> SEQUENCE: 431 caggc                                                              5

<210> SEQ ID NO 432
<211> LENGTH: 5
<212> TYPE: DNA
<213> ORGANISM: Artificial Sequence
<220> FEATURE:
<223> OTHER INFORMATION: Element 2

<400> SEQUENCE: 432 ccagg                                                              5

<210> SEQ ID NO 433
<211> LENGTH: 5
```

```
<212> TYPE: DNA
<213> ORGANISM: Artificial Sequence
<220> FEATURE:
<223> OTHER INFORMATION: Element 2

<400> SEQUENCE: 433 ccgag                                                               5

<210> SEQ ID NO 434
<211> LENGTH: 5
<212> TYPE: DNA
<213> ORGANISM: Artificial Sequence
<220> FEATURE:
<223> OTHER INFORMATION: Element 2

<400> SEQUENCE: 434 aactg                                                               5

<210> SEQ ID NO 435
<211> LENGTH: 5
<212> TYPE: DNA
<213> ORGANISM: Artificial Sequence
<220> FEATURE:
<223> OTHER INFORMATION: Element 2

<400> SEQUENCE: 435 aagct                                                               5

<210> SEQ ID NO 436
<211> LENGTH: 5
<212> TYPE: DNA
<213> ORGANISM: Artificial Sequence
<220> FEATURE:
<223> OTHER INFORMATION: Element 2

<400> SEQUENCE: 436 aagtc                                                               5

<210> SEQ ID NO 437
<211> LENGTH: 5
<212> TYPE: DNA
<213> ORGANISM: Artificial Sequence
<220> FEATURE:
<223> OTHER INFORMATION: Element 2

<400> SEQUENCE: 437 aatcg                                                               5

<210> SEQ ID NO 438
<211> LENGTH: 5
<212> TYPE: DNA
<213> ORGANISM: Artificial Sequence
<220> FEATURE:
<223> OTHER INFORMATION: Element 2

<400> SEQUENCE: 438 aatgc                                                               5

<210> SEQ ID NO 439
<211> LENGTH: 5
<212> TYPE: DNA
<213> ORGANISM: Artificial Sequence
<220> FEATURE:
<223> OTHER INFORMATION: Element 2

<400> SEQUENCE: 439
```

```
acagt                                                          5

<210> SEQ ID NO 440
<211> LENGTH: 5
<212> TYPE: DNA
<213> ORGANISM: Artificial Sequence
<220> FEATURE:
<223> OTHER INFORMATION: Element 2

<400> SEQUENCE: 440 acatg                                                          5

<210> SEQ ID NO 441
<211> LENGTH: 5
<212> TYPE: DNA
<213> ORGANISM: Artificial Sequence
<220> FEATURE:
<223> OTHER INFORMATION: Element 2

<400> SEQUENCE: 441 acgat                                                          5

<210> SEQ ID NO 442
<211> LENGTH: 5
<212> TYPE: DNA
<213> ORGANISM: Artificial Sequence
<220> FEATURE:
<223> OTHER INFORMATION: Element 2

<400> SEQUENCE: 442 acgta                                                          5

<210> SEQ ID NO 443
<211> LENGTH: 5
<212> TYPE: DNA
<213> ORGANISM: Artificial Sequence
<220> FEATURE:
<223> OTHER INFORMATION: Element 2

<400> SEQUENCE: 443 actag                                                          5

<210> SEQ ID NO 444
<211> LENGTH: 5
<212> TYPE: DNA
<213> ORGANISM: Artificial Sequence
<220> FEATURE:
<223> OTHER INFORMATION: Element 2

<400> SEQUENCE: 444 actga                                                          5

<210> SEQ ID NO 445
<211> LENGTH: 5
<212> TYPE: DNA
<213> ORGANISM: Artificial Sequence
<220> FEATURE:
<223> OTHER INFORMATION: Element 2

<400> SEQUENCE: 445 agact                                                          5

<210> SEQ ID NO 446
<211> LENGTH: 5
<212> TYPE: DNA
<213> ORGANISM: Artificial Sequence
```

```
<220> FEATURE:
<223> OTHER INFORMATION: Element 2

<400> SEQUENCE: 446 agatc                                                                    5

<210> SEQ ID NO 447
<211> LENGTH: 5
<212> TYPE: DNA
<213> ORGANISM: Artificial Sequence
<220> FEATURE:
<223> OTHER INFORMATION: Element 2

<400> SEQUENCE: 447 agcat                                                                    5

<210> SEQ ID NO 448
<211> LENGTH: 5
<212> TYPE: DNA
<213> ORGANISM: Artificial Sequence
<220> FEATURE:
<223> OTHER INFORMATION: Element 2

<400> SEQUENCE: 448 agcta                                                                    5

<210> SEQ ID NO 449
<211> LENGTH: 5
<212> TYPE: DNA
<213> ORGANISM: Artificial Sequence
<220> FEATURE:
<223> OTHER INFORMATION: Element 2

<400> SEQUENCE: 449 agtac                                                                    5

<210> SEQ ID NO 450
<211> LENGTH: 5
<212> TYPE: DNA
<213> ORGANISM: Artificial Sequence
<220> FEATURE:
<223> OTHER INFORMATION: Element 2

<400> SEQUENCE: 450 gtaac                                                                    5

<210> SEQ ID NO 451
<211> LENGTH: 5
<212> TYPE: DNA
<213> ORGANISM: Artificial Sequence
<220> FEATURE:
<223> OTHER INFORMATION: Element 2

<400> SEQUENCE: 451 gtaca                                                                    5

<210> SEQ ID NO 452
<211> LENGTH: 5
<212> TYPE: DNA
<213> ORGANISM: Artificial Sequence
<220> FEATURE:
<223> OTHER INFORMATION: Element 2

<400> SEQUENCE: 452 gtcaa                                                                    5
```

```
<210> SEQ ID NO 453
<211> LENGTH: 5
<212> TYPE: DNA
<213> ORGANISM: Artificial Sequence
<220> FEATURE:
<223> OTHER INFORMATION: Element 2

<400> SEQUENCE: 453 gtccc                                                                  5

<210> SEQ ID NO 454
<211> LENGTH: 5
<212> TYPE: DNA
<213> ORGANISM: Artificial Sequence
<220> FEATURE:
<223> OTHER INFORMATION: Element 2

<400> SEQUENCE: 454 gtctt                                                                  5

<210> SEQ ID NO 455
<211> LENGTH: 5
<212> TYPE: DNA
<213> ORGANISM: Artificial Sequence
<220> FEATURE:
<223> OTHER INFORMATION: Element 2

<400> SEQUENCE: 455 gttct                                                                  5

<210> SEQ ID NO 456
<211> LENGTH: 5
<212> TYPE: DNA
<213> ORGANISM: Artificial Sequence
<220> FEATURE:
<223> OTHER INFORMATION: Element 2

<400> SEQUENCE: 456 gtttc                                                                  5

<210> SEQ ID NO 457
<211> LENGTH: 5
<212> TYPE: DNA
<213> ORGANISM: Artificial Sequence
<220> FEATURE:
<223> OTHER INFORMATION: Element 2

<400> SEQUENCE: 457 taacg                                                                  5

<210> SEQ ID NO 458
<211> LENGTH: 5
<212> TYPE: DNA
<213> ORGANISM: Artificial Sequence
<220> FEATURE:
<223> OTHER INFORMATION: Element 2

<400> SEQUENCE: 458 taagc                                                                  5

<210> SEQ ID NO 459
<211> LENGTH: 5
<212> TYPE: DNA
<213> ORGANISM: Artificial Sequence
<220> FEATURE:
<223> OTHER INFORMATION: Element 2
```

```
<400> SEQUENCE: 459 tacag                                                                    5

<210> SEQ ID NO 460
<211> LENGTH: 5
<212> TYPE: DNA
<213> ORGANISM: Artificial Sequence
<220> FEATURE:
<223> OTHER INFORMATION: Element 2

<400> SEQUENCE: 460 tacga                                                                    5

<210> SEQ ID NO 461
<211> LENGTH: 5
<212> TYPE: DNA
<213> ORGANISM: Artificial Sequence
<220> FEATURE:
<223> OTHER INFORMATION: Element 2

<400> SEQUENCE: 461 tagac                                                                    5

<210> SEQ ID NO 462
<211> LENGTH: 5
<212> TYPE: DNA
<213> ORGANISM: Artificial Sequence
<220> FEATURE:
<223> OTHER INFORMATION: Element 2

<400> SEQUENCE: 462 tagca                                                                    5

<210> SEQ ID NO 463
<211> LENGTH: 5
<212> TYPE: DNA
<213> ORGANISM: Artificial Sequence
<220> FEATURE:
<223> OTHER INFORMATION: Element 2

<400> SEQUENCE: 463 tcaag                                                                    5

<210> SEQ ID NO 464
<211> LENGTH: 5
<212> TYPE: DNA
<213> ORGANISM: Artificial Sequence
<220> FEATURE:
<223> OTHER INFORMATION: Element 2

<400> SEQUENCE: 464 tcaga                                                                    5

<210> SEQ ID NO 465
<211> LENGTH: 5
<212> TYPE: DNA
<213> ORGANISM: Artificial Sequence
<220> FEATURE:
<223> OTHER INFORMATION: Element 2

<400> SEQUENCE: 465 tcccg                                                                    5

<210> SEQ ID NO 466
```

```
<211> LENGTH: 5
<212> TYPE: DNA
<213> ORGANISM: Artificial Sequence
<220> FEATURE:
<223> OTHER INFORMATION: Element 2

<400> SEQUENCE: 466 ccacc                                                                      5

<210> SEQ ID NO 467
<211> LENGTH: 5
<212> TYPE: DNA
<213> ORGANISM: Artificial Sequence
<220> FEATURE:
<223> OTHER INFORMATION: Element 2

<400> SEQUENCE: 467 ccatt                                                                      5

<210> SEQ ID NO 468
<211> LENGTH: 5
<212> TYPE: DNA
<213> ORGANISM: Artificial Sequence
<220> FEATURE:
<223> OTHER INFORMATION: Element 2

<400> SEQUENCE: 468 cccac                                                                      5

<210> SEQ ID NO 469
<211> LENGTH: 5
<212> TYPE: DNA
<213> ORGANISM: Artificial Sequence
<220> FEATURE:
<223> OTHER INFORMATION: Element 2

<400> SEQUENCE: 469 cccca                                                                      5

<210> SEQ ID NO 470
<211> LENGTH: 5
<212> TYPE: DNA
<213> ORGANISM: Artificial Sequence
<220> FEATURE:
<223> OTHER INFORMATION: Element 2

<400> SEQUENCE: 470 cctat                                                                      5

<210> SEQ ID NO 471
<211> LENGTH: 5
<212> TYPE: DNA
<213> ORGANISM: Artificial Sequence
<220> FEATURE:
<223> OTHER INFORMATION: Element 2

<400> SEQUENCE: 471 cctta                                                                      5

<210> SEQ ID NO 472
<211> LENGTH: 5
<212> TYPE: DNA
<213> ORGANISM: Artificial Sequence
<220> FEATURE:
<223> OTHER INFORMATION: Element 2

<400> SEQUENCE: 472
``` ctact                                                                  5

<210> SEQ ID NO 473
<211> LENGTH: 5
<212> TYPE: DNA
<213> ORGANISM: Artificial Sequence
<220> FEATURE:
<223> OTHER INFORMATION: Element 2

<400> SEQUENCE: 473 ctatc                                                                  5

<210> SEQ ID NO 474
<211> LENGTH: 5
<212> TYPE: DNA
<213> ORGANISM: Artificial Sequence
<220> FEATURE:
<223> OTHER INFORMATION: Element 2

<400> SEQUENCE: 474 ctcat                                                                  5

<210> SEQ ID NO 475
<211> LENGTH: 5
<212> TYPE: DNA
<213> ORGANISM: Artificial Sequence
<220> FEATURE:
<223> OTHER INFORMATION: Element 2

<400> SEQUENCE: 475 ctcta                                                                  5

<210> SEQ ID NO 476
<211> LENGTH: 5
<212> TYPE: DNA
<213> ORGANISM: Artificial Sequence
<220> FEATURE:
<223> OTHER INFORMATION: Element 2

<400> SEQUENCE: 476 cttac                                                                  5

<210> SEQ ID NO 477
<211> LENGTH: 5
<212> TYPE: DNA
<213> ORGANISM: Artificial Sequence
<220> FEATURE:
<223> OTHER INFORMATION: Element 2

<400> SEQUENCE: 477 cttca                                                                  5

<210> SEQ ID NO 478
<211> LENGTH: 5
<212> TYPE: DNA
<213> ORGANISM: Artificial Sequence
<220> FEATURE:
<223> OTHER INFORMATION: Element 2

<400> SEQUENCE: 478 taaat                                                                  5

<210> SEQ ID NO 479
<211> LENGTH: 5
<212> TYPE: DNA

```
<213> ORGANISM: Artificial Sequence
<220> FEATURE:
<223> OTHER INFORMATION: Element 2

<400> SEQUENCE: 479 taata                                                                      5

<210> SEQ ID NO 480
<211> LENGTH: 5
<212> TYPE: DNA
<213> ORGANISM: Artificial Sequence
<220> FEATURE:
<223> OTHER INFORMATION: Element 2

<400> SEQUENCE: 480 tacct                                                                      5

<210> SEQ ID NO 481
<211> LENGTH: 5
<212> TYPE: DNA
<213> ORGANISM: Artificial Sequence
<220> FEATURE:
<223> OTHER INFORMATION: Element 2

<400> SEQUENCE: 481 tactc                                                                      5

<210> SEQ ID NO 482
<211> LENGTH: 5
<212> TYPE: DNA
<213> ORGANISM: Artificial Sequence
<220> FEATURE:
<223> OTHER INFORMATION: Element 2

<400> SEQUENCE: 482 ccgga                                                                      5

<210> SEQ ID NO 483
<211> LENGTH: 5
<212> TYPE: DNA
<213> ORGANISM: Artificial Sequence
<220> FEATURE:
<223> OTHER INFORMATION: Element 2

<400> SEQUENCE: 483 cgacg                                                                      5

<210> SEQ ID NO 484
<211> LENGTH: 5
<212> TYPE: DNA
<213> ORGANISM: Artificial Sequence
<220> FEATURE:
<223> OTHER INFORMATION: Element 2

<400> SEQUENCE: 484 cgagc                                                                      5

<210> SEQ ID NO 485
<211> LENGTH: 5
<212> TYPE: DNA
<213> ORGANISM: Artificial Sequence
<220> FEATURE:
<223> OTHER INFORMATION: Element 2

<400> SEQUENCE: 485 cgcag                                                                      5
```

```
<210> SEQ ID NO 486
<211> LENGTH: 5
<212> TYPE: DNA
<213> ORGANISM: Artificial Sequence
<220> FEATURE:
<223> OTHER INFORMATION: Element 2

<400> SEQUENCE: 486 cgcga                                                                    5

<210> SEQ ID NO 487
<211> LENGTH: 5
<212> TYPE: DNA
<213> ORGANISM: Artificial Sequence
<220> FEATURE:
<223> OTHER INFORMATION: Element 2

<400> SEQUENCE: 487 cggac                                                                    5

<210> SEQ ID NO 488
<211> LENGTH: 5
<212> TYPE: DNA
<213> ORGANISM: Artificial Sequence
<220> FEATURE:
<223> OTHER INFORMATION: Element 2

<400> SEQUENCE: 488 cggca                                                                    5

<210> SEQ ID NO 489
<211> LENGTH: 5
<212> TYPE: DNA
<213> ORGANISM: Artificial Sequence
<220> FEATURE:
<223> OTHER INFORMATION: Element 2

<400> SEQUENCE: 489 gaaag                                                                    5

<210> SEQ ID NO 490
<211> LENGTH: 5
<212> TYPE: DNA
<213> ORGANISM: Artificial Sequence
<220> FEATURE:
<223> OTHER INFORMATION: Element 2

<400> SEQUENCE: 490 gaaga                                                                    5

<210> SEQ ID NO 491
<211> LENGTH: 5
<212> TYPE: DNA
<213> ORGANISM: Artificial Sequence
<220> FEATURE:
<223> OTHER INFORMATION: Element 2

<400> SEQUENCE: 491 gaccg                                                                    5

<210> SEQ ID NO 492
<211> LENGTH: 5
<212> TYPE: DNA
<213> ORGANISM: Artificial Sequence
<220> FEATURE:
```

```
<223> OTHER INFORMATION: Element 2

<400> SEQUENCE: 492 gacgc                                                                    5

<210> SEQ ID NO 493
<211> LENGTH: 5
<212> TYPE: DNA
<213> ORGANISM: Artificial Sequence
<220> FEATURE:
<223> OTHER INFORMATION: Element 2

<400> SEQUENCE: 493 gagaa                                                                    5

<210> SEQ ID NO 494
<211> LENGTH: 5
<212> TYPE: DNA
<213> ORGANISM: Artificial Sequence
<220> FEATURE:
<223> OTHER INFORMATION: Element 2

<400> SEQUENCE: 494 gagcc                                                                    5

<210> SEQ ID NO 495
<211> LENGTH: 5
<212> TYPE: DNA
<213> ORGANISM: Artificial Sequence
<220> FEATURE:
<223> OTHER INFORMATION: Element 2

<400> SEQUENCE: 495 gagtt                                                                    5

<210> SEQ ID NO 496
<211> LENGTH: 5
<212> TYPE: DNA
<213> ORGANISM: Artificial Sequence
<220> FEATURE:
<223> OTHER INFORMATION: Element 2

<400> SEQUENCE: 496 gatgt                                                                    5

<210> SEQ ID NO 497
<211> LENGTH: 5
<212> TYPE: DNA
<213> ORGANISM: Artificial Sequence
<220> FEATURE:
<223> OTHER INFORMATION: Element 2

<400> SEQUENCE: 497 gattg                                                                    5

<210> SEQ ID NO 498
<211> LENGTH: 5
<212> TYPE: DNA
<213> ORGANISM: Artificial Sequence
<220> FEATURE:
<223> OTHER INFORMATION: Element 2

<400> SEQUENCE: 498 agtca                                                                    5
```

```
<210> SEQ ID NO 499
<211> LENGTH: 5
<212> TYPE: DNA
<213> ORGANISM: Artificial Sequence
<220> FEATURE:
<223> OTHER INFORMATION: Element 2

<400> SEQUENCE: 499 atacg                                                                    5

<210> SEQ ID NO 500
<211> LENGTH: 5
<212> TYPE: DNA
<213> ORGANISM: Artificial Sequence
<220> FEATURE:
<223> OTHER INFORMATION: Element 2

<400> SEQUENCE: 500 atagc                                                                    5

<210> SEQ ID NO 501
<211> LENGTH: 5
<212> TYPE: DNA
<213> ORGANISM: Artificial Sequence
<220> FEATURE:
<223> OTHER INFORMATION: Element 2

<400> SEQUENCE: 501 atcag                                                                    5

<210> SEQ ID NO 502
<211> LENGTH: 5
<212> TYPE: DNA
<213> ORGANISM: Artificial Sequence
<220> FEATURE:
<223> OTHER INFORMATION: Element 2

<400> SEQUENCE: 502 atcga                                                                    5

<210> SEQ ID NO 503
<211> LENGTH: 5
<212> TYPE: DNA
<213> ORGANISM: Artificial Sequence
<220> FEATURE:
<223> OTHER INFORMATION: Element 2

<400> SEQUENCE: 503 atgac                                                                    5

<210> SEQ ID NO 504
<211> LENGTH: 5
<212> TYPE: DNA
<213> ORGANISM: Artificial Sequence
<220> FEATURE:
<223> OTHER INFORMATION: Element 2

<400> SEQUENCE: 504 atgca                                                                    5

<210> SEQ ID NO 505
<211> LENGTH: 5
<212> TYPE: DNA
<213> ORGANISM: Artificial Sequence
<220> FEATURE:
<223> OTHER INFORMATION: Element 2
```

```
<400> SEQUENCE: 505 caagt                                                              5

<210> SEQ ID NO 506
<211> LENGTH: 5
<212> TYPE: DNA
<213> ORGANISM: Artificial Sequence
<220> FEATURE:
<223> OTHER INFORMATION: Element 2

<400> SEQUENCE: 506 caatg                                                              5

<210> SEQ ID NO 507
<211> LENGTH: 5
<212> TYPE: DNA
<213> ORGANISM: Artificial Sequence
<220> FEATURE:
<223> OTHER INFORMATION: Element 2

<400> SEQUENCE: 507 cagat                                                              5

<210> SEQ ID NO 508
<211> LENGTH: 5
<212> TYPE: DNA
<213> ORGANISM: Artificial Sequence
<220> FEATURE:
<223> OTHER INFORMATION: Element 2

<400> SEQUENCE: 508 cagta                                                              5

<210> SEQ ID NO 509
<211> LENGTH: 5
<212> TYPE: DNA
<213> ORGANISM: Artificial Sequence
<220> FEATURE:
<223> OTHER INFORMATION: Element 2

<400> SEQUENCE: 509 catag                                                              5

<210> SEQ ID NO 510
<211> LENGTH: 5
<212> TYPE: DNA
<213> ORGANISM: Artificial Sequence
<220> FEATURE:
<223> OTHER INFORMATION: Element 2

<400> SEQUENCE: 510 catga                                                              5

<210> SEQ ID NO 511
<211> LENGTH: 5
<212> TYPE: DNA
<213> ORGANISM: Artificial Sequence
<220> FEATURE:
<223> OTHER INFORMATION: Element 2

<400> SEQUENCE: 511 cccgt                                                              5

<210> SEQ ID NO 512
<211> LENGTH: 5
```

```
<212> TYPE: DNA
<213> ORGANISM: Artificial Sequence
<220> FEATURE:
<223> OTHER INFORMATION: Element 2

<400> SEQUENCE: 512 ccctg                                                                    5

<210> SEQ ID NO 513
<211> LENGTH: 5
<212> TYPE: DNA
<213> ORGANISM: Artificial Sequence
<220> FEATURE:
<223> OTHER INFORMATION: Element 2

<400> SEQUENCE: 513 ccgct                                                                    5

<210> SEQ ID NO 514
<211> LENGTH: 5
<212> TYPE: DNA
<213> ORGANISM: Artificial Sequence
<220> FEATURE:
<223> OTHER INFORMATION: Element 2

<400> SEQUENCE: 514 tccgc                                                                    5

<210> SEQ ID NO 515
<211> LENGTH: 5
<212> TYPE: DNA
<213> ORGANISM: Artificial Sequence
<220> FEATURE:
<223> OTHER INFORMATION: Element 2

<400> SEQUENCE: 515 tcgaa                                                                    5

<210> SEQ ID NO 516
<211> LENGTH: 5
<212> TYPE: DNA
<213> ORGANISM: Artificial Sequence
<220> FEATURE:
<223> OTHER INFORMATION: Element 2

<400> SEQUENCE: 516 tcgcc                                                                    5

<210> SEQ ID NO 517
<211> LENGTH: 5
<212> TYPE: DNA
<213> ORGANISM: Artificial Sequence
<220> FEATURE:
<223> OTHER INFORMATION: Element 2

<400> SEQUENCE: 517 tcgtt                                                                    5

<210> SEQ ID NO 518
<211> LENGTH: 5
<212> TYPE: DNA
<213> ORGANISM: Artificial Sequence
<220> FEATURE:
<223> OTHER INFORMATION: Element 2

<400> SEQUENCE: 518
``` tctgt                                                                         5

<210> SEQ ID NO 519
<211> LENGTH: 5
<212> TYPE: DNA
<213> ORGANISM: Artificial Sequence
<220> FEATURE:
<223> OTHER INFORMATION: Element 2

<400> SEQUENCE: 519 tcttg                                                                         5

<210> SEQ ID NO 520
<211> LENGTH: 5
<212> TYPE: DNA
<213> ORGANISM: Artificial Sequence
<220> FEATURE:
<223> OTHER INFORMATION: Element 2

<400> SEQUENCE: 520 tgaac                                                                         5

<210> SEQ ID NO 521
<211> LENGTH: 5
<212> TYPE: DNA
<213> ORGANISM: Artificial Sequence
<220> FEATURE:
<223> OTHER INFORMATION: Element 2

<400> SEQUENCE: 521 tgaca                                                                         5

<210> SEQ ID NO 522
<211> LENGTH: 5
<212> TYPE: DNA
<213> ORGANISM: Artificial Sequence
<220> FEATURE:
<223> OTHER INFORMATION: Element 2

<400> SEQUENCE: 522 tgcaa                                                                         5

<210> SEQ ID NO 523
<211> LENGTH: 5
<212> TYPE: DNA
<213> ORGANISM: Artificial Sequence
<220> FEATURE:
<223> OTHER INFORMATION: Element 2

<400> SEQUENCE: 523 tgccc                                                                         5

<210> SEQ ID NO 524
<211> LENGTH: 5
<212> TYPE: DNA
<213> ORGANISM: Artificial Sequence
<220> FEATURE:
<223> OTHER INFORMATION: Element 2

<400> SEQUENCE: 524 tgctt                                                                         5

<210> SEQ ID NO 525
<211> LENGTH: 5
<212> TYPE: DNA
<213> ORGANISM: Artificial Sequence

```
<220> FEATURE:
<223> OTHER INFORMATION: Element 2

<400> SEQUENCE: 525 tgtct                                                                    5

<210> SEQ ID NO 526
<211> LENGTH: 5
<212> TYPE: DNA
<213> ORGANISM: Artificial Sequence
<220> FEATURE:
<223> OTHER INFORMATION: Element 2

<400> SEQUENCE: 526 tgttc                                                                    5

<210> SEQ ID NO 527
<211> LENGTH: 5
<212> TYPE: DNA
<213> ORGANISM: Artificial Sequence
<220> FEATURE:
<223> OTHER INFORMATION: Element 2

<400> SEQUENCE: 527 ttcgt                                                                    5

<210> SEQ ID NO 528
<211> LENGTH: 5
<212> TYPE: DNA
<213> ORGANISM: Artificial Sequence
<220> FEATURE:
<223> OTHER INFORMATION: Element 2

<400> SEQUENCE: 528 ttctg                                                                    5

<210> SEQ ID NO 529
<211> LENGTH: 5
<212> TYPE: DNA
<213> ORGANISM: Artificial Sequence
<220> FEATURE:
<223> OTHER INFORMATION: Element 2

<400> SEQUENCE: 529 ttgct                                                                    5

<210> SEQ ID NO 530
<211> LENGTH: 5
<212> TYPE: DNA
<213> ORGANISM: Artificial Sequence
<220> FEATURE:
<223> OTHER INFORMATION: Element 2

<400> SEQUENCE: 530 tataa                                                                    5

<210> SEQ ID NO 531
<211> LENGTH: 5
<212> TYPE: DNA
<213> ORGANISM: Artificial Sequence
<220> FEATURE:
<223> OTHER INFORMATION: Element 2

<400> SEQUENCE: 531 tatcc                                                                    5
```

```
<210> SEQ ID NO 532
<211> LENGTH: 5
<212> TYPE: DNA
<213> ORGANISM: Artificial Sequence
<220> FEATURE:
<223> OTHER INFORMATION: Element 2

<400> SEQUENCE: 532 tattt                                                                    5

<210> SEQ ID NO 533
<211> LENGTH: 5
<212> TYPE: DNA
<213> ORGANISM: Artificial Sequence
<220> FEATURE:
<223> OTHER INFORMATION: Element 2

<400> SEQUENCE: 533 tcact                                                                    5

<210> SEQ ID NO 534
<211> LENGTH: 5
<212> TYPE: DNA
<213> ORGANISM: Artificial Sequence
<220> FEATURE:
<223> OTHER INFORMATION: Element 2

<400> SEQUENCE: 534 tcatc                                                                    5

<210> SEQ ID NO 535
<211> LENGTH: 5
<212> TYPE: DNA
<213> ORGANISM: Artificial Sequence
<220> FEATURE:
<223> OTHER INFORMATION: element 2

<400> SEQUENCE: 535 tccat                                                                    5

<210> SEQ ID NO 536
<211> LENGTH: 5
<212> TYPE: DNA
<213> ORGANISM: Artificial Sequence
<220> FEATURE:
<223> OTHER INFORMATION: Element 2

<400> SEQUENCE: 536 tccta                                                                    5

<210> SEQ ID NO 537
<211> LENGTH: 5
<212> TYPE: DNA
<213> ORGANISM: Artificial Sequence
<220> FEATURE:
<223> OTHER INFORMATION: Element 2

<400> SEQUENCE: 537 tctac                                                                    5

<210> SEQ ID NO 538
<211> LENGTH: 5
<212> TYPE: DNA
<213> ORGANISM: Artificial Sequence
<220> FEATURE:
<223> OTHER INFORMATION: Element 2
```

```
<400> SEQUENCE: 538 tctca                                                              5

<210> SEQ ID NO 539
<211> LENGTH: 3
<212> TYPE: DNA
<213> ORGANISM: Artificial Sequence
<220> FEATURE:
<223> OTHER INFORMATION: Element 3

<400> SEQUENCE: 539 aag                                                                3

<210> SEQ ID NO 540
<211> LENGTH: 3
<212> TYPE: DNA
<213> ORGANISM: Artificial Sequence
<220> FEATURE:
<223> OTHER INFORMATION: Element 3

<400> SEQUENCE: 540 ctc                                                                3

<210> SEQ ID NO 541
<211> LENGTH: 3
<212> TYPE: DNA
<213> ORGANISM: Artificial Sequence
<220> FEATURE:
<223> OTHER INFORMATION: Element 3

<400> SEQUENCE: 541 ggt                                                                3

<210> SEQ ID NO 542
<211> LENGTH: 3
<212> TYPE: DNA
<213> ORGANISM: Artificial Sequence
<220> FEATURE:
<223> OTHER INFORMATION: Element 3

<400> SEQUENCE: 542 tca                                                                3

<210> SEQ ID NO 543
<211> LENGTH: 3
<212> TYPE: DNA
<213> ORGANISM: Artificial Sequence
<220> FEATURE:
<223> OTHER INFORMATION: Element 3

<400> SEQUENCE: 543 act                                                                3

<210> SEQ ID NO 544
<211> LENGTH: 3
<212> TYPE: DNA
<213> ORGANISM: Artificial Sequence
<220> FEATURE:
<223> OTHER INFORMATION: Element 3

<400> SEQUENCE: 544 cga                                                                3

<210> SEQ ID NO 545
```

```
<211> LENGTH: 3
<212> TYPE: DNA
<213> ORGANISM: Artificial Sequence
<220> FEATURE:
<223> OTHER INFORMATION: Element 3

<400> SEQUENCE: 545 gtg                                                                        3

<210> SEQ ID NO 546
<211> LENGTH: 3
<212> TYPE: DNA
<213> ORGANISM: Artificial Sequence
<220> FEATURE:
<223> OTHER INFORMATION: Element 3

<400> SEQUENCE: 546 tac                                                                        3

<210> SEQ ID NO 547
<211> LENGTH: 3
<212> TYPE: DNA
<213> ORGANISM: Artificial Sequence
<220> FEATURE:
<223> OTHER INFORMATION: Element 3

<400> SEQUENCE: 547 agc                                                                        3

<210> SEQ ID NO 548
<211> LENGTH: 3
<212> TYPE: DNA
<213> ORGANISM: Artificial Sequence
<220> FEATURE:
<223> OTHER INFORMATION: Element 3

<400> SEQUENCE: 548 ccg                                                                        3

<210> SEQ ID NO 549
<211> LENGTH: 3
<212> TYPE: DNA
<213> ORGANISM: Artificial Sequence
<220> FEATURE:
<223> OTHER INFORMATION: Element 3

<400> SEQUENCE: 549 gaa                                                                        3

<210> SEQ ID NO 550
<211> LENGTH: 3
<212> TYPE: DNA
<213> ORGANISM: Artificial Sequence
<220> FEATURE:
<223> OTHER INFORMATION: Element 3

<400> SEQUENCE: 550 ttt                                                                        3

<210> SEQ ID NO 551
<211> LENGTH: 3
<212> TYPE: DNA
<213> ORGANISM: Artificial Sequence
<220> FEATURE:
<223> OTHER INFORMATION: Element 3

<400> SEQUENCE: 551
```

```
ata                                                              3

<210> SEQ ID NO 552
<211> LENGTH: 3
<212> TYPE: DNA
<213> ORGANISM: Artificial Sequence
<220> FEATURE:
<223> OTHER INFORMATION: Element 3

<400> SEQUENCE: 552 cat                                                              3

<210> SEQ ID NO 553
<211> LENGTH: 3
<212> TYPE: DNA
<213> ORGANISM: Artificial Sequence
<220> FEATURE:
<223> OTHER INFORMATION: Element 3

<400> SEQUENCE: 553 gcc                                                              3

<210> SEQ ID NO 554
<211> LENGTH: 3
<212> TYPE: DNA
<213> ORGANISM: Artificial Sequence
<220> FEATURE:
<223> OTHER INFORMATION: Element 3

<400> SEQUENCE: 554 tgg                                                              3

<210> SEQ ID NO 555
<211> LENGTH: 12
<212> TYPE: DNA
<213> ORGANISM: Artificial Sequence
<220> FEATURE:
<223> OTHER INFORMATION: Element 4

<400> SEQUENCE: 555
acccacacca aa                                                   12

<210> SEQ ID NO 556
<211> LENGTH: 12
<212> TYPE: DNA
<213> ORGANISM: Artificial Sequence
<220> FEATURE:
<223> OTHER INFORMATION: Element 4

<400> SEQUENCE: 556
caaacacaac cc                                                   12

<210> SEQ ID NO 557
<211> LENGTH: 12
<212> TYPE: DNA
<213> ORGANISM: Artificial Sequence
<220> FEATURE:
<223> OTHER INFORMATION: Element 4

<400> SEQUENCE: 557
gtgtgggttg tt                                                   12

<210> SEQ ID NO 558
<211> LENGTH: 12
<212> TYPE: DNA
```

```
<213> ORGANISM: Artificial Sequence
<220> FEATURE:
<223> OTHER INFORMATION: Element 4

<400> SEQUENCE: 558
tgtgtttggt gg                                                          12

<210> SEQ ID NO 559
<211> LENGTH: 12
<212> TYPE: DNA
<213> ORGANISM: Artificial Sequence
<220> FEATURE:
<223> OTHER INFORMATION: Element 4

<400> SEQUENCE: 559
tttggtgtgg gt                                                          12

<210> SEQ ID NO 560
<211> LENGTH: 12
<212> TYPE: DNA
<213> ORGANISM: Artificial Sequence
<220> FEATURE:
<223> OTHER INFORMATION: Element 4

<400> SEQUENCE: 560
gggttgtgtt tg                                                          12

<210> SEQ ID NO 561
<211> LENGTH: 12
<212> TYPE: DNA
<213> ORGANISM: Artificial Sequence
<220> FEATURE:
<223> OTHER INFORMATION: Element 4

<400> SEQUENCE: 561
aacaacccac ac                                                          12

<210> SEQ ID NO 562
<211> LENGTH: 12
<212> TYPE: DNA
<213> ORGANISM: Artificial Sequence
<220> FEATURE:
<223> OTHER INFORMATION: Element 4

<400> SEQUENCE: 562
ccaccaaaca ca                                                          12
```